(12) United States Patent
Koyuncu et al.

(10) Patent No.: US 9,168,269 B2
(45) Date of Patent: Oct. 27, 2015

(54) INHIBITORS OF LONG AND VERY LONG CHAIN FATTY ACID METABOLISM AS BROAD SPECTRUM ANTI-VIRALS

(75) Inventors: Emre Koyuncu, Princeton, NJ (US); Joshua D. Rabinowitz, Princeton, NJ (US); Thomas Shenk, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 0 days.

(21) Appl. No.: 13/579,967

(22) PCT Filed: Feb. 18, 2011

(86) PCT No.: PCT/US2011/025558
§ 371 (c)(1),
(2), (4) Date: Apr. 1, 2013

(87) PCT Pub. No.: WO2011/103516
PCT Pub. Date: Aug. 25, 2011

(65) Prior Publication Data
US 2013/0190381 A1    Jul. 25, 2013

Related U.S. Application Data

(60) Provisional application No. 61/305,862, filed on Feb. 18, 2010.

(51) Int. Cl.
| | |
|---|---|
| *A61K 31/415* | (2006.01) |
| *A61K 31/40* | (2006.01) |
| *A61K 31/713* | (2006.01) |
| *A61K 31/536* | (2006.01) |
| *A61K 45/06* | (2006.01) |
| *A61K 31/4155* | (2006.01) |
| *A61K 31/439* | (2006.01) |
| *A61K 31/445* | (2006.01) |
| *A61K 31/46* | (2006.01) |

(52) U.S. Cl.
CPC ........... *A61K 31/713* (2013.01); *A61K 31/4155* (2013.01); *A61K 31/439* (2013.01); *A61K 31/445* (2013.01); *A61K 31/46* (2013.01); *A61K 31/536* (2013.01); *A61K 45/06* (2013.01)

(58) Field of Classification Search
None
See application file for complete search history.

(56) References Cited

U.S. PATENT DOCUMENTS

| | | |
|---|---|---|
| 2001/0033864 A1 | 10/2001 | Colonno et al. |
| 2008/0045482 A1 | 2/2008 | Robbins et al. |
| 2009/0304634 A1 | 12/2009 | Erickson-Miller et al. |

FOREIGN PATENT DOCUMENTS

| | | |
|---|---|---|
| EP | 1914237 A3 | 4/2008 |
| WO | 95/29688 A1 | 11/1995 |

OTHER PUBLICATIONS

Rider et al. PLoS ONE 2011 (6) 1-15.*
Munger et al. Nature Biotechnology 2008 (26) 1179-1186.*
PCT International Search Report and Written Opinion for PCT/US11/25558 mailed Aug. 10, 2011.
Morikawa et al., "Complete inhibition of Human Immunodeficiency Virus Gag Myristoylation is Necessary for Inhibition of Particle Budding", JBC 1996, 271(5):2868-2873.
Yao et al., "Long chain acyl-CoA synthetase 3-mediated phosphalidylcholine synthesis is required for assembly of very low density lipoproteins in human hepatoma Huh7 cells", J. Biol Chem 2006, 283(2):849-54.
Gortmaker et al., "Effect of Combination Therapy Including Protease Inhibitors on Mortality Among Children and Adolescents Infected with HIV-1", N Engl J Med 2001, 345:1522-8.
Tornodo et al., "Evidence for an Essential Role of Long Chian Acyl-CoA Synthetase in Animal Cell Proliferation", The Journal of Biological Chemistry 1991, 266(7):4214-9.
Pub Chem CID:9576787. Oct. 24, 2006. Triascin c -compound summary.

* cited by examiner

*Primary Examiner* — Jeffrey S Lundgren
*Assistant Examiner* — Michael Schmitt
(74) *Attorney, Agent, or Firm* — Kenyon & Kenyon LLP

(57) ABSTRACT

The present invention provides methods and compounds for treating viral infections using modulators of host cell enzymes relating to long chain fatty acid and lipid droplet metabolism. It includes a method of treating viral infections using triacsin C and its relatives, analogs and derivatives as well as other inhibitors of long chain fatty acid metabolism and lipid droplet metabolism.

4 Claims, 18 Drawing Sheets

INHIBITORS OF LONG AND VERY LONG CHAIN FATTY ACID METABOLISM AS BROAD SPECTRUM ANTI-VIRALS

STATEMENT OF GOVERNMENT INTEREST

This invention was made with government support under Grants #1 R01 AI 078063 and #5 R01 CA085786 awarded by the National Institutes of Health. The government has certain rights in the invention.

CROSS-REFERENCE TO RELATED APPLICATIONS

This application is a 371 of International Patent Application No.: PCT/US2011/025558 filed Feb. 18, 2011, which claims the benefit of priority to U.S. patent application Ser. No. 61/305,862 filed Feb. 18, 2010, all of which are incorporated herein by reference in their entireties.

FIELD OF THE INVENTION

The present invention provides methods and compounds for treating viral infections using modulators of host cell enzymes relating to long chain fatty acid and lipid droplet metabolism. It includes a method of treating viral infections using triacsin C and its relatives, analogues and derivatives as well as other inhibitors of long chain fatty acid metabolism and lipid droplet metabolism.

BACKGROUND OF THE INVENTION

There is a great unmet medical need for agents that more safely, effectively, and reliably treat viral infections, from HIV to the common cold. This includes a major need for better agents to treat human cytomegalovirus (where current agents suffer from significant toxicity and lack of efficacy), herpes simplex virus (where current agents are beneficial but provide incomplete relief), influenza A (where resistance to current agents is rampant), and hepatitis C virus (where many patients die from poor disease control). It further includes a major need for agents that work across a spectrum of viruses, facilitating their clinical use without necessarily requiring identification of the underlying pathogen.

SUMMARY OF THE INVENTION

The invention provides a method of treating or preventing viral infection in a mammal, comprising administering to a mammalian subject in need thereof a therapeutically effective amount of a compound or prodrug thereof, or pharmaceutically acceptable salt or ester of said compound or prodrug, wherein the compound is a compound of Formula I:

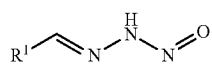
(I)

wherein $R^1$ is a carbon chain having from 3 to 23 atoms (including optional heteroatoms) in the chain, wherein the chain comprises 0-10 double bonds within the chain, and 0-4 heteroatoms within the chain, and wherein 0-8 of the carbon atoms of $R^1$ are optionally substituted. If one or more optional heteroatoms occur within the $R^1$ chain, in preferred embodiments each heteroatom is independently selected from O, S, and $NR^2$, wherein $R^2$ is selected from H, $C_{1-6}$ alkyl, and $C_{3-6}$ cycloalkyl. When the carbon atoms of $R^1$ are substituted, it is preferred that from 0-8 hydrogen atoms along the chain may be replaced by a substituent selected from halo, $OR^2$, $SR^2$, lower alkyl, and cycloalkyl, wherein $R^2$ is H, $C_{1-6}$ alkyl, and $C_{3-6}$ cycloalkyl. In certain preferred embodiments, $R^1$ is unsubstituted (i.e., $R^1$ is unbranched, and none of the hydrogens have been replaced by a substituent). In preferred embodiments for compounds of the formula I, $R^1$ has a chain length of 8 to 12 atoms. More preferably, $R^1$ has a total chain length of $R^1$ has a chain length of 9 to 11 atoms. Most preferably $R^1$ has a chain length of 10 atoms. In other preferred embodiments, $R^1$ has 2 to 4 double bonds. In another embodiment of the invention, the compound of Formula I is a triacsin. In yet another embodiment of the invention, the compound of Formula I is triacsin C. In still another embodiment of the invention, the compound is an inhibitor of acyl-CoA synthetase long-chain family member 1 (ACSL1). In still another embodiment of the invention, the compound is an inhibitor of another enzyme inhibited by triacsin C, including without limitation arachidonoyl-CoA synthase or enzymes of triglyceride (TG) or cholesterol ester (CE) synthesis.

Compounds of Formula I are broad spectrum antivirals useful for treating or preventing infection by a wide range of viruses. In one embodiment, the compounds of Formula I are used to treat or prevent viral infection by an enveloped virus. In certain embodiments of the invention, the compounds are used to treat or prevent infection by human cytomegalovirus (HCMV), herpes simplex virus-1 (HSV-1), influenza A, or hepatitis C virus.

The invention also provides a pharmaceutical composition for treatment or prevention of a viral infection comprising a therapeutically effective amount of a composition comprising a compound or prodrug thereof, or pharmaceutically acceptable salt of said compound or prodrug; and a pharmaceutically acceptable carrier, wherein the compound is a compound of Formula I.

In one embodiment, the invention provides a method of treating or preventing viral infection in a mammal, comprising administering to a mammalian subject in need thereof a therapeutically effective amount of a compound or prodrug thereof, or pharmaceutically acceptable salt or ester of said compound or prodrug, wherein the compound is a compound of formula V

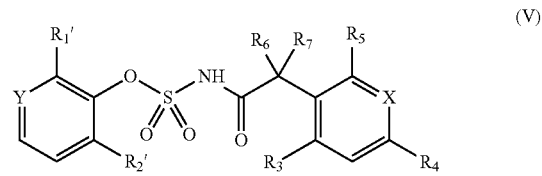
(V)

wherein
X and Y are independently selected from N and CH;
$R_{1'}$ and $R_{2'}$ are independently selected from H, $C_{1-6}$ alkyl which may be optionally substituted with F, $OCH_3$ and OH, and $C_{1-6}$ cycloalkyl;
$R_6$ and $R_7$ are independently selected from H, and $C_{1-3}$ alkyl, or $R_6$ and $R_7$ taken together may form a C3-6 cycloalkyl,
$R_3$, $R_4$ and $R_5$ are independently selected from H, $C_{1-6}$ alkyl which may be optionally substituted with F, $OCH_3$ and OH, and $C_{1-6}$ cycloalkyl;
additionally or alternatively, one of $R_6$ or $R_7$ may be taken together with $R_5$ to form a $C_{5-11}$ cycloalkyl ring.

In one embodiment, the compound of formula V is avasimibe. In one embodiment the compound of formula V is an inhibitor of Acyl-CoA cholesterol acyltransferase (ACAT).

In one embodiment, the invention provides a method of treating or preventing viral infection in a mammal, comprising administering to a mammalian subject in need thereof a therapeutically effective amount of a compound or prodrug thereof, or pharmaceutically acceptable salt or ester of said compound or prodrug, wherein the compound is selected from the group consisting of eflucimibe, pactimibe, Compound 1, Compound 21, Compound 12g, SMP-797, CL-283, 546, and Wu-V-23. In one embodiment the compound inhibitor of Acyl-CoA cholesterol acyltransferase (ACAT).

In one embodiment, the invention provides a method of treating or preventing viral infection in a mammal, comprising administering to a mammalian subject in need thereof a therapeutically effective amount of a compound or prodrug thereof, or pharmaceutically acceptable salt or ester of said compound or prodrug, wherein the compound is selected from the group consisting of PF-1052, spylidone, rubimaillin, sespendole, terpendole C, Compound 7, Compound 8, Compound 9, vermisporin, beauveriolides, phenochalasins, isobisvertinol, and K97-0239. In one embodiment, the compound is PF-1052. In one embodiment, compound is spylidone. In one embodiment, the compound is rubimaillin. In one embodiment compound inhibits lipid droplet formation.

In one embodiment, the invention provides a method of treating or preventing viral infection in a mammal, comprising administering to a mammalian subject in need thereof a therapeutically effective amount of an agent that inhibits a long chain fatty acid synthesis enzyme.

The invention also provides a method of treating or preventing viral infection in a mammal, comprising administering to a mammalian subject in need thereof a therapeutically effective amount of an agent that inhibits the activity of a long chain fatty acid synthesis enzyme. In one embodiment, the enzyme is a long or very long chain acyl-CoA synthetases. In another embodiment, the enzyme is an elongase. In certain embodiments of the invention, the enzyme is ACSL1, ELOVL2, ELOVL3, ELOVL6, or SLC27A3. Inhibitors of such enzymes include inhibitory polynucleotides, small molecule, and biological molecules including, but not limited to, antibodies.

In an embodiment of the invention, the agent is a compound of Formula VI:

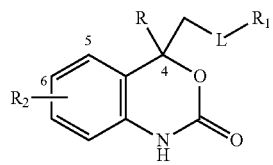
(VI)

wherein L is selected from carbamate, urea, amide,

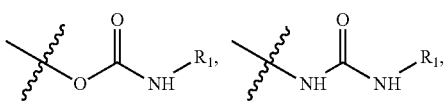

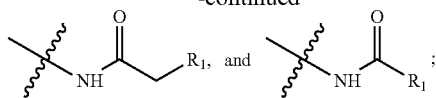

wherein R is selected from halo, $CF_3$, cyclopropyl, optionally substituted $C_{1-5}$ alkyl, wherein the $C_{1-5}$ alkyl may be substituted with halo, oxo, —OH, —CN, —$NH_2$, $CO_2H$, and C1-3 alkoxy; wherein $R_1$ is selected from substituted phenyl where the substituents are selected from F, $CF_3$, Me, OMe, or isopropyl, $R_2$ is Cl, Ph, 1-(2-pyridone), 4-isoxazol, 3-pyrazol, 4-pyrazol, 1-pyrazol, 5-(1,2,4-triazol), 1-(1,2,4-triaol), 2-imidazolo, 1-(2-pyrrolidone), 3-(1,3-oxazolidin-2-one); and wherein the chiral center at C4 can be racemic, (S), (R), or any ratio of enantiomers, or prodrug thereof, or pharmaceutically acceptable salt or ester of said compound or prodrug thereof.

In an embodiment of the invention, the compound of Formula VI is selected from the group consisting of

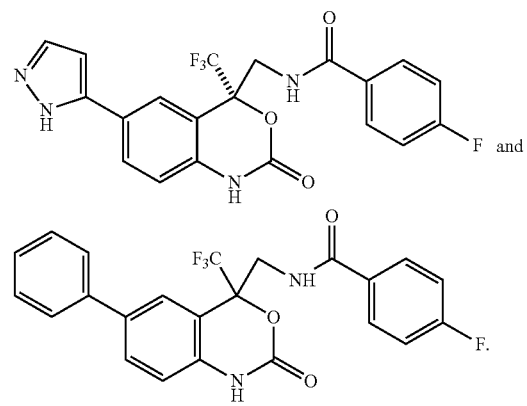

In an embodiment of the invention, the agent is a compound of Formula VIIa or VIIb:

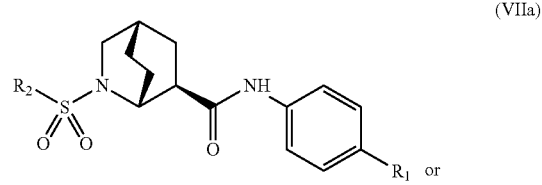
(VIIa)

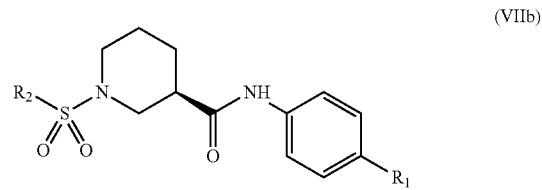
(VIIb)

wherein $R_1$ is selected from OMe, OiPr, $OCF_3$, OPh, $CH_2Ph$, F, $CH_3$, $CF_3$, and benzyl; and $R_2$ is selected from $C_{1-4}$ alkyl (such as nBu, nPr, and iPr); phenyl; substituted phenyl where substitutents are selected from OMe, $CF_3$, F, tBu, iPr and thio; 2-pyridine; 3-pyridine; and N-methy imidazole, or prodrug thereof, or pharmaceutically acceptable salt or ester of said compound or prodrug thereof.

In an embodiment of the invention, the compound of Formula VIIa and VIIb is selected from the group consisting of

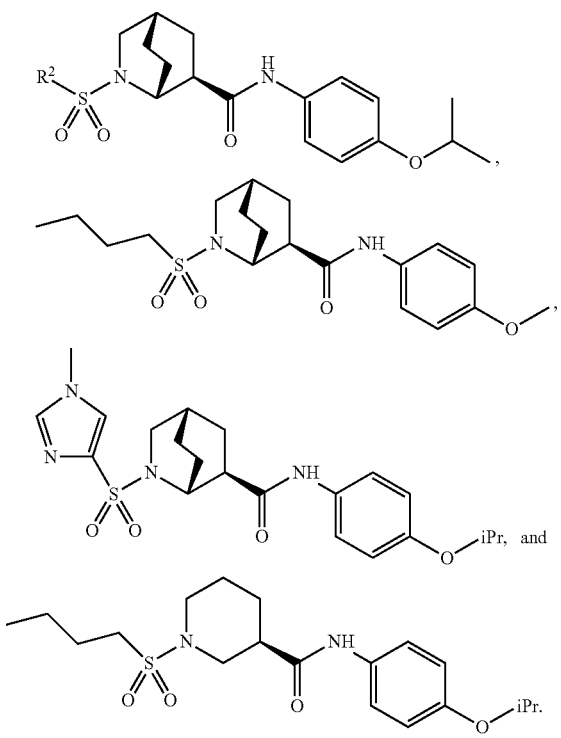

In another embodiment the agent is a compound of Formula VIII

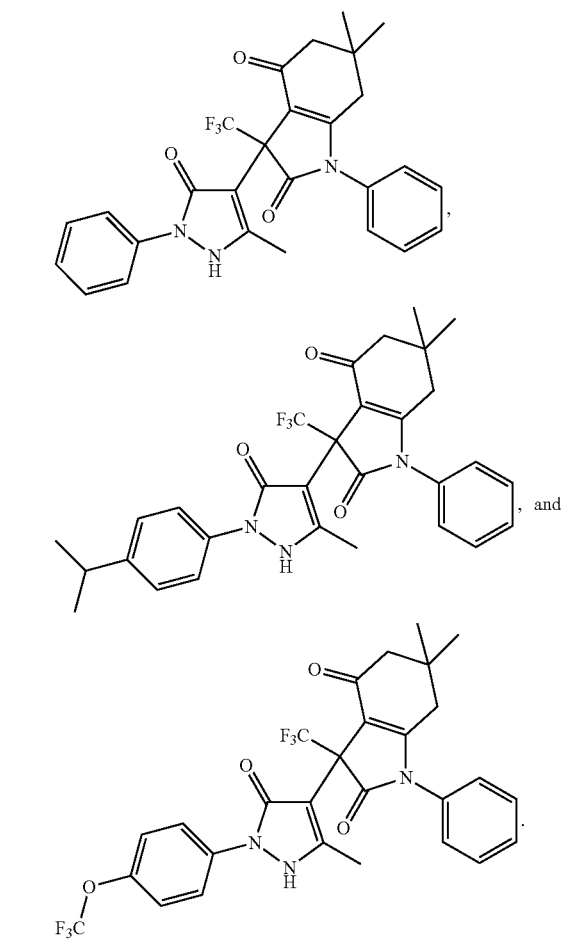

(VIII)

wherein $R_1$ is selected from H, unsubstituted phenyl, substituted phenyl where substitutents are selected from F, Me, Et, Cl, OMe, $OCF_3$, and $CF_3$; $C_{1-6}$ alkyl (such as Me, Et, iPr, and n-propyl); and $C_{3-6}$ cycloalkyl (cyclopropyl, cyclobutyl, cyclopentyl, cyclohexyl), $R_3$ and $R_4$ are independently selected from H, $C_{1-3}$ alkyl, and phenyl; or $R_3$ and $R_4$ taken together form a cycloalkyl of formula —$(CH2)_n$— where n=2, 3, 4 and 5, wherein $R_5$ is selected from methyl; $CF_3$; cyclopropyl; unsubstituted phenyl; mono- and disubstituted phenyl where substitutents are selected from F, Me, Et, CN, iPr, Cl, OMe, OPh, $OCF_3$, and $CF_3$; unsubstituted heteroaromatic groups (such as 2, 3, or 4-pyridine, isoxazol, pyrazol, triazol); and imidazolo or prodrug thereof, or pharmaceutically acceptable salt or ester of said compound or prodrug thereof.

In an embodiment of the invention, the compound of Formula VIII is selected from the group consisting of In yet another embodiment, the agent is a compound of Formula IX:

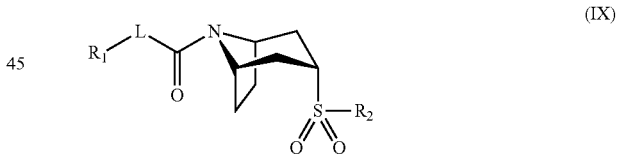

(IX)

wherein L is selected from urea or an amide, for example

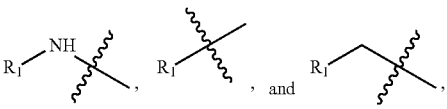

wherein $R_1$ is selected form 2-, 3-, and 4-pyridine; pyrimidine; unsubstituted heteroaryls such as isoxazol, pyrazol, triazol, imidazole; and unsubstituted phenyl; ortho, meta or para-substituted phenyl where substitutents are F, Me, Et, Cl, OMe, $OCF_3$, and $CF_3$, Cl, iPr and phenyl; and wherein $R_2$ is selected from Cl; iPr; phenyl; ortho, meta or para-substituted phenyl where substitutents are F, Me, Et, Cl, OMe, $OCF_3$, and $CF_3$; and heteroaryls such as 2-, 3-, and 4-pyridine, pyrimidine, and isoxazol, pyrazol, triazol, and imidazo, or a prodrug thereof, or pharmaceutically acceptable salt or ester of said compound or prodrug thereof.

In one embodiment, the compound of Formula IX is selected from the group consisting of

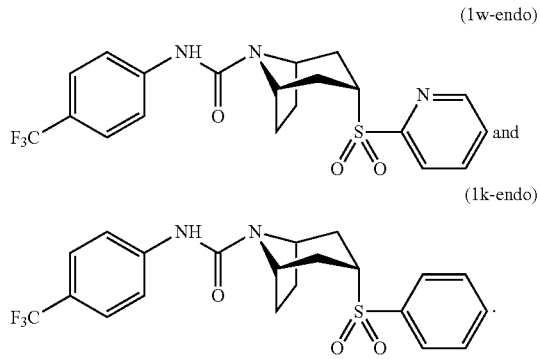

The invention also provides a method of treating or preventing viral infection in a mammal, comprising administering to a mammalian subject in need thereof a therapeutically effective amount of an agent that inhibits acyl-coenzyme A cholesterol acyltransferase (ACAT). In one embodiment, the agent is a dual inhibitor of acyl-coenzyme A cholesterol acyltransferase 1 (ACAT1) and acyl-coenzyme A cholesterol acyltransferase 2 (ACAT2). In another embodiment, the agent is avasimibe. In yet another embodiment, the agent is rubimaillin.

The invention provides a method of treating or preventing viral infection in a mammal, comprising administering to a mammalian subject in need thereof a therapeutically effective amount of an agent that inhibits ADP-ribosyltransferase 1 (ART1). In one embodiment, the method comprises administering to a mammalian subject in need thereof a therapeutically effective amount of meta-iodo-benzylguanidine (MIBG).

The invention further provides a method of treating or preventing viral infection in a mammal, comprising administering to a mammalian subject in need thereof a therapeutically effective amount of an agent that inhibits alanine-glyoxylate aminotransferase 2 (AGXT2). In one embodiment, the method comprises administering to a mammalian subject in need thereof a therapeutically effective amount of aminooxyacetic acid (AOAA).

The invention also provides for treatment of viral infections using combinations of such agents. In one embodiment, the invention provides a method of treating or preventing HCMV infection in a mammal, which comprises administering to a mammalian subject in need thereof a therapeutically effective amount of an agent that inhibits HCMV-encoded DNA polymerase and an agent that inhibits lipid droplet formation or inhibits an enzyme selected from the group consisting of ACSL1, ELOVL2, ELOVL3, ELOVL6, SLC27A3, FAS, ACC, or HMG-CoA.

In another embodiment, a method of treating or preventing HSV infection in a mammal is provided, which comprises administering to a mammalian subject in need thereof a therapeutically effective amount of an agent that inhibits HSV-encoded DNA polymerase and an agent that inhibits lipid droplet formation or inhibits an enzyme selected from the group consisting of ACSL1, ELOVL2, ELOVL3, ELOVL6, SLC27A3, FAS, ACC, or HMG-CoA.

In still another embodiment, the invention provides a method of treating or preventing influenza infection in a mammal, which comprises administering to a mammalian subject in need thereof a therapeutically effective amount of an agent that inhibits influenza-encoded M2 protein and an agent that inhibits lipid droplet formation or inhibits an enzyme selected from the group consisting of ACSL1, ELOVL2, ELOVL3, ELOVL6, SLC27A3, FAS, ACC, or HMG-CoA.

In yet another embodiment, the invention provides a method of treating or preventing HCV infection in a mammal, which comprises administering to a mammalian subject in need thereof a therapeutically effective amount of an agent that inhibits HCV RNA synthesis and an agent that inhibits lipid droplet formation or a cellular long or inhibits an enzyme selected from the group consisting of ACSL1, ELOVL2, ELOVL3, ELOVL6, SLC27A3, FAS, ACC, or HMG-CoA.

The invention also provides a method of treating or preventing HBV infection in a mammal, which comprises administering to a mammalian subject in need thereof a therapeutically effective amount of an agent that inhibits HBV-encoded reverse transcriptase and an agent that inhibits lipid droplet formation or inhibits an enzyme selected from the group consisting of ACSL1, ELOVL2, ELOVL3, ELOVL6, SLC27A3, FAS, ACC, or HMG-CoA.

The invention further provides a method of treating or preventing HIV infection in a mammal, which comprises administering to a mammalian subject in need thereof a therapeutically effective amount of an agent that inhibits HIV-encoded transcriptase and an agent that inhibits lipid droplet formation or inhibits an enzyme selected from the group consisting of ACSL1, ELOVL2, ELOVL3, ELOVL6, SLC27A3, FAS, ACC, or HMG-CoA.

The invention also provides a method for treating or preventing viral infection in a mammal, comprising administering to a mammalian subject in need thereof a therapeutically effective amount of an agent that inhibits the activity of an enzyme selected from ADP-ribosyltransferase 1 (ART1), 1-acylglycerol-3-phosphate O-acyltransferase 7 (AGPAT7), alanine-glyoxylate aminotransferase 2 (AGXT2), ADP-ribosyltransferase 3 (ART3), leukotriene C4 synthase (LTC4S) transcript variant 2, coactivator-associated arginine methyltransferase 1 (CARM1), chromodomain protein, Y-linked, 2A (CDY2A), FKBP6-like (LOC541473), coagulation factor XIII A1 polypeptide (F13A1), transaldolase 1 (TALDO1), gamma-glutamyltransferase 3 (GGT3), heparan sulfate 6-O-sulfotransferase 1 (HS6ST1), uronyl-2-sulfotransferase (UST), transketolase-like 1 (TKTL1), phospholipase A2, group VII (platelet-activating factor acetylhydrolase, plasma) (PLA2G7), alanine-glyoxylate aminotransferase 2-like 1 (AGXT2L1), heparan sulfate 6-O-sulfotransferase 2 (HS6ST2) transcript variant S, methylcrotonoyl-Coenzyme A carboxylase 2 (beta) (MCCC2), protein disulfide isomerase family A member 6 (PDIA6), phenylethanolamine N-methyltransferase (PNMT), acetyl-Coenzyme A carboxylase alpha (ACACA) transcript variant 6, UDP glycosyltransferase 3 family polypeptide A2 (UGT3A2), glycine amidinotransferase (L-arginine: glycine amidinotransferase) (GATM), glycerol-3-phosphate acyltransferase, mitochondrial (GPAM), microsomal glutathione S-transferase 3 (MGST3), carbonic anhydrase VII (CA7), otopetrin 2 (OTOP2), otopetrin 3 (OTOP3), thromboxane A synthase 1 (TBXAS1), thymidylate synthase (TYMS), thioredoxin domain containing 11 (TXNDC11), protein disulfide isomerase family A, member 5 (PDIA5), prostaglandin-endoperoxide synthase 2 (PTGS2), syntaxin 6 (STX6), and syntaxin 8 (STX8).

The invention provides a pharmaceutical composition for carrying out the above methods. The invention also provides a pharmaceutical composition for treatment or prevention of a viral infection comprising a therapeutically effective amount of an inhibitor of an enzyme involved in elongation of very long chain fatty acids and an inhibitor of a second enzyme that controls virus replication.

The invention provides a method of identifying a compound for treating or preventing a virus infection, which comprises selecting a compound that inhibits a long chain fatty acid synthesis enzyme. According to the invention, the long chain fatty acid synthesis enzyme can have been identified as a regulator of viral replication by treating a test cell infected with a virus with an agent that inhibits the long chain fatty acid synthesis enzyme, such that virus replication in the treated test cell is reduced as compared to virus replication in an untreated test cell, thus identifying the long chain fatty acid synthesis enzyme as a regulator of viral replication. In an embodiment of the invention, the long chain fatty acid synthesis enzyme is selected from an acyl-CoA synthetase long-chain family member, an elongation of very long chain fatty acids enzyme, and solute carrier family 27 (fatty acid transporter), member 3 (SLC27A3).

The invention also provides a method of identifying a compound for treating or preventing a viral infection, which comprises selecting a compound that inhibits a long chain fatty acid synthesis enzyme, wherein the long chain fatty acid synthesis enzyme was identified as a regulator of viral replication by treating a test cell infected with a virus with an agent that inhibits the long chain fatty acid synthesis enzyme, wherein virus replication in the treated test cell is reduced as compared to virus replication in an untreated test cell, thus identifying the long chain fatty acid synthesis enzyme as a regulator of viral replication. In an embodiment of the invention, the virus is selected from human cytomegalovirus (HCMV), herpes simplex virus-1 (HSV-1), influenza A, and hepatitis C virus. The invention further provides agents for treatment or prevention of a viral infection and pharmaceutical compositions thereof that are selected as inhibitors of a long chain fatty acid synthesis enzyme.

DETAILED DESCRIPTION

Figure 1:
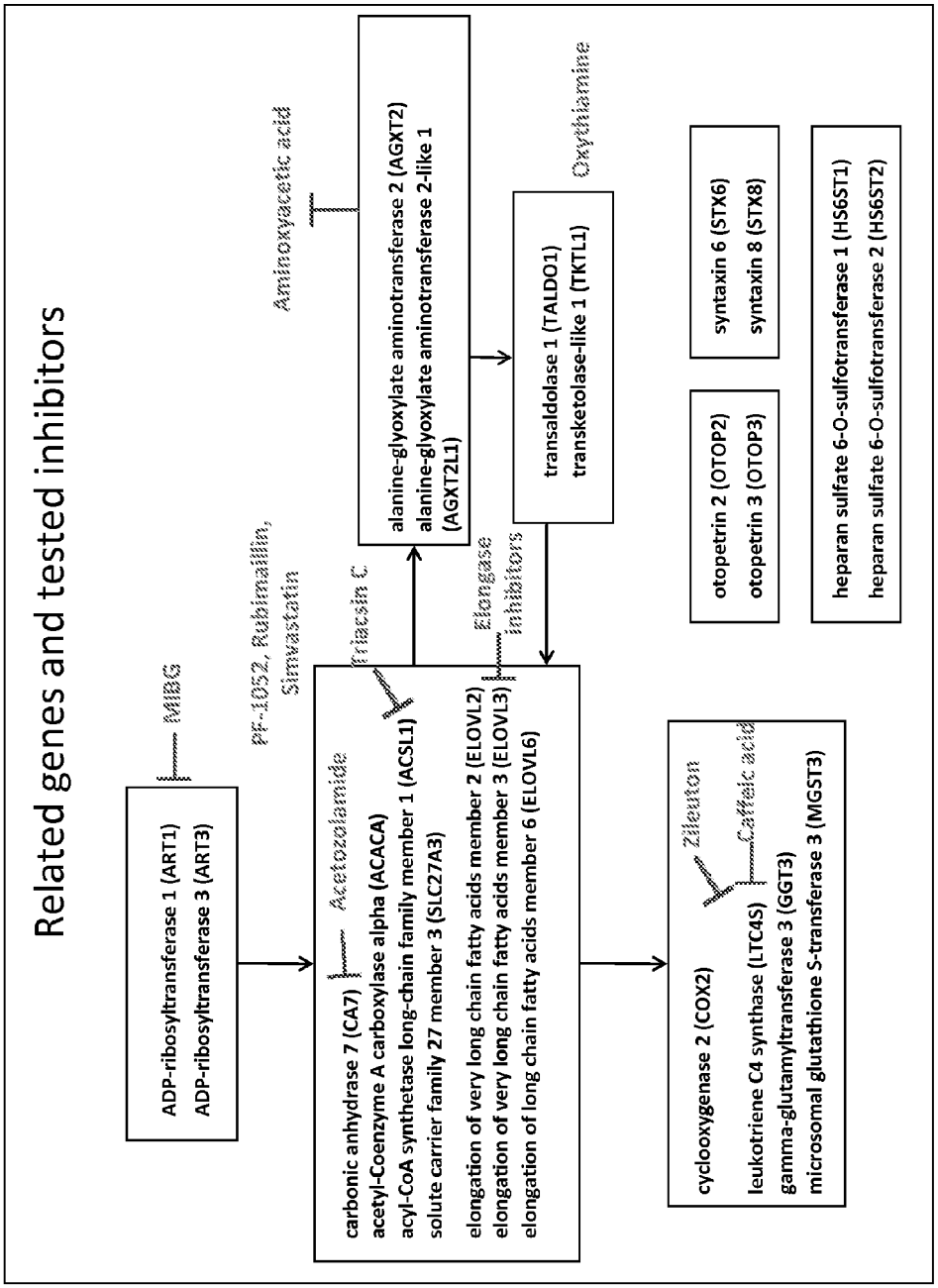
FIG. 1. Inhibitors of viral replication. The figure depicts genes for which inhibition of their expression by siRNA resulted in reduced HCMV replication. The genes are grouped by function. Specific inhibitors also shown to reduce viral replication are also depicted.

Viral replication requires energy and macromolecular precursors derived from the metabolic network of the host cell. Using an integrated approach to profiling metabolic flux, the inventors discovered alterations of certain metabolite concentrations and fluxes in response to viral infection. Details of the profiling methods are described in PCT/US2008/006959, which is incorporated by reference in its entirety. Using this approach, certain enzymes in the various metabolic pathways, especially those which serve as key "switches," have been discovered to be useful targets for intervention; i.e., as targets for redirecting the metabolic flux to disadvantage viral replication and restore normal metabolic flux profiles, thus serving as targets for antiviral therapies. Enzymes involved in initial steps in a metabolic pathway are preferred enzyme targets. In addition, enzymes that catalyze "irreversible" reactions or committed steps in metabolic pathways can be advantageously used as enzyme targets for antiviral therapy.

The subsections below describe in more detail the antiviral compounds and target enzymes of the invention, screening assays for identifying and characterizing new antiviral compounds, and methods for their use as antiviral therapeutics to treat and prevent viral infections.

In certain embodiments, compounds of the invention may exist in several tautomeric forms. Accordingly, the chemical structures depicted herein encompass all possible tautomeric forms of the illustrated compounds. Compounds of the invention may exist in various hydrated forms.

Definitions of the more commonly recited chemical groups are set forth below. Certain variables in classes of compounds disclosed herein recite other chemical groups. Chemical groups recited herein, but not specifically defined, have their ordinary meaning as would be known by a chemist skilled in the art.

A "$C_{1-X}$ alkyl" group is a saturated straight chain or branched non-cyclic hydrocarbon having from 1 to x carbon atoms. Representative —($C_{1-8}$ alkyls) include -methyl, -ethyl, -n-propyl, -n-butyl, -n-pentyl, -n-hexyl, -n-heptyl and -n-octyl; while saturated branched alkyls include -isopropyl, -sec-butyl, -isobutyl, -tert-butyl, -isopentyl, 2-methylpentyl, 3-methylpentyl, 4-methylpentyl, 2,3-dimethylbutyl and the like. A —($C_{1-X}$ alkyl) group can be substituted or unsubstituted.

The terms "halogen" and "halo" mean fluorine, chlorine, bromine and iodine.

An "aryl" group is an unsaturated aromatic carbocyclic group of from 6 to 14 carbon atoms having a single ring (e.g., phenyl) or multiple condensed rings (e.g., naphthyl or anthryl). Particular aryls include phenyl, biphenyl, naphthyl and the like. An aryl group can be substituted or unsubstituted.

A "heteroaryl" group is an aryl ring system having one to four heteroatoms as ring atoms in a heteroaromatic ring system, wherein the remainder of the atoms are carbon atoms. Suitable heteroatoms include oxygen, sulfur and nitrogen. In certain embodiments, the heterocyclic ring system is monocyclic or bicyclic. Non-limiting examples include aromatic groups selected from the following:

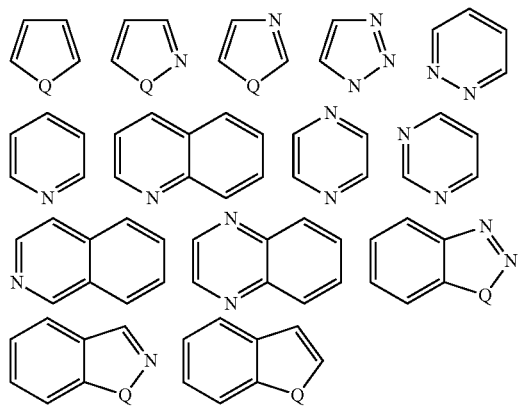

wherein Q is CH2, CH=CH, O, S or NH. Further representative examples of heteroaryl groups include, but are not limited to, benzofuranyl, benzothienyl, indolyl, benzopyrazolyl, coumarinyl, furanyl, isothiazolyl, imidazolyl, isoxazolyl, thiazolyl, triazolyl, tetrazolyl, thiophenyl, pyrimidinyl, isoquinolinyl, quinolinyl, pyridinyl, pyrrolyl, pyrazolyl, 1H-indolyl, 1H-indazolyl, benzo[d]thiazolyl and pyrazinyl. Heteroaryls can be bonded at any ring atom (i.e., at any carbon atom or heteroatom of the heteroaryl ring) A heteroaryl group can be substituted or unsubstituted. In one embodiment, the heteroaryl group is a C3-10 heteroaryl.

A "cycloalkyl" group is a saturated or unsaturated non-aromatic carbocyclic ring. Representative cycloalkyl groups include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, and cyclooctadienyl. A cycloalkyl group can be substituted or unsubstituted. In one embodiment, the cycloalkyl group is a C3-8 cycloalkyl group.

A "heterocycloalkyl" group is a non-aromatic cycloalkyl in which one to four of the ring carbon atoms are independently replaced with a heteroatom from the group consisting of O, S and N. Representative examples of a heterocycloalkyl group include, but are not limited to, morpholinyl, pyrrolyl, pyrrolidinyl, thienyl, furanyl, thiazolyl, imidazolyl, pyrazolyl, triazolyl, piperizinyl, isothiazolyl, isoxazolyl, (1,4)-dioxane, (1,3)-dioxolane, 4,5-dihydro-1H-imidazolyl and tetrazolyl. Heterocycloalkyls can also be bonded at any ring atom (i.e., at any carbon atom or heteroatom of the Heteroaryl ring). A heterocycloalkyl group can be substituted or unsubstituted. In one embodiment, the heterocycloalkyl is a 3-7 membered heterocycloalkyl.

In one embodiment, when groups described herein are said to be "substituted," they may be substituted with any suitable substituent or substituents. Illustrative examples of substituents include those found in the exemplary compounds and embodiments disclosed herein, as well as halogen (chloro, iodo, bromo, or fluoro); $C_{1-6}$ alkyl; $C_{2-6}$ alkenyl; $C_{2-6}$ alkynyl; hydroxyl; $C_{1-6}$ alkoxyl; amino; nitro; thiol; thioether; imine; cyano; amido; phosphonato; phosphine; carboxyl; thiocarbonyl; sulfonyl; sulfonamide; ketone; aldehyde; ester; oxygen (=O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); o-lower alkyl; o-aryl, aryl; aryl-lower alkyl; $CO_2CH_3$; $CONH_2$; $OCH_2CONH_2$; $NH_2$; $SO_2NH_2$; $OCHF_2$; $CF_3$; $OCF_3$.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the compounds include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, See for example, Remington's Pharmaceutical Sciences, 18th eds., Mack Publishing, Easton Pa. (1990) or Remington: The Science and Practice of Pharmacy, 19th eds., Mack Publishing, Easton Pa. (1995).

As used herein and unless otherwise indicated, the term "hydrate" means a compound, or a salt thereof, that further includes a stoichiometric or non-stoichiometric amount of water bound by non-covalent intermolecular forces.

As used herein and unless otherwise indicated, the term "solvate" means a compound, or a salt thereof, that further includes a stoichiometric or non-stoichiometric amount of a solvent bound by non-covalent intermolecular forces.

As used herein and unless otherwise indicated, the term "prodrug" means a compound derivative that can hydrolyze, oxidize, or otherwise react under biological conditions (in vitro or in vivo) to provide compound. Examples of prodrugs include, but are not limited to, derivatives and metabolites of a compound that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers Gmfh).

As used herein and unless otherwise indicated, the term "stereoisomer" or "stereomerically pure" means one stereoisomer of a compound, in the context of an organic or inorganic molecule, that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The compounds can have chiral centers and can occur as racemates, individual enantiomers or diastereomers, and mixtures thereof. All such isomeric forms are included within the embodiments disclosed herein, including mixtures thereof.

Various compounds contain one or more chiral centers, and can exist as racemic mixtures of enantiomers, mixtures of diastereomers or enantiomerically or optically pure compounds. The use of stereomerically pure forms of such compounds, as well as the use of mixtures of those forms are encompassed by the embodiments disclosed herein. For example, mixtures comprising equal or unequal amounts of the enantiomers of a particular compound may be used in methods and compositions disclosed herein. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al., Tetrahedron 33:2725 (1977); Eliel, E. L., Stereochemistry of Carbon Compounds (McGraw-Hill, NY, 1962); and Wilen, S. H., Tables of Resolving Agents and Optical Resolutions p. 268 (E. L. Eliel, Ed., Univ. of Notre Dame Press, Notre Dame, Ind., 1972).

It should also be noted that compounds, in the context of organic and inorganic molecules, can include E and Z isomers, or a mixture thereof, and cis and trans isomers or a mixture thereof. In certain embodiments, compounds are isolated as either the E or Z isomer. In other embodiments, compounds are a mixture of the E and Z isomers.

As used herein, the term "effective amount" in the context of administering a therapy to a subject refers to the amount of a therapy which is sufficient to achieve one, two, three, four, or more of the following effects: (i) reduce or ameliorate the severity of a viral infection or a symptom associated therewith; (ii) reduce the duration of a viral infection or a symptom associated therewith; (iii) prevent the progression of a viral infection or a symptom associated therewith; (iv) cause regression of a viral infection or a symptom associated therewith; (v) prevent the development or onset of a viral infection or a symptom associated therewith; (vi) prevent the recurrence of a viral infection or a symptom associated therewith; (vii) reduce or prevent the spread of a virus from one cell to another cell, or one tissue to another tissue; (ix) prevent or reduce the spread of a virus from one subject to another subject; (x) reduce organ failure associated with a viral infection; (xi) reduce hospitalization of a subject; (xii) reduce hospitalization length; (xiii) increase the survival of a subject with a viral infection; (xiv) eliminate a virus infection; and/or (xv) enhance or improve the prophylactic or therapeutic effect(s) of another therapy.

As used herein, the term "effective amount" in the context of a compound for use in cell culture-related products refers to an amount of a compound which is sufficient to reduce the viral titer in cell culture or prevent the replication of a virus in cell culture.

A preferred dose of a triacsin used to treat or prevent viral infections in mammals is <100 mg/kg, <50 mg/kg, <20 mg/kg, <10 mg/kg, <5 mg/kg, <2 mg/kg, <1 mg/kg, <0.5 mg/kg, <0.2 mg/kg, <0.1 mg/kg, <0.05 mg/kg, <0.02 mg/kg, or <0.01 mg/kg. A preferred dose of a triacsin used to treat or prevent viral infections in mammals results in total serum concentrations of <100 µM, <50 µM, <20 µM, <10 µM, <5 µM, <1 µM, <500 nM, or <250 nM. It is noted that higher triacsin C concentrations, e.g., >5 µM, >10 µM, >20 µM, >50 µM, or >100 µM, increase the risk of side effects including vasodilation (another effect of triacsin C).

The present invention also provides for the use of Triacsin compounds in cell culture-related products in which it is desirable to have antiviral activity. In one embodiment, a triacsin compound is added to cell culture media. The triacsin compounds used in cell culture media include compounds that may otherwise be found too toxic for treatment of a subject.

1. Host Cell Target Enzymes

The invention further provides cellular target enzymes for reducing virus production. As described below, an siRNA screen was performed to test the effects of inhibiting specific enzymes on the infectious yield of HCMV. The siRNA which were found to inhibit HCMV replication are shown in Table 1. Accordingly, the present invention provides methods of treating viral infections using inhibitors or other modulators of these enzymes. Inhibitors and modulators include without limitation small molecules, nucleic acids, and proteins. As used herein, "small molecule" refers to a substances that has a molecular weight up to 2000 atomic mass units (Daltons). Exemplary nucleic acid-based inhibitors include siRNA and shRNA. Exemplary protein-based inhibitors include antibodies. Additional small molecule inhibitors can be found by screening of compound libraries and/or design of molecules that bind to specific pockets in the structures of these enzymes. The properties of these molecules can be optimized through derivitization, including iterative rounds of synthesis and experimental testing.

TABLE 1

Enzyme knockdown by siRNA inhibits HCMV replication

| Fold reduction | Enzyme |
|---|---|
| 41.43 | ADP-ribosyltransferase 1 (ART1) |
| 14.70 | 1-acylglycerol-3-phosphate O-acyltransferase 7 (AGPAT7) |
| 10.73 | alanine-glyoxylate aminotransferase 2 (AGXT2) |
| 10.46 | solute carrier family 27 (fatty acid transporter), member 3 (SLC27A3) |
| 9.83 | ADP-ribosyltransferase 3 (ART3) |
| 3.45 | leukotriene C4 synthase (LTC4S), transcript variant 2 |
| 3.22 | coactivator-associated arginine methyltransferase 1 (CARM1) |
| 3.06 | chromodomain protein, Y-linked, 2A (CDY2A) |
| 2.72 | FKBP6-like (LOC541473) |
| 2.63 | carbonic anhydrase VII (CA7) |
| 2.63 | otopetrin 3 (OTOP3) |
| 2.62 | coagulation factor XIII, A1 polypeptide (F13A1) |
| 2.57 | acyl-CoA synthetase long-chain family member 1 (ACSL1) |
| 2.56 | thromboxane A synthase 1 (TBXAS1) |
| 2.56 | thymidylate synthase (TYMS) |
| 2.53 | transaldolase 1 (TALDO1) |
| 2.51 | gamma-glutamyltransferase 3 (GGT3) |
| 2.49 | heparan sulfate 6-O-sulfotransferase 1 (HS6ST1) |
| 2.46 | uronyl-2-sulfotransferase (UST) |
| 2.39 | transketolase-like 1 (TKTL1) |
| 2.33 | phospholipase A2, group VII (platelet-activating factor acetylhydrolase, plasma) (PLA2G7) |
| 2.27 | thioredoxin domain containing 11 (TXNDC11) |
| 2.25 | alanine-glyoxylate aminotransferase 2-like 1 (AGXT2L1) |
| 2.25 | heparan sulfate 6-O-sulfotransferase 2 (HS6ST2), transcript variant S |
| 2.23 | methylcrotonoyl-Coenzyme A carboxylase 2 (beta) (MCCC2) |
| 2.23 | elongation of very long chain fatty acids (ELOVL2) |
| 2.22 | protein disulfide isomerase family A, member 5 (PDIA5) |
| 2.10 | protein disulfide isomerase family A, member 6 (PDIA6) |
| 2.06 | elongation of very long chain fatty acids (ELOVL3) |
| 2.05 | ELOVL family member 6, elongation of long chain fatty acids (ELOVL6) |
| 2.04 | phenylethanolamine N-methyltransferase (PNMT) |
| 2.02 | acetyl-Coenzyme A carboxylase alpha (ACACA), transcript variant 6 |
| 2.01 | UDP glycosyltransferase 3 family, polypeptide A2 (UGT3A2) |
| 1.97 | glycine amidinotransferase (L-arginine:glycine amidinotransferase) (GATM) |
| 1.96 | prostaglandin-endoperoxide synthase 2 (PTGS2) |
| 1.96 | syntaxin 8 (STX8) |
| 1.96 | glycerol-3-phosphate acyltransferase, mitochondrial (GPAM) |
| 1.94 | microsomal glutathione S-transferase 3 (MGST3) |
| 1.92 | otopetrin 2 (OTOP2) |
| 1.92 | syntaxin 6 (STX6) |

As depicted in FIG. 1, several of the above enzymes have related functions. For example, acyl-CoA synthetase long chain family member 1 (ACSL1), elongation of very long chain fatty acids 2, 3 and 6 (ELOVL2, ELOVL3 and ELOVL6), and solute carrier family 27 (fatty acid transporter) member 3 (SLC27A3) (which despite its name has long chain and very long chain acyl-CoA ligase activity) all are enzymes involved in synthesis of long and very long chain acyl-CoA species. The observation that knockdown of any of these enzymes inhibited the production of infectious HCMV leads to the conclusion that HCMV requires acyl-CoA derivatives of long chain fatty acids and very long chain fatty acids for the efficient production of progeny virus.

Accordingly, the invention provides two classes of enzymes (long and very long chain acyl-CoA synthetases and elongases) as antiviral targets, including, but not limited to ACSL1, ELOVL2, ELOVL3, ELOVL6, and SLC27A3. Long-chain acyl-CoA synthetases (ACSLs) (E.C.6.2.1.3) catalyze esterification of long-chain fatty acids, mediating the partitioning of fatty acids in mammalian cells. ACSL isoforms (ACSL1, ACSL3, ACSL4, ACSL5, and ACSL6) generate bioactive fatty acyl-CoAs from CoA, ATP, and long-chain (C12-C20) fatty acids. In many instances, the enzymes are tissue specific and/or substrate specific. For example, ACSLs exhibit different tissue distribution, subcellular localization, fatty acid preference, and transcriptional regulation. Similarly, seven distinct fatty acid condensing enzymes (elongases) have been identified in mouse, rat, and human, with different substrate specificities and expression patterns. ELOVL-1, ELOVL-3, and ELOVL-6 elongate saturated and monounsaturated fatty acids, whereas ELOVL-2, ELOVL-4, and ELOVL-5 elongate polyunsaturated fatty acids. ELOVL-5 also elongates some monounsaturated fatty acids, like palmitoleic acid and specifically elongates γ-linolenoyl-CoA (18:3,n-6 CoA). ELOVL-2 specifically elongates 22-carbon PUFA. Also, the elongases (ELOVL) are expressed differentially in mammalian tissues. For example, five elongases are expressed in rat and mouse liver, including ELOVL-1, -2, -3, -5, -6. In contrast, the heart expresses ELOVL-1, -5, and -6, but not ELOVL-2.

Another means of inhibiting virus production is by targeting a cellular component with a small molecule or other inhibitor of enzyme function. For example, long and very long chain acyl-CoA synthetases can be targeted with triacsin C and its relatives, derivatives, and analogues. As discussed herein, nanomolar concentrations of triacsin C inhibit the replication of HCMV, herpes simplex virus-1 (HSV-1), and influenza A.

Another set of related enzymes are leukotriene C4 synthase (LTC4S), gamma-glutamyltransferase 3 (GGT3), and microsomal glutathione-S-transferase 3 (MGST3). These enzymes each contribute to the synthesis of cysteinyl leukotrienes, with LTC4S being the pivotal enzyme. The observation that knockdown of any of these enzymes inhibited the production of infectious HCMV leads to the conclusion that HCMV requires cysteinyl leukotrienes for the efficient production of progeny virus, and identifies enzymes of cysteinyl leukotriene synthesis as antiviral targets. In addition to siRNA, another inhibitor of cysteinyl leukotriene synthesis is caffeic acid. Synthesis of the cysteinyl leukotriene precursor leukotriene A4 can be inhibited with zileuton, and 100 µM zileuton reduced HCMV replication by ~90% without evidence of host cell toxicity. According to the invention, antiviral agents also include inhibitors of leukotriene and cysteinyl leukotriene signaling, such as, but not limited to zafirlukast or montelukast.

A pair of related enzymes that are both required for HCMV replication are ADP-ribosyltransferase 1 and 3 (ART1 and ART3). Inhibition of either of these enzymes led to a marked reduction in HCMV replication, ~40-fold for ART1 and ~10-fold for ART3. Without being bound by any particular mechanism, although ADP-ribosyltransfer is not per se a reaction of lipid metabolism, ADP ribosylation plays a key role in regulating lipid storage via targets including the protein CtBP1/BARS. Mono-ADP ribosylation of this protein results in loss of lipid droplets due to a dramatic efflux of fatty acids. Monitoring lipid droplets via microscopy with oil red O staining demonstrates that HCMV infection results initially in accumulation of lipid droplets in the infected hosts, and thereafter (by 72 hours post infection) in a dramatic depletion of lipid droplets. Accordingly, ADP-ribosylation appears to play a key role in regulating these lipid storage events during HCMV infection, and siRNA data indicates that such regulation is essential for HCMV replication. The observation that knockdown of either of these enzymes inhibited that production of infectious HCMV suggests that HCMV requires ADP-ribosyltransfer activity for efficient production of progeny virus. In addition to siRNA, another means of inhibiting ADP-ribosyltransferase is with the compound meta-iodobenzylguanidine (MIBG), and 100 µM MIBG inhibited the replication of HCMV in fibroblasts by 13-fold with no evidence of host cell toxicity.

The observations of lipid droplet accumulation and depletion during HCMV infection in an ordered temporal manner indicates that HCMV hijacks the host cell machinery involved in lipid droplet production and consumption. Thus host cell components involved in lipid droplet production and consumption provide antiviral targets. In addition to siRNA against the relevant cellular machinery, other means of inhibiting lipid droplet formation include the compounds spylidone, PF-1052 (a fungal natural product isolated from *Phoma* species), vermisporin, beauveriolides, phenochalasins, isobisvertinol, K97-0239, and rubimaillin. PF-1052 (10 µM) profoundly inhibited HCMV late protein synthesis (>99%) and similarly profoundly inhibits HMCV replication. In addition, triacsin C also resulted in depletion of lipid droplets, with 100 nM triacsin C causing >90% depletion of lipid droplets in HCMV infected cells and 250 nM resulting in no detectable lipid droplets by oil red O staining Normally patterns of HCMV-induced accumulation and depletion of lipid droplets were also blocked by 100 µM MIBG.

The loss of lipid droplets in HCMV infected cells is followed by the induction of lipid droplet formation in the neighboring uninfected cells. This indicates that HCMV infection results in the enhanced uptake or synthesis of lipids in the surrounding cells. Note that, HCMV spread occurs mainly from cell to cell in vivo and lipid accumulation in uninfected cells next to the infected cells can be considered as a facilitating event for the secondary infections. Triacsin C resulted in depletion of lipid droplets both in HCMV infected and surrounding uninfected cells with 100 nM triacsin C causing >90% depletion of lipid droplets and 250 nM resulting in no detectable lipid droplets by oil red O staining.

The major constituents of lipid droplets are CEs and TGs (estimated percentages in macrophages are ~58 and ~27 w/w respectively). Among the compounds indicated above, PF-1052 inhibits both CE and TG synthesis in a dose dependent manner, whereas, rubimaillin (also referred as mollugin) selectively inhibits CE synthesis. Rubimaillin is a naphthohydroquinone isolated from the plant *Rubia Cordifoila*. The inhibitory effect of rubimaillin on CE synthesis and lipid droplet formation is linked to its activity on acyl-CoA:cholesterol acyl-transferases (ACATs). It is a dual inhibitor of ACAT1 and ACAT2 enzymes (Matsuda et al., 2009, Biol. Pharm. Bull., 32, 1317-1320) and 10 µM of rubimaillin reduced HCMV replication by >80%. Thus targeting ACAT enzymes, which leads to the inhibition of lipid droplet formation, can be used in treating virus infections. The examples of dual ACAT inhibitors include the compounds pactimibe and avasimibe.

Another pair of related enzymes that are both required for HCMV replication are alanine-glyoxylate aminotransferase 2 (AGXT2) and alanine-glyoxylate aminotransferase 2-like 1 (AGXT2L1), with knockdown of AGXT2 having a particularly strong impact on viral replication. Without being bound by any particular mechanism, although alanine-glyoxylate aminotransferase is not a reaction of lipid metabolism per se, a major route of glyoxylate production in mammals is during lipid degradation. Accordingly, the antiviral effects of knockdown of AGXT2 and AGXT2L1 may arise from HCMV triggering excessive glyoxylate production which is highly reactive and toxic in biological systems from pathways including lipid degradation, and from this glyoxylate needing to be converted to glycine and pyruvate for viral replication to proceed normally. The observation that knockdown of either of these enzymes inhibits production of infectious HCMV indicates that glyoxylate degradation and/or glycine synthesis activity is required for efficient production of progeny virus and identifies alanine-glyoxylate aminotransferases as antiviral targets. In addition to siRNA, another means of inhibiting alanine-glyoxylate aminotransferase activity, which also impacts other aminotransferases, is via the compound aminooxyacetic acid (AOAA). AOAA inhibited the replication of each of three different viruses tested: HCMV, influenza A, and adenovirus. See Example 2.

Yet another pair of related enzymes are transaldolase 1 (TALDO1) and transketolase-like 1 (TKTL1). Although not catalyzing reactions of lipid metabolism per se, and without being bound by any particular mechanism, these enzymes both sit in the pentose phosphate pathway, which has among its major functions production of NADPH, which is used substantially for fatty acid biosynthesis. Another function of the pentose phosphate pathway which may be important for viral replication is ribose-5-phosphate synthesis. The observation that knockdown of either of these enzymes inhibited that production of infectious HCMV indicates that HCMV requires pentose phosphate pathway activity for efficient production of progeny virus. Accordingly, antiviral targets include transaldolase, transketolase, and transketolase-like enzymes.

Fatty acid elongation requires the condensation between fatty acyl-CoA and malonyl-CoA to generate β-ketoacyl-CoA which is the rate limiting step for the synthesis of long and very long chain fatty acids. This step is catalyzed by ELOVL enzymes and requires a fatty-acyl-CoA as a precursor, which is generated by ACSLs, and malonyl-CoA, which is produced by acetyl-coA carboxylase alpha (ACACA; also referred as ACCT). Therefore, in addition to ELOVLs and ACSLs, inhibition of ACACA also provides another means of inhibiting virus production. Consistently, ACACA is identified as an enzyme required for HCMV replication by the siRNA screen. In addition to siRNA, another means of inhibiting aacetyl-CoA-carboxylase activity, is via the compound TOFA. TOFA inhibited the replication of each of the two different viruses: HCMV and HCV (see Example 11).

An enzyme which is required for HCMV replication is carbonic anhydrase 7 (CA7). Although not catalyzing the reactions of lipid metabolism per se, this enzyme catalysis the hydration of carbon dioxide to produce bicarbonate which is substantially required for the synthesis of malonyl-CoA from acetyl-coA, which is the rate limiting step of fatty acid biosynthesis. Carbonic anhydrases can be inhibited by acetazolamide, and 25 µM acetazolamide inhibited HCMV replication by ~80% without evidence of host cell cytotoxicity.

2. Targeting Combinations of Host Cell Enzymes

Lipid-related processes are essential to viral growth, replication and/or other elements of infection. Consequently, it is likely that multiple cellular enzymes that function in lipid metabolism are needed for successful infection, and it is possible that simultaneous inhibition of multiple enzymes (e.g., two or more different enzymes) will produce a synergistic inhibition of infection or allow the use of lower doses of each compound to achieve a desirable therapeutic effect. Accordingly, the present invention relates to the prevention and treatment of viral infection in a mammal in need thereof, via administering to the mammal two or more compounds described herein, wherein each compound targets one or more different enzymes described herein. In some embodiments, such combination therapy is sequential; in other embodiments, it is simultaneous. In some embodiments, the two or more agents are formulated together to create a composition comprising two or more compounds for the prevention and/or treatment of viral infection via modulation of host cell lipid and/or cholesterol metabolism. In some embodiments, the dose of one of the compounds is substantially less, e.g., 1.5, 2, 3, 5, 7, or 10-fold less, than required when used independently for the prevention and/or treatment of viral infection. In some embodiments, the dose of both agents is reduced by 1.5, 2, 3, 5, 7, or 10-fold or more.

As used herein, the term "in combination," in the context of the administration of two or more therapies to a subject, refers to the use of more than one therapy (e.g., more than one prophylactic agent and/or therapeutic agent). The use of the term "in combination" does not restrict the order in which therapies are administered to a subject with a viral infection. A first therapy (e.g., a first prophylactic or therapeutic agent) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject with a viral infection.

In one embodiment, a triacsin compound or relative or analog is combined with an inhibitor of a long or very long chain fatty acid synthesis enzyme, including, but not limited to, an inhibitor of ACSL1, ELOVL2, ELOVL6, or SLC27A3. In another embodiment, the triacsin compound or relative or analog is combined with an inhibitor of HMG-CoA reductase. In another embodiment, the triacsin compound or relative or analog is combined with an inhibitor of acetyl-CoA carboxylase. In still another embodiment, the triacsin compound or relative or analog is combined with an inhibitor of a fatty acid synthase. In certain embodiments of the invention, the triacsin compound is triacsin C.

In certain embodiments of the invention, combinations include one or more drugs from group A and one or more drugs from group B, wherein group A comprises inhibitors of the HCMV-encoded DNA polymerase including, but not limited to, gancyclovir, valgancyclovir, cidofovir, and foscarnet, and group B compromises inhibitors of cellular long and very long chain fatty acid metabolic enzymes and processes including, but not limited to, ACSL1, ELOVL2, ELOVL3, ELOVL6, FAS, SLC27A3, ACC, HMG-CoA reductase, and lipid droplet formation, for the treatment of pathological manifestations of HCMV infection, such as retinitis, colitis, hepatitis, pneumonitis, esophagitis, polyradiculopathy, transverse myelitis, subacute encephalitis, mononucleosis and congenital HCMV infection.

In another combination, group A comprises inhibitors of the HSV-encoded DNA polymerase including, but not limited to, acyclovir, valacyclovir, pencyclovir, and famcyclovir, and group B compromises inhibitors of cellular long and very long chain fatty acid metabolic enzymes and processes including, but not limited to, ACSL1, ELOVL2, ELOVL3, ELOVL6, FAS, SLC27A3, ACC, HMG-CoA reductase, and lipid droplet formation, for the treatment of pathological manifestations of HSV-1 or HSV-2 infection, such as herpes labialis, herpes genitalis, encephalitis, meningitis, esophagitis, herpetic gingivostomatitis, herpetic keratoconjunctivitis, herpetic sycosis, eczema herpeticum and congenital herpes simplex infection.

In another combination, group A comprises inhibitors of the influenza-encoded M2 protein including, but not limited to, amantadine and rimantadine, and inhibitors of the influenza-encoded neuraminidase, including, but not limited to, oseltamivir, peramivir and zanamivir, and group B compromises inhibitors of cellular long and very long chain fatty acid metabolic enzymes and processes including, but not limited to, ACSL1, ELOVL2, ELOVL3, ELOVL6, FAS, SLC27A3, ACC, HMG-CoA reductase, and lipid droplet formation, for the treatment of pathological infections of influenza A, influenza B or influenza C.

In another combination, group A comprises the HCV RNA synthesis inhibitor ribavirin, and the immunomodulators peginterferon alfa-2a (PEGASYS™) and peginterferon alfa-2b (PEG-INTRON™), and group B compromises inhibitors of cellular long and very long chain fatty acid metabolic enzymes and processes including, but not limited to, ACSL1, ELOVL2, ELOVL3, ELOVL6, FAS, SLC27A3, ACC, HMG-CoA reductase, and lipid droplet formation, for the treatment of either hepatitis C or chronic, asymptomatic HCV infection.

In another combination, group A comprises the nucleoside or nucleotide inhibitors of HBV reverse transcriptase, including, but not limited to, lamivudine, adefovir, tenofovir, telbivudine, and entecavir, and the immunomodulators peginterferon alfa-2a (PEGASYS™) and peginterferon alfa-2b (PEG-INTRON™), and group B compromises inhibitors of cellular long and very long chain fatty acid metabolic enzymes and processes including, but not limited to, ACSL1, ELOVL2, ELOVL3, ELOVL6, FAS, SLC27A3, ACC, HMG-CoA reductase, and lipid droplet formation, for the treatment of either hepatitis B or chronic, asymptomatic HBV infection.

In another combination, group A comprises nucleoside or nucleotide analog inhibitors of the HIV-encoded reverse transcriptase including, but not limited to, abacavir, didanosine, emtricitabine, lamivudine, stavudine, tenofovir and zidovudine; non-nucleotide analog inhibitors of the HIV-encoded reverse transcriptase including, but not limited to, delavirdine, efavirenz, etravirine and nevirapine; inhibitors of the HIV-encoded protease, including, but not limited to, amprenavir, atazanavir, darunavir, fosamprenavir, indinavir, lopinavir, ritonavir, nelfinavir, saquinavir and tipranavir; inhibitors of the HIV-encoded integrase, including, but not limited to, raltegravir; or inhibitors of HIV entry, including, but not limited to, enfuvirtide and maraviroc, and group B compromises inhibitors of cellular long and very long chain fatty acid metabolic enzymes and processes including, but not limited to, ACSL1, ELOVL2, ELOVL3, ELOVL6, FAS, SLC27A3, ACC, HMG-CoA reductase, and lipid droplet formation, for the treatment of pathological manifestations of HIV-1 or HIV-2 infection, such as acquired immunodeficiency syndrome (AIDS). Of particular interest are combinations between drugs of group B and the group A combination therapies currently recommended for Highly Active Antiretroviral Therapy (HAART), which include efavirenz/emtricitabine/tenofovir (ATRIPLA™); emtricitabine/tenofovir (TRUVADA™) plus raltegravir (ISENTRESS™); darunavir (PREZISTA™) plus ritonavir (NORVIR™) and emtricitabine/tenofovir (TRUVADA™); and atazanavir (REYATAZ™) plus ritonavir (NORVIR™) and emtricitabine/tenofovir (TRUVADA™).

In certain embodiments of the invention, an inhibitor of cellular long and very long chain fatty acid metabolic enzymes and processes including, but not limited to, ACSL1, ELOVL2, ELOVL3, ELOVL6, FAS, SLC27A3, ACC, HMG-CoA reductase, and lipid droplet formation, is used in combination with another such inhibitor for the treatment or prevention of viral infection including but not limited to infection by HCMV, HSV-1, HSV-2, influenza A, influenza B, influenza C, HCV, HBV, HIV-1 or HIV-2. Non-limiting examples of such combinations include an ACSL1 inhibitor and an ELOVL2 inhibitor, an ACSL1 inhibitor and an ELOVL3 inhibitor, an ACSL1 inhibitor and an ELOVL6 inhibitor, an ACSL1 inhibitor and an SLC27A3 inhibitor, an ACSL1 inhibitor and an ACC inhibitor, an ACSL1 inhibitor and an FAS inhibitor, an ACSL1 inhibitor and an HMG-CoA reductase inhibitor. Further examples include an ELOVL2 inhibitor and an SLC27A3 inhibitor, an ELOVL2 inhibitor and an ACC inhibitor, an ELOVL2 inhibitor and an FAS inhibitor, an ELOVL2 inhibitor and an HMG-CoA reductase inhibitor, an ELOVL3 inhibitor and an SLC27A3 inhibitor, an ELOVL3 inhibitor and an ACC inhibitor, an ELOVL3 inhibitor and an FAS inhibitor, an ELOVL3 inhibitor and an HMG-CoA reductase inhibitor, an ELOVL6 inhibitor and an SLC27A3 inhibitor, an ELOVL6 inhibitor and an ACC inhibitor, an ELOVL6 inhibitor and an FAS inhibitor, an ELOVL6 inhibitor and an HMG-CoA reductase inhibitor, an SLC27A3 inhibitor and an ACC inhibitor, an SLC27A3 inhibitor and an FAS inhibitor, an SLC27A3 inhibitor and an HMG-CoA reductase inhibitor, an ELOVL2 inhibitor and an ELOVL3 inhibitor, an ELOVL2 inhibitor and an ELOVL 6 inhibitor, and an ELOVL3 inhibitor and an ELOVL6 inhibitor.

2.1 Inhibitors of Host Cell Enzymes
2.1.1 RNAi Molecules

According to the invention, RNA interference is used to reduce expression of a target enzyme in a cell in order to reduce yield of infectious virus. siRNAs were designed to inhibit expression of a variety of enzyme targets. 30 targets for which infection yields of HCMV were reduced by the an siRNA, along with descriptions of the interfering RNA, are provided below in Example 1. In certain embodiments, a compound is an RNA interference (RNAi) molecule that can decrease the expression level of a target enzyme. RNAi molecules include, but are not limited to, small-interfering RNA (siRNA), short hairpin RNA (shRNA), microRNA (miRNA), and any molecule capable of mediating sequence-specific RNAi.

RNA interference (RNAi) is a sequence specific post-transcriptional gene silencing mechanism triggered by double-stranded RNA (dsRNA) that have homologous sequences to the target mRNA. RNAi is also called post-transcriptional gene silencing or PTGS. See, e.g., Couzin, 2002, Science 298:2296-2297; McManus et al., 2002, Nat. Rev. Genet. 3, 737-747; Hannon, G. J., 2002, Nature 418, 244-251; Paddison et al., 2002, Cancer Cell 2, 17-23. dsRNA is recognized and targeted for cleavage by an RNaseIII-type enzyme termed Dicer. The Dicer enzyme "dices" the RNA into short duplexes of about 21 to 23 nucleotides, termed siRNAs or short-interfering RNAs (siRNAs), composed of 19 nucleotides of perfectly paired ribonucleotides with about two three unpaired nucleotides on the 3' end of each strand. These short duplexes associate with a multiprotein complex termed RISC, and direct this complex to mRNA transcripts with sequence similarity to the siRNA. As a result, nucleases present in the RNA-induced silencing complex (RISC) cleave and degrade the target mRNA transcript, thereby abolishing expression of the gene product.

Numerous reports in the literature purport the specificity of siRNAs, suggesting a requirement for near-perfect identity with the siRNA sequence (Elbashir et al., 2001. EMBO J. 20:6877-6888; Tuschl et al., 1999, Genes Dev. 13:3191-3197; Hutvagner et al., Sciencexpress 297:2056-2060). One report suggests that perfect sequence complementarity is required for siRNA-targeted transcript cleavage, while partial complementarity will lead to translational repression without transcript degradation, in the manner of microRNAs (Hutvagner et al., Sciencexpress 297:2056-2060).

miRNAs are regulatory RNAs expressed from the genome, and are processed from precursor stem-loop (short hairpin) structures (approximately 80 nucleotide in length) to produce single-stranded nucleic acids (approximately 22 nucleotide in length) that bind (or hybridizes) to complementary sequences in the 3' UTR of the target mRNA (Lee et al., 1993, Cell 75:843-854; Reinhart et al., 2000, Nature 403:901-906; Lee et al., 2001, Science 294:862-864; Lau et al., 2001, Science 294:858-862; Hutvagner et al., 2001, Science 293:834-838).

miRNAs bind to transcript sequences with only partial complementarity (Zeng et al., 2002, Molec. Cell 9:1327-1333) and repress translation without affecting steady-state RNA levels (Lee et al., 1993, Cell 75:843-854; Wightman et al., 1993, Cell 75:855-862). Both miRNAs and siRNAs are processed by Dicer and associate with components of the RNA-induced silencing complex (Hutvagner et al., 2001, Science 293:834-838; Grishok et al., 2001, Cell 106: 23-34; Ketting et al., 2001, Genes Dev. 15:2654-2659; Williams et al., 2002, Proc. Natl. Acad. Sci. USA 99:6889-6894; Hammond et al., 2001, Science 293:1146-1150; Mourlatos et al., 2002, Genes Dev. 16:720-728).

Short hairpin RNA (shRNA) is a single-stranded RNA molecule comprising at least two complementary portions hybridized or capable of hybridizing to form a double-stranded (duplex) structure sufficiently long to mediate RNAi upon processing into double-stranded RNA with overhangs, e.g., siRNAs and miRNAs. shRNA also contains at least one noncomplementary portion that forms a loop structure upon hybridization of the complementary portions to form the double-stranded structure. shRNAs serve as precursors of miRNAs and siRNAs.

Usually, sequence encoding an shRNA is cloned into a vector and the vector is introduced into a cell and transcribed by the cell's transcription machinery (Chen et al., 2003, *Biochem Biophys Res Commun* 311:398-404). The shRNAs can then be transcribed, for example, by RNA polymerase III (Pol III) in response to a Pol III-type promoter in the vector (Yuan et al., 2006, *Mol Biol Rep* 33:33-41 and Scherer et al., 2004, *Mol Ther* 10:597-603). The expressed shRNAs are then exported into the cytoplasm where they are processed by proteins such as Dicer into siRNAs, which then trigger RNAi (Amarzguioui et al., 2005, *FEBS Letter* 579:5974-5981). It has been reported that purines are required at the 5' end of a newly initiated RNA for optimal RNA polymerase III transcription. More detailed discussion can be found in Zecherle et al., 1996, *Mol. Cell. Biol.* 16:5801-5810; Fruscoloni et al., 1995, *Nucleic Acids Res,* 23:2914-2918; and Mattaj et al., 1988, *Cell,* 55:435-442. The shRNAs core sequences can be expressed stably in cells, allowing long-term gene silencing in cells both in vitro and in vivo, e.g., in animals (see, McCaffrey et al., 2002, *Nature* 418:38-39; Xia et al., 2002, *Nat. Biotech.* 20:1006-1010; Lewis et al., 2002, *Nat. Genetics* 32:107-108; Rubinson et al., 2003, *Nat. Genetics* 33:401-406; and Tiscornia et al., 2003, *Proc. Natl. Acad. Sci. USA* 100:1844-1848).

Martinez et al. reported that RNA interference can be used to selectively target oncogenic mutations (Martinez et al., 2002, Proc. Natl. Acad. Sci. USA 99:14849-14854). In this report, an siRNA that targets the region of the R248W mutant of p53 containing the point mutation was shown to silence the expression of the mutant p53 but not the wild-type p53.

Wilda et al. reported that an siRNA targeting the M-BCR/ABL fusion mRNA can be used to deplete the M-BCR/ABL mRNA and the M-BCR/ABL oncoprotein in leukemic cells (Wilda et al., 2002, Oncogene 21:5716-5724).

U.S. Pat. No. 6,506,559 discloses a RNA interference process for inhibiting expression of a target gene in a cell. The process comprises introducing partially or fully doubled-stranded RNA having a sequence in the duplex region that is identical to a sequence in the target gene into the cell or into the extracellular environment.

U.S. Patent Application Publication No. US 2002/0086356 discloses RNA interference in a *Drosophila* in vitro system using RNA segments 21-23 nucleotides (nt) in length. The patent application publication teaches that when these 21-23 nt fragments are purified and added back to *Drosophila* extracts, they mediate sequence-specific RNA interference in the absence of long dsRNA. The patent application publication also teaches that chemically synthesized oligonucleotides of the same or similar nature can also be used to target specific mRNAs for degradation in mammalian cells.

International Patent Application Publication No. WO 2002/44321 discloses that double-stranded RNA (dsRNA) 19-23 nt in length induces sequence-specific post-transcriptional gene silencing in a *Drosophila* in vitro system. The PCT publication teaches that short interfering RNAs (siRNAs) generated by an RNase III-like processing reaction from long dsRNA or chemically synthesized siRNA duplexes with overhanging 3' ends mediate efficient target RNA cleavage in the lysate, and the cleavage site is located near the center of the region spanned by the guiding siRNA.

U.S. Patent Application Publication No. US 2002/016216 discloses a method for attenuating expression of a target gene in cultured cells by introducing double stranded RNA (dsRNA) that comprises a nucleotide sequence that hybridizes under stringent conditions to a nucleotide sequence of the target gene into the cells in an amount sufficient to attenuate expression of the target gene.

International Patent Application Publication No. WO 2003/006477 discloses engineered RNA precursors that when expressed in a cell are processed by the cell to produce targeted small interfering RNAs (siRNAs) that selectively silence targeted genes (by cleaving specific mRNAs) using the cell's own RNA interference (RNAi) pathway. The PCT publication teaches that by introducing nucleic acid molecules that encode these engineered RNA precursors into cells in vivo with appropriate regulatory sequences, expression of the engineered RNA precursors can be selectively controlled both temporally and spatially, i.e., at particular times and/or in particular tissues, organs, or cells.

International Patent Application Publication No. WO 02/44321 discloses that double-stranded RNAs (dsRNAs) of 19-23 nt in length induce sequence-specific post-transcriptional gene silencing in a *Drosophila* in vitro system. The PCT publication teaches that siRNAs duplexes can be generated by an RNase III-like processing reaction from long dsRNAs or by chemically synthesized siRNA duplexes with overhanging 3' ends mediating efficient target RNA cleavage in the lysate where the cleavage site is located near the center of the region spanned by the guiding siRNA. The PCT publication also provides evidence that the direction of dsRNA processing determines whether sense or antisense-identical target RNA can be cleaved by the produced siRNA complex. Systematic analyses of the effects of length, secondary structure, sugar backbone and sequence specificity of siRNAs on RNA interference have been disclosed to aid siRNA design. In addition, silencing efficacy has been shown to correlate with the GC content of the 5' and 3' regions of the 19 base pair target sequence. It was found that siRNAs targeting sequences with a GC rich 5' and GC poor 3' perform the best. More detailed discussion may be found in Elbashir et al., 2001, *EMBO J.* 20:6877-6888 and Aza-Blanc et al., 2003, *Mol. Cell.* 12:627-637; each of which is hereby incorporated by reference herein in its entirety.

The invention provides specific siRNAs to target cellular components and inhibit virus replication as follows:

TABLE 2

Targets for Inhibition of Virus Replication and Inhibitory Polynucleotides

| Gene Symbol (Accession No.) | siRNA (5' to 3' sense) | SEQ ID NO | siRNA (5' to 3' antisense) | SEQ ID NO |
|---|---|---|---|---|
| ACACA, transcript variant 6 (NM_000664) | GUUUGAUUGUGCCAUACUUTT | 1 | AAGUAUGGCACAAUCAAACUTT | 2 |
| | CAUGUCUGGCUUGCACCUATT | 3 | UAGGUGCAAGCCAGACAUGTT | 4 |
| | GAUUGAGAAGGUUCUUAUUTT | 5 | AAUAAGAACCUUCUCAAUCTT | 6 |
| ACSL1 (NM_001995) | GUGUGAAGAAGAAAGCUCATT | 7 | UGAGCUUUCUUCUUCACACTT | 8 |
| | GAACAAGGAUGCUUUGCUUTT | 9 | AAGCAAAGCAUCCUUGUUCTT | 10 |
| | GAAAUGAAGCCAUCACGUATT | 11 | UACGUGAUGGCUUCAUUUCTT | 12 |
| AGPAT7 (NM_153613) | CCCUCUAUGCCAACAAUGUTT | 13 | ACAUUGUUGGCAUAGAGGGTT | 14 |
| | GGGUUUGGUGGACUUCCGATT | 15 | UCGGAAGUCCACCAAACCCTT | 16 |
| | CCAACAAUGUUCAGAGGGUTT | 17 | ACCCUCUGAACAUUGUUGGTT | 18 |
| AGXT2 (NM_031900) | CAAGCUAAAGAUCAGUAUATT | 19 | UAUACUGAUCUUUAGCUUGTT | 20 |
| | GUGUGAAUGGAGUUGUCCATT | 21 | UGGACAACUCCAUUCACACTT | 22 |
| | GUCUCAUGAUAGGCAUAGATT | 23 | UCUAUGCCUAUCAUGAGACTT | 24 |
| AGXT2L1 (NM_031279) | CACCUAUGUGCUUCACUGATT | 25 | UCAGUGAAGCACAUAGGUGTT | 26 |
| | GGAAUUGUCAGUUUAGAUUTT | 27 | AAUCUAAACUGACAAUUCCTT | 28 |
| | GGUUAAUAGCUCUAUUAUATT | 29 | UAUAAUAGAGCUAUUAACCTT | 30 |
| ART1 (NM_004314) | CAACUGCGAGUACAUCAAATT | 31 | UUUGAUGUACUCGCAGUUGTT | 32 |
| | CCAACCAGGUGUAUGCAGATT | 33 | UCUGCAUACACCUGGUUGGTT | 34 |
| | CAAGUCUGGGCCUUGCCAUTT | 35 | AUGGCAAGGCCCAGACUUGTT | 36 |
| ART3 (NM_001179) | GCCAUUAUGAGUGUGCAUUTT | 37 | AAUGCACACUCAUAAUGGCTT | 38 |
| | GCCAAAUGGGCAGCCCGAATT | 39 | UUCGGGCUGCCCAUUUGGCTT | 40 |
| | CUCAAAUCUUUCUCCCUAUTT | 41 | AUAGGGAGAAAGAUUUGAGTT | 42 |
| CARM1 (NM_199141) | GUAACCUCCUGGAUCUGAATT | 43 | UUCAGAUCCAGGAGGUUACTT | 44 |
| | CCAGUAACCUCCUGGAUCUTT | 45 | AGAUCCAGGAGGUUACUGGTT | 46 |
| | CCUAUGACUUGAGCAGUGUTT | 47 | ACACUGCUCAAGUCAUAGGTT | 48 |
| CDY2A (NM_004825) | GUAAUUAAAGAAAUGGUUATT | 49 | UAACCAUUUCUUUAAUUACTT | 50 |
| | GCUAUCAACUAGAUCGACATT | 51 | UGUCGAUCUAGUUGAUAGCTT | 52 |
| | GAUAAUAAAUUCAACUAUUTT | 53 | AAUAGUUGAAUUUAUUAUCTT | 54 |
| ELOVL2 (NM_017770) | GCUACAACUUACAGUGUCATT | 55 | UGACACUGUAAGUUGUAGCTT | 56 |
| | CAAAGUUUCUUUGGACCAATT | 57 | UUGGUCCAAAGAAACUUUGTT | 58 |
| | CGUUAGUCAUCCUCUUCUUTT | 59 | AAGAAGAGGAUGACUAACGTT | 60 |
| ELOVL3 (NM_152310) | GGAGUAUUGGGCAACCUCATT | 61 | UGAGGUUGCCCAAUACUCCTT | 62 |
| | GAAUGAUUAGGUUGCCUUATT | 63 | UAAGGCAACCUAAUCAUUCTT | 64 |
| | CACUUAUUCUGGUCCUUCATT | 65 | UGAAGGACCAGAAUAAGUGTT | 66 |
| ELOVL6 (NM_024090) | GGCUUAUGCAUUUGUGCUATT | 67 | UAGCACAAAUGCAUAAGCCTT | 68 |
| | CAAUGGACCUGUCAGCAAATT | 69 | UUUGCUGACAGGUCCAUUGTT | 70 |
| | CAUGUCAGUGUUGACUUUATT | 71 | UAAAGUCAACACUGACAUGTT | 72 |
| F13A1 (NM_000129) | CUAACAAGGUGGACCACCATT | 73 | UGGUGGUCCACCUUGUUAGTT | 74 |
| | CUAACCAUCCCUGAGAUCATT | 75 | UGAUCUCAGGGAUGGUUAGTT | 76 |
| | GCCUAUAGUCUCAGAGUUATT | 77 | UAACUCUGAGACUAUAGGCTT | 78 |
| GATM (NM_001482) | GAGACAUCCUGAUAGUUGUTT | 79 | ACAACUAUCAGGAUGUCUCTT | 80 |
| | CAAAUGGCUUUCCAUGAAUTT | 81 | AUUCAUGGAAAGCCAUUUGTT | 82 |
| | CAUUAAAGUUAACAUUCGUTT | 83 | ACGAAUGUUAACUUUAAUGTT | 84 |
| GGT3 (NR_003267) | CACUCAUGACUGAGGUCAUTT | 85 | AUGACCUCAGUCAUGAGUGTT | 86 |
| | CCUGUCUUGUGUGAGGUGUTT | 87 | ACACCUCACACAAGACAGGTT | 88 |
| | CCAGCAUUCACCAAUGAGUTT | 89 | ACUCAUUGGUGAAUGCUGGTT | 90 |
| GPAM (NM_020918) | GUUAUUAGAAUGUUACGAATT | 91 | UUCGUAACAUUCUAAUAACTT | 92 |
| | GAGUGUAGCAAGAGGUGUUTT | 93 | AACACCUCUUGCUACACUCTT | 94 |
| | GCAUGUUUGCCACCAAUGUTT | 95 | ACAUUGGUGGCAAACAUGCTT | 96 |
| HS6ST1 (NM_004807) | GACGUCUUUGCAUAUGUGUTT | 97 | ACACAUAUGCAAAGACGUCTT | 98 |
| | CUGUUCGAGCGGACGUUCATT | 99 | UGAACGUCCGCUCGAACAGTT | 100 |
| | CAGUACCUGUUCGAGCGGATT | 101 | UCCGCUCGAACAGGUACUGTT | 102 |
| HS6ST2 (NM_147175) | GCCAUUUACCCAGUAUAAUTT | 103 | AUUAUACUGGGUAAAUGGCTT | 104 |
| | GGAUCAGUUUAUGAGGCAUTT | 105 | UGCCUCAUAAACUGAUCCTT | 106 |
| | CAUGAACUUUAUUUCGCCAUTT | 107 | UGGCGAAAUAAAGUUCAUGTT | 108 |

TABLE 2-continued

Targets for Inhibition of Virus Replication and Inhibitory Polynucleotides

| Gene Symbol (Accession No.) | siRNA (5' to 3' sense) | SEQ ID NO | siRNA (5' to 3' antisense) | SEQ ID NO |
|---|---|---|---|---|
| LOC541473 (NR_003602) | GUCCCUGUACGAGCGGUUATT | 109 | UAACCGCUCGUACAGGGACTT | 110 |
| | GCGGUUAAGUCAGAGGAUGTT | 111 | CAUCCUCUGACUUAACCGCTT | 112 |
| | CUGUACGAGCGGUUAAGUCTT | 113 | GACUUAACCGCUCGUACAGTT | 114 |
| LTC4S (NM_000897) | GCGAGUACUUCCCGCUGUUTT | 115 | AACAGCGGGAAGUACUCGCTT | 116 |
| | GCCGGCAUCUUCUUUCAUGTT | 117 | CAUGAAAGAAGAUGCCGGCTT | 118 |
| | GGGUCGCCGGCAUCUUCUUTT | 119 | AAGAAGAUGCCGGCGACCCTT | 120 |
| MCCC2 (NM_022132) | CCAAGAUUUCUCUACAUUUTT | 121 | AAAUGUAGAGAAAUCUUGGTT | 122 |
| | GAUUUAUGGUUGGUAGAGATT | 123 | UCUCUACCAACCAUAAAUCTT | 124 |
| | CAUCAUGCCCUUCACUUAATT | 125 | UUAAGUGAAGGGCAUGAUGTT | 126 |
| MGST3 (NM_004528) | GUGUAUCCUCCCUUCUUAUTT | 127 | AUAAGAAGGGAGGAUACACTT | 128 |
| | CUGGAUUGUUGGACGAGUUTT | 129 | AACUCGUCCAACACAUCCAGTT | 130 |
| | GUGUUUACCACCCGCGUAUTT | 131 | AUACGCGGGUGGUAAACACTT | 132 |
| PDIA6 (NM_005742) | CAUCGAAUUUCAACCGAGATT | 133 | UCUCGGUUGAAAUUCGAUGTT | 134 |
| | GUGAUAGUUCAAGUAAGAATT | 135 | UUCUUACUUGAACUAUCACTT | 136 |
| | CCAUCAAUGCACGCAAGAUTT | 137 | AUCUUGCGUGCAUUGAUGGTT | 138 |
| PLA2G7 (NM_005084) | CAGAGAUUCAGAUGUGGUATT | 139 | UACCACAUCUGAAUCUCUGTT | 140 |
| | GCCUUAUUCCGUUGGUUGUTT | 141 | ACAACCAACGGAAUAAGGCTT | 142 |
| | GAAAUGAGCAGGUACGGCATT | 143 | UGCCGUACCUGCUCAUUUCTT | 144 |
| PNMT (NM_002686) | CCUUCAACUGGAGCAUGUATT | 145 | UACAUGCUCCAGUUGAAGGTT | 146 |
| | GACAUCACCAUGACAGAUUTT | 147 | AAUCUGUCAUGGUGAUGUCTT | 148 |
| | CCCUCAUCGACAUUGGUUCTT | 149 | GAACCAAUGUCGAUGAGGGTT | 150 |
| SLC27A3 (NM_024330) | GCAACGUGGCCACCAUCAATT | 151 | UUGAUGGUGGCCACGUUGCTT | 152 |
| | CCAGAUACCUGGGAGCGUUTT | 153 | AACGCUCCCAGGUAUCUGGTT | 154 |
| | CGCUGAAGUGGAUGGGCCATT | 155 | UGGCCCAUCCACUUCAGCGTT | 156 |
| TALDO1 (NM_006755) | CACAAGAGGACCAGAUUAATT | 157 | UUAAUCUGGUCCUCUUGUGTT | 158 |
| | GCAACACGGGCGAGAUCAATT | 159 | UUGAUCUCGCCCGUGUUGCTT | 160 |
| | CGAAUUCUUAUAAAGCUGUTT | 161 | ACAGCUUUAUAAGAAUUCGTT | 162 |
| TKTL1 (NM_012253) | GUCGUUUGUGGAUGUGGCATT | 163 | UGCCACAUCCACAAACGACTT | 164 |
| | CAUGCAAAGCCAAUGCCGATT | 165 | UCGGCAUUGGCUUUGCAUGTT | 166 |
| | GGUAUUCUGGCAGGCUUCUTT | 167 | AGAAGCCUGCCAGAAUACCTT | 168 |
| UGT3A2 (NM_174914) | GUUUCUAUUCAGUUAAAGATT | 169 | UCUUUAACUGAAUAGAAACTT | 170 |
| | GAGACAUUGGCUCUUAAGATT | 171 | UCUUAAGAGCCAAUGUCUCTT | 172 |
| | GAACUUCGACAUGGUGAUATT | 173 | UAUCACCAUGUCGAAGUUCTT | 174 |
| UST (NM_005715) | CCUAUUUAUUCACUCGACATT | 175 | UGUCGAGUGAAUAAAUAGGTT | 176 |
| | GAGAUACGAGUACGAGUUUTT | 177 | AAACUCGUACUCGUAUCUCTT | 178 |
| | CCUAAGGGACUAAAUUAATT | 179 | UUAAUUUAGUCCCUUAAGGTT | 180 |
| SOAT1 (NM_003101) | CGUCAUACUCCAACUAUUATT | 196 | UAAUAGUUGGAGUAUGACGTT | 197 |
| | CAAAUCUGCUGCCAUGUUTT | 198 | UAACAUGGCAGCAGAUUUGTT | 199 |
| | CGAAUAUGCCUUGGCUGUUTT | 200 | AACAGCCAAGGCAUAUUCGTT | 201 |
| SOAT2 (NM_003578) | GCUAUACAAUCCUACCCAU | 202 | AUGGGUAGGAUUGUAUAGC | 203 |
| | CUGAUACUCUUCCUUGUCA | 204 | UGACAAGGAAGAGUAUCAG | 205 |
| | CGAUCUUGGUCCUGCCAUA | 206 | UAUGGCAGGACCAAGAUCG | 207 |
| CA7 (NM_005182) | CCAGUUUGCUCCUUGGUCATT | 208 | UGACCAAGGAGCAAACUGGTT | 209 |
| | CACUGAAGGGCCGCGUGGUTT | 210 | ACCACGCGGCCCUUCAGUGTT | 211 |
| | GAGACUCAAGCAAUAAUUATT | 212 | UAAUUAUUGCUUGAGUCUCTT | 213 |
| OTOP3 (NM_178233) | CCCUGAAUGUGGUGUUCCUTT | 214 | AGGAACACCACAUUCAGGGTT | 215 |
| | GAGGCUUCCUGAUGCUCUATT | 216 | UAGAGCAUCAGGAAGCCUCTT | 217 |
| | GGCAAUGAGACCAACACCUTT | 218 | AGGUGUUGGUCUCAUUGCCTT | 219 |
| TBXAS1 (NM_001061) | CAAUAAGAACCGAGACGAATT | 220 | UUCGUCUCGGUUCUUAUUGTT | 221 |
| | GUGAAACACUGCAAGCGUUTT | 222 | AACGCUUGCAGUGUUUCACTT | 223 |
| | GAGACUUCCUCCAAAUGGUTT | 224 | ACCAUUUGGAGGAAGUCUCTT | 225 |
| TYMS (NM_001071) | CAAUGGAUCCCGAGACUUUTT | 226 | AAAGUCUCGGGAUCCAUUGTT | 227 |
| | GUACAAUCCGCAUCCAACUTT | 228 | AGUUGGAUGCGGAUUGUACTT | 229 |
| | GAGAUAUGGAAUCAGAUUATT | 230 | UAAUCUGAUUCCAUAUCUCTT | 231 |

TABLE 2-continued

Targets for Inhibition of Virus Replication and Inhibitory Polynucleotides

| Gene Symbol (Accession No.) | siRNA (5' to 3' sense) | SEQ ID NO | siRNA (5' to 3' antisense) | SEQ ID NO |
|---|---|---|---|---|
| TXNDC11 (NM_015914) | GCAUAGAAUGCAGCAAUUUTT | 232 | AAAUUGCUGCAUUCUAUGCTT | 233 |
|  | GAAAGAAUUUGCGGCAAUUTT | 234 | AAUUGCCGCAAAUUCUUUCTT | 235 |
|  | CAGAGUACGUUCGACGGGATT | 236 | UCCCGUCGAACGUACUCUGTT | 237 |
| PDIA5 (NM_006810) | GACGGUUCUUGUUCCAGUATT | 238 | UACUGGAACAAGAACCGUCTT | 239 |
|  | CCAUUACCAGGAUGGUGCATT | 2406 | UGCACCAUCCUGGUAAUGGTT | 241 |
|  | CCGUUUAUCACCUGACCGATT | 242 | UCGGUCAGGUGAUAAACGGTT | 243 |
| PTGS2 (NM_000963) | GAGUAUGCGAUGUGCUUAATT | 244 | UUAAGCACAUCGCAUACUCTT | 245 |
|  | CAGUAUAAGUGCGAUUGUATT | 246 | UACAAUCGCACUUAUACUGTT | 247 |
|  | GUAUGAGUGUGGGAUUUGATT | 248 | UCAAAUCCCACACUCAUACTT | 249 |
| STX8 (NM_004853) | GACUACUUCUGGCAUCCUUTT | 250 | AAGGAUGCCAGAAGUAGUCTT | 251 |
|  | CAACCUAGUGGAGAACACATT | 252 | UGUGUUCUCCACUAGGUGTT | 253 |
|  | CAAAGCUUACCGUGACAAUTT | 254 | AUUGUCACGGUAAGCUUUGTT | 255 |
| OTOP2 (NM_178160) | CUGUCAGCCUCUUCCGGGATT | 256 | UCCCGGAAGAGGCUGACAGTT | 257 |
|  | CCCUUCAGACCAGCGGGAATT | 258 | UUCCCGCUGGUCUGAAGGGTT | 259 |
|  | CUGACCUGGUGUGGUCUCATT | 260 | UGAGACCACACCAGGUCAGTT | 261 |
| STX6 (NM_005819) | CAAGUUGUCAGGGACAUGATT | 262 | UCAUGUCCCUGACAACUUGTT | 263 |
|  | GAAAUAACCUCCGGAGCAUTT | 264 | AUGCUCCGGAGGUUAUUUCTT | 265 |
|  | CAGUUAUGUUGGAAGAUUUTT | 266 | AAAUCUUCCAACAUAACUGTT | 267 |

In addition, siRNA design algorithms are disclosed in PCT publications WO 2005/018534 A2 and WO 2005/042708 A2; each of which is hereby incorporated by reference herein in its entirety. Specifically, International Patent Application Publication No. WO 2005/018534 A2 discloses methods and compositions for gene silencing using siRNA having partial sequence homology to its target gene. The application provides methods for identifying common and/or differential responses to different siRNAs targeting a gene. The application also provides methods for evaluating the relative activity of the two strands of an siRNA. The application further provides methods of using siRNAs as therapeutics for treatment of diseases. International Patent Application Publication No. WO 2005/042708 A2 provides a method for identifying siRNA target motifs in a transcript using a position-specific score matrix approach. It also provides a method for identifying off-target genes of an siRNA using a position-specific score matrix approach. The application further provides a method for designing siRNAs with improved silencing efficacy and specificity as well as a library of exemplary siRNAs.

Design software can be use to identify potential sequences within the target enzyme mRNA that can be targeted with siRNAs in the methods described herein. See, for example, http://www.ambion.com/techlib/misc/siRNA_finder.html ("Ambion siRNA Target Finder Software"). For example, the nucleotide sequence of ACSL1, which is known in the art (GenBank Accession No. NM_001995) is entered into the Ambion siRNA Target Finder Software (http://www.ambion.com/techlib/misc/siRNA_finder.html), and the software identifies potential ACSL1 target sequences and corresponding siRNA sequences that can be used in assays to inhibit human ACSL1 activity by downregulation of ACSL1 expression. Using this method, non-limiting examples of ACSL1 target sequence (5' to 3') and corresponding sense and antisense strand siRNA sequences (5' to 3') for inhibiting ACSL1 are identified and presented below:

|   | ACSL1 Target Sequence | Sense Strand siRNA | Antisense Strand siRNA |
|---|---|---|---|
| 1. | AAGAACCAAGGGCATATAAAG (SEQ ID NO: 181) | GAACCAAGGGCAUAUAAAGtt (SEQ ID NO: 182) | CUUUAUAUGCCCUUGGUUCtt (SEQ ID NO: 183) |
| 2. | AACCAAGGGCATATAAAGACA (SEQ ID NO: 184) | CCAAGGGCAUAUAAAGACAtt (SEQ ID NO: 185) | UGUCUUUAUAUGCCCUUGGtt (SEQ ID NO: 186) |
| 3. | AAGGGCATATAAAGACAGATG (SEQ ID NO: 187) | GGGCAUAUAAAGACAGAUGtt (SEQ ID NO: 188) | CAUCUGUCUUUAUAUGCCCtt (SEQ ID NO: 189) |
| 4. | AAAGACAGATGGGAGGAGACC (SEQ ID NO: 190) | AGACAGAUGGGAGGAGACCtt (SEQ ID NO: 191) | GGUCUCCUCCCAUCUGUCUtt (SEQ ID NO: 192) |
| 5. | AAGAAGCATCTACATAGGTAC (SEQ ID NO: 193) | GAAGCAUCUACAUAGGUACtt (SEQ ID NO: 194) | GUACCUAUGUAGAUGCUUCtt (SEQ ID NO: 195) |

The same method can be applied to identify target sequences of any enzyme and the corresponding siRNA sequences (sense and antisense strands) to obtain RNAi molecules.

In certain embodiments, a compound is an siRNA effective to inhibit expression of a target enzyme, e.g., ACSL1 or ART1, wherein the siRNA comprises a first strand comprising a sense sequence of the target enzyme mRNA and a second strand comprising a complement of the sense sequence of the target enzyme, and wherein the first and second strands are about 21 to 23 nucleotides in length. In some embodiments, the siRNA comprises first and second strands comprise sense and complement sequences, respectively, of the target enzyme mRNA that is about 17, 18, 19, or 20 nucleotides in length.

The RNAi molecule (e.g., siRNA, shRNA, miRNA) can be both partially or completely double-stranded, and can encompass fragments of at least 18, at least 19, at least 20, at least 21, at least 22, at least 23, at least 24, at least 25, at least 30, at least 35, at least 40, at least 45, at least 50 or more nucleotides per strand. The RNAi molecule (e.g., siRNA, shRNA, miRNA) can also comprise 3' overhangs of at least 1, at least

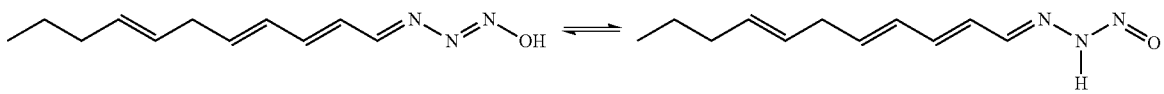

2, at least 3, or at least 4 nucleotides. The RNAi molecule (e.g., siRNA, shRNA, miRNA) can be of any length desired by the user as long as the ability to inhibit target gene expression is preserved.

RNAi molecules can be obtained using any of a number of techniques known to those of ordinary skill in the art. Generally, production of RNAi molecules can be carried out by chemical synthetic methods or by recombinant nucleic acid techniques. Methods of preparing a dsRNA are described, for example, in Ausubel et al., Current Protocols in Molecular Biology (Supplement 56), John Wiley & Sons, New York (2001); Sambrook et al., Molecular Cloning: A Laboratory Manual, 3.sup.rd ed., Cold Spring Harbor Press, Cold Spring Harbor (2001); and can be employed in the methods described herein. For example, RNA can be transcribed from PCR products, followed by gel purification. Standard procedures known in the art for in vitro transcription of RNA from PCR templates. For example, dsRNA can be synthesized using a PCR template and the Ambion T7 MEGASCRIPT, or other similar, kit (Austin, Tex.); the RNA can be subsequently precipitated with LiCl and resuspended in a buffer solution.

To assay for RNAi activity in cells, any of a number of techniques known to those of ordinary skill in the art can be employed. For example, the RNAi molecules are introduced into cells, and the expression level of the target enzyme can be assayed using assays known in the art, e.g., ELISA and immunoblotting. Also, the mRNA transcript level of the target enzyme can be assayed using methods known in the art, e.g., Northern blot assays and quantitative real-time PCR. Further the activity of the target enzyme can be assayed using methods known in the art and/or described herein in section 5.3. In a specific embodiment, the RNAi molecule reduces the protein expression level of the target enzyme by at least about 10%, 20%, 30%, 40%, 50%, 60%, 70%, 80%, 90%, or 95%. In one embodiment, the RNAi molecule reduces the mRNA transcript level of the target enzyme by at least about 10%, 20%, 30%, 40%, 50%, 60%, 70%, 80%, 90%, or 95%. In a particular embodiment, the RNAi molecule reduces the enzymatic activity of the target enzyme by at least about 10%, 20%, 30%, 40%, 50%, 60%, 70%, 80%, 90%, or 95%.

2.1.2 Small Molecules 2.1.2.1 Triacsin Compounds

In one embodiment, the present invention provides a method of treating or preventing a viral infection in a mammal, comprising administering to a subject in need therefore a therapeutically effective amount of triacsin C or a relative, analogue, or derivative thereof.

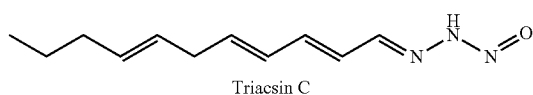

Triacsin C

Triacsin C exists in two tautomeric forms as follows:

Triacsin C is a fungal antimetabolite that inhibits long chain acyl-CoA synthetases (ACSLs), arachidonoyl-CoA synthetase, and triglyceride and cholesterol ester biosynthesis. It is a member of a family of related compounds (Triacsins A-D) isolated from the culture filtrate of Streptomyces sp. SK-1894 (Omura et al., J Antibiot 39, 1211-8, 1986; Tomoda et al., Biochim Biophys Acta, 921, 595-8, 1987), all of which consist of 11-carbon alkenyl chains with a common triazenol moiety at their termini. Structures of triacsins A, B, and D are as follows:

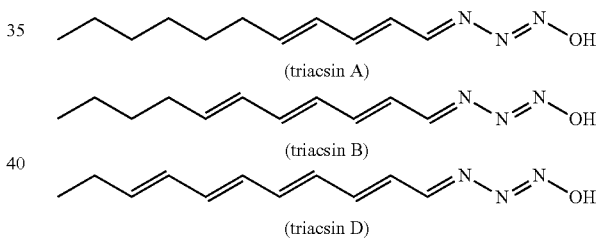

(triacsin A)

(triacsin B)

(triacsin D)

According to the invention, Triacsin C or a related compound or analog or prodrug thereof, is used for treating or preventing infection by a wide range of viruses, such as, but not limited to, DNA viruses (double stranded and single stranded), double-stranded RNA viruses, single-stranded RNA viruses (negative-sense and positive-sense), single-stranded RNA retroviruses, and double stranded viruses with RNA intermediates. For example, as exemplified herein, nanomolar concentrations of triacsin C inhibit the replication of HCMV (a Herpesvirus; comprising a double stranded DNA genome), herpes simplex virus-1 (HSV-1), influenza A (an Orthomyxovirus; a negative-sense single-stranded RNA virus) and hepatitis C virus (HCV). Further, triacsin C exhibits broad spectrum anti-viral activity against enveloped viruses. Accordingly, in one embodiment of the invention, Triacsin C is used for treating or preventing infection by an enveloped virus. Also, triacsin C is active against non-enveloped viruses whose replication occurs on host cell membrane structures and against viruses that induce increases in host cell membrane.

Triacsin C inhibits ACSLs and also inhibits arachidonoyl-CoA synthase. Triacsin C inhibits triacylglycerol (TG) and cholesterol ester (CE) synthesis with an $IC_{50}$ of 100 nM and 190 nM, respectively. Triacsin C inhibits ACSLs in rat liver cell sonicates with an $IC_{50}$ of about 8.7 μM and also inhibits arachidonoyl-CoA sythethase.

Nanomolar concentrations of triacsin C inhibited by >10-fold the replication of 3 of 4 viruses tested: HCMV, herpes simplex virus-1 (HSV-1), and influenza A (but not adenovirus). HCMV, HSV-1, and influenza A (but not adenovirus) have a lipid envelope. See Example 1.

Triacsin C relatives that the present invention include without limitation triacsins A, C, D and WS-1228 A and B (Omura et al., *J Antibiot* 39, 1211-8, 1986). Triacsin C analogues of the present invention include without limitation 3 to 25 carbon unbranched (linear) carbon chains with the triazenol moiety of triacsin C at their termini and with any combination of cis or trans double bonds in the carbon chain. In certain embodiments of the invention, the carbon chain is no shorter than 4, 5, 6, 7, 8, 9, 10, or 11 carbon atoms. In certain embodiments, the carbon chain is no longer than 24, 23, 22, 21, 20, 19, 18, 17, 16, 15, 14, 13, 12, or 11 atoms. In certain embodiments, the carbon chain contains exactly 0, 1, 2, 3, or 4 cis double bonds. In certain embodiments, the carbon chain contains exactly 0, 1, 2, 3, 4, 5, or 6 trans double bonds. In certain embodiments, as in triacsin C, there is a trans double bond at the $2^{nd}$ carbon-carbon bond in the chain (numbering where the carbon-nitrogen bound is bond 0). In other embodiments, there are one or more trans double bonds at bonds 3, 4, 5, 6, 7, 8, 9, 10, 11, or 12 in the chain. In certain embodiments, as in triacsin C, there is a cis-double bond at the $7^{th}$ carbon-carbon bond in the chain. In other embodiments, there are one or more cis double bonds at bonds 3, 4, 5, 6, 7, 8, 9, 10, 11, or 12 in the chain. Triacsin C derivatives of the present invention include without limitation triacsin or its analogues with insertion of heteroatoms or methyl or ethyl groups in place of hydrogen atoms at any point in the carbon chain. They further include variants where a portion of the linear chain of carbon-carbon bonds is replaced by one or more 3, 4, 5, or 6 membered rings, comprised of saturated or unsaturated carbon atoms or heteroatoms. A synthetic route to this class of compounds is described in U.S. Pat. No. 4,297,096 to Yoshida et al.

In certain embodiments, the triacin analogs of the invention include compounds of formula I:

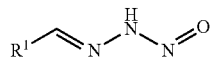

(I)

wherein $R^1$ is a carbon chain having from 3 to 23 atoms (including optional heteroatoms) in the chain, wherein the chain comprises
0-10 double bonds within the chain; and
0-4 heteroatoms within the chain;
and wherein 0-8 of the carbon atoms of $R^1$ are optionally substituted.

If one or more optional heteroatoms occur within the $R^1$ chain, in preferred embodiments each heteroatom is independently selected from O, S, and $NR^2$, wherein $R^2$ is selected from H, $C_{1-6}$ alkyl, and $C_{3-6}$ cycloalkyl.

When the carbon atoms of $R^1$ are substituted, it is preferred that from 0-8 hydrogen atoms along the chain may be replaced by a substituent selected from halo, $OR^2$, $SR^2$, lower alkyl, and cycloalkyl, wherein $R^2$ is H, $C_{1-6}$ alkyl, and $C_{3-6}$ cycloalkyl. In certain preferred embodiments, $R^1$ is unsubstituted (i.e., $R^1$ is unbranched, and none of the hydrogens have been replaced by a substituent).

In preferred embodiments for compounds of the formula I, $R^1$ has a chain length of 8 to 12 atoms. More preferably, $R^1$ has a total chain length of $R^1$ has a chain length of 9 to 11 atoms. Most preferably $R^1$ has a chain length of 10 atoms. In other preferred embodiments, $R^1$ has 2 to 4 double bonds.

In certain embodiments, the triacin anolog is selected from

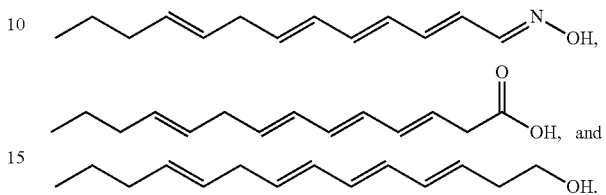

In certain embodiments, the triacin analogs of the invention include compounds of formula II:

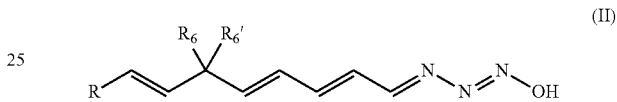

(II)

wherein R is selected from $C_{1-6}$ alkyl; and wherein $R_6$ and $R_{6'}$ are independently selected from H, $C_{1-3}$ alkyl; or $R_6$ and $R_{6'}$ taken together form a cycloalkyl group of formula $-(CH_2)_n$ wherein n is 2-6. In certain embodiments R may be selected from Me, Et, n-butyl, i-propyl, n-pentyl to n-hexyl. In certain embodiments, $R_6$ and $R_{6'}$ are independently selected from Me and F; or $R_6$ and $R_{6'}$ taken together form a cycloalkyl group of formula $-(CH_2)_n$ wherein n is 2, 3, 4, and 6.

For example, in certain embodiments the triacin analog of formula II is one of the following compounds:

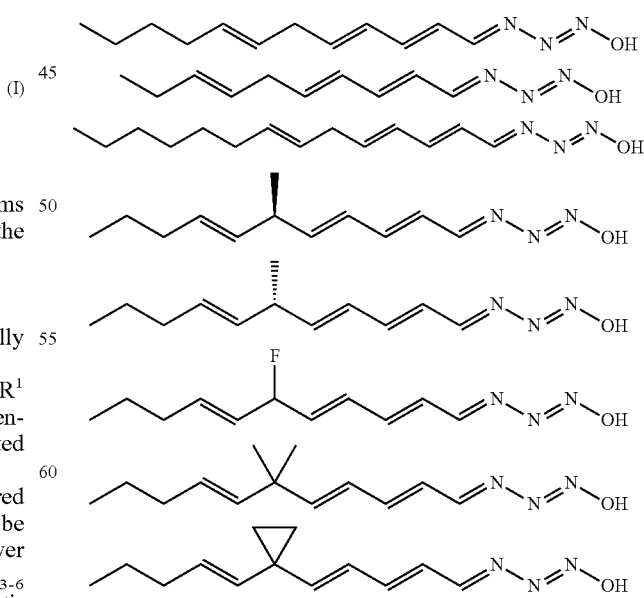

In certain embodiments, the triacin analogs of the invention include compounds of formula III:

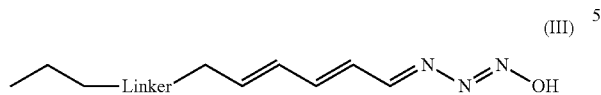
(III)

Wherein the Linker is selected from Z or E-olefin, alkyne, optionally substituted phenyl ring or optionally substituted heteroaryl ring (such as pyridine).

For example, compounds of formula III include:

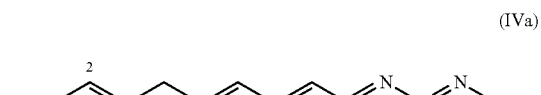
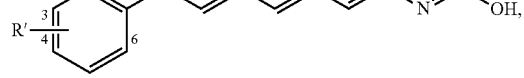

In another embodiment triacin analogs of the invention include compounds of formula IVa and IVb:

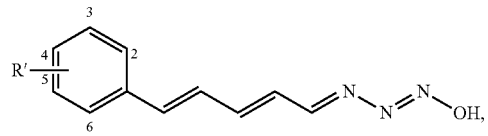
(IVa)

(IVb)

Wherein R' is $C_{1-4}$ alkyl. In certain embodiments R' is Me, Et, nPr, iPr, nBu. In certain embodiments one of the phenyl carbons at positions 2-6 may be replaced by N.

For example, in certain embodiments compounds of formula IVa include:

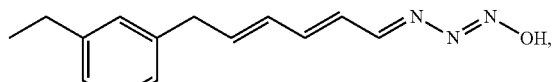
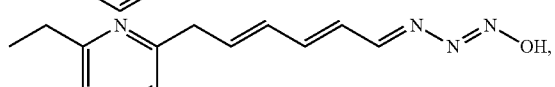
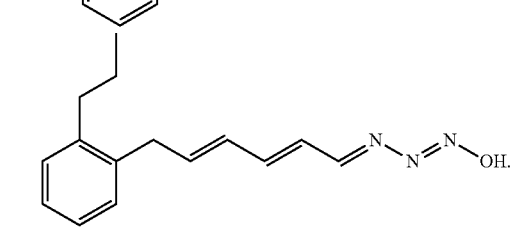

In certain embodiments compounds of formula IVb include:

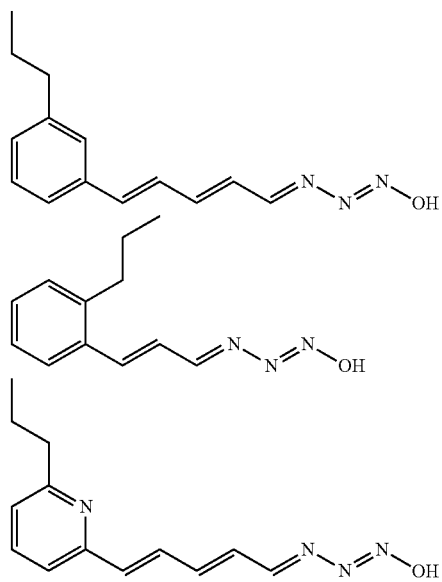

In one embodiment triacsin C analogs are designed from corresponding lipophillic tail groups, spacer groups, and polar groups

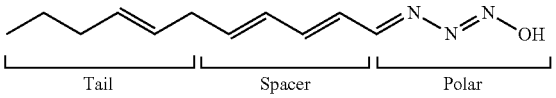

wherein the lipophilic tail group is selected from the tail group of traicin A-D and

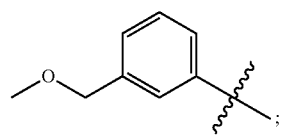 [SMILES: *c1cccc(COC)c1 ; ";"]

wherein the spacer group is selected from the spacer group of traicin A-D and

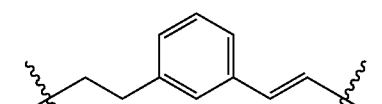
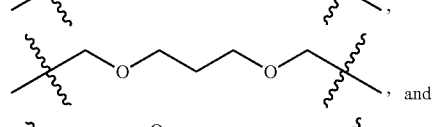
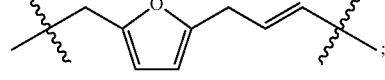

and
wherein the polar group is selected from the polar group of traicin A-D and

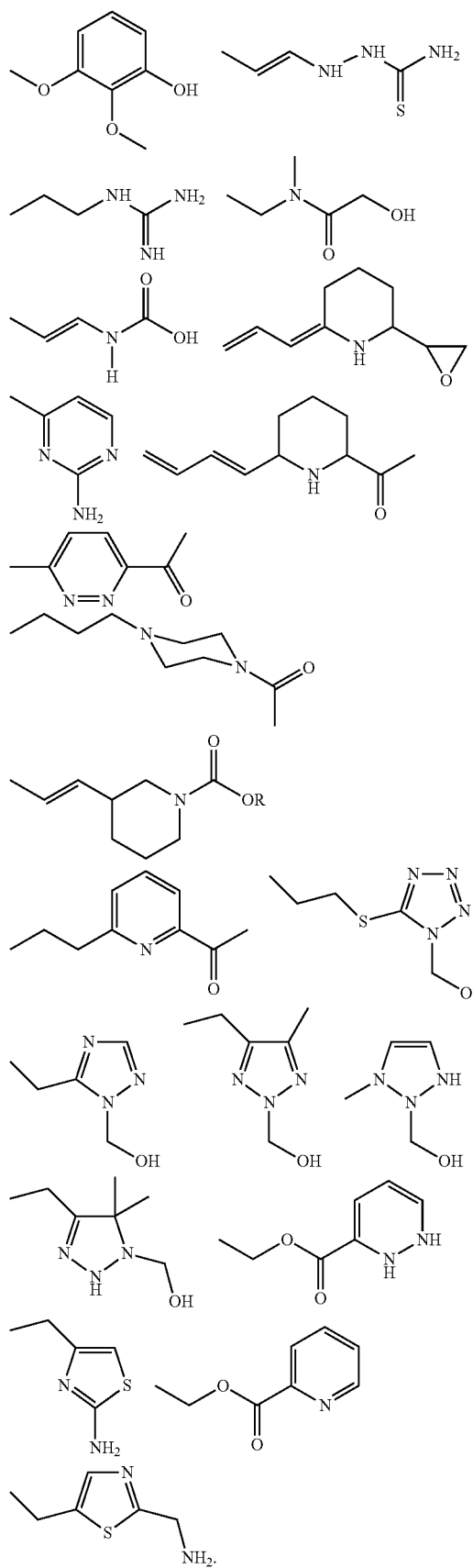
In one embodiment, the triacin C analog composed of the tail, spacer and polar group is
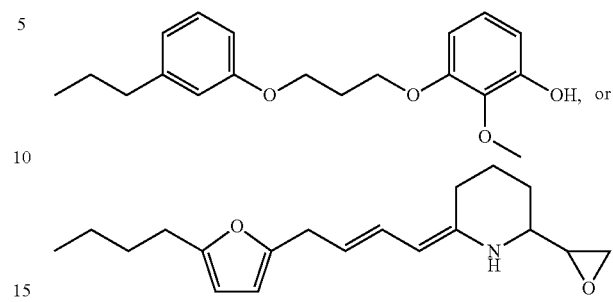
2.1.2.2 Inhibitors of Lipid Drop Formation
Inhibitors of lipid drop formation include, but are not limited to the following compounds:
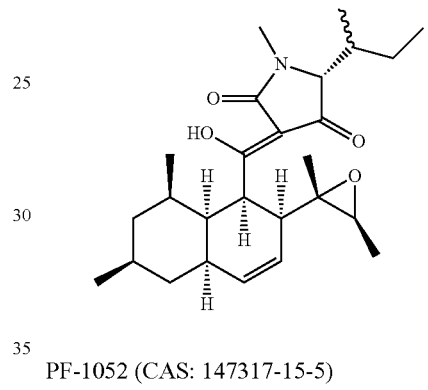
PF-1052 (CAS: 147317-15-5)
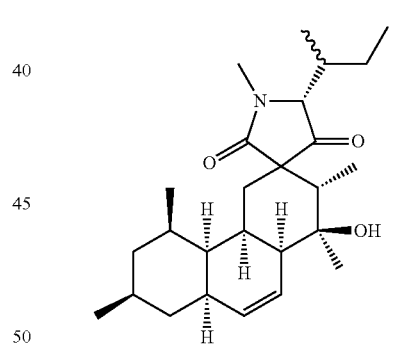
Spylidone (Liquid Droplet inhibition IC$_{50}$ 42 uM) (Tomoda et al., 2007, *Pharmacol. Ther.* 115:375-89);
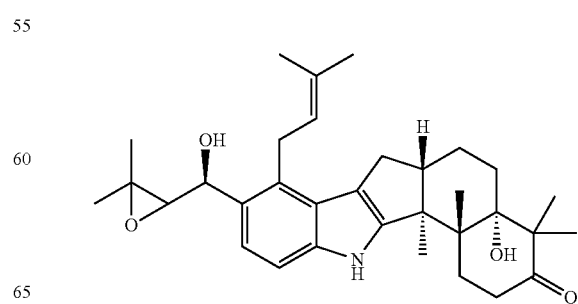

Sespendole (Liquid Droplet inhibition IC50 4 uM) (Tomoda et al., 2007, *Pharmacol. Ther.* 115:375-89)

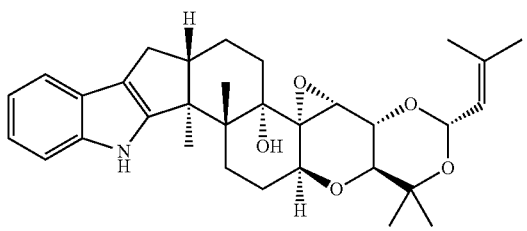

Terpendole C (Liquid Droplet inhibition IC$_{50}$ 2.5 μM)(Tomoda et al., 2007, *Pharmacol. Ther.* 115:375-89);

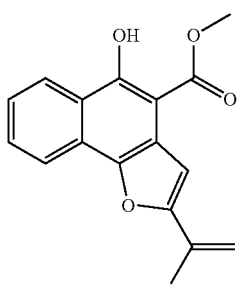 [SMILES: C=C(C)c1cc2c(C(=O)OC)c(O)c3ccccc3c2o1]

Compound 7 (Sastry et al., 2010, *J. Org. Chem.* 75:2274-80);

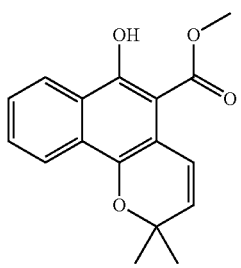 [SMILES: COC(=O)c1c2c(c3ccccc3c1O)OC(C)(C)C=C2]

Rubimaillin;

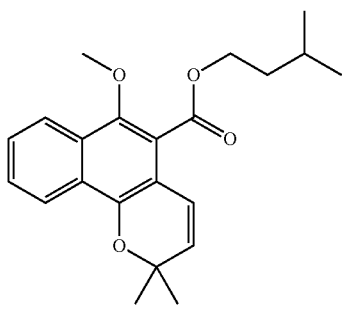 [SMILES: COc1c(C(=O)OCCC(C)C)c2c(c3ccccc13)OC(C)(C)C=C2]

Compound 8 (Ho, L. K. et al., 1996, *J. Nat. Prod.* 59:330-3); and

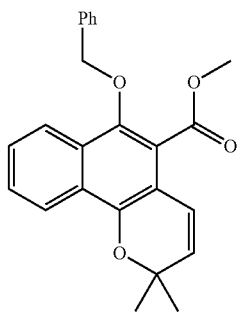 [SMILES: COC(=O)c1c2c(c3ccccc3c1OCc1ccccc1)OC(C)(C)C=C2]

Compound 9 (Ho, L. K. et al., 1996, *J. Nat. Prod.* 59:330-3).

Analogs of PF-1052 and Spylidone useful in the present invention include

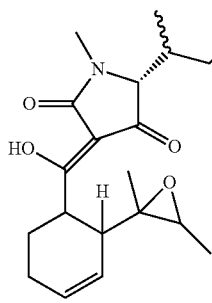 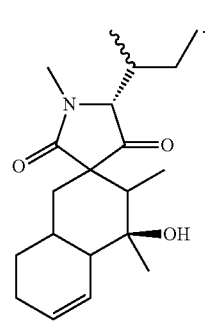

Additional inhibitors of lipid droplet formation include Vermisporin; Beauveriolides; Phenochalasins; Isobisvertinol; and K97-0239.

2.1.2.3 ACAT Inhibitors

In certain embodiments, the ACAT inhibitors of the invention include compounds of formula V

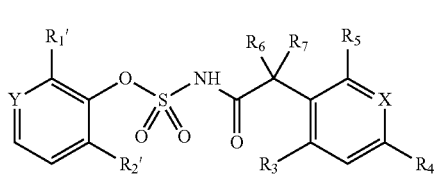

(V)

wherein

X and Y are independently selected from N and CH;

$R_{1'}$ and $R_{2'}$ are independently selected from H, $C_{1-6}$ alkyl which may be optionally substituted with F, $OCH_3$ and OH, and $C_{1-6}$ cycloalkyl;

$R_6$ and $R_7$ are independently selected from H, and $C_{1-3}$ alkyl, or $R_6$ and $R_7$ taken together may form a $C_{3-6}$ cycloalkyl, $R_3$, $R_4$ and $R_5$ are independently selected from H, $C_{1-6}$ alkyl which may be optionally substituted with F, $OCH_3$ and OH, and $C_{1-6}$ cycloalkyl;

additionally or alternatively, one of $R_6$ or $R_7$ may be taken together with $R_5$ to form a $C_{5-11}$ cycloalkyl ring.

In certain embodiments, $R_{1'}$ and/or $R_{2'}$ are independently selected from branched $C_{3-5}$ alkyl and particularly isopropyl.

In certain embodiments, $R_3$, $R_4$ and/or $R_5$ are independently selected from branched $C_{3-5}$ alkyl and particularly isopropyl.

In certain embodiments, $R_6$ and $R_7$ are both H.

In certain embodiments, the ACAT inhibitors of the invention include compounds of formula Va

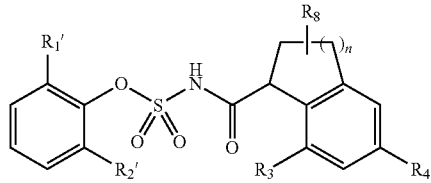

(Va)

wherein $R_{1'}$ and $R_{2'}$ are independently selected from H, $C_{1-6}$ alkyl which may be optionally substituted with F, $OCH_3$ and OH, and $C_{1-6}$ cycloalkyl;

$R_3$ and $R_4$ are independently selected from H, $C_{1-6}$ alkyl which may be optionally substituted with F, $OCH_3$ and OH, and $C_{1-6}$ cycloalkyl;

n is selected from 1 to 7; and $R_8$ is selected from H and $C_{1-3}$ alkyl.

In certain embodiments, $R_{1'}$ and/or $R_{2'}$ are independently selected from branched $C_{3-5}$ alkyl and particularly isopropyl.

In certain embodiments, $R_3$ and/or $R_4$ are independently selected from branched $C_{3-5}$ alkyl and particularly isopropyl.

In certain embodiments, $R_8$ is methyl.

In one embodiment the compound of formula V is

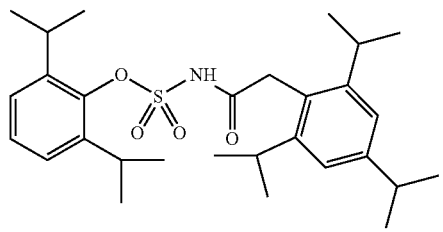 [SMILES: CC(C)c1cc(C(C)C)c(CC(=O)NS(=O)(=O)Oc2c(C(C)C)cccc2C(C)C)c(C(C)C)c1]

Avasimibe (ACAT $IC_{50}$ 479 nM).

Additional ACAT inhibitors of the invention include, but are not limited to the following compounds:

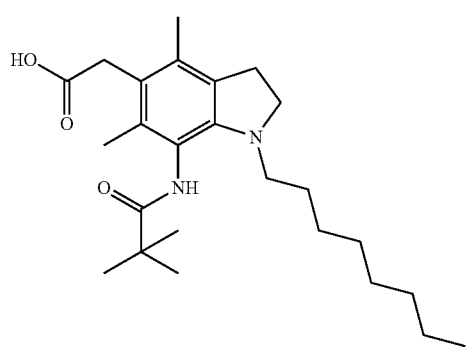 [SMILES: CCCCCCCCN1CCc2c(C)c(CC(=O)O)c(C)c(NC(=O)C(C)(C)C)c21]

Pactimibe (Liver ACAT $IC_{50}$ 312 nM) (Ohta et al., 2010, *Chem. Pharm. Bull.* 58:1066-76);

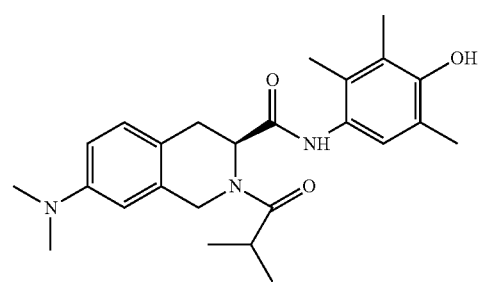

Compound I (Liver ACAT $IC_{50}$ 120 nM) (Takahashi et al., 2008, *J. Med. Chem.* 51:4823-33);

Compound 21 (Liver ACAT $IC_{50}$ 113 nM) (Ohta et al., 2010, *Chem. Pharm. Bull.* 58:1066-76);

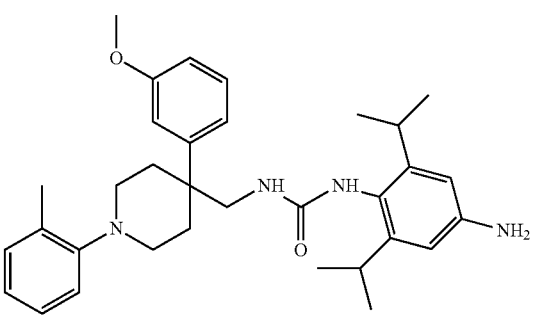 [SMILES: COc1cccc(C2(CNC(=O)Nc3c(C(C)C)cc(N)cc3C(C)C)CCN(c3ccccc3C)CC2)c1]

Compound 12g (ACAT $IC_{50}$ 68 nM) (Asano et al., 2009, *Bioorg. Med. Chem. Lett.* 19:1062-5);

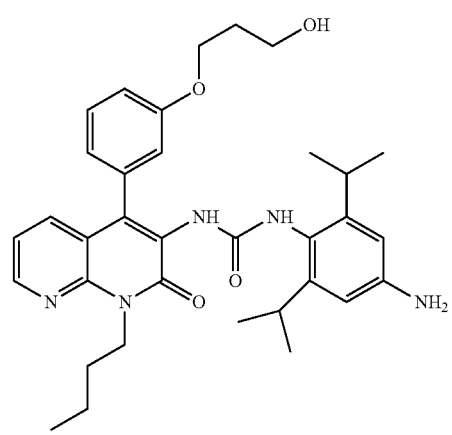 [SMILES: CCCCn1c(=O)c(NC(=O)Nc2c(C(C)C)cc(N)cc2C(C)C)c(-c2cccc(OCCCO)c2)c2cccnc21]

SMP-797 (ACAT $IC_{50}$ 31 nM) (Asano et al., 2009, *Bioorg. Med. Chem. Lett.* 19:1062-5);

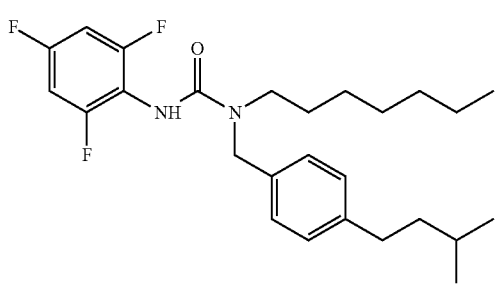 [SMILES: CCCCCCCN(Cc1ccc(CCC(C)C)cc1)C(=O)Nc1c(F)cc(F)cc1F]

CL-283,546 (Liquid Droplet inhibition IC$_{50}$ 35 nM) (Tomoda et al., 2007, *Pharmacol. Ther.* 115:375-89);

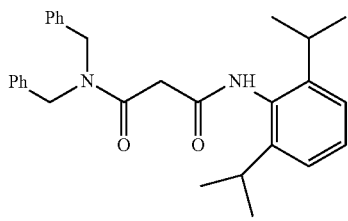 [SMILES: CC(C)c1cccc(C(C)C)c1NC(=O)CC(=O)N(Cc1ccccc1)Cc1ccccc1]

Wu-V-23 (Tomoda et al., 2007, *Pharmacol. Ther.* 115:375-89); and

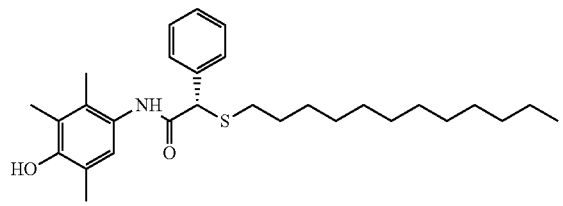 [SMILES: CCCCCCCCCCCCS[C@H](C(=O)Nc1cc(C)c(O)c(C)c1C)c1ccccc1]

Eflucimibe.

2.1.2.4 Elongase Inhibitors

One example of an elongase inhibitor is a compound of formula VI:

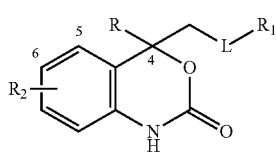

(VI)

wherein L is selected from carbamate, urea, or amide including, for example

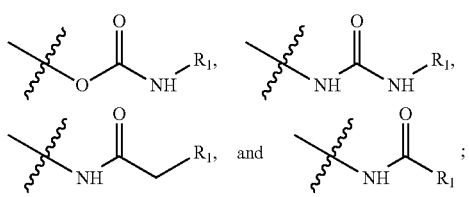

and wherein R is selected from halo; CF$_3$; cyclopropyl; optionally substituted C$_{1-5}$ alkyl, wherein the C$_{1-5}$ alkyl may be substituted with halo, oxo, —OH, —CN, —NH$_2$, CO$_2$H, and C$_{1-3}$ alkoxy;

wherein R$_1$ is selected from substituted phenyl where the substituents are selected from F, CF$_3$, Me, OMe, or isopropyl;

wherein R$_2$ is Cl, Ph, 1-(2-pyridone), 4-isoxazol, 3-pyrazol, 4-pyrazol, 1-pyrazol, 5-(1,2,4-triazol), 1-(1,2,4-triaol), 2-imidazolo, 1-(2-pyrrolidone), 3-(1,3-oxazolidin-2-one).

The chiral center at C4 can be racemic, (S), (R), or any ratio of enantiomers. In one embodiment, L is an amide. In certain embodiments, R is selected from C$_1$, CF$_3$, methyl, ethyl, isopropyl and, cyclopropyl. In certain embodiments R1 is para-substituted wherein the substituent is selected from F, CF$_3$, Me, OMe, or isopropyl, In one embodiment, the compound of formula VIa is

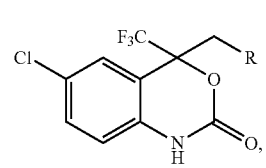

(VIa)

wherein R is selected from

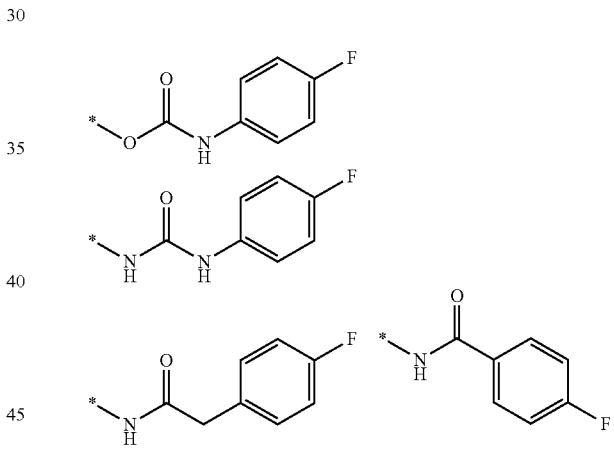

In another embodiment, the elongase inhibitor is a compound of formula VIb

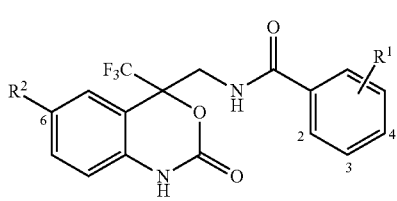

(VIb)

wherein R$^1$ is substituted at position 2, 3, or 4 with F, or Me, or R$^1$ is substituted at position 4 with MeO, or CF$_3$. R$^2$ is Cl, H, Ph, 4-isoxazol, 4-pyrazol, 3-pyrazol, 1-pyrazol, 5-(1,2,4-triazol), 1-(1,2,4-triazol), 2-imidazol, 1-(2-pyrrolidone), or 3-(1,3-oxazolidin-2-one). In one embodiment the compound of formula VI is

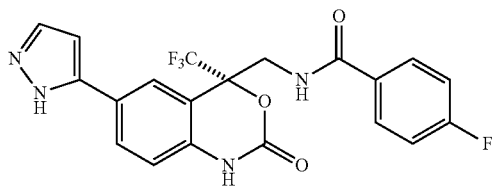 [SMILES: O=C1Nc2ccc(-c3ccn[nH]3)cc2[C@](CNC(=O)c2ccc(F)cc2)(C(F)(F)F)O1]

(S)-y. (See, Mizutani et al., 2009, *J. Med. Chem.* 52:7289-7300).

In another embodiment, the compound of formula VI is

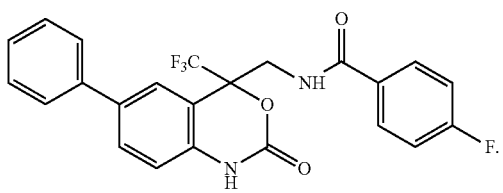 [SMILES: O=C1Nc2ccc(-c3ccccc3)cc2C(CNC(=O)c2ccc(F)cc2)(C(F)(F)F)O1]

Additional examples of an elongase inhibitors are compounds of formula VIIa and VIIb

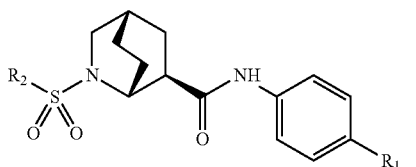
(VIIa)

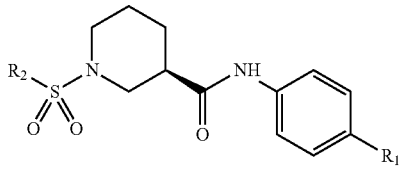
(VIIb)

wherein $R_1$ is selected from OMe, OiPr, OCF$_3$, OPh, CH$_2$Ph, F, CH$_3$, CF$_3$, and benzyl; and wherein $R_2$ is selected from C$_{1-4}$ alkyl (such as nBu, nPr, and iPr); phenyl; substituted phenyl where substitutents are selected from OMe, CF$_3$, F, tBu, iPr and thio; 2-pyridine; 3-pyridine; and N-methy imidazole. (See, Sasaki et al., 2009, *Biorg. Med. Chem.* 17:5639-47).

In one embodiment, $R_1$ is selected from OiPr and OCF$_3$. In one embodiment $R_2$ is selected from nBu, unsubstituted phenyl, fluorophenyl and thiophenyl.

In one embodiment the inhibitor of formula VIIa is

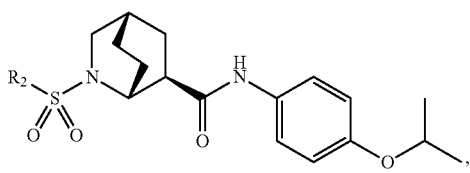

wherein $R^2$ is selected from butyl, propyl, phenyl, pyridyl, and imidazole.

In one embodiment the inhibitor of formula VIIa is selected from

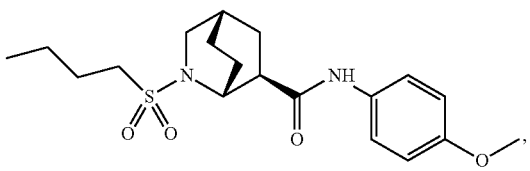 [SMILES: CCCCS(=O)(=O)N1C[C@H]2CC[C@@H]1[C@H](C(=O)Nc1ccc(OC)cc1)C2]

which has hELOVL6 IC$_{50}$ of 1710 nM;

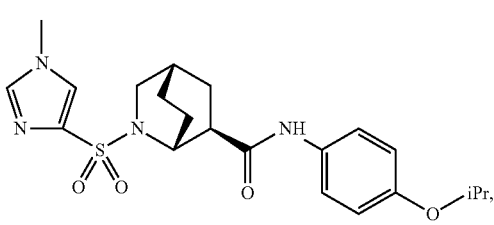 [SMILES: CC(C)Oc1ccc(NC(=O)[C@@H]2C[C@@H]3CC[C@H]2N(S(=O)(=O)c2cn(C)cn2)C3)cc1]

which has hELOVL6 IC$_{50}$ of 220 nM and a hELOVL3 IC$_{50}$ of 1510 nM; and

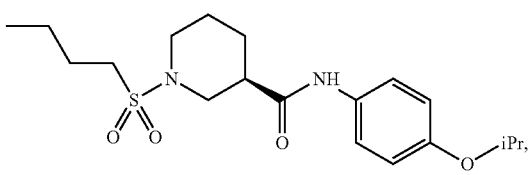 [SMILES: CCCCS(=O)(=O)N1CCC[C@@H](C(=O)Nc2ccc(OC(C)C)cc2)C1]

which has hELOVL6 IC$_{50}$ of 930 nM.

Yet another example of an elongase inhibitor is a compound of formula VIII

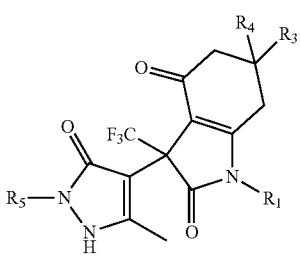
(VIII)

wherein $R_1$ is selected from H, unsubstituted phenyl; substituted phenyl where substitutents are selected from F, Me, Et, Cl, OMe, OCF$_3$, and CF$_3$; C$_{1-6}$ alkyl (such as Me, Et, iPr, and n-propyl); and C$_{3-6}$ cycloalkyl (cyclopropyl, cyclobutyl, cyclopentyl, cyclohexyl);

wherein $R_3$ and $R_4$ are independently selected from H; C$_{1-3}$ alkyl; and phenyl; or $R_3$ and $R_4$ taken together form a cycloalkyl of formula —(CH2)$_n$— where n=2, 3, 4 and 5;

wherein $R_5$ is selected from methyl; CF$_3$; cyclopropyl; unsubstituted phenyl; mono- and disubstituted phenyl where substitutents are selected from F, Me, Et, CN, iPr, Cl, OMe, OPh, OCF$_3$, and CF$_3$; unsubstituted heteroaromatic groups (such as 2, 3, or 4-pyridine, isoxazol, pyrazol, triazol); and imidazolo.

In other embodiments the compound of formula VIII is

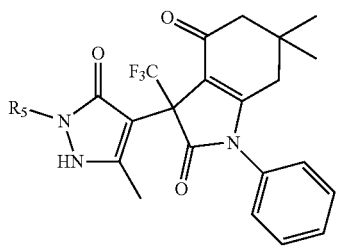

wherein R⁵ is a substituted phenyl ring, including, but not limited to

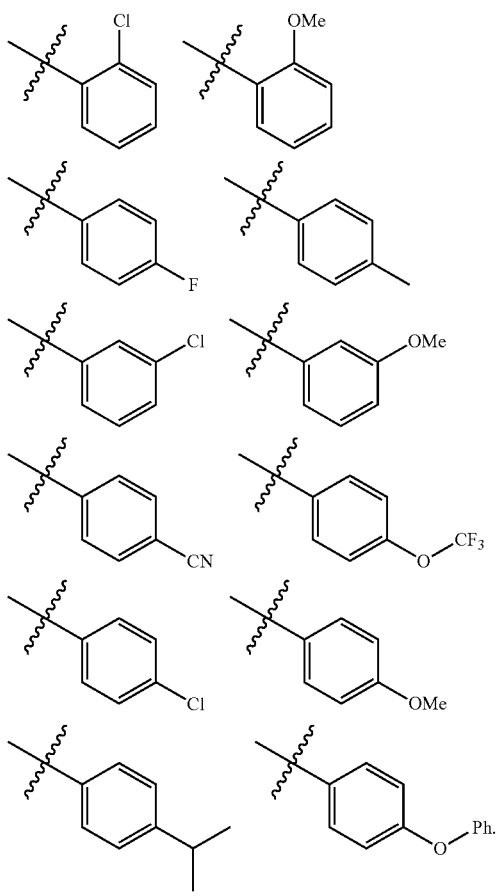

(See Takahashi et al., 2009, J. Med. Chem. 52:3142-5.)

In other embodiments compound of formula VIII is one of the following compounds:

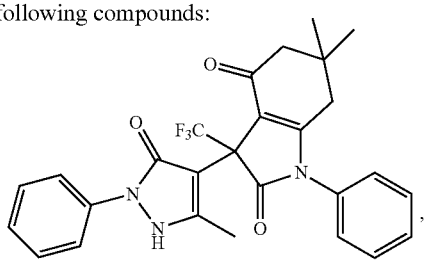

which has a hELOVL6 IC50 of 290 nM,

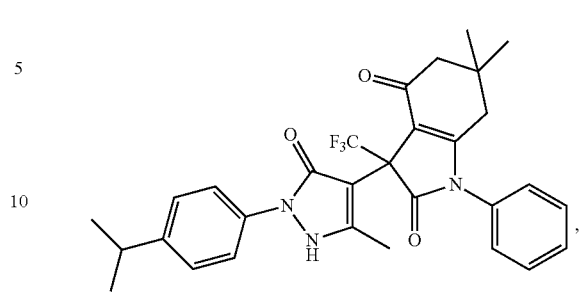

which has a hELOVL6 IC50 of 10 nM and a hELOVL3 IC50 of 59 nM, and

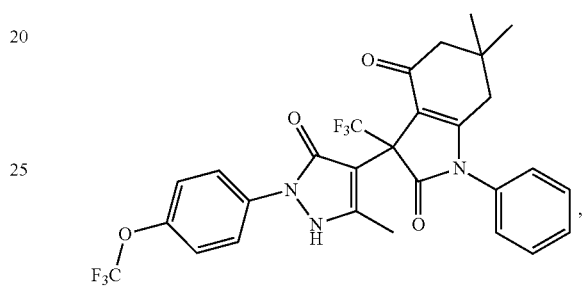

Compound 37, which has a hELOVL6 IC50 of 8.9 nM and a hELOVL3 IC50 of 337 nM.

In one embodiment the elongase inhibitor is a compound of formula IX

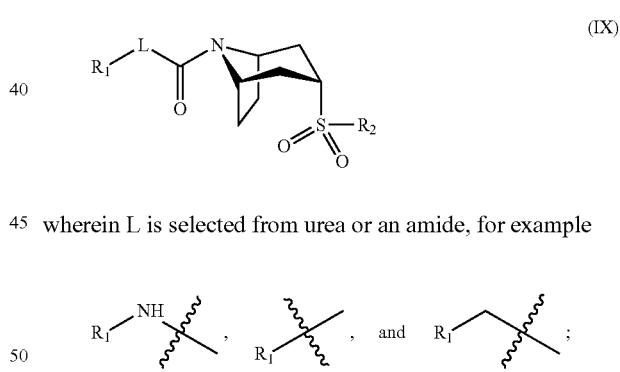

wherein L is selected from urea or an amide, for example

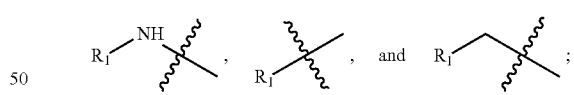

wherein $R_1$ is selected form 2-, 3-, and 4-pyridine; pyrimidine; unsubstituted heteroaryls such as isoxazol, pyrazol, triazol, imidazole; and unsubstituted phenyl; ortho, meta or para-substituted phenyl where substitutents are F, Me, Et, Cl, OMe, OCF₃, and CF₃, Cl, iPr and phenyl;

wherein $R_2$ is selected from Cl; iPr; phenyl; ortho, meta or para-substituted phenyl where substitutents are F, Me, Et, Cl, OMe, OCF₃, and CF₃; and heteroaryls such as 2-, 3-, and 4-pyridine, pyrimidine, and isoxazol, pyrazol, triazol, and imidazo.

In one embodiment L is urea. In one embodiment, $R_1$ is para-substituted CF₃ phenyl. In one embodiment, $R_2$ is phenyl. In another embodiment, $R_2$ is 2-pyridyl.

In one embodiment the compound of formula IX is selected from

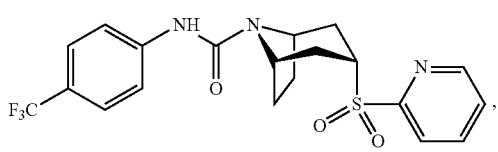

(endo-1w) which has a hELOVL6 IC50 of 79 nM and a hELOVL3 IC50 of 6940 nM, and

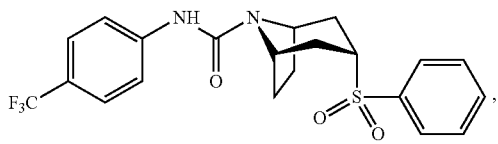

(endo-1k) which has a hELOVL6 IC50 of 78 nM.

2.1.2.5 ART1 Inhibitors

Meta-iodo-benzylguanidine (MIBG) is an inhibitor of ADP-ribosyltransferase 1 (ART1). 50 µM MIBG reduced HCMV titer from infected MRC5 fibroblasts by about 70% with little or no effect on cell morphology.

2.1.2.6 AGXT2 Inhibitors

Aminooxyacetic acid (AOAA) is an inhibitor of alanine-glyoxylate aminotransferase 2 (AGXT2). 0.5 mM AOAA decreases HCMV replication by 100-fold with no measurable decrease in cell viability at concentrations up to 2.5 mM. 0.5 mM and 1 mM AOAA decreases influenza A replication in MDCK cells by at least 1000-fold after 24 hours with no evidence of host cell toxicity. 0.5 mM and 1 mM concentrations of AOAA decrease adenovirus titer in MRC2 cells by 20-fold and 500-fold respectively.

3. Screening Assays to Identify Inhibitors of Host Cell Target Enzymes

Compounds known to be inhibitors of the host cell target enzymes can be directly screened for antiviral activity using assays known in the art and/or described infra (see, e.g., Section 4 et seq.). While optional, derivatives or congeners of such enzyme inhibitors, or any other compound can be tested for their ability to modulate the enzyme targets using assays known to those of ordinary skill in the art and/or described below. Compounds found to modulate these targets can be further tested for antiviral activity. Compounds found to modulate these targets or to have antiviral activity (or both) can also be tested in the metabolic flux assays described in Section 4.2.8 in order to confirm the compound's effect on the metabolic flux of the cell. This is particularly useful for determining the effect of the compound in blocking the ability of the virus to alter cellular metabolic flux, and to identify other possible metabolic pathways that may be targeted by the compound.

Alternatively, compounds can be tested directly for antiviral activity. Those compounds which demonstrate anti-viral activity, or that are known to be antiviral but have unacceptable specificity or toxicity, can be screened against the enzyme targets of the invention. Antiviral compounds that modulate the enzyme targets can be optimized for better activity profiles.

Any host cell enzyme, known in the art and/or described in Section 5.1, is contemplated as a potential target for antiviral intervention. Further, additional host cell enzymes that have a role, directly or indirectly, in regulating the cell's metabolism are contemplated as potential targets for antiviral intervention. Compounds, such as the compounds disclosed herein or any other compounds, e.g., a publicly available library of compounds, can be tested for their ability to modulate (activate or inhibit) the activity of these host cell enzymes. If a compound is found to modulate the activity of a particular enzyme, then a potential antiviral compound has been identified.

In one embodiment, an enzyme that affects or is involved in synthesis of long and very long chain fatty acids is tested as a target for the compound, for example, ACSL1, ELOVL2, ELOVL3, ELOVL6, or SLC27A3. In one embodiment, long and very long chain acyl-CoA synthases are tested for modulation by the compound. In another embodiment, fatty acid elongases are tested for modulation by the compound. In one embodiment, an enzyme involved in synthesis of cysteinyl leukotrienes is tested for modulation by the compound. In one embodiment, an enzyme that plays role in lipid storage (including but not limited to ADP-ribosyltransferase 1 or 3) is tested for modulation by the compound. In another embodiment, an alanine-glyoxylate aminotransferase is tested for modulation by the compound. In yet another embodiment, an enzyme in the pentose phosphosphate pathway is tested for modulation by the compound.

In preferred embodiments, a compound is tested for its ability to modulate host metabolic enzymes by contacting a composition comprising the compound with a composition comprising the enzyme and measuring the enzyme's activity. If the enzyme's activity is altered in the presence of the compound compared to a control, then the compound modulates the enzyme's activity. In some embodiments of the invention, the compound increases an enzyme's activity (for example, an enzyme that is a negative regulator of fatty acid biosynthesis might have its activity increased by a potential antiviral compound). In specific embodiments, the compound increases an enzyme's activity by at least approximately 10%, 15%, 20%, 25%, 30%, 40%, 50%, 60%, 70%, 80% or 90%. In some embodiments, the compound decreases an enzyme's activity. In particular embodiments, the compound decreases an enzyme's activity by at least approximately 10%, 15%, 20%, 25%, 30%, 40%, 50%, 60%, 70%, 80%, 90%, 95% or 100%. In certain embodiments, the compound exclusively modulates a single enzyme. In some embodiments, the compound modulates multiple enzymes, although it might modulate one enzyme to a greater extent than another. Using the standard enzyme activity assays described herein, the activity of the compounds could be characterized. In one embodiment, a compound exhibits an irreversible inhibition or activation of a particular enzyme. In some embodiments, a compound reversibly inhibits or activates an enzyme. In some embodiments, a compound alters the kinetics of the enzyme.

In one embodiment, for example, evaluating the interaction between the test compound and host target enzyme includes one or more of (i) evaluating binding of the test compound to the enzyme; (ii) evaluating a biological activity of the enzyme; (iii) evaluating an enzymatic activity (e.g., elongase activity) of the enzyme in the presence and absence of test compound. The in vitro contacting can include forming a reaction mixture that includes the test compound, enzyme, any required cofactor (e.g., biotin) or energy source (e.g., ATP, or radiolabeled ATP), a substrate (e.g., acetyl-CoA, a sugar, a polypeptide, a nucleoside, or any other metabolite, with or without label) and evaluating conversion of the substrate into a product. Evaluating product formation can include, for example, detecting the transfer of carbons or phosphate (e.g., chemically or using a label, e.g., a radiolabel), detecting the reaction product, detecting a secondary reaction dependent on the first reaction, or detecting a physical property of the substrate, e.g., a change in molecular weight, charge, or pI.

Target enzymes for use in screening assays can be purified from a natural source, e.g., cells, tissues or organs comprising adipocytes (e.g., adipose tissue), liver, etc. Alternatively, target enzymes can be expressed in any of a number of different recombinant DNA expression systems and can be obtained in large amounts and tested for biological activity. For expression in recombinant bacterial cells, for example E. coli, cells are grown in any of a number of suitable media, for example LB, and the expression of the recombinant polypeptide induced by adding IPTG to the media or switching incubation to a higher temperature. After culturing the bacteria for a further period of between 2 and 24 hours, the cells are collected by centrifugation and washed to remove residual media. The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars such as sucrose into the buffer and centrifugation at a selective speed. If the recombinant polypeptide is expressed in the inclusion, these can be washed in any of several solutions to remove some of the contaminating host proteins, then solubilized in solutions containing high concentrations of urea (e.g., 8 M) or chaotropic agents such as guanidine hydrochloride in the presence of reducing agents such as beta-mercaptoethanol or DTT (dithiothreitol). At this stage it may be advantageous to incubate the polypeptide for several hours under conditions suitable for the polypeptide to undergo a refolding process into a conformation which more closely resembles that of the native polypeptide. Such conditions generally include low polypeptide (concentrations less than 500 mg/ml), low levels of reducing agent, concentrations of urea less than 2 M and often the presence of reagents such as a mixture of reduced and oxidized glutathione which facilitate the interchange of disulphide bonds within the protein molecule. The refolding process can be monitored, for example, by SDS-PAGE or with antibodies which are specific for the native molecule. Following refolding, the polypeptide can then be purified further and separated from the refolding mixture by chromatography on any of several supports including ion exchange resins, gel permeation resins or on a variety of affinity columns.

Isolation and purification of host cell expressed polypeptide, or fragments thereof may be carried out by conventional means including, but not limited to, preparative chromatography and immunological separations involving monoclonal or polyclonal antibodies.

These polypeptides may be produced in a variety of ways, including via recombinant DNA techniques, to enable large scale production of pure, biologically active target enzyme useful for screening compounds for the purposes of the invention. Alternatively, the target enzyme to be screened could be partially purified or tested in a cellular lysate or other solution or mixture.

Target enzyme activity assays are preferably in vitro assays using the enzymes in solution or using cell or cell lysates that express such enzymes, but the invention is not to be so limited. In certain embodiments, the enzyme is in solution. In other embodiments, the enzyme is associated with microsomes or in detergent. In other embodiments, the enzyme is immobilized to a solid or gel support. In certain embodiments, the enzyme is labeled to facilitate purification and/or detection. In other embodiments, a substrate is labeled to facilitate purification and or detection. Labels include polypeptide tags, biotin, radiolabels, fluorescent labels, or a colorimetric label. Any art-accepted assay to test the activity of metabolic enzymes can be used in the practice of this invention. Preferably, many compounds are screened against multiple targets with high throughput screening assays.

Substrate and product levels can be evaluated in an in vitro system, e.g., in a biochemical extract, e.g., of proteins. For example, the extract may include all soluble proteins or a subset of proteins (e.g., a 70% or 50% ammonium sulfate cut), the useful subset of proteins defined as the subset that includes the target enzyme. The effect of a test compound can be evaluated, for example, by measuring substrate and product levels at the beginning of a time course, and then comparing such levels after a predetermined time (e.g., 0.5, 1, or 2 hours) in a reaction that includes the test compound and in a parallel control reaction that does not include the test compound. This is one method for determining the effect of a test compound on the substrate-to-product ratio in vitro. Reaction rates can obtained by linear regression analysis of radioactivity or other label incorporated vs. reaction time for each incubation. $K_M$ and $V_{max}$ values can be determined by non-linear regression analysis of initial velocities, according to the standard Henri-Michaelis-Menten equation. $k_{cat}$ can be obtained by dividing $V_{max}$ values by reaction concentrations of enzyme, e.g., derived by colorimetric protein determinations (e.g., Bio-RAD protein assay, Bradford assay, Lowry method). In one embodiment, the compound irreversibly inactivates the target enzyme. In another embodiment, the compound reversibly inhibits the target enzyme. In some embodiments, the compound reversibly inhibits the target enzyme by competitive inhibition. In some embodiments, the compound reversibly inhibits the target enzyme by noncompetitive inhibition. In some embodiments, the compound reversibly inhibits the target enzyme by uncompetitive inhibition. In a further embodiment, the compound inhibits the target enzyme by mixed inhibition. The mechanism of inhibition by the compound can be determined by standard assays known by those of ordinary skill in the art.

Methods for the quantitative measurement of enzyme activity utilizing a phase partition system are described in U.S. Pat. No. 6,994,956, which is incorporated by reference herein in its entirety. Specifically, a radiolabeled substrate and the product of the reaction are differentially partitioned into an aqueous phase and an immiscible scintillation fluid-containing organic phase, and enzyme activity is assessed either by incorporation of a radiolabeled-containing organic-soluble moiety into product molecules (gain of signal assay) or loss of a radiolabel-containing organic-soluble moiety from substrate molecules (loss of signal assay). Scintillations are only detected when the radionuclide is in the organic, scintillant-containing phase. Such methods can be employed to test the ability of a compound to inhibit the activity of a target enzyme.

Cellular assays may be employed. An exemplary cellular assay includes contacting a test compound to a culture cell (e.g., a mammalian culture cell, e.g., a human culture cell) and then evaluating substrate and product levels in the cell, e.g., using any method described herein, such as Reverse Phase HPLC, LC-MS, or LC-MS/MS.

Substrate and product levels can be evaluated, e.g., by NMR, HPLC (See, e.g., Bak, M. I., and Ingwall, J. S. (1994) J. Clin. Invest. 93, 40-49), mass spectrometry, thin layer chromatography, or the use of radiolabeled components (e.g., radiolabeled ATP for a kinase assay). For example, $^{31}P$ NMR can be used to evaluate ATP and AMP levels. In one implementation, cells and/or tissue can be placed in a 10-mm NMR sample tube and inserted into a 1H/31P double-tuned probe situated in a 9.4-Tesla superconducting magnet with a bore of 89 cm. If desired, cells can be contacted with a substance that provides a distinctive peak in order to index the scans. Six $^{31}$P NMR spectra—each obtained by signal averaging of 104 free induction decays—can be collected using a 60° flip angle, 15-microsecond pulse, 2.14-second delay, 6,000 Hz sweep width, and 2048 data points using a GE-400 Omega NMR spectrometer (Bruker Instruments, Freemont, Calif., USA). Spectra are analyzed using 20-Hz exponential multiplication and zero- and first-order phase corrections. The resonance peak areas can be fitted by Lorentzian line shapes using NMR1 software (New Methods Research Inc., Syracuse, N.Y., USA). By comparing the peak areas of fully relaxed spectra (recycle time: 15 seconds) and partially saturated spectra (recycle time: 2.14 seconds), the correction factor for saturation can be calculated for the peaks. Peak areas can be normalized to cell and/or tissue weight or number and expressed in arbitrary area units. Another method for evaluating, e.g., ATP and AMP levels includes lysing cells in a sample to form an extract, and separating the extract by Reversed Phase HPLC, while monitoring absorbance at 260 nm.

Another type of in vitro assay evaluates the ability of a test compound to modulate interaction between a first enzyme pathway component and a second enzyme pathway component This type of assay can be accomplished, for example, by coupling one of the components with a radioisotope or enzymatic label such that binding of the labeled component to the second pathway component can be determined by detecting the labeled compound in a complex. An enzyme pathway component can be labeled with $^{125}$I, $^{35}$S, $^{14}$C, or $^{3}$H, either directly or indirectly, and the radioisotope detected by direct counting of radio-emission or by scintillation counting. Alternatively, a component can be enzymatically labeled with, for example, horseradish peroxidase, alkaline phosphatase, or luciferase, and the enzymatic label detected by determination of conversion of an appropriate substrate to product. Competition assays can also be used to evaluate a physical interaction between a test compound and a target.

Soluble and/or membrane-bound forms of isolated proteins (e.g., enzyme pathway components and their receptors or biologically active portions thereof) can be used in the cell-free assays of the invention. When membrane-bound forms of the enzyme are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton X-100, Triton X-114, Thesit, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl-N,N-dimethyl-3-ammonio-1-propane sulfonate. In another example, the enzyme pathway component can reside in a membrane, e.g., a liposome or other vesicle.

Cell-free assays involve preparing a reaction mixture of the target enzyme and the test compound under conditions and for a time sufficient to allow the two components to interact and bind, thus forming a complex that can be removed and/or detected. In one embodiment, the target enzyme is mixed with a solution containing one or more, and often many hundreds or thousands, of test compounds. The target enzyme, including any bound test compounds, is then isolated from unbound (i.e., free) test compounds, e.g., by size exclusion chromatography or affinity chromoatography. The test compound(s) bound to the target can then be separated from the target enzyme, e.g., by denaturing the enzyme in organic solvent, and the compounds identified by appropriate analytical approaches, e.g., LC-MS/MS.

The interaction between two molecules, e.g., target enzyme and test compound, can also be detected, e.g., using a fluorescence assay in which at least one molecule is fluorescently labeled, e.g., to evaluate an interaction between a test compound and a target enzyme. One example of such an assay includes fluorescence energy transfer (FET or FRET for fluorescence resonance energy transfer) (See, for example, Lakowicz et al., U.S. Pat. No. 5,631,169; Stavrianopoulos, et al., U.S. Pat. No. 4,868,103). A fluorophore label on the first, "donor" molecule is selected such that its emitted fluorescent energy will be absorbed by a fluorescent label on a second, "acceptor" molecule, which in turn is able to fluoresce due to the absorbed energy. Alternately, a proteinaceous "donor" molecule may simply utilize the natural fluorescent energy of tryptophan residues. Labels are chosen that emit different wavelengths of light, such that the "acceptor" molecule label may be differentiated from that of the "donor." Since the efficiency of energy transfer between the labels is related to the distance separating the molecules, the spatial relationship between the molecules can be assessed. In a situation in which binding occurs between the molecules, the fluorescent emission of the "acceptor" molecule label in the assay should be maximal. A FET binding event can be conveniently measured through standard fluorometric detection means well known in the art (e.g., using a fluorimeter).

Another example of a fluorescence assay is fluorescence polarization (FP). For FP, only one component needs to be labeled. A binding interaction is detected by a change in molecular size of the labeled component. The size change alters the tumbling rate of the component in solution and is detected as a change in FP. See, e.g., Nasir et al. (1999) Comb Chem HTS 2:177-190; Jameson et al. (1995) Methods Enzymol 246:283; See Anal Biochem. 255:257 (1998). Fluorescence polarization can be monitored in multi-well plates. See, e.g., Parker et al. (2000) Journal of Biomolecular Screening 5:77-88; and Shoeman, et al. (1999) 38, 16802-16809.

In another embodiment, determining the ability of the target enzyme to bind to a target molecule can be accomplished using real-time Biomolecular Interaction Analysis (BIA) (See, e.g., Sjolander, S, and Urbaniczky, C. (1991) Anal. Chem. 63:2338-2345 and Szabo et al. (1995) Curr. Opin. Struct. Biol. 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target enzyme is anchored onto a solid phase. The target enzyme/test compound complexes anchored on the solid phase can be detected at the end of the reaction, e.g., the binding reaction. For example, the target enzyme can be anchored onto a solid surface, and the test compound (which is not anchored), can be labeled, either directly or indirectly, with detectable labels discussed herein.

It may be desirable to immobilize either the target enzyme or an anti-target enzyme antibody to facilitate separation of complexed from uncomplexed forms of one or both of the proteins, as well as to accommodate automation of the assay. Binding of a test compound to target enzyme, or interaction of a target enzyme with a second component in the presence and absence of a candidate compound, can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase/target enzyme fusion proteins can be adsorbed onto glutathione sepharose beads (Sigma Chemical, St. Louis, Mo., USA) or glutathione derivatized microtiter plates, which are then combined with the test compound or the test compound and either the non-adsorbed target enzyme, and the mixture incubated under conditions conducive to complex formation (e.g., at physiological conditions for salt and pH). Following incubation, the beads or microtiter plate wells are washed to remove any unbound components, the matrix immobilized in the case of beads, and the complex determined either directly or indirectly, for example, as described above. Alternatively, the complexes can be dissociated from the matrix, and the level of target enzyme binding or activity is determined using standard techniques.

Other techniques for immobilizing either a target enzyme or a test compound on matrices include using conjugation of biotin and streptavidin. Biotinylated target enzyme or test compounds can be prepared from biotin-NHS (N-hydroxysuccinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface, e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with a target enzyme but which do not interfere with binding of the target enzyme to the test compound and/or substrate. Such antibodies can be derivatized to the wells of the plate, and unbound target enzyme trapped in the wells by antibody conjugation. Methods for detecting such complexes, in addition to those described above for the GST-immobilized complexes, include immunodetection of complexes using antibodies reactive with the target enzyme, as well as enzyme-linked assays which rely on detecting an enzymatic activity associated with the target enzyme.

Alternatively, cell free assays can be conducted in a liquid phase. In such an assay, the reaction products are separated from unreacted components, by any of a number of standard techniques, including but not limited to: differential centrifugation (See, for example, Rivas, G., and Minton, A. P., (1993) Trends Biochem Sci 18:284-7); chromatography (gel filtration chromatography, ion-exchange chromatography); electrophoresis (See, e.g., Ausubel, F. et al., eds. Current Protocols in Molecular Biology 1999, J. Wiley: New York); and immunoprecipitation (See, for example, Ausubel, F. et al., eds. (1999) Current Protocols in Molecular Biology, J. Wiley: New York). Such resins and chromatographic techniques are known to one skilled in the art (See, e.g., Heegaard, N.H., (1998) J Mol Recognit 11:141-8; Hage, D. S., and Tweed, S. A. (1997) J Chromatogr B Biomed Sci Appl. 699:499-525). Further, fluorescence energy transfer may also be conveniently utilized, as described herein, to detect binding without further purification of the complex from solution.

In a preferred embodiment, the assay includes contacting the target enzyme or biologically active portion thereof with a known compound which binds the target enzyme to form an assay mixture, contacting the assay mixture with a test compound, and determining the ability of the test compound to interact with the target enzyme, wherein determining the ability of the test compound to interact with the target enzyme includes determining the ability of the test compound to preferentially bind to the target enzyme, or to modulate the activity of the target enzyme, as compared to the known compound (e.g., a competition assay). In another embodiment, the ability of a test compound to bind to and modulate the activity of the target enzyme is compared to that of a known activator or inhibitor of such target enzyme.

The target enzymes of the invention can, in vivo, interact with one or more cellular or extracellular macromolecules, such as proteins, which are either heterologous to the host cell or endogenous to the host cell, and which may or may not be recombinantly expressed. For the purposes of this discussion, such cellular and extracellular macromolecules are referred to herein as "binding partners." Compounds that disrupt such interactions can be useful in regulating the activity of the target enzyme. Such compounds can include, but are not limited to molecules such as antibodies, peptides, and small molecules. In an alternative embodiment, the invention provides methods for determining the ability of the test compound to modulate the activity of a target enzyme through modulation of the activity of a downstream effector of such target enzyme. For example, the activity of the effector molecule on an appropriate target can be determined, or the binding of the effector to an appropriate target can be determined, as previously described.

To identify compounds that interfere with the interaction between the target enzyme and its cellular or extracellular binding partner(s), a reaction mixture containing the target enzyme and the binding partner is prepared, under conditions and for a time sufficient, to allow the two products to form a complex. In order to test an inhibitory compound, the reaction mixture is provided in the presence and absence of the test compound. The test compound can be initially included in the reaction mixture, or can be added at a time subsequent to the addition of the target and its cellular or extracellular binding partner. Control reaction mixtures are incubated without the test compound or with a placebo. The formation of any complexes between the target product and the cellular or extracellular binding partner is then detected. The formation of a complex in the control reaction, but not in the reaction mixture containing the test compound, indicates that the compound interferes with the interaction of the target product and the interactive binding partner. Additionally, complex formation within reaction mixtures containing the test compound and normal target enzyme can also be compared to complex formation within reaction mixtures containing the test compound and mutant target enzyme. This comparison can be important in those cases wherein it is desirable to identify compounds that disrupt interactions of mutant but not normal target enzymes.

The assays described herein can be conducted in a heterogeneous or homogeneous format. Heterogeneous assays involve anchoring either the target enzyme or the binding partner, substrate, or tests compound onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target enzyme and a binding partners or substrate, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target enzyme or the interactive cellular or extracellular binding partner or substrate, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target enzyme and the interactive cellular or extracellular binding partner product or substrate is prepared in that either the target enzyme or their binding partners or substrates are labeled, but the signal generated by the label is quenched due to complex formation (See, e.g., U.S. Pat. No. 4,109,496 that utilizes this approach for immunoassays). The addition of a test substance that competes with and displaces one of the species from the preformed complex will result in the generation of a signal above background. In this way, test compounds that disrupt target enzyme-binding partner or substrate contact can be identified.

In yet another aspect, the target enzyme can be used as "bait protein" in a two-hybrid assay or three-hybrid assay (See, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent, International patent application Publication No. WO94/10300), to identify other proteins that bind to or interact with target enzyme ("target enzyme binding protein" or "target enzyme-bp") and are involved in target enzyme pathway activity. Such target enzyme-bps can be activators or inhibitors of the target enzyme or target enzyme targets as, for example, downstream elements of the target enzyme pathway.

In another embodiment, modulators of a target enzyme's gene expression are identified. For example, a cell or cell free mixture is contacted with a candidate compound and the expression of the target enzyme mRNA or protein evaluated relative to the level of expression of target enzyme mRNA or protein in the absence of the candidate compound. When expression of the target enzyme component mRNA or protein is greater in the presence of the candidate compound than in its absence, the candidate compound is identified as a stimulator of target enzyme mRNA or protein expression. Alternatively, when expression of the target enzyme mRNA or protein is less (statistically significantly less) in the presence of the candidate compound than in its absence, the candidate compound is identified as an inhibitor of the target enzyme mRNA or protein expression. The level of the target enzyme mRNA or protein expression can be determined by methods for detecting target enzyme mRNA or protein, e.g., Westerns, Northerns, PCR, mass spectroscopy, 2-D gel electrophoresis, and so forth, all which are known to those of ordinary skill in the art.

Assays for producing enzyme targets, testing their activity, and conducting screens for their inhibition or activation are described below using examples of enzymes related to fatty acid biosynthesis. These assays can be adapted by one of ordinary skill in the art, or other assays known in the art can be used, to test the activity of other targets of the invention.

3.1 High Throughput Screening of Compounds and Target Enzymes

In one embodiment, high throughput screening using, e.g., mass spectrometry can be used to screen a number of compounds and a number of potential target enzymes simultaneously. Mass spectrometry can be utilized for determination of metabolite levels and enzymatic activity.

The levels of specific metabolites (e.g. AMP, ATP) can be quantified by liquid chromatography-mass spectrometry (LC-MS/MS). A metabolite of interest will have a specific chromatographic retention time at which point the mass spectrometer performs a selected reaction monitoring scan event (SRM) that consists of three identifiers:

1) The metabolite's mass (the parent ion);
2) The energy required to fragment the parent ion in a collision with argon to yield a fragment with a specific mass; and
3) The mass of the specific fragment ion.

Utilizing the above identifiers, the accumulation of a metabolite can be measured whose production depends on the activity of a metabolic enzyme of interest. By adding an excess of enzyme substrate to a cellular lysate, so as to make the activity of the enzyme rate limiting, the accumulation of enzymatic product over time is then measured by LC-MS/MS as outlined above, and serves as a function of the metabolic enzyme's activity. An example of such an assay is reported in Munger et al, 2006 PLoS Pathogens, 2: 1-11, incorporated herein by reference in its entirety, in which the activity of phosphofructokinase present in infected lysates was measured by adding an excess of the phosphofructokinase substrates ATP and fructose phosphate and measuring fructose bisphosphate accumulation by LC-MS/MS. This approach can be adopted to measure the activities of numerous host target enzymes.

3.2 Kinetic Flux Profiling (KFP) to Assess Potential Antiviral Compounds

In a further embodiment of the invention, cellular metabolic fluxes are profiled in the presence or absence of a virus using kinetic flux profiling (KFP) (See Munger et al. 2008 Nature Biotechnology, 26: 1179-1186) in the presence or absence of a compound found to inhibit a target enzyme in one of the aforementioned assays. Such metabolic flux profiling provides additional (i) guidance about which components of a host's metabolism can be targeted for antiviral intervention; (ii) guidance about the metabolic pathways targeted by different viruses; and (iii) validation of compounds as potential antiviral agents based on their ability to offset the metabolic flux caused by a virus or trigger cell-lethal metabolic derangements specifically in virally infected cells. In one embodiment, the kinetic flux profiling methods of the invention can be used for screening to determine (i) the specific alterations in metabolism caused by different viruses and (ii) the ability of a compound to offset (or specifically augment) alterations in metabolic flux caused by different viruses.

Thus, in one embodiment of the invention, cells are infected with a virus and metabolic flux is assayed at different time points after virus infection, such time points known to one of skill in the art. For example, for HCMV, flux can be measured 24, 48, or 72 hours post-infection, whereas for a faster growing virus like HSV, flux can be measured at 6, 12, or 18 hours post-infection. If the metabolic flux is altered in the presence of the virus, then the virus alters cellular metabolism during infection. The type of metabolic flux alteration observed (See above and examples herein) will provide guidance as to the cellular pathways that the virus acts on. Assays well known to those of skill in the art and described herein below can then be employed to confirm the target of the virus. Similarly, compounds can be tested for the ability to interfere with the virus in the assays for antiviral activity described in Section 4 below. If it appears that a virus modulates the level and/or activity of a particular enzyme, inhibitors of that enzyme can be tested for their antiviral effect. If well-characterized compounds are observed to be effective antivirals, other compounds that modulate the same target can similarly be assessed as potential antivirals.

In one embodiment of the invention, a virus infected cell is contacted with a compound and metabolic flux is measured. If the metabolic flux in the presence of the compound is different from the metabolic flux in the absence of the compound, in a manner wherein the metabolic effects of the virus have been inhibited or augmented, then a compound that modulates the virus' ability to alter the metabolic flux has been identified. The type of metabolic flux alteration observed will provide guidance as to the cellular pathway that the compound is acting on. Assays well known to those of skill in the art and described herein can then be employed to confirm the target of the antiviral compound.

In one embodiment, high throughput metabolome quantitation mass spectrometry can be used to screen for changes in metabolism caused by infection of a virus and whether or not a compound or library of compounds offsets these changes. See Munger et al. 2006. PLoS Pathogens, 2: 1-11.

3.3 Identification of Compounds

Using metabolome and fluxome-based analysis of virus infected cells, the inventors have identified host cell target enzymes listed in Table 1 (Section 1) and demonstrated that virus replication can be reduced by reducing expression of the target enzymes. Further, any compound of interest can be tested for its ability to modulate the activity of these enzymes. Alternatively, compounds can be tested for their ability to inhibit any other host cell enzyme related to metabolism. Once such compounds are identified as having metabolic enzyme-modulating activity, they can be further tested for their antiviral activity as described in Section 4. Alternatively, compounds can be screened for antiviral activity and optionally characterized using the metabolic screening assays described herein.

In one embodiment, high throughput screening methods are used to provide a combinatorial chemical or peptide library (e.g., a publicly available library) containing a large number of potential therapeutic compounds (potential modulators or ligand compounds). Such "combinatorial chemical libraries" or "ligand libraries" are then screened in one or more assays, as described in Section 3 herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (See, e.g., U.S. Pat. No. 5,010,175, Furka, Int. J. Pept. Prot. Res. 37:487-493 (1991) and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (See Ausubel, Berger and Sambrook, all supra), peptide nucleic acid libraries (See, e.g., U.S. Pat. No. 5,539,083), antibody libraries (See, e.g., Vaughn et al., Nature Biotechnology, 14(3):309-314 (1996) and PCT/US96/10287), carbohydrate libraries (See, e.g., Liang et al., Science, 274:1520-1522 (1996) and International Patent Application Publication NO. WO 1997/000271), small organic molecule libraries (See, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like). Additional examples of methods for the synthesis of molecular libraries can be found in the art, for example in: DeWitt et al. (1993) Proc. Natl. Acad. Sci. U.S.A. 90:6909; Erb et al.

(1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Some exemplary libraries are used to generate variants from a particular lead compound. One method includes generating a combinatorial library in which one or more functional groups of the lead compound are varied, e.g., by derivatization. Thus, the combinatorial library can include a class of compounds which have a common structural feature (e.g., scaffold or framework). Devices for the preparation of combinatorial libraries are commercially available (See, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (See, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.). The test compounds can also be obtained from: biological libraries; peptoid libraries (libraries of molecules having the functionalities of peptides, but with a novel, non-peptide backbone which are resistant to enzymatic degradation but which nevertheless remain bioactive; See, e.g., Zuckermann, R. N. et al. (1994) J. Med. Chem. 37:2678-85); spatially addressable parallel solid phase or solution phase libraries; synthetic library methods requiring deconvolution; the 'one-bead one-compound' library method; and synthetic library methods using affinity chromatography selection. The biological libraries include libraries of nucleic acids and libraries of proteins. Some nucleic acid libraries encode a diverse set of proteins (e.g., natural and artificial proteins; others provide, for example, functional RNA and DNA molecules such as nucleic acid aptamers or ribozymes. A peptoid library can be made to include structures similar to a peptide library. (See also Lam (1997) Anticancer Drug Des. 12:145). A library of proteins may be produced by an expression library or a display library (e.g., a phage display library). Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner, U.S. Pat. No. 5,223,409), spores (Ladner U.S. Pat. No. 5,223,409), plasmids (Cull et al. (1992) Proc Natl Acad Sci USA 89:1865-1869) or on phage (Scott and Smith (1990) Science 249:386-390; Devlin (1990) Science 249: 404-406; Cwirla et al. (1990) Proc. Natl. Acad. Sci. 87:6378-6382; Felici (1991) J. Mol. Biol. 222:301-310; Ladner supra.). Enzymes can be screened for identifying compounds which can be selected from a combinatorial chemical library or any other suitable source (Hogan, Jr., Nat. Biotechnology 15:328, 1997).

Any assay herein, e.g., an in vitro assay or an in vivo assay, can be performed individually, e.g., just with the test compound, or with appropriate controls. For example, a parallel assay without the test compound, or other parallel assays without other reaction components, e.g., without a target or without a substrate. Alternatively, it is possible to compare assay results to a reference, e.g., a reference value, e.g., obtained from the literature, a prior assay, and so forth. Appropriate correlations and art known statistical methods can be used to evaluate an assay result. See Section 3.1 above.

Once a compound is identified as having a desired effect, production quantities of the compound can be synthesized, e.g., producing at least 50 mg, 500 mg, 5 g, or 500 g of the compound. Although a compound that is able to penetrate a host cell is preferable in the practice of the invention, a compound may be combined with solubilizing agents or administered in combination with another compound or compounds to maintain its solubility, or help it enter a host cell, e.g., by mixture with lipids. The compound can be formulated, e.g., for administration to a subject, and may also be administered to the subject.

4. Characterization of Antiviral Activity of Compounds 4.1 Viruses

The present invention provides compounds for use in the prevention, management and/or treatment of viral infection. The antiviral activity of compounds against any virus can be tested using techniques described in Section 4.2 herein below. The virus may be enveloped or naked, have a DNA or RNA genome, or have a double-stranded or single-stranded genome. See, e.g., FIG. 1 modified from Flint et al., Principles of Virology: Molecular Biology, Pathogenesis and Control of Animal Viruses. 2nd edition, ASM Press, 2003, for a subset of virus families and their classification, as well as a subset of viruses against which compounds can be assessed for antiviral activity. In specific embodiments, the virus infects human. In other embodiments, the virus infects non-human animals. In a specific embodiment, the virus infects pigs, fowl, other livestock, or pets.

In certain embodiments, the virus is an enveloped virus. Enveloped viruses include, but are not limited to viruses that are members of the hepadnavirus family, herpesvirus family, iridovirus family, poxvirus family, flavivirus family, togavirus family, retrovirus family, coronavirus family, filovirus family, rhabdovirus family, bunyavirus family, orthomyxovirus family, paramyxovirus family, and arenavirus family. Non-limiting examples of viruses that belong to these families are included in Table 3.

TABLE 3

Families of Enveloped Viruses

| Virus Family | Members |
| --- | --- |
| Hepadnavirus (Hepadnaviridae) | hepatitis B virus (HBV), woodchuck hepatitis virus, ground squirrel hepatitis virus, duck hepatitis B virus, heron hepatitis B virus |
| Herpesvirus (Herpesviridae) | herpes simplex virus (HSV) types 1 and 2, varicella-zoster virus, cytomegalovirus (CMV), human cytomegalovirus (HCMV), Epstein-Barr virus (EBV), human herpesvirus 6 (variants A and B), human herpesvirus 7, human herpesvirus 8, Kaposi's sarcoma—associated herpes virus (KSHV), B virus |
| Poxvirus (Poxviridae) | vaccinia virus, variola virus, smallpox virus, monkeypox virus, cowpox virus, camelpox virus, mousepox virus, raccoonpox viruses, molluscum contagiosum virus, orf virus, milker's nodes virus, bovin papular stomatitis virus, sheeppox virus, goatpox virus, lumpy skin disease virus, fowlpox virus, canarypox virus, pigeonpox virus, |

TABLE 3-continued

Families of Enveloped Viruses

| Virus Family | Members |
|---|---|
| | sparrowpox virus, myxoma virus, hare fibroma virus, rabbit fibroma virus, squirrel fibroma viruses, swinepox virus, tanapox virus, Yabapox virus |
| Flavivirus (Flaviviridae) | dengue virus, hepatitis C virus (HCV), GB hepatitis viruses (GBV-A, GBV-B and GBV-C), West Nile virus, yellow fever virus, St. Louis encephalitis virus, Japanese encephalitis virus, Powassan virus, tick-borne encephalitis virus, Kyasanur Forest disease virus |
| Togavirus (Togaviridae) | Venezuelan equine encephalitis virus, chikungunya virus, Ross River virus, Mayaro virus, Sindbis virus, rubella virus |
| Retrovirus (Retroviridae) | human immunodeficiency virus (HIV) types 1 and 2, human T cell leukemia virus (HTLV) types 1, 2, and 5, mouse mammary tumor virus (MMTV), Rous sarcoma virus (RSV), lentiviruses |
| Coronavirus (Coronaviridae) | severe acute respiratory syndrome (SARS) virus |
| Filovirus (Filoviridae) | Ebola virus, Marburg virus |
| Rhabdovirus (Rhabdoviridae) | rabies virus, vesicular stomatitis virus |
| Bunyavirus (Bunyaviridae) | Crimean-Congo hemorrhagic fever virus, Rift Valley fever virus, La Crosse virus, Hantaan virus |
| Orthomyxovirus (Orthomyxoviridae) | influenza virus (types A, B, and C) |
| Paramyxovirus (Paramyxoviridae) | parainfluenza virus, respiratory syncytial virus (types A and B), measles virus, mumps virus |
| Arenavirus (Arenaviridae) | lymphocytic choriomeningitis virus, Junin virus, Machupo virus, Guanarito virus, Lassa virus, Ampari virus, Flexal virus, Ippy virus, Mobala virus, Mopeia virus, Latino virus, Parana virus, Pichinde virus, Tacaribe virus, Tamiami virus |

In some embodiments, the virus is a non-enveloped virus, i.e., the virus does not have an envelope and is naked. Non-limiting examples of such viruses include viruses that are members of the parvovirus family, circovirus family, polyoma virus family, papillomavirus family, adenovirus family, iridovirus family, reovirus family, birnavirus family, calicivirus family, and picornavirus family. Examples of viruses that belong to these families include, but are not limited to, those set forth in Table 4.

In certain embodiments, the virus is a DNA virus. In other embodiments, the virus is a RNA virus. In one embodiment, the virus is a DNA or a RNA virus with a single-stranded genome. In another embodiment, the virus is a DNA or a RNA virus with a double-stranded genome.

In some embodiments, the virus has a linear genome. In other embodiments, the virus has a circular genome. In some embodiments, the virus has a segmented genome. In other embodiments, the virus has a non-segmented genome.

TABLE 4

Families of Non-Enveloped (Naked) Viruses

| Virus Family | Members |
|---|---|
| Parvovirus (Parvoviridae) | canine parvovirus, parvovirus B19 |
| Circovirus (Circoviridae) | porcine circovirus type 1 and 2, BFDV (Beak and Feather Disease Virus), chicken anaemia virus |
| Polyomavirus (Polyomaviridae) | simian virus 40 (SV40), JC virus, BK virus, Budgerigar fledgling disease virus |
| Papillomavirus (Papillomaviridae) | human papillomavirus, bovine papillomavirus (BPV) type 1 |
| Adenovirus (Adenoviridae) | human adenovirus (HAdV-A, HAdV-B, HAdV-C, HAdV-D, HAdV-E, and HAdV-F), fowl adenovirus A, ovine adenovirus D, frog adenovirus |
| Reovirus (Reoviridae) | human orbivirus, human coltivirus, mammalian orthoreovirus, bluetongue virus, rotavirus A, rotaviruses (groups B to G), Colorado tick fever virus, aquareovirus A, cypovirus 1, Fiji disease virus, rice dwarf virus, rice ragged stunt virus, idnoreovirus 1, mycoreovirus 1 |
| Birnavirus (Birnaviridae) | bursal disease virus, pancreatic necrosis virus |
| Calicivirus (Caliciviridae) | swine vesicular exanthema virus, rabbit hemorrhagic disease virus, Norwalk virus, Sapporo virus |
| Picornavirus (Picornaviridae) | human polioviruses (1-3), human coxsackieviruses A1-22, 24 (CA1-22 and CA24, CA23 = echovirus 9), human coxsackieviruses (B1-6 (CB1-6)), human echoviruses 1-7, 9, 11-27, 29-33, vilyuish virus, simian enteroviruses 1-18 (SEV1-18), porcine enteroviruses 1-11 (PEV1-11), bovine enteroviruses 1-2 (BEV1-2), hepatitis A virus, rhinoviruses, hepatoviruses, cardioviruses, aphthoviruses, echoviruses |

In some embodiments, the virus is a positive-stranded RNA virus. In other embodiments, the virus is a negative-stranded RNA virus. In one embodiment, the virus is a segmented, negative-stranded RNA virus. In another embodiment, the virus is a non-segmented negative-stranded RNA virus.

In some embodiments, the virus is an icosahedral virus. In other embodiments, the virus is a helical virus. In yet other embodiments, the virus is a complex virus.

In certain embodiments, the virus is a herpes virus, e.g., HSV-1, HSV-2, and CMV. In other embodiments, the virus is not a herpes virus (e.g., HSV-1, HSV-2, and CMV). In a specific embodiment, the virus is HSV. In an alternative embodiment, the virus is not HSV. In another embodiment, the virus is HCMV. In a further alternative embodiment, the virus is not HCMV. In another embodiment, the virus is a liver trophic virus. In an alternative embodiment, the virus is not a liver trophic virus. In another embodiment, the virus is a hepatitis virus. In an alternate embodiment, the virus is not a hepatitis virus. In another embodiment, the virus is a hepatitis C virus. In a further alternative embodiment, the virus is not a hepatitis C virus. In another specific embodiment, the virus is an influenza virus. In an alternative embodiment, the virus is not an influenza virus. In some embodiments, the virus is a retrovirus. In some embodiments, the virus is not a retrovirus. In some embodiments, the virus is HIV. In other embodiments, the virus is not HIV. In certain embodiments, the virus is a hepatitis B virus. In another alternative embodiment, the virus is not a hepatitis B virus. In a specific embodiment, the virus is EBV. In a specific alternative embodiment, the virus is not EBV. In some embodiments, the virus is Kaposi's sarcoma-associated herpes virus (KSHV). In some alternative embodiments, the virus is not KSHV. In certain embodiments the virus is a variola virus. In certain alternative embodiments, the virus is not variola virus. In one embodiment, the virus is a Dengue virus. In one alternative embodiment, the virus is not a Dengue virus. In other embodiments, the virus is a SARS virus. In other alternative embodiments, the virus is not a SARS virus. In a specific embodiment, the virus is an Ebola virus. In an alternative embodiment, the virus is not an Ebola virus. In some embodiments the virus is a Marburg virus. In an alternative embodiment, the virus is not a Marburg virus. In certain embodiments, the virus is a measles virus. In some alternative embodiments, the virus is not a measles virus. In particular embodiments, the virus is a vaccinia virus. In alternative embodiments, the virus is not a vaccinia virus. In some embodiments, the virus is varicella-zoster virus (VZV). In an alternative embodiment the virus is not VZV. In some embodiments, the virus is a picornavirus. In alternative embodiments, the virus is not a picornavirus. In certain embodiments the virus is not a rhinovirus. In certain embodiments, the virus is a poliovirus. In alternative embodiments, the virus is not a poliovirus. In some embodiments, the virus is an adenovirus. In alternative embodiments, the virus is not adenovirus. In particular embodiments, the virus is a coxsackievirus (e.g., coxsackievirus B3). In other embodiments, the virus is not a coxsackievirus (e.g., coxsackievirus B3). In some embodiments, the virus is a rhinovirus. In other embodiments, the virus is not a rhinovirus. In certain embodiments, the virus is a human papillomavirus (HPV). In other embodiments, the virus is not a human papillomavirus. In certain embodiments, the virus is a virus selected from the group consisting of the viruses listed in Tables 3 and 4. In other embodiments, the virus is not a virus selected from the group consisting of the viruses listed in Tables 3 and 4. In one embodiment, the virus is not one or more viruses selected from the group consisting of the viruses listed in Tables 3 and 4.

The antiviral activities of compounds against any type, subtype or strain of virus can be assessed. For example, the antiviral activity of compounds against naturally occurring strains, variants or mutants, mutagenized viruses, reassortants and/or genetically engineered viruses can be assessed.

The lethality of certain viruses, the safety issues concerning working with certain viruses and/or the difficulty in working with certain viruses may preclude (at least initially) the characterization of the antiviral activity of compounds on such viruses. Under such circumstances, other animal viruses that are representative of such viruses may be utilized. For example, SIV may be used initially to characterize the antiviral activity of compounds against HIV. Further, Pichinde virus may be used initially to characterize the antiviral activity of compounds against Lassa fever virus.

In some embodiments, the virus achieves peak titer in cell culture or a subject in 4 hours or less, 6 hours or less, 8 hours or less, 12 hours or less, 16 hours or less, or 24 hours or less. In other embodiments, the virus achieves peak titers in cell culture or a subject in 48 hours or less, 72 hours or less, or 1 week or less. In other embodiments, the virus achieves peak titers after about more than 1 week. In accordance with these embodiments, the viral titer may be measured in the infected tissue or serum.

In some embodiments, the virus achieves in cell culture a viral titer of $10^4$ pfu/ml or more, $5\times10^4$ pfu/ml or more, $10^5$ pfu/ml or more, $5\times10^5$ pfu/ml or more, $10^6$ pfu/ml or more, $5\times10^6$ pfu/ml or more, $10^7$ pfu/ml or more, $5\times10^7$ pfu/ml or more, $10^8$ pfu/ml or more, $5\times10^8$ pfu/ml or more, $10^9$ pfu/ml or more, $5\times10^9$ pfu/ml or more, or $10^{10}$ pfu/ml or more. In certain embodiments, the virus achieves in cell culture a viral titer of $10^4$ pfu/ml or more, $5\times10^4$ pfu/ml or more, $10^5$ pfu/ml or more, $5\times10^5$ pfu/ml or more, $10^6$ pfu/ml or more, $5\times10^6$ pfu/ml or more, $10^7$ pfu/ml or more, $5\times10^7$ pfu/ml or more, $10^8$ pfu/ml or more, $5\times10^8$ pfu/ml or more, $10^9$ pfu/ml or more, $5\times10^9$ pfu/ml or more, or $10^{10}$ pfu/ml or more within 4 hours, 6 hours, 8 hours, 12 hours, 16 hours, or 24 hours or less. In other embodiments, the virus achieves in cell culture a viral titer of $10^4$ pfu/ml or more, $5\times10^4$ pfu/ml or more, $10^5$ pfu/ml or more, $5\times10^5$ pfu/ml or more, $10^6$ pfu/ml or more, $5\times10^6$ pfu/ml or more, $10^7$ pfu/ml or more, $5\times10^7$ pfu/ml or more, $10^8$ pfu/ml or more, $5\times10^8$ pfu/ml or more, $10^9$ pfu/ml or more, $5\times10^9$ pfu/ml or more, or $10^{10}$ pfu/ml or more within 48 hours, 72 hours, or 1 week.

In some embodiments, the virus achieves a viral yield of 1 pfu/ml or more, 10 pfu/ml or more, $5\times10^1$ pfu/ml or more, $10^2$ pfu/ml or more, $5\times10^2$ pfu/ml or more, $10^3$ pfu/ml or more, $2.5\times10^3$ pfu/ml or more, $5\times10^3$ pfu/ml or more, $10^4$ pfu/ml or more, $2.5\times10^4$ pfu/ml or more, $5\times10^4$ pfu/ml or more, or $10^5$ pfu/ml or more in a subject. In certain embodiments, the virus achieves a viral yield of 1 pfu/ml or more, 10 pfu/ml or more, $5\times10^1$ pfu/ml or more, $10^2$ pfu/ml or more, $5\times10^2$ pfu/ml or more, $10^3$ pfu/ml or more, $2.5\times10^3$ pfu/ml or more, $5\times10^3$ pfu/ml or more, $10^4$ pfu/ml or more, $2.5\times10^4$ pfu/ml or more, $5\times10^4$ pfu/ml or more, or $10^5$ pfu/ml or more in a subject within 4 hours, 6 hours, 8 hours, 12 hours, 16 hours, 24 hours, or 48 hours. In certain embodiments, the virus achieves a viral yield of 1 pfu/ml or more, 10 pfu/ml or more, $10^1$ pfu/ml or more, $5\times10^1$ pfu/ml or more, $10^2$ pfu/ml or more, $5\times10^2$ pfu/ml or more, $10^3$ pfu/ml or more, $2.5\times10^3$ pfu/ml or more, $5\times10^3$ pfu/ml or more, $10^4$ pfu/ml or more, $2.5\times10^4$ pfu/ml or more, $5\times10^4$ pfu/ml or more, or $10^5$ pfu/ml or more in a subject within 48 hours, 72 hours, or 1 week. In accordance with these embodiments, the viral yield may be measured in the infected tissue or serum. In a specific embodiment, the subject is immunocompetent. In another embodiment, the subject is immunocompromised or immunosuppressed.

In some embodiments, the virus achieves a viral yield of 1 pfu or more, 10 pfu or more, $5\times10^1$ pfu or more, $10^2$ pfu or more, $5\times10^2$ pfu or more, $10^3$ pfu or more, $2.5\times10^3$ pfu or more, $5\times10^3$ pfu or more, $10^4$ pfu or more, $2.5\times10^4$ pfu or more, $5\times10^4$ pfu or more, or $10^5$ pfu or more in a subject. In certain embodiments, the virus achieves a viral yield of 1 pfu or more, 10 pfu or more, $5\times10^1$ pfu or more, $10^2$ pfu or more, $5\times10^2$ pfu or more, $10^3$ pfu or more, $2.5\times10^3$ pfu or more, $5\times10^3$ pfu or more, $10^4$ pfu or more, $2.5\times10^4$ pfu or more, $5\times10^4$ pfu or more, or $10^5$ pfu or more in a subject within 4 hours, 6 hours, 8 hours, 12 hours, 16 hours, 24 hours, or 48 hours. In certain embodiments, the virus achieves a viral yield of 1 pfu or more, 10 pfu or more, $10^1$ pfu or more, $5\times10^1$ pfu or more, $10^2$ pfu or more, $5\times10^2$ pfu or more, $10^3$ pfu or more, $2.5\times10^3$ pfu or more, $5\times10^3$ pfu or more, $10^4$ pfu or more, $2.5\times10^4$ pfu or more, $5\times10^4$ pfu or more, or $10^5$ pfu or more in a subject within 48 hours, 72 hours, or 1 week. In accordance with these embodiments, the viral yield may be measured in the infected tissue or serum. In a specific embodiment, the subject is immunocompetent. In another embodiment, the subject is immunocompromised or immunosuppressed.

In some embodiments, the virus achieves a viral yield of 1 infectious unit or more, 10 infectious units or more, $5\times10^1$ infectious units or more, $10^2$ infectious units or more, $5\times10^2$ infectious units or more, $10^3$ infectious units or more, $2.5\times10^3$ infectious units or more, $5\times10^3$ infectious units or more, $10^4$ infectious units or more, $2.5\times10^4$ infectious units or more, $5\times10^4$ infectious units or more, or $10^5$ infectious units or more in a subject. In certain embodiments, the virus achieves a viral yield of 1 infectious unit or more, 10 infectious units or more, $5\times10^1$ infectious units or more, $10^2$ infectious units or more, $5\times10^2$ infectious units or more, $10^3$ infectious units or more, $2.5\times10^3$ infectious units or more, $5\times10^3$ infectious units or more, $10^4$ infectious units or more, $2.5\times10^4$ infectious units or more, $5\times10^4$ infectious units or more, or $10^5$ infectious units or more in a subject within 4 hours, 6 hours, 8 hours, 12 hours, 16 hours, 24 hours, or 48 hours. In certain embodiments, the virus achieves a viral yield of 1 infectious unit or more, 10 infectious units or more, $10^1$ infectious units or more, $5\times10^1$ infectious units or more, $10^2$ infectious units or more, $5\times10^2$ infectious units or more, $10^3$ infectious units or more, $2.5\times10^3$ infectious units or more, $5\times10^3$ infectious units or more, $10^4$ infectious units or more, $2.5\times10^4$ infectious units or more, $5\times10^4$ infectious units or more, or $10^5$ infectious units or more in a subject within 48 hours, 72 hours, or 1 week. In accordance with these embodiments, the viral yield may be measured in the infected tissue or serum. In a specific embodiment, the subject is immunocompetent. In another embodiment, the subject is immunocompromised or immunosuppressed. In a specific embodiment, the virus achieves a yield of less than $10^4$ infectious units. In other embodiments the virus achieves a yield of $10^5$ or more infectious units.

In some embodiments, the virus achieves a viral titer of 1 infectious unit per ml or more, 10 infectious units per ml or more, $5\times10^1$ infectious units per ml or more, $10^2$ infectious units per ml or more, $5\times10^2$ infectious units per ml or more, $10^3$ infectious units per ml or more, $2.5\times10^3$ infectious units per ml or more, $5\times10^3$ infectious units per ml or more, $10^4$ infectious units per ml or more, $2.5\times10^4$ infectious units per ml or more, $5\times10^4$ infectious units per ml or more, or $10^5$ infectious units per ml or more in a subject. In certain embodiments, the virus achieves a viral titer of 10 infectious units per ml or more, $5\times10^1$ infectious units per ml or more, $10^2$ infectious units per ml or more, $5\times10^2$ infectious units per ml or more, $10^3$ infectious units per ml or more, $2.5\times10^3$ infectious units per ml or more, $5\times10^3$ infectious units per ml or more, $10^4$ infectious units per ml or more, $2.5\times10^4$ infectious units per ml or more, $5\times10^4$ infectious units per ml or more, or $10^5$ infectious units per ml or more in a subject within 4 hours, 6 hours, 8 hours, 12 hours, 16 hours, 24 hours, or 48 hours. In certain embodiments, the virus achieves a viral titer of 1 infectious unit per mL or more, 10 infectious units per ml or more, $5\times10^1$ infectious units per ml or more, $10^2$ infectious units per ml or more, $5\times10^2$ infectious units per ml or more, $10^3$ infectious units per mL or more, $2.5\times10^3$ infectious units per ml or more, $5\times10^3$ infectious units per ml or more, $10^4$ infectious units per ml or more, $2.5\times10^4$ infectious units per ml or more, $5\times10^4$ infectious units per ml or more, or $10^5$ infectious units per ml or more in a subject within 48 hours, 72 hours, or 1 week. In accordance with these embodiments, the viral titer may be measured in the infected tissue or serum. In a specific embodiment, the subject is immunocompetent. In another embodiment, the subject is immunocompromised or immunosuppressed. In a specific embodiment, the virus achieves a titer of less than $10^4$ infectious units per ml. In some embodiments, the virus achieves $10^5$ or more infectious units per ml.

In some embodiments, the virus infects a cell and produces, $10^1$ or more, $2.5\times10^1$ or more, $5\times10^1$ or more, $7.5\times10^1$ or more, $10^2$ or more, $2.5\times10^2$ or more, $5\times10^2$ or more, $7.5\times10^2$ or more, $10^3$ or more, $2.5\times10^3$ or more, $5\times10^3$ or more, $7.5\times10^3$ or more, $10^4$ or more, $2.5\times10^4$ or more, $5\times10^4$ or more, $7.5\times10^4$ or more, or $10^5$ or more viral particles per cell. In certain embodiments, the virus infects a cell and produces 10 or more, $10^1$ or more, $2.5\times10^1$ or more, $5\times10^1$ or more, $7.5\times10^1$ or more, $10^2$ or more, $2.5\times10^2$ or more, $5\times10^2$ or more, $7.5\times10^2$ or more, $10^3$ or more, $2.5\times10^3$ or more, $5\times10^3$ or more, $7.5\times10^3$ or more, $10^4$ or more, $2.5\times10^4$ or more, $5\times10^4$ or more, $7.5\times10^4$ or more, or $10^5$ or more viral particles per cell within 4 hours, 6 hours, 8 hours, 12 hours, 16 hours, or 24 hours. In other embodiments, the virus infects a cell and produces 10 or more, $10^1$ or more, $2.5\times10^1$ or more, $5\times10^1$ or more, $7.5\times10^1$ or more, $10^2$ or more, $2.5\times10^2$ or more, $5\times10^2$ or more, $7.5\times10^2$ or more, $10^3$ or more, $2.5\times10^3$ or more, $5\times10^3$ or more, $7.5\times10^3$ or more, $10^4$ or more, $2.5\times10^4$ or more, $5\times10^4$ or more, $7.5\times10^4$ or more, or $10^5$ or more viral particles per cell within 48 hours, 72 hours, or 1 week.

In other embodiments, the virus is latent for a period of about at least 1 day, 2 days, 3 days, 4 days, 5 days, 6 days, 7 days, 8 days, 9 days, 10 days, 11 days, 12 days, 13 days, 14 days, or 15 days. In another embodiment, the virus is latent for a period of about at least 1 week, or 2 weeks, 3 weeks, 4 weeks, 5 weeks, 6 weeks, 7 weeks, 8 weeks, 9 weeks, or weeks. In a further embodiment, the virus is latent for a period of about at least 1 month, 2 months, 3 months, 4 months, 5 months, 6 months, 7 months, 8 months, 9 months, 10 months, or 11 months. In yet another embodiment, the virus is latent for a period of about at least 1 year, 2 years, 3 years, 4 years, 5 years, 6 years, 7 years, 8 years, 9 years, 10 years, 11 years, 12 years, 13 years, 14 years, or 15 years. In some embodiments, the virus is latent for a period of greater than 15 years.

4.2 In Vitro Assays to Detect Antiviral Activity

The antiviral activity of compounds may be assessed in various in vitro assays described herein or others known to one of skill in the art. Non-limiting examples of the viruses that can be tested for compounds with antiviral activities against such viruses are provided in Section 4.1, supra. In specific embodiments, compounds exhibit an activity profile that is consistent with their ability to inhibit viral replication while maintaining low toxicity with respect to eukaryotic cells, preferably mammalian cells. For example, the effect of a compound on the replication of a virus may be determined by infecting cells with different dilutions of a virus in the presence or absence of various dilutions of a compound, and assessing the effect of the compound on, e.g., viral replication, viral genome replication, and/or the synthesis of viral proteins. Alternatively, the effect of a compound on the replication of a virus may be determined by contacting cells with various dilutions of a compound or a placebo, infecting the cells with different dilutions of a virus, and assessing the effect of the compound on, e.g., viral replication, viral genome replication, and/or the synthesis of viral proteins. Altered viral replication can be assessed by, e.g., plaque formation. The production of viral proteins can be assessed by, e.g., ELISA, Western blot, immunofluorescence, or flow cytometry analysis. The production of viral nucleic acids can be assessed by, e.g., RT-PCR, PCR, Northern blot analysis, or Southern blot.

In certain embodiments, compounds reduce the replication of a virus by approximately 10%, preferably 15%, 25%, 30%, 45%, 50%, 60%, 75%, 95% or more relative to a negative control (e.g., PBS, DMSO) in an assay described herein or others known to one of skill in the art. In some embodiments, compounds reduce the replication of a virus by about at least 1.5 fold, 2, fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 75 fold, 100 fold, 500 fold, or 1000 fold relative to a negative control (e.g., PBS, DMSO) in an assay described herein or others known to one of skill in the art. In other embodiments, compounds reduce the replication of a virus by about at least 1.5 to 3 fold, 2 to 4 fold, 3 to 5 fold, 4 to 8 fold, 6 to 9 fold, 8 to 10 fold, 2 to 10 fold, 5 to 20 fold, 10 to 40 fold, 10 to 50 fold, 25 to 50 fold, 50 to 100 fold, 75 to 100 fold, 100 to 500 fold, 500 to 1000 fold, or 10 to 1000 fold relative to a negative control (e.g., PBS, DMSO) in an assay described herein or others known to one of skill in the art. In other embodiments, compounds reduce the replication of a virus by about 1 log, 1.5 logs, 2 logs, 2.5 logs, 3 logs, 3.5 logs, 4 logs, 4.5 logs, 5 logs or more relative to a negative control (e.g., PBS, DMSO) in an assay described herein or others known to one of skill in the art. In accordance with these embodiments, such compounds may be further assessed for their safety and efficacy in assays such as those described in Section 4, infra.

In certain embodiments, compounds reduce the replication of a viral genome by approximately 10%, preferably 15%, 25%, 30%, 45%, 50%, 60%, 75%, 95% or more relative to a negative control (e.g., PBS, DMSO) in an assay described herein or others known to one of skill in the art. In some embodiments, compounds reduce the replication of a viral genome by about at least 1.5 fold, 2, fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 75 fold, 100 fold, 500 fold, or 1000 fold relative to a negative control (e.g., PBS, DMSO) in an assay described herein or others known to one of skill in the art. In other embodiments, compounds reduce the replication of a viral genome by about at least 1.5 to 3 fold, 2 to 4 fold, 3 to 5 fold, 4 to 8 fold, 6 to 9 fold, 8 to 10 fold, 2 to 10 fold, 5 to 20 fold, 10 to 40 fold, 10 to 50 fold, 25 to 50 fold, 50 to 100 fold, 75 to 100 fold, 100 to 500 fold, 500 to 1000 fold, or 10 to 1000 fold relative to a negative control (e.g., PBS, DMSO) in an assay described herein or others known to one of skill in the art. In other embodiments, compounds reduce the replication of a viral genome by about 1 log, 1.5 logs, 2 logs, 2.5 logs, 3 logs, 3.5 logs, 4 logs, 4.5 logs, 5 logs or more relative to a negative control (e.g., PBS, DMSO) in an assay described herein or others known to one of skill in the art. In accordance with these embodiments, such compounds may be further assessed for their safety and efficacy in assays such as those described in Section 4, infra.

In certain embodiments, compounds reduce the synthesis of viral proteins by approximately 10%, preferably 15%, 25%, 30%, 45%, 50%, 60%, 75%, 95% or more relative to a negative control (e.g., PBS, DMSO) in an assay described herein or others known to one of skill in the art. In some embodiments, compounds reduce the synthesis of viral proteins by approximately at least 1.5 fold, 2, fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 75 fold, 100 fold, 500 fold, or 1000 fold relative to a negative control (e.g., PBS, DMSO) in an assay described herein or others known to one of skill in the art. In other embodiments, compounds reduce the synthesis of viral proteins by approximately at least 1.5 to 3 fold, 2 to 4 fold, 3 to 5 fold, 4 to 8 fold, 6 to 9 fold, 8 to 10 fold, 2 to 10 fold, 5 to 20 fold, 10 to 40 fold, 10 to 50 fold, 25 to 50 fold, 50 to 100 fold, 75 to 100 fold, 100 to 500 fold, 500 to 1000 fold, or 10 to 1000 fold relative to a negative control (e.g., PBS, DMSO) in an assay described herein or others known to one of skill in the art. In other embodiments, compounds reduce the synthesis of viral proteins by approximately 1 log, 1.5 logs, 2 logs, 2.5 logs, 3 logs, 3.5 logs, 4 logs, 4.5 logs, 5 logs or more relative to a negative control (e.g., PBS, DMSO) in an assay described herein or others known to one of skill in the art. In accordance with these embodiments, such compounds may be further assessed for their safety and efficacy in assays such as those described in Section 4.3, infra.

In some embodiments, compounds result in about a 1.5 fold or more, 2 fold or more, 3 fold or more, 4 fold or more, 5 fold or more, 6 fold or more, 7 fold or more, 8 fold or more, 9 fold or more, 10 fold or more, 15 fold or more, 20 fold or more, 25 fold or more, 30 fold or more, 35 fold or more, 40 fold or more, 45 fold or more, 50 fold or more, 60 fold or more, 70 fold or more, 80 fold or more, 90 fold or more, or 100 fold or more inhibition/reduction of viral yield per round of viral replication. In certain embodiments, compounds result in about a 2 fold or more reduction inhibition/reduction of viral yield per round of viral replication. In specific embodiments, compounds result in about a 10 fold or more inhibition/reduction of viral yield per round of viral replication.

The in vitro antiviral assays can be conducted using any eukaryotic cell, including primary cells and established cell lines. The cell or cell lines selected should be susceptible to infection by a virus of interest. Non-limiting examples of mammalian cell lines that can be used in standard in vitro antiviral assays (e.g., viral cytopathic effect assays, neutral red update assays, viral yield assay, plaque reduction assays) for the respective viruses are set out in Table 5.

TABLE 5

Examples of Mammalian Cell Lines in Antiviral Assays

| Virus | Cell Line |
|---|---|
| herpes simplex virus (HSV) | primary fibroblasts (MRC-5 cells) Vero cells |

TABLE 5-continued

Examples of Mammalian Cell Lines in Antiviral Assays

| Virus | Cell Line |
| --- | --- |
| human cytomegalovirus (HCMV) | primary fibroblasts (MRC-5 cells) |
| Influenza | primary fibroblasts (MRC-5 cells) |
| | Madin Darby canine kidney (MDCK) |
| | primary chick embryo |
| | chick kidney |
| | calf kidney |
| | African green monkey kidney (Vero) cells |
| | mink lung |
| | human respiratory epithelia cells |
| hepatitis C virus | Huh7 (or Huh7.7) |
| | Huh7.5 |
| | primary human hepatocytes (PHH) |
| | immortalized human hepatocytes (IHH) |
| HIV-1 | MT-2 cells (T cells) |
| Dengue virus | Vero cells |
| Measles virus | African green monkey kidney (CV-1) cells |
| SARS virus | Vero 76 cells |
| Respiratory syncytial virus | African green monkey kidney (MA-104) cells |
| Venezuelan equine encephalitis virus | Vero cells |
| West Nile virus | Vero cells |
| yellow fever virus | Vero cells |
| HHV-6 | Cord Blood Lymphocytes (CBL) |
| | Human T cell lymphoblastoid cell lines (HSB-2 and SupT-1) |
| HHV-8 | B-cell lymphoma cell line (BCBL-1) |
| EBV | umbilical cord blood lymphocytes |

Sections 4.2.1 to 4.2.7 below provide non-limiting examples of antiviral assays that can be used to characterize the antiviral activity of compounds against the respective virus. One of skill in the art will know how to adapt the methods described in Sections 4.2.1 to 4.2.7 to other viruses by, e.g., changing the cell system and viral pathogen, such as described in Table 5.

4.2.1 Viral Cytopathic Effect (CPE) Assay

CPE is the morphological changes that cultured cells undergo upon being infected by most viruses. These morphological changes can be observed easily in unfixed, unstained cells by microscopy. Forms of CPE, which can vary depending on the virus, include, but are not limited to, rounding of the cells, appearance of inclusion bodies in the nucleus and/or cytoplasm of infected cells, and formation of syncytia, or polykaryocytes (large cytoplasmic masses that contain many nuclei). For adenovirus infection, crystalline arrays of adenovirus capsids accumulate in the nucleus to form an inclusion body.

The CPE assay can provide a measure of the antiviral effect of a compound. In a non-limiting example of such an assay, compounds are serially diluted (e.g. 1000, 500, 100, 50, 10, 1 µg/ml) and added to 3 wells containing a cell monolayer (preferably mammalian cells at 80-100% confluent) of a 96-well plate. Within 5 minutes, viruses are added and the plate sealed, incubated at 37° C. for the standard time period required to induce near-maximal viral CPE (e.g., approximately 48 to 120 hours, depending on the virus and multiplicity of infection). CPE is read microscopically after a known positive control drug is evaluated in parallel with compounds in each test. Non-limiting examples of positives controls are ribavirin for dengue, influenza, measles, respiratory syncytial, parainfluenza, Pichinde, Punta Toro and Venezuelan equine encephalitis viruses; cidofovir for adenovirus; pirodovir for rhinovirus; 6-azauridine for West Nile and yellow fever viruses; and alferon (interferon α-n3) for SARS virus. The data are expressed as 50% effective concentrations or approximated virus-inhibitory concentration, 50% end-point (EC50) and cell-inhibitory concentration, 50% end-point (IC50). General selectivity index ("SI") is calculated as the IC50 divided by the EC50. These values can be calculated using any method known in the art, e.g., the computer software program MacSynergy II by M. N. Prichard, K. R. Asaltine, and C. Shipman, Jr., University of Michigan, Ann Arbor, Mich.

In one embodiment, a compound has an SI of greater than 3, or 4, or 5, or 6, or 7, or 8, or 9, or 10, or 11, or 12, or 13, or 14, or 15, or 20, or 21, or 22, or 23, or 24, or 25, or 30, or 35, or 40, or 45, or 50, or 60, or 70, or 80, or 90, or 100, or 200, or 300, or 400, or 500, 1,000, or 10,000. In some embodiments, a compound has an SI of greater than 10. In a specific embodiment, compounds with an SI of greater than 10 are further assessed in other in vitro and in vivo assays described herein or others known in the art to characterize safety and efficacy.

4.2.2 Neutral Red (NR) Dye Uptake Assay

The NR Dye Uptake assay can be used to validate the CPE inhibition assay (See Section 4.2.1). In a non-limiting example of such an assay, the same 96-well microplates used for the CPE inhibition assay can be used. Neutral red is added to the medium, and cells not damaged by virus take up a greater amount of dye. The percentage of uptake indicating viable cells is read on a microplate autoreader at dual wavelengths of 405 and 540 nm, with the difference taken to eliminate background. (See McManus et al., Appl. Environment. Microbiol. 31:35-38, 1976). An EC50 is determined for samples with infected cells and contacted with compounds, and an IC50 is determined for samples with uninfected cells contacted with compounds.

4.2.3 Virus Yield Assay

Lysed cells and supernatants from infected cultures such as those in the CPE inhibition assay (See section 4.2.1) can be used to assay for virus yield (production of viral particles after the primary infection). In a non-limiting example, these supernatants are serial diluted and added onto monolayers of susceptible cells (e.g., Vero cells). Development of CPE in these cells is an indication of the presence of infectious viruses in the supernatant. The 90% effective concentration (EC90), the test compound concentration that inhibits virus yield by 1 $\log_{10}$, is determined from these data using known calculation methods in the art. In one embodiment, the EC90 of compound is at least 1.5 fold, 2 fold, 3 fold, 4 fold, 5 fold, 6 fold, 7 fold, 8 fold, 9 fold, 10 fold, 20 fold, 30 fold, 40 fold, or 50 fold less than the EC90 of the negative control sample.

4.2.4 Plaque Reduction Assay

In a non-limiting example of such an assay, the virus is diluted into various concentrations and added to each well containing a monolayer of the target mammalian cells in triplicate. The plates are then incubated for a period of time to achieve effective infection of the control sample (e.g., 1 hour with shaking every fifteen minutes). After the incubation period, an equal amount of 1% agarose is added to an equal volume of each compound dilution prepared in 2× concentration. In certain embodiments, final compound concentrations between 0.03 µg/ml to 100 µg/ml can be tested with a final agarose overlay concentration of 0.5%. The drug agarose mixture is applied to each well in 2 ml volume and the plates are incubated for three days, after which the cells are stained with a 1.5% solution of neutral red. At the end of the 4-6 hour incubation period, the neutral red solution is aspirated, and plaques counted using a stereomicroscope. Alternatively, a final agarose concentration of 0.4% can be used. In other embodiments, the plates are incubated for more than three days with additional overlays being applied on day four and on day 8 when appropriate. In another embodiment, the overlay medium is liquid rather than semi-solid.

4.2.5 Virus Titer Assay

In this non-limiting example, a monolayer of the target mammalian cell line is infected with different amounts (e.g., multiplicity of 3 plaque forming units (pfu) or 5 pfu) of virus (e.g., HCMV or HSV) and subsequently cultured in the presence or absence of various dilutions of compounds (e.g., 0.1 µg/ml, 1 µg/ml, 5 µg/ml, or 10 µg/ml). Infected cultures are harvested 48 hours or 72 hours post infection and titered by standard plaque assays known in the art on the appropriate target cell line (e.g., Vero cells, MRCS cells). In certain embodiments, culturing the infected cells in the presence of compounds reduces the yield of infectious virus by at least 1.5 fold, 2, fold, 3, fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 100 fold, 500 fold, or 1000 fold relative to culturing the infected cells in the absence of compounds. In a specific embodiment, culturing the infected cells in the presence of compounds reduces the PFU/ml by at least 10 fold relative to culturing the infected cells in the absence of compounds.

In certain embodiments, culturing the infected cells in the presence of compounds reduces the yield of infectious virus by at least 0.5 log 10, 1 log 10, 1.5 log 10, 2 log 10, 2.5 log 10, 3 log 10, 3.5 log 10, 4 log 10, 4.5 log 10, 5 log 10, 5.5 log 10, 6 log 10, 6.5 log 10, 7 log 10, 7.5 log 10, 8 log 10, 8.5 log 10, or 9 log 10 relative to culturing the infected cells in the absence of compounds. In a specific embodiment, culturing the infected cells in the presence of compounds reduces the yield of infectious virus by at least 1 log 10 or 2 log 10 relative to culturing the infected cells in the absence of compounds. In another specific embodiment, culturing the infected cells in the presence of compounds reduces the yield of infectious virus by at least 2 log 10 relative to culturing the infected cells in the absence of compounds.

4.2.6 Flow Cytometry Assay

Flow cytometry can be utilized to detect expression of virus antigens in infected target cells cultured in the presence or absence of compounds (See, e.g., McSharry et al., Clinical Microbiology Rev., 1994, 7:576-604). Non-limiting examples of viral antigens that can be detected on cell surfaces by flow cytometry include, but are not limited to gB, gC, gC, and gE of HSV; E protein of Japanese encephalitis; virus gp52 of mouse mammary tumor virus; gpI of varicella-zoster virus; gB of HCMV; gp160/120 of HIV; HA of influenza; gp110/60 of HHV-6; and H and F of measles virus. In other embodiments, intracellular viral antigens or viral nucleic acid can be detected by flow cytometry with techniques known in the art.

4.2.7 Genetically Engineered Cell Lines for Antiviral Assays

Various cell lines for use in antiviral assays can be genetically engineered to render them more suitable hosts for viral infection or viral replication and more convenient substrates for rapidly detecting virus-infected cells (See, e.g., Olivo, P. D., Clin. Microbiol. Rev., 1996, 9:321-334). In some aspects, these cell lines are available for testing the antiviral activity of compound on blocking any step of viral replication, such as, transcription, translation, pregenome encapsidation, reverse transcription, particle assembly and release. Nonlimiting examples of genetically engineered cells lines for use in antiviral assays with the respective virus are discussed below.

HepG2-2.2.15 is a stable cell line containing the hepatitis B virus (HBV) ayw strain genome that is useful in identifying and characterizing compounds blocking any step of viral replication, such as, transcription, translation, pregenome encapsidation, reverse transcription, particle assembly and release. In one aspect, compounds can be added to HepG2-2.2.15 culture to test whether compound will reduce the production of secreted HBV from cells utilizing real time quantitative PCR (TaqMan) assay to measure HBV DNA copies. Specifically, confluent cultures of HepG2-2.2.15 cells cultured on 96-well flat-bottomed tissue culture plates and are treated with various concentration of daily doses of compounds. HBV virion DNA in the culture medium can be assessed 24 hours after the last treatment by quantitative blot hybridization or real time quantitative PCR (TaqMan) assay. Uptake of neutral red dye (absorbance of internalized dye at 510 nM [A510]) can be used to determine the relative level of toxicity 24 hours following the last treatment. Values are presented as a percentage of the average A510 values for separate cultures of untreated cells maintained on the same plate. Intracellular HBV DNA replication intermediates can be assessed by quantitative Southern blot hybridization. Intracellular HBV particles can be isolated from the treated HepG2-2.2.15 cells and the pregenomic RNA examined by Southern blot analysis. ELISAs can be used to quantify the amounts of the HBV envelope protein, surface antigen (HBsAg), and secreted e-antigen (HBeAg) released from cultures. Lamivudine (3TC) can be used as a positive assay control. (See Korba & Gerin, Antivir. Res. 19:55-70, 1992).

In one aspect, the cell line Huh7 ET (luc-ubi-neo/ET), which contains a new HCV RNA replicon with a stable luciferase (LUC) reporter, can be used to assay compounds antiviral activity against hepatitis C viral replication (See Krieger, N., V. Lohmann, and R. Bartenschlager J. Virol., 2001, 75:4614-4624). The activity of the LUC reporter is directly proportional to HCV RNA levels and positive control antiviral compounds behave comparably using either LUC or RNA endpoints. Subconfluent cultures of Huh7 ET cells are plated onto 96-well plates, compounds are added to the appropriate wells the next day, and the samples as well as the positive (e.g., human interferon-alpha 2b) and negative control samples are processed 72 hr later when the cells are still subconfluent. The HCV RNA levels can also be assessed using quantitative PCR (TaqMan). In some embodiments, compounds reduce the LUC signal (or HCV RNA levels) by 20%, 35%, 30%, 35%, 40%, 45%, 50%, 55%, 60%, 65%, 70%, 75%, 80%, 90%, or 95% or more relative to the untreated sample controls. In a preferred embodiment, compounds reduce the LUC signal (or HCV RNA levels) by 50% or more relative to the untreated cell controls. Other relevant cell culture models to study HCV have been described, e.g., See Durantel et al., J. Hepatology, 2007, 46:1-5.

The antiviral effect of compound can be assayed against EBV by measuring the level of viral capsid antigen (VCA) production in Daudi cells using an ELISA assay. Various concentrations of compounds are tested (e.g., 50 mg/ml to 0.03 mg/ml), and the results obtained from untreated and compound treated cells are used to calculate an EC50 value. Selected compounds that have good activity against EBV VCA production without toxicity will be tested for their ability to inhibit EBV DNA synthesis.

For assays with HSV, the BHKICP6LacZ cell line, which was stably transformed with the *E. coli* lacZ gene under the transcriptional control of the HSV-1 UL39 promoter, can be used (See Stabell et al., 1992, Methods 38:195-204). Infected cells are detected using β-galactosidase assays known in the art, e.g., colorimetric assay.

Standard antiviral assays for influenza virus has been described, See, e.g., Sidwell et al., Antiviral Research, 2000, 48:1-16. These assays can also be adapted for use with other viruses.

4.2.8 Approach to Identifying and Measuring Metabolic Fluxes Regulated by Viral Infection and Anti-Viral Compounds Viruses can alter cellular metabolic activity through a variety of routes. These include affecting transcription, translation, and/or degradation of mRNAs and/or proteins, relocalization of mRNAs and/or proteins, covalent modification of proteins, and allosteric regulation of enzymes or other proteins; and alterations to the composition of protein-containing complexes that modify their activity. The net result of all of these changes is modulation of metabolic fluxes to meet the needs of the virus. Thus, metabolic flux changes represent the ultimate endpoint of the virus' efforts to modulate host cell metabolism. Accordingly, fluxes that are increased by the virus are especially likely to be critical to viral survival and replication and to represent valuable drug targets.

A novel approach has been developed to profile metabolic fluxes. It builds upon an approach to measuring nitrogen metabolic fluxes in *E. coli* developed by Rabinowitz and colleagues (Yuan et al., 2006, Nat. Chem. Biol. 2:529-530), which is incorporated herein by reference. The essence of this kinetic flux profiling (KFP) approach is as follows:

(1) Cells (either uninfected or infected with virus) are rapidly switched from unlabeled to isotope-labeled nutrient (or vice versa); for the present purposes, preferred nutrients include uniformly or partially $^{13}$C-labeled or $^{15}$N-labeled glucose, glutamine, glutamate, or related compounds including without limitation pyruvate, lactate, glycerol, acetate, aspartate, arginine, and urea. Labels can include all known isotopes of H, C, N, O, P, or S, including both stable and radioactive labels. Results are dependent on the interplay between the host cell type and the viral pathogen, including the viral load and time post infection.

(2) Metabolism is quenched at various time points following the isotope-switch (e.g., 0.2, 0.5, 1, 2, 5, 10, 20, 30 min and 1, 2, 4, 8, 12, 16, 24, 36, 48 h or a subset or variant thereof). One convenient means of metabolism quenching is addition of cold (e.g., dry-ice temperature) methanol, although other solvents and temperatures, including also boiling solvents, are possible.

(3) The metabolome, including its extent of isotope labeling, is quantified for each collected sample. One convenient means of such quantitation is extraction of metabolites from the cells followed by liquid chromatography-tandem mass spectrometry (LC-MS/MS) analysis of the extract. Appropriate extraction protocols and LC-MS/MS methods are known in the art. See the following citations, which are herein incorporated by reference (Bajad et al., 2006, J. Chromatogr. A 1125:76-88; Bolling and Fiehn, 2005, Plant Physiol. 139: 1995-2005; Coulier et al., 2006, Anal Chem. 78:6573-6582; Kimball and Rabinowitz, 2006, Anal Biochem. 358:273-280; Lu et al., 2006, J. Am. Soc. Mass Spectrom. 17:37-50; Lu et al., 2007, J Am Soc Mass Spectrom. 18:898-909; Luo et al., 2007, J. Chromatogr. A 1147:153-164; Maharjan and Ferenci, 2003, Anal Biochem 313:145-154; Milne et al., 2006, Methods 39:92-103; Munger et al., 2006, PLoS Pathog. 2:e132; Olsson et al., 2004, Anal Chem. 76:2453-2461; Rabinowitz and Kimball, 2007, Anal Chem. 79:6167-73; Schaub et al., 2006, Biotechnol. Prog. 22:1434-1442; van Winden et al., 2005, FEMS Yeast Research 5:559-568; Villas-Boas et al., 2005, Yeast 22:1155-1169; Wittmann et al., 2004, Anal Biochem. 327:135-139; Wu et al., 2005, Anal Biochem. 336:164-171; Yuan et al., 2006, Nat. Chem. Biol. 2:529-530).

(4) The resulting data is analyzed to determine the cellular metabolic fluxes.

The KFP data is analyzed based on the following principles, through whose application those skilled in the art of cellular metabolism can identify flux changes associated with viral infection by comparing results for infected versus uninfected samples:

(1) Metabolites closer to the added nutrient in the metabolic network will become labeled before their downstream products. Thus, the pattern of labeling provides insight into the route taken to forming a particular metabolite. For example, more rapid labeling of oxaloacetate than citrate upon switching cells from unlabeled to uniformly $^{13}$C-labeled glucose would imply formation of oxaloacetate via phosphoenolpyruvate carboxylase or phosphoenolpyruvate carboxykinase rather than via clockwise turning of the tricarboxylic acid cycle.

(2) The speed of labeling provides insight into the quantitative flux through different metabolic pathways, with fast labeling of a metabolite pool resulting from large flux through that pool and/or low absolute pool size of it. For the ideal case of a well-mixed system in which a nutrient is being directly converted into an intracellular metabolite, instantaneous switching of the nutrient input into isotope-labeled form, without other modulation of the system, results over time in disappearance of the unlabeled metabolite:

$$dX^U/dt = -f_X X^U/X^T \qquad \text{Eq. (A)}$$

where $X^T$ is the total pool of metabolite X; $X^U$ the unlabeled form; and $f_X$ is the sum of all fluxes consuming the metabolite. For $f_X$ and $X^T$ constant (i.e., the system at pseudo-steady-state prior to the isotope switch), $$X^U/X^T = \exp(-f_X t/X^T) \qquad \text{Eq. (B)}$$

and $$f_X = X^T k_X \qquad \text{Eq. (C)}$$

where $k_X$ is the apparent first-order rate constant for disappearance of the unlabeled metabolite. According to Eq. (C), the total flux through metabolite X can be determined based on two parameters that can be measured directly experimentally: the intracellular pool size of the metabolite and the rate of disappearance of the unlabeled form. While in practice isotope switching is not instantaneous and slightly more complex equations are required, the full differential equations can still often be solved analytically and typically involve only two free parameters, with one of these, $k_X$, directly yielding total metabolic flux as shown above (Yuan et al., 2006, Nat. Chem. Biol. 2:529-530).

In certain cases involving branched and cyclic pathways, however, the mathematics become more complex and use of more sophisticated computational algorithms to facilitate data analysis may be beneficial. The cellular metabolic network can be described by a system of differential equations describing changes in metabolite levels over time (including changes in isotopic labeling patterns). See the following citations, which are hereby incorporated by reference (Reed et al., 2003, Genome Biol. 4:R54; Sauer, 2006, Mol. Syst. Biol. 2:62; Stephanopoulos, 1999, Metab. Eng. 1:1-11; Szyperski et al., 1999, Metab. Eng. 1:189-197; Zupke et al., 1995). Such descriptions, wherein the form of the equations is parallel to Eq. (A) above, can be solved for fluxes $f_{x1}$, $f_{x2}$, etc. based on experimentally observed data describing metabolite concentrations and labeling kinetics ($X^T$ at pseudo-steady-state and $X^U/X^T$ as a function of time). One appropriate class of algorithm for obtaining such solutions is described in the following citations, which are hereby incorporated by reference (Feng and Rabitz, 2004, Biophys. J. 86:1270-1281; Feng et al., 2006, J. Phys. Chem. A. Mol. Spectrosc. Kinet. Environ. Gen. Theory 110:7755-7762).

In general, changes in fluxes induced by viral infections occur slowly relative to the turnover of metabolites. Accordingly, the steady-state assumption generally applies to virally perturbed metabolic networks over short to moderate timescales (e.g., for CMV, up to ~2 h; the exact length of time depends on the nature of the viral pathogen, with more aggressive pathogens generally associated with shorter time scales).

At steady-state, the flux through all steps of a linear metabolic pathway must be equal. Accordingly, if flux through one step of a pathway is markedly increased by viral infection, the flux through the other steps is likely also increased. A complication arises due to branching, however. While the effect of branching is small in the case that the side branches are associated with low relative flux, the possibility of branching (as well as non-steady-state conditions) points to the need for more experimental data than just one measured pathway flux to implicate other pathway steps as viable drug targets. If increased flux is experimentally demonstrated at both steps upstream and downstream of an unmeasured step of the pathway, however, then one can have greatly increased confidence that the flux at the (unmeasured) intermediate step is also increased. Accordingly, herein we consider demonstration of increased flux at both the upstream and downstream steps (but, in selected embodiments, neither individually) to be adequate to validate the intermediate flux (and associated catalyzing enzyme) as a valid antiviral drug target.

4.3 Characterization of Safety and Efficacy of Compounds

The safety and efficacy of compounds can be assessed using technologies known to one of skill in the art. Sections 4.4 and 4.5 below provide non-limiting examples of cytotoxicity assays and animal model assays, respectively, to characterize the safety and efficacy of compounds. In certain embodiments, the cytotoxicity assays described in Section 4.4 are conducted following the in vitro antiviral assays described in Section 4, supra. In other embodiments, the cytotoxicity assays described in Section 4.4 are conducted before or concurrently with the in vitro antiviral assays described in Section 4, supra.

In some embodiments, compounds differentially affect the viability of uninfected cells and cells infected with virus. The differential effect of a compound on the viability of virally infected and uninfected cells may be assessed using techniques such as those described in Section 4.4, infra, or other techniques known to one of skill in the art. In certain embodiments, compounds are more toxic to cells infected with a virus than uninfected cells. In specific embodiments, compounds preferentially affect the viability of cells infected with a virus. Without being bound by any particular concept, the differential effect of a compound on the viability of uninfected and virally infected cells may be the result of the compound targeting a particular enzyme or protein that is differentially expressed or regulated or that has differential activities in uninfected and virally infected cells. For example, viral infection and/or viral replication in an infected host cells may alter the expression, regulation, and/or activities of enzymes and/or proteins. Accordingly, in some embodiments, other compounds that target the same enzyme, protein or metabolic pathway are examined for antiviral activity. In other embodiments, congeners of compounds that differentially affect the viability of cells infected with virus are designed and examined for antiviral activity. Non-limiting examples of antiviral assays that can be used to assess the antiviral activity of compound are provided in Section 4, supra.

4.4 Cytotoxicity Studies

In a preferred embodiment, the cells are animal cells, including primary cells and cell lines. In some embodiments, the cells are human cells. In certain embodiments, cytotoxicity is assessed in one or more of the following cell lines: U937, a human monocyte cell line; primary peripheral blood mononuclear cells (PBMC); Huh7, a human hepatoblastoma cell line; 293T, a human embryonic kidney cell line; and THP-1, monocytic cells. Other non-limiting examples of cell lines that can be used to test the cytotoxicity of compounds are provided in Table 5.

Many assays well-known in the art can be used to assess viability of cells (infected or uninfected) or cell lines following exposure to a compound and, thus, determine the cytotoxicity of the compound. For example, cell proliferation can be assayed by measuring Bromodeoxyuridine (BrdU) incorporation (See, e.g., Hoshino et al., 1986, Int. J. Cancer 38, 369; Campana et al., 1988, J. Immunol. Meth. 107:79), (3H) thymidine incorporation (See, e.g., Chen, J., 1996, Oncogene 13:1395-403; Jeoung, J., 1995, J. Biol. Chem. 270:18367 73), by direct cell count, or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription. Cell viability can be assessed by using trypan-blue staining or other cell death or viability markers known in the art. In a specific embodiment, the level of cellular ATP is measured to determined cell viability.

In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes may include enlargement, granularity, cells with ragged edges, a filmy appearance, rounding, detachment from the surface of the well, or other changes. These changes are given a designation of T (100% toxic), PVH (partially toxic—very heavy—80%), PH (partially toxic—heavy—60%), P (partially toxic—40%), Ps (partially toxic—slight—20%), or 0 (no toxicity—0%), conforming to the degree of cytotoxicity seen. A 50% cell inhibitory (cytotoxic) concentration (IC50) is determined by regression analysis of these data.

Compounds can be tested for in vivo toxicity in animal models. For example, animal models, described herein and/or others known in the art, used to test the antiviral activities of compounds can also be used to determine the in vivo toxicity of these compounds. For example, animals are administered a range of concentrations of compounds. Subsequently, the animals are monitored over time for lethality, weight loss or failure to gain weight, and/or levels of serum markers that may be indicative of tissue damage (e.g., creatine phosphokinase level as an indicator of general tissue damage, level of glutamic oxalic acid transaminase or pyruvic acid transaminase as indicators for possible liver damage). These in vivo assays may also be adapted to test the toxicity of various administration mode and/or regimen in addition to dosages.

The toxicity and/or efficacy of a compound in accordance with the invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. A compound identified in accordance with the invention that exhibits large therapeutic indices is preferred. While a compound identified in accordance with the invention that exhibits toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of a compound identified in accordance with the invention for use in humans. The dosage of such agents lies preferably within a range of circulating concentrations that include the ED50 with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high-performance liquid chromatography. Additional information concerning dosage determination is provided in Section 6.4, infra.

4.5 Animal Models

Compounds and compositions are preferably assayed in vivo for the desired therapeutic or prophylactic activity prior to use in humans. For example, in vivo assays can be used to determine whether it is preferable to administer a compound and/or another therapeutic agent. For example, to assess the use of a compound to prevent a viral infection, the compound can be administered before the animal is infected with the virus. In another embodiment, a compound can be administered to the animal at the same time that the animal is infected with the virus. To assess the use of a compound to treat or manage a viral infection, in one embodiment, the compound is administered after a viral infection in the animal. In another embodiment, a compound is administered to the animal at the same time that the animal is infected with the virus to treat and/or manage the viral infection. In a specific embodiment, the compound is administered to the animal more than one time.

Compounds can be tested for antiviral activity against virus in animal models systems including, but are not limited to, rats, mice, chicken, cows, monkeys, pigs, goats, sheep, dogs, rabbits, guinea pigs, etc. In a specific embodiment of the invention, compounds are tested in a mouse model system. Such model systems are widely used and well-known to the skilled artisan.

Animals are infected with virus and concurrently or subsequently treated with a compound or placebo. Samples obtained from these animals (e.g., serum, urine, sputum, semen, saliva, plasma, or tissue sample) can be tested for viral replication via well known methods in the art, e.g., those that measure altered viral replication (as determined, e.g., by plaque formation) or the production of viral proteins (as determined, e.g., by Western blot, ELISA, or flow cytometry analysis) or viral nucleic acids (as determined, e.g., by RT-PCR, northern blot analysis or southern blot). For quantitation of virus in tissue samples, tissue samples are homogenized in phosphate-buffered saline (PBS), and dilutions of clarified homogenates are adsorbed for 1 hour at 37° C. onto monolayers of cells (e.g., Vero, CEF or MDCK cells). In other assays, histopathologic evaluations are performed after infection, preferably evaluations of the organ(s) the virus is known to target for infection. Virus immunohistochemistry can be performed using a viral-specific monoclonal antibody. Non-limiting exemplary animal models described below (Sections 4.5.1-4.5.5) can be adapted for other viral systems.

The effect of a compound on the virulence of a virus can also be determined using in vivo assays in which the titer of the virus in an infected subject administered a compound, the length of survival of an infected subject administered a compound, the immune response in an infected subject administered a compound, the number, duration and/or severity of the symptoms in an infected subject administered a compound, and/or the time period before onset of one or more symptoms in an infected subject administered a compound is assessed. Techniques known to one of skill in the art can be used to measure such effects.

4.5.1 Herpes Simplex Virus (HSV)

Mouse models of herpes simplex virus type 1 or type 2 (HSV-1 or HSV-2) can be employed to assess the antiviral activity of compounds in vivo. BALB/c mice are commonly used, but other suitable mouse strains that are susceptible can also be used. Mice are inoculated by various routes with an appropriate multiplicity of infection of HSV (e.g., $10^5$ pfu of HSV-1 strain E-377 or $4 \times 10^4$ pfu of HSV-2 strain MS) followed by administration of compounds and placebo. For i.p. inoculation, HSV-1 replicates in the gut, liver, and spleen and spreads to the CNS. For i.n. inoculation, HSV-1 replicates in the nasopharynx and spreads to the CNS. Any appropriate route of administration (e.g., oral, topical, systemic, nasal), frequency and dose of administration can be tested to determine the optimal dosages and treatment regimens using compounds, optionally in combination with other therapies.

In a mouse model of HSV-2 genital disease, intravaginal inoculation of female Swiss Webster mice with HSV-1 or HSV-2 is carried out, and vaginal swabs are obtained to evaluate the effect of therapy on viral replication (See, e.g., Crute et al., Nature Medicine, 2002, 8:386-391). For example, viral titers by plaque assays are determined from the vaginal swabs. A mouse model of HSV-1 using SKH-1 mice, a strain of immunocompetent hairless mice, to study cutaneous lesions is also described in the art (See, e.g., Crute et al., Nature Medicine, 2002, 8:386-391 and Bolger et al., Antiviral Res., 1997, 35:157-165). Guinea pig models of HSV have also been described, See, e.g., Chen et al., Virol. J, 2004 Nov. 23, 1:11. Statistical analysis is carried out to calculate significance (e.g., a P value of 0.05 or less).

4.5.2 HCMV

Since HCMV does not generally infect laboratory animals, mouse models of infection with murine CMV (MCMV) can be used to assay antiviral activity compounds in vivo. For example, a MCMV mouse model with BALB/c mice can be used to assay the antiviral activities of compounds in vivo when administered to infected mice (See, e.g., Kern et al., Antimicrob. Agents Chemother., 2004, 48:4745-4753). Tissue homogenates isolated from infected mice treated or untreated with compounds are tested using standard plaque assays with mouse embryonic fibroblasts (MEFs). Statistical analysis is then carried out to calculate significance (e.g., a P value of 0.05 or less).

Alternatively, human tissue (i.e., retinal tissue or fetal thymus and liver tissue) is implanted into SCID mice, and the mice are subsequently infected with HCMV, preferably at the site of the tissue graft (See, e.g., Kern et al., Antimicrob. Agents Chemother., 2004, 48:4745-4753). The pfu of HCMV used for inoculation can vary depending on the experiment and virus strain. Any appropriate routes of administration (e.g., oral, topical, systemic, nasal), frequency and dose of administration can be tested to determine the optimal dosages and treatment regimens using compounds, optionally in combination with other therapies. Implant tissue homogenates isolated from infected mice treated or untreated with compounds at various time points are tested using standard plaque assays with human foreskin fibroblasts (HFFs). Statistical analysis is then carried out to calculate significance (i.e., a P value of 0.05 or less).

Guinea pig models of CMV to study antiviral agents have also been described, See, e.g., Bourne et al., Antiviral Res., 2000, 47:103-109; Bravo et al., Antiviral Res., 2003, 60:41-49; and Bravo et al, J. Infectious Diseases, 2006, 193:591-597.

4.5.3 Influenza

Animal models, such as ferret, mouse and chicken, developed for use to test antiviral agents against influenza virus have been described, See, e.g., Sidwell et al., Antiviral Res., 2000, 48:1-16; and McCauley et al., Antiviral Res., 1995, 27:179-186. For mouse models of influenza, non-limiting examples of parameters that can be used to assay antiviral activity of compounds administered to the influenza-infected mice include pneumonia-associated death, serum $\alpha$1-acid glycoprotein increase, animal weight, lung virus assayed by hemagglutinin, lung virus assayed by plaque assays, and histopathological change in the lung. Statistical analysis is carried out to calculate significance (e.g., a P value of 0.05 or less).

Nasal turbinates and trachea may be examined for epithelial changes and subepithelial inflammation. The lungs may be examined for bronchiolar epithelial changes and peribronchiolar inflammation in large, medium, and small or terminal bronchioles. The alveoli are also evaluated for inflammatory changes. The medium bronchioles are graded on a scale of 0 to 3+ as follows: 0 (normal: lined by medium to tall columnar epithelial cells with ciliated apical borders and basal pseudostratified nuclei; minimal inflammation); 1+ (epithelial layer columnar and even in outline with only slightly increased proliferation; cilia still visible on many cells); 2+ (prominent changes in the epithelial layer ranging from attenuation to marked proliferation; cells disorganized and layer outline irregular at the luminal border); 3+ (epithelial layer markedly disrupted and disorganized with necrotic cells visible in the lumen; some bronchioles attenuated and others in marked reactive proliferation).

The trachea is graded on a scale of 0 to 2.5+ as follows: 0 (normal: Lined by medium to tall columnar epithelial cells with ciliated apical border, nuclei basal and pseudostratified. Cytoplasm evident between apical border and nucleus. Occasional small focus with squamous cells); 1+ (focal squamous metaplasia of the epithelial layer); 2+ (diffuse squamous metaplasia of much of the epithelial layer, cilia may be evident focally); 2.5+ (diffuse squamous metaplasia with very few cilia evident).

Virus immunohistochemistry is performed using a viral-specific monoclonal antibody (e.g. NP-, N- or HN-specific monoclonal antibodies). Staining is graded 0 to 3+ as follows: 0 (no infected cells); 0.5+ (few infected cells); 1+ (few infected cells, as widely separated individual cells); 1.5+ (few infected cells, as widely separated singles and in small clusters); 2+ (moderate numbers of infected cells, usually affecting clusters of adjacent cells in portions of the epithelial layer lining bronchioles, or in small sublobular foci in alveoli); 3+ (numerous infected cells, affecting most of the epithelial layer in bronchioles, or widespread in large sublobular foci in alveoli).

4.5.4 Hepatitis

A HBV transgenic mouse model, lineage 1.3.46 (official designation, Tg[HBV 1.3 genome] Chi46) has been described previously and can be used to test the in vivo antiviral activities of compounds as well as the dosing and administration regimen (See, e.g., Cavanaugh et al., J. Virol., 1997, 71:3236-3243; and Guidotti et al., J. Virol., 1995, 69:6158-6169). In these HBV transgenic mice, a high level of viral replication occurs in liver parenchymal cells and in the proximal convoluted tubules in the kidneys of these transgenic mice at levels comparable to those observed in the infected liver of patients with chronic HBV hepatitis. HBV transgenic mice that have been matched for age (i.e., 6-10 weeks), sex (i.e., male), and levels of hepatitis B surface antigen (HBsAg) in serum can be treated with compounds or placebo followed by antiviral activity analysis to assess the antiviral activity of compounds. Non-limiting examples of assays that can be performed on these mice treated and untreated with compounds include Southern analysis to measure HBV DNA in the liver, quantitative reverse transcriptase PCR (qRT-PCR) to measure HBV RNA in liver, immunoassays to measure hepatitis e antigen (HBeAg) and HBV surface antigen (HBsAg) in the serum, immunohistochemistry to measure HBV antigens in the liver, and quantitative PCR (qPCR) to measure serum HBV DNA. Gross and microscopic pathological examinations can be performed as needed.

Various hepatitis C virus (HCV) mouse models described in the art can be used in assessing the antiviral activities of compounds against HCV infection (See Zhu et al., Antimicrobial Agents and Chemother., 2006, 50:3260-3268; Bright et al., Nature, 2005, 436:973-978; Hsu et al., Nat. Biotechnol., 2003, 21:519-525; Ilan et al., J. Infect. Dis. 2002, 185: 153-161; Kneteman et al., Hepatology, 2006, 43:1346-1353; Mercer et al., Nat. Med., 2001, 7:927-933; and Wu et al., Gastroenterology, 2005, 128:1416-1423). For example, mice with chimeric human livers are generated by transplanting normal human hepatocytes into SCID mice carrying a plasminogen activator transgene (Alb-uPA) (See Mercer et al., Nat. Med., 2001, 7:927-933). These mice can develop prolonged HCV infections with high viral titers after inoculation with HCV (e.g., from infected human serum). Thus, these mice can be administered a compound or placebo prior to, concurrently with, or subsequent to HCV infection, and replication of the virus can be confirmed by detection of negative-strand viral RNA in transplanted livers or expression of HCV viral proteins in the transplanted hepatocyte nodules. The statistical significance of the reductions in the viral replication levels are determined.

Another example of a mouse model of HCV involves implantation of the HuH7 cell line expressing a luciferase reporter linked to the HCV subgenome into SCID mice, subcutaneously or directly into the liver (See Zhu et al., Antimicrobial Agents and Chemother., 2006, 50:3260-3268). The mice are treated with a compound or placebo, and whole-body imaging is used to detect and quantify bioluminescence signal intensity. Mice treated with a compound that is effective against HCV have less bioluminescence signal intensity relative to mice treated with placebo or a negative control.

4.5.5 HIV

The safety and efficacy of compounds against HIV can be assessed in vivo with established animal models well known in the art. For example, a Trimera mouse model of HIV-1 infection has been developed by reconstituting irradiated normal BALB/c mice with murine SCID bone marrow and engrafted human peripheral blood mononuclear cells (See Ayash-Rashkovsky et al., FASEB J., 2005, 19:1149-1151). These mice are injected intraperitoneally with T- and M-tropic HIV-1 laboratory strains. After HIV infection, rapid loss of human $CD4^+$ T cells, decrease in CD4/CD8 ratio, and increased T cell activation can be observed. A compound can be administered to these mice and standard assays known in the art can be used to determine the viral replication capacity in animals treated or untreated with a compound. Non-limiting examples of such assays include the COBAS AMPLICOR® RT-PCR assay (Roche Diagnostics, Branchberg, N.J.) to determine plasma viral load (HIV-1 RNA copies/ml); active HIV-1 virus replication assay where human lymphocytes recovered from infected Trimera mice were cocultured with target T cells (MT-2 cells) and HIV-dependent syncytia formation was examined; and human lymphocytes recovered from infected Trimera mice were cocultured with cMAGI indicator cells, where HIV-1 LTR driven trans-activation of β-galactosidase was measured. Levels of anti-HIV-1 antibodies produced in these mice can also be measured by ELISA. Other established mouse models described in the art can also be used to test the antiviral activity of compounds in vivo (See, Mosier et al., Semin. Immunol., 1996, 8:255-262; Mosier et al., Hosp. Pract. (Off Ed)., 1996, 31:41-48, 53-55, 59-60; Bonyhadi et al., Mol. Med. Today, 1997, 3:246-253; Jolicoeur et al., Leukemia, 1999, 13:S78-S80; Browning et al., Proc. Natl. Acad. Sci. USA, 1997, 94:14637-14641; and Sawada et al., J. Exp. Med., 1998, 187:1439-1449). A simian immunodeficiency virus (SIV) nonhuman primate model has also been described (See Schito et al., Curr. HIV Res., 2006, 4:379-386).

5. Pharmaceutical Compositions

Any compound described or incorporated by referenced herein may optionally be in the form of a composition comprising the compound.

In certain embodiments provided herein, compositions (including pharmaceutical compositions) comprise a compound and a pharmaceutically acceptable carrier, excipient, or diluent.

In other embodiments, provided herein are pharmaceutical compositions comprising an effective amount of a compound and a pharmaceutically acceptable carrier, excipient, or diluent. The pharmaceutical compositions are suitable for veterinary and/or human administration.

The pharmaceutical compositions provided herein can be in any form that allows for the composition to be administered to a subject, said subject preferably being an animal, including, but not limited to a human, mammal, or non-human animal, such as a cow, horse, sheep, pig, fowl, cat, dog, mouse, rat, rabbit, guinea pig, etc., and is more preferably a mammal, and most preferably a human.

In a specific embodiment and in this context, the term "pharmaceutically acceptable carrier, excipient or diluent" means a carrier, excipient or diluent approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E.W. Martin.

Typical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents.

Lactose free compositions can comprise excipients that are well known in the art and are listed, for example, in the U.S. Pharmacopeia (USP)SP(XXI)/NF (XVI). In general, lactose free compositions comprise an active ingredient, a binder/filler, and a lubricant in pharmaceutically compatible and pharmaceutically acceptable amounts. Preferred lactose free dosage forms comprise a compound, microcrystalline cellulose, pre gelatinized starch, and magnesium stearate.

Further provided herein are anhydrous pharmaceutical compositions and dosage forms comprising one or more compounds, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, NY, N.Y., 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous compositions and dosage forms provided herein can be prepared using anhydrous or low moisture containing ingredients and low moisture or low humidity conditions. Compositions and dosage forms that comprise lactose and at least one compound that comprises a primary or secondary amine are preferably anhydrous if substantial contact with moisture and/or humidity during manufacturing, packaging, and/or storage is expected.

An anhydrous composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Further provided herein are compositions and dosage forms that comprise one or more agents that reduce the rate by which a compound will decompose. Such agents, which are referred to herein as "stabilizers," include, but are not limited to, antioxidants such as ascorbic acid, pH buffers, or salt buffers.

The compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a compound preferably in purified form, together with a suitable amount of carrier so as to provide the form for proper administration to the patient. The formulation should suit the mode of administration. In a preferred embodiment, the compositions or single unit dosage forms are sterile and in suitable form for administration to a subject, preferably an animal subject, more preferably a mammalian subject, and most preferably a human subject.

Compositions provided herein are formulated to be compatible with the intended route of administration. Examples of routes of administration include, but are not limited to, parenteral, e.g., intravenous, intradermal, subcutaneous, oral (e.g., inhalation), intranasal, transdermal (topical), transmucosal, intra-synovial, ophthalmic, and rectal administration. In a specific embodiment, the composition is formulated in accordance with routine procedures as a composition adapted for intravenous, subcutaneous, intramuscular, oral, intranasal, ophthalmic, or topical administration to human beings. In a preferred embodiment, a composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non aqueous liquid suspensions, oil in water emulsions, or a water in oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use.

Generally, the ingredients of compositions provided herein are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Pharmaceutical compositions provided herein that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Typical oral dosage forms provided herein are prepared by combining a compound in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions provided herein is typically present in from about 50 to about 99 weight percent of the pharmaceutical composition or dosage form.

Suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC 581. Suitable anhydrous or low moisture excipients or additives include AVICEL PH 103™ and Starch 1500 LM.

Disintegrants are used in the compositions provided herein to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms provided herein. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms provided herein include, but are not limited to, agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB 0 SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A compound can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased patient compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or agents.

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms provided herein are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non aqueous vehicles such as, but not limited to, corn oil, cottonseed oil, peanut oil, sesame oil, ethyl oleate, isopropyl myristate, and benzyl benzoate.

Agents that increase the solubility of one or more of the compounds provided herein can also be incorporated into the parenteral dosage forms provided herein.

Transdermal, topical, and mucosal dosage forms provided herein include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, 16th and 18th eds., Mack Publishing, Easton Pa. (1980 &

1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms provided herein are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are non toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16th and 18th eds., Mack Publishing, Easton Pa. (1980 & 1990).

Depending on the specific tissue to be treated, additional components may be used prior to, in conjunction with, or subsequent to treatment with a compound. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more compounds. Similarly, the polarity of a solvent carrier, its ionic strength, or tonicity can be adjusted to improve delivery. Agents such as stearates can also be added to pharmaceutical compositions or dosage forms to advantageously alter the hydrophilicity or lipophilicity of one or more compounds so as to improve delivery. In this regard, stearates can serve as a lipid vehicle for the formulation, as an emulsifying agent or surfactant, and as a delivery enhancing or penetration enhancing agent. Different salts, hydrates or solvates of the compounds can be used to further adjust the properties of the resulting composition.

In certain specific embodiments, the compositions are in oral, injectable, or transdermal dosage forms. In one specific embodiment, the compositions are in oral dosage forms. In another specific embodiment, the compositions are in the form of injectable dosage forms. In another specific embodiment, the compositions are in the form of transdermal dosage forms.

6. Prophylactic and Therapeutic Methods

The present invention provides methods of preventing, treating and/or managing a viral infection, said methods comprising administering to a subject in need thereof one or more compounds. In a specific embodiment, the invention provides a method of preventing, treating and/or managing a viral infection, said method comprising administering to a subject in need thereof a dose of a prophylactically or therapeutically effective amount of one or more compounds or a composition comprising a compound. A compound or a composition comprising a compound may be used as any line of therapy (e.g., a first, second, third, fourth or fifth line therapy) for a viral infection.

In another embodiment, the invention relates to a method for reversing or redirecting metabolic flux altered by viral infection in a human subject by administering to a human subject in need thereof, an effective amount of one or more compounds or a composition comprising one or more compounds. For example, viral infection can be treated using combinations of the enzyme inhibition compounds that produce beneficial results, e.g., synergistic effect; reduction of side effects; a higher therapeutic index. In one such embodiment, a citrate lyase inhibitor can be used in combination with an Acetyl-CoA Carboxylase (ACC).

In specific embodiments, a compound is the only active ingredient administered to prevent, treat, manage or ameliorate said viral infection. In a certain embodiment, a composition comprising a compound is the only active ingredient.

The choice of compounds to be used depends on a number of factors, including but not limited to the type of viral infection, health and age of the patient, and toxicity or side effects. For example, treatments that inhibit enzymes required for core ATP production, such as proton ATPase are not preferred unless given in a regimen that compensates for the toxicity; e.g., using a localized delivery system that limits systemic distribution of the drug.

The present invention encompasses methods for preventing, treating, and/or managing a viral infection for which no antiviral therapy is available. The present invention also encompasses methods for preventing, treating, and/or managing a viral infection as an alternative to other conventional therapies.

The present invention also provides methods of preventing, treating and/or managing a viral infection, said methods comprising administering to a subject in need thereof one or more of the compounds and one or more other therapies (e.g., prophylactic or therapeutic agents). In a specific embodiment, the other therapies are currently being used, have been used or are known to be useful in the prevention, treatment and/or management of a viral infection. Non-limiting examples of such therapies are provided in Section 6, infra. In a specific embodiment, one or more compounds are administered to a subject in combination with one or more of the therapies described in Section 6, infra. In another embodiment, one or more compounds are administered to a subject in combination with a supportive therapy, a pain relief therapy, or other therapy that does not have antiviral activity.

The combination therapies of the invention can be administered sequentially or concurrently. In one embodiment, the combination therapies of the invention comprise a compound and at least one other therapy which has the same mechanism of action. In another embodiment, the combination therapies of the invention comprise a compound and at least one other therapy which has a different mechanism of action than the compound.

In a specific embodiment, the combination therapies of the present invention improve the prophylactic and/or therapeutic effect of a compound by functioning together with the compound to have an additive or synergistic effect. In another embodiment, the combination therapies of the present invention reduce the side effects associated with each therapy taken alone.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

6.1 Patient Population

According to the invention, compounds, compositions comprising a compound, or a combination therapy is administered to a subject suffering from a viral infection. In other embodiments, compounds, compositions comprising a compound, or a combination therapy is administered to a subject predisposed or susceptible to a viral infection. In some embodiments, compounds, compositions comprising a compound, or a combination therapy is administered to a subject that lives in a region where there has been or might be an outbreak with a viral infection. In some embodiments, the viral infection is a latent viral infection. In one embodiment, a compound or a combination therapy is administered to a human infant. In one embodiment, a compound or a combination therapy is administered to a premature human infant. In other embodiments, the viral infection is an active infection. In yet other embodiments, the viral infection is a chronic viral infection. Non-limiting examples of types of virus infections include infections caused by those provided in Section 4.1, supra.

In a specific embodiment, the viral infection is an enveloped virus infection. In some embodiments, the enveloped virus is a DNA virus. In other embodiments, the enveloped virus is a RNA virus. In some embodiments, the enveloped virus has a double stranded DNA or RNA genome. In other embodiments, the enveloped virus has a single-stranded DNA or RNA genome. In a specific embodiment, the virus infects humans.

In certain embodiments, a compound, a composition comprising a compound, or a combination therapy is administered to a mammal which is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In certain embodiments, a compound, a composition comprising a compound, or a combination therapy is administered to a human at risk for a virus infection. In certain embodiments, a compound, a composition comprising a compound, or a combination therapy is administered to a human with a virus infection. In certain embodiments, the patient is a human 0 to 6 months old, 6 to 12 months old, 1 to 5 years old, 5 to 10 years old, 5 to 12 years old, 10 to 15 years old, 15 to 20 years old, 13 to 19 years old, 20 to 25 years old, 25 to 30 years old, 20 to 65 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In some embodiments, a compound, a composition comprising a compound, or a combination therapy is administered to a human infant. In other embodiments, a compound, or a combination therapy is administered to a human child. In other embodiments, a compound, a composition comprising a compound, or a combination therapy is administered to a human adult. In yet other embodiments, a compound, a composition comprising a compound, or a combination therapy is administered to an elderly human.

In certain embodiments, a compound, a composition comprising a compound, or a combination therapy is administered to a pet, e.g., a dog or cat. In certain embodiments, a compound, a composition comprising a compound, or a combination therapy is administered to a farm animal or livestock, e.g., pig, cows, horses, chickens, etc. In certain embodiments, a compound, a composition comprising a compound, or a combination therapy is administered to a bird, e.g., ducks or chicken.

In certain embodiments, a compound, a composition comprising a compound, or a combination therapy is administered to a primate, preferably a human, or another mammal, such as a pig, cow, horse, sheep, goat, dog, cat and rodent, in an immunocompromised state or immunosuppressed state or at risk for becoming immunocompromised or immunosuppressed. In certain embodiments, a compound, a composition comprising a compound, or a combination therapy is administered to a subject receiving or recovering from immunosuppressive therapy. In certain embodiments, a compound, a composition comprising a compound, or a combination therapy is administered to a subject that has or is at risk of getting cancer, AIDS, another viral infection, or a bacterial infection. In certain embodiments, a subject that is, will or has undergone surgery, chemotherapy and/or radiation therapy. In certain embodiments, a compound, a composition comprising a compound, or a combination therapy is administered to a subject that has cystic fibrosis, pulmonary fibrosis, or another disease which makes the subject susceptible to a viral infection. In certain embodiments, a compound, a composition comprising a compound, or a combination therapy is administered to a subject that has, will have or had a tissue transplant. In some embodiments, a compound, a composition comprising a compound, or a combination therapy is administered to a subject that lives in a nursing home, a group home (i.e., a home for 10 or more subjects), or a prison. In some embodiments, a compound, a composition comprising a compound, or a combination therapy is administered to a subject that attends school (e.g., elementary school, middle school, junior high school, high school or university) or daycare. In some embodiments, a compound, a composition comprising a compound, or a combination therapy is administered to a subject that works in the healthcare area, such as a doctor or a nurse, or in a hospital. In certain embodiments, a compound, a composition comprising a compound, or a combination therapy is administered to a subject that is pregnant or will become pregnant.

In some embodiments, a patient is administered a compound or a composition comprising a compound, or a combination therapy before any adverse effects or intolerance to therapies other than compounds develops. In some embodiments, compounds or compositions comprising one or more compounds, or combination therapies are administered to refractory patients. In a certain embodiment, refractory patient is a patient refractory to a standard antiviral therapy. In certain embodiments, a patient with a viral infection, is refractory to a therapy when the infection has not significantly been eradicated and/or the symptoms have not been significantly alleviated. The determination of whether a patient is refractory can be made either in vivo or in vitro by any method known in the art for assaying the effectiveness of a treatment of infections, using art-accepted meanings of "refractory" in such a context. In various embodiments, a patient with a viral infection is refractory when viral replication has not decreased or has increased.

In some embodiments, compounds or compositions comprising one or more compounds, or combination therapies are administered to a patient to prevent the onset or reoccurrence of viral infections in a patient at risk of developing such infections. In some embodiments, compounds or compositions comprising one or more compounds, or combination therapies are administered to a patient who are susceptible to adverse reactions to conventional therapies.

In some embodiments, one or more compounds or compositions comprising one or more compounds, or combination therapies are administered to a patient who has proven refractory to therapies other than compounds, but are no longer on these therapies. In certain embodiments, the patients being managed or treated in accordance with the methods of this invention are patients already being treated with antibiotics, anti-virals, anti-fungals, or other biological therapy/immunotherapy. Among these patients are refractory patients, patients who are too young for conventional therapies, and patients with reoccurring viral infections despite management or treatment with existing therapies.

In some embodiments, the subject being administered one or more compounds or compositions comprising one or more compounds, or combination therapies has not received a therapy prior to the administration of the compounds or compositions or combination therapies. In other embodiments, one or more compounds or compositions comprising one or more compounds, or combination therapies are administered to a subject who has received a therapy prior to administration of one or more compounds or compositions comprising one or more compounds, or combination therapies. In some embodiments, the subject administered a compound or a composition comprising a compound was refractory to a prior therapy or experienced adverse side effects to the prior therapy or the prior therapy was discontinued due to unacceptable levels of toxicity to the subject.

6.2 Mode of Administration

When administered to a patient, a compound is preferably administered as a component of a composition that optionally comprises a pharmaceutically acceptable vehicle. The composition can be administered orally, or by any other convenient route, for example, by infusion or bolus injection, by absorption through epithelial or mucocutaneous linings (e.g., oral mucosa, rectal, and intestinal mucosa) and may be administered together with another biologically active agent. Administration can be systemic or local. Various delivery systems are known, e.g., encapsulation in liposomes, microparticles, microcapsules, capsules, and can be used to administer the compound and pharmaceutically acceptable salts thereof.

Methods of administration include but are not limited to parenteral, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration is left to the discretion of the practitioner. In most instances, administration will result in the release of a compound into the bloodstream.

In specific embodiments, it may be desirable to administer a compound locally. This may be achieved, for example, and not by way of limitation, by local infusion, topical application, e.g., in conjunction with a wound dressing, by injection, by means of a catheter, by means of a suppository, or by means of an implant, said implant being of a porous, non-porous, or gelatinous material, including membranes, such as sialastic membranes, or fibers. In such instances, administration may selectively target a local tissue without substantial release of a Compound into the bloodstream.

In certain embodiments, it may be desirable to introduce a compound into the central nervous system by any suitable route, including intraventricular, intrathecal and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, a compound is formulated as a suppository, with traditional binders and vehicles such as triglycerides.

For viral infections with cutaneous manifestations, the compound can be administered topically. Similarly, for viral infections with ocular manifestation, the compounds can be administered ocularly.

In another embodiment, a compound is delivered in a vesicle, in particular a liposome (See Langer, 1990, Science 249:1527 1533; Treat et al., in Liposomes in the Therapy of Infectious Disease and Bacterial infection, Lopez-Berestein and Fidler (eds.), Liss, New York, pp. 353 365 (1989); Lopez Berestein, ibid., pp. 317 327; See generally ibid.).

In another embodiment, a compound is delivered in a controlled release system (See, e.g., Goodson, in Medical Applications of Controlled Release, supra, vol. 2, pp. 115 138 (1984)). Examples of controlled-release systems are discussed in the review by Langer, 1990, Science 249:1527 1533 may be used. In one embodiment, a pump may be used (See Langer, supra; Sefton, 1987, CRC Crit. Ref Biomed. Eng. 14:201; Buchwald et al., 1980, Surgery 88:507; Saudek et al., 1989, N. Engl. J. Med. 321:574). In another embodiment, polymeric materials can be used (See Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; See also Levy et al., 1985, Science 228:190; During et al., 1989, Ann. Neurol. 25:351; Howard et al., 1989, J. Neurosurg. 71:105). In a specific embodiment, a controlled-release system comprising a compound is placed in close proximity to the tissue infected with a virus to be prevented, treated and/or managed. In accordance with this embodiment, the close proximity of the controlled-release system to the infection may result in only a fraction of the dose of the compound required if it is systemically administered.

In certain embodiments, it may be preferable to administer a compound via the natural route of infection of the virus against which a compound has antiviral activity. For example, it may be desirable to administer a compound of the invention into the lungs by any suitable route to treat or prevent an infection of the respiratory tract by viruses (e.g., influenza virus). Pulmonary administration can also be employed, e.g., by use of an inhaler or nebulizer, and formulation with an aerosolizing agent for use as a spray.

6.3 Agents for Use in Combination with Compounds

Therapeutic or prophylactic agents that can be used in combination with compounds for the prevention, treatment and/or management of a viral infection include, but are not limited to, small molecules, synthetic drugs, peptides (including cyclic peptides), polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides), antibodies, synthetic or natural inorganic molecules, mimetic agents, and synthetic or natural organic molecules. Specific examples of such agents include, but are not limited to, immunomodulatory agents (e.g., interferon), anti-inflammatory agents (e.g., adrenocorticoids, corticosteroids (e.g., beclomethasone, budesonide, flunisolide, fluticasone, triamcinolone, methylprednisolone, prednisolone, prednisone, hydrocortisone), glucocorticoids, steriods, and non-steriodal anti-inflammatory drugs (e.g., aspirin, ibuprofen, diclofenac, and COX-2 inhibitors), pain relievers, leukotreine antagonists (e.g., montelukast, methyl xanthines, zafirlukast, and zileuton), beta2-agonists (e.g., albuterol, biterol, fenoterol, isoetharie, metaproterenol, pirbuterol, salbutamol, terbutalin formoterol, salmeterol, and salbutamol terbutaline), anticholinergic agents (e.g., ipratropium bromide and oxitropium bromide), sulphasalazine, penicillamine, dapsone, antihistamines, anti-malarial agents (e.g., hydroxychloroquine), anti-viral agents (e.g., nucleoside analogs (e.g., zidovudine, acyclovir, gancyclovir, vidarabine, idoxuridine, trifluridine, and ribavirin), foscarnet, amantadine, rimantadine, saquinavir, indinavir, ritonavir, and AZT) and antibiotics (e.g., dactinomycin (formerly actinomycin), bleomycin, erythomycin, penicillin, mithramycin, and anthramycin (AMC)).

Any therapy which is known to be useful, or which has been used or is currently being used for the prevention, management, and/or treatment of a viral infection or can be used in combination with compounds in accordance with the invention described herein. See, e.g., Gilman et al., Goodman and Gilman's: The Pharmacological Basis of Therapeutics, 10th ed., McGraw-Hill, New York, 2001; The Merck Manual of Diagnosis and Therapy, Berkow, M. D. et al. (eds.), 17th Ed., Merck Sharp & Dohme Research Laboratories, Rahway, N.J., 1999; Cecil Textbook of Medicine, 20th Ed., Bennett and Plum (eds.), W.B. Saunders, Philadelphia, 1996, and Physicians' Desk Reference ($61^{st}$ ed. 1007) for information regarding therapies (e.g., prophylactic or therapeutic agents) which have been or are currently being used for preventing, treating and/or managing viral infections.

6.3.1 Antiviral Agents

Antiviral agents that can be used in combination with compounds include, but are not limited to, non-nucleoside reverse transcriptase inhibitors, nucleoside reverse transcriptase inhibitors, protease inhibitors, and fusion inhibitors. In one embodiment, the antiviral agent is selected from the group consisting of amantadine, oseltamivir phosphate, rimantadine, and zanamivir. In another embodiment, the antiviral agent is a non-nucleoside reverse transcriptase inhibitor selected from the group consisting of delavirdine, efavirenz, and nevirapine. In another embodiment, the antiviral agent is a nucleoside reverse transcriptase inhibitor selected from the group consisting of abacavir, didanosine, emtricitabine, emtricitabine, lamivudine, stavudine, tenofovir DF, zalcitabine, and zidovudine. In another embodiment, the antiviral agent is a protease inhibitor selected from the group consisting of amprenavir, atazanavir, fosamprenav, indinavir, lopinavir, nelfinavir, ritonavir, and saquinavir. In another embodiment, the antiviral agent is a fusion inhibitor such as enfuvirtide.

Additional, non-limiting examples of antiviral agents for use in combination compounds include the following: rifampicin, nucleoside reverse transcriptase inhibitors (e.g., AZT, ddI, ddC, 3TC, d4T), non-nucleoside reverse transcriptase inhibitors (e.g., delavirdine efavirenz, nevirapine), protease inhibitors (e.g., aprenavir, indinavir, ritonavir, and saquinavir), idoxuridine, cidofovir, acyclovir, ganciclovir, zanamivir, amantadine, and palivizumab. Other examples of anti-viral agents include but are not limited to acemannan; acyclovir; acyclovir sodium; adefovir; alovudine; alvircept sudotox; amantadine hydrochloride (SYMMETREL™); aranotin; arildone; atevirdine mesylate; pyridine; cidofovir; cipamfylline; cytarabine hydrochloride; delavirdine mesylate; desciclovir; didanosine; disoxaril; edoxudine; enviradene; enviroxime; famciclovir; famotine hydrochloride; fiacitabine; fialuridine; fosarilate; foscamet sodium; fosfonet sodium; ganciclovir; ganciclovir sodium; idoxuridine; kethoxal; lamivudine; lobucavir; memotine hydrochloride; methisazone; nevirapine; oseltamivir phosphate (TAMIFLU™); penciclovir; pirodavir; ribavirin; rimantadine hydrochloride (FLUMADINE™); saquinavir mesylate; somantadine hydrochloride; sorivudine; statolon; stavudine; tilorone hydrochloride; trifluridine; valacyclovir hydrochloride; vidarabine; vidarabine phosphate; vidarabine sodium phosphate; viroxime; zalcitabine; zanamivir (RELENZA™); zidovudine; and zinviroxime.

6.3.2 Antibacterial Agents

Antibacterial agents, including antibiotics, that can be used in combination with compounds include, but are not limited to, aminoglycoside antibiotics, glycopeptides, amphenicol antibiotics, ansamycin antibiotics, cephalosporins, cephamycins oxazolidinones, penicillins, quinolones, streptogamins, tetracycline, and analogs thereof. In some embodiments, antibiotics are administered in combination with a compound to prevent and/or treat a bacterial infection.

In a specific embodiment, compounds are used in combination with other protein synthesis inhibitors, including but not limited to, streptomycin, neomycin, erythromycin, carbomycin, and spiramycin.

In one embodiment, the antibacterial agent is selected from the group consisting of ampicillin, amoxicillin, ciprofloxacin, gentamycin, kanamycin, neomycin, penicillin G, streptomycin, sulfanilamide, and vancomycin. In another embodiment, the antibacterial agent is selected from the group consisting of azithromycin, cefonicid, cefotetan, cephalothin, cephamycin, chlortetracycline, clarithromycin, clindamycin, cycloserine, dalfopristin, doxycycline, erythromycin, linezolid, mupirocin, oxytetracycline, quinupristin, rifampin, spectinomycin, and trimethoprim.

Additional, non-limiting examples of antibacterial agents for use in combination with compounds include the following: aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefinetazole, and cefminox), folic acid analogs (e.g., trimethoprim), glycopeptides (e.g., vancomycin), lincosamides (e.g., clindamycin, and lincomycin), macrolides (e.g., azithromycin, carbomycin, clarithomycin, dirithromycin, erythromycin, and erythromycin acistrate), monobactams (e.g., aztreonam, carumonam, and tigemonam), nitrofurans (e.g., furaltadone, and furazolium chloride), oxacephems (e.g., flomoxef, and moxalactam), oxazolidinones (e.g., linezolid), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o benethamine, penicillin 0, penicillin V, penicillin V benzathine, penicillin V hydrabamine, penimepicycline, and phencihicillin potassium), quinolones and analogs thereof (e.g., cinoxacin, ciprofloxacin, clinafloxacin, flumequine, grepagloxacin, levofloxacin, and moxifloxacin), streptogramins (e.g., quinupristin and dalfopristin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), and tetracyclines (e.g., apicycline, chlortetracycline, clomocycline, and demeclocycline). Additional examples include cycloserine, mupirocin, tuberin amphomycin, bacitracin, capreomycin, colistin, enduracidin, enviomycin, and 2,4 diaminopyrimidines (e.g., brodimoprim).

6.4 Dosages & Frequency of Administration

The amount of a compound, or the amount of a composition comprising a compound, that will be effective in the prevention, treatment and/or management of a viral infection can be determined by standard clinical techniques. In vitro or in vivo assays may optionally be employed to help identify optimal dosage ranges. The precise dose to be employed will also depend, e.g., on the route of administration, the type of invention, and the seriousness of the infection, and should be decided according to the judgment of the practitioner and each patient's or subject's circumstances.

In some embodiments, the dosage of a compound is determined by extrapolating from the no observed adverse effective level (NOAEL), as determined in animal studies. This extrapolated dosage is useful in determining the maximum recommended starting dose for human clinical trials. For instance, the NOAELs can be extrapolated to determine human equivalent dosages (HED). Typically, HED is extrapolated from a non-human animal dosage based on the doses that are normalized to body surface area (i.e., mg/m$^2$). In specific embodiments, the NOAELs are determined in mice, hamsters, rats, ferrets, guinea pigs, rabbits, dogs, primates, primates (monkeys, marmosets, squirrel monkeys, baboons), micropigs or minipigs. For a discussion on the use of NOAELs and their extrapolation to determine human equivalent doses, *See Guidance for Industry Estimating the Maximum Safe Starting Dose in Initial Clinical Trials for Therapeutics in Adult Healthy Volunteers*, U.S. Department of Health and Human Services Food and Drug Administration Center for Drug Evaluation and Research (CDER), Pharmacology and Toxicology, July 2005. In one embodiment, a compound or composition thereof is administered at a dose that is lower than the human equivalent dosage (HED) of the NOAEL over a period of 1 week, 2 weeks, 3 weeks, 1 month, 2 months, three months, four months, six months, nine months, 1 year, 2 years, 3 years, 4 years or more.

In certain embodiments, a dosage regime for a human subject can be extrapolated from animal model studies using the dose at which 10% of the animals die (LD10). In general the starting dose of a Phase I clinical trial is based on preclinical testing. A standard measure of toxicity of a drug in preclinical testing is the percentage of animals that die because of treatment. It is well within the skill of the art to correlate the LD10 in an animal study with the maximal-tolerated dose (MTD) in humans, adjusted for body surface area, as a basis to extrapolate a starting human dose. In some embodiments, the interrelationship of dosages for one animal model can be converted for use in another animal, including humans, using conversion factors (based on milligrams per meter squared of body surface) as described, e.g., in Freireich et al., Cancer Chemother. Rep., 1966, 50:219-244. Body surface area may be approximately determined from height and weight of the patient. See, e.g., Scientific Tables, Geigy Pharmaceuticals, Ardley, N.Y., 1970, 537. In certain embodiments, the adjustment for body surface area includes host factors such as, for example, surface area, weight, metabolism, tissue distribution, absorption rate, and excretion rate. In addition, the route of administration, excipient usage, and the specific disease or virus to target are also factors to consider. In one embodiment, the standard conservative starting dose is about $\frac{1}{10}$ the murine LD10, although it may be even lower if other species (i.e., dogs) were more sensitive to the compound. In other embodiments, the standard conservative starting dose is about $\frac{1}{100}$, $\frac{1}{95}$, $\frac{1}{90}$, $\frac{1}{85}$, $\frac{1}{80}$, $\frac{1}{75}$, $\frac{1}{70}$, $\frac{1}{65}$, $\frac{1}{60}$, $\frac{1}{55}$, $\frac{1}{50}$, $\frac{1}{45}$, $\frac{1}{40}$, $\frac{1}{35}$, $\frac{1}{30}$, $\frac{1}{25}$, $\frac{1}{20}$, $\frac{1}{15}$, $\frac{2}{10}$, $\frac{3}{10}$, $\frac{4}{10}$, or $\frac{5}{10}$ of the murine LD10. In other embodiments, an starting dose amount of a compound in a human is lower than the dose extrapolated from animal model studies. In another embodiment, an starting dose amount of a compound in a human is higher than the dose extrapolated from animal model studies. It is well within the skill of the art to start doses of the active composition at relatively low levels, and increase or decrease the dosage as necessary to achieve the desired effect with minimal toxicity.

Exemplary doses of compounds or compositions include milligram or microgram amounts per kilogram of subject or sample weight (e.g., about 1 microgram per kilogram to about 500 milligrams per kilogram, about 5 micrograms per kilogram to about 100 milligrams per kilogram, or about 1 microgram per kilogram to about 50 micrograms per kilogram). In specific embodiments, a daily dose is at least 50 mg, 75 mg, 100 mg, 150 mg, 250 mg, 500 mg, 750 mg, or at least 1 g.

In one embodiment, the dosage is a concentration of 0.01 to 5000 mM, 1 to 300 mM, 10 to 100 mM and 10 mM to 1 M. In another embodiment, the dosage is a concentration of at least 5 μM, at least 10 μM, at least 50 μM, at least 100 μM, at least 500 μM, at least 1 mM, at least 5 mM, at least 10 mM, at least 50 mM, at least 100 mM, or at least 500 mM.

In one embodiment, the dosage is a concentration of 0.01 to 5000 mM, 1 to 300 mM, 10 to 100 mM and 10 mM to 1 M. In another embodiment, the dosage is a concentration of at least 5 μM, at least 10 μM, at least 50 μM, at least 100 μM, at least 500 μM, at least 1 mM, at least 5 mM, at least 10 mM, at least 50 mM, at least 100 mM, or at least 500 mM. In a specific embodiment, the dosage is 0.25 μg/kg or more, preferably 0.5 μg/kg or more, 1 μg/kg or more, 2 μg/kg or more, 3 μg/kg or more, 4 μg/kg or more, 5 μg/kg or more, 6 μg/kg or more, 7 μg/kg or more, 8 μg/kg or more, 9 μg/kg or more, or 10 μg/kg or more, 25 μg/kg or more, preferably 50 μg/kg or more, 100 μg/kg or more, 250 μg/kg or more, 500 μg/kg or more, 1 mg/kg or more, 5 mg/kg or more, 6 mg/kg or more, 7 mg/kg or more, 8 mg/kg or more, 9 mg/kg or more, or 10 mg/kg or more of a patient's body weight.

In another embodiment, the dosage is a unit dose of 5 mg, preferably 10 mg, 50 mg, 100 mg, 150 mg, 200 mg, 250 mg, 300 mg, 350 mg, 400 mg, 500 mg, 550 mg, 600 mg, 650 mg, 700 mg, 750 mg, 800 mg or more. In another embodiment, the dosage is a unit dose that ranges from about 5 mg to about 100 mg, about 100 mg to about 200 μg, about 150 mg to about 300 mg, about 150 mg to about 400 mg, 250 μg to about 500 mg, about 500 mg to about 800 mg, about 500 mg to about 1000 mg, or about 5 mg to about 1000 mg.

In certain embodiments, suitable dosage ranges for oral administration are about 0.001 milligram to about 500 milligrams of a compound, per kilogram body weight per day. In specific embodiments of the invention, the oral dose is about 0.01 milligram to about 100 milligrams per kilogram body weight per day, about 0.1 milligram to about 75 milligrams per kilogram body weight per day or about 0.5 milligram to 5 milligrams per kilogram body weight per day. The dosage amounts described herein refer to total amounts administered; that is, if more than one compound is administered, then, in some embodiments, the dosages correspond to the total amount administered. In a specific embodiment, oral compositions contain about 10% to about 95% a compound of the invention by weight.

Suitable dosage ranges for intravenous (i.v.) administration are about 0.01 milligram to about 100 milligrams per kilogram body weight per day, about 0.1 milligram to about 35 milligrams per kilogram body weight per day, and about 1 milligram to about 10 milligrams per kilogram body weight per day. In some embodiments, suitable dosage ranges for intranasal administration are about 0.01 pg/kg body weight per day to about 1 mg/kg body weight per day. Suppositories generally contain about 0.01 milligram to about 50 milligrams of a compound of the invention per kilogram body weight per day and comprise active ingredient in the range of about 0.5% to about 10% by weight.

Recommended dosages for intradermal, intramuscular, intraperitoneal, subcutaneous, epidural, sublingual, intracerebral, intravaginal, transdermal administration or administration by inhalation are in the range of about 0.001 milligram to about 500 milligrams per kilogram of body weight per day. Suitable doses for topical administration include doses that are in the range of about 0.001 milligram to about 50 milligrams, depending on the area of administration. Effective doses may be extrapolated from dose-response curves derived from in vitro or animal model test systems. Such animal models and systems are well known in the art.

In another embodiment, a subject is administered one or more doses of a prophylactically or therapeutically effective amount of a compound or a composition, wherein the prophylactically or therapeutically effective amount is not the same for each dose. In another embodiment, a subject is administered one or more doses of a prophylactically or therapeutically effective amount of a compound or a composition, wherein the dose of a prophylactically or therapeutically effective amount administered to said subject is increased by, e.g., 0.01 µg/kg, 0.02 µg/kg, 0.04 µg/kg, 0.05 µg/kg, 0.06 µg/kg, 0.08 µg/kg, 0.1 µg/kg, 0.2 µg/kg, 0.25 µg/kg, 0.5 µg/kg, 0.75 µg/kg, 1 µg/kg, 1.5 µg/kg, 2 µg/kg, 4 µg/kg, 5 µg/kg, 10 µg/kg, 15 µg/kg, 20 µg/kg, 25 µg/kg, 30 µg/kg, 35 µg/kg, 40 µg/kg, 45 µg/kg, or 50 µg/kg, as treatment progresses. In another embodiment, a subject is administered one or more doses of a prophylactically or therapeutically effective amount of a compound or composition, wherein the dose is decreased by, e.g., 0.01 µg/kg, 0.02 µg/kg, 0.04 µg/kg, 0.05 µg/kg, 0.06 µg/kg, 0.08 µg/kg, 0.1 µg/kg, 0.2 µg/kg, 0.25 µg/kg, 0.5 µg/kg, 0.75 µg/kg, 1 µg/kg, 1.5 µg/kg, 2 µg/kg, 4 µg/kg, 5 µg/kg, 10 µg/kg, 15 µg/kg, 20 µg/kg, 25 µg/kg, 30 µg/kg, 35 µg/kg, 40 µg/kg, 45 µg/kg, or 50 µg/kg, as treatment progresses.

In certain embodiments, a subject is administered a compound or a composition in an amount effective to inhibit or reduce viral genome replication by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In other embodiments, a subject is administered a compound or a composition in an amount effective to inhibit or reduce viral genome replication by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In certain embodiments, a subject is administered a compound or a composition in an amount effective to inhibit or reduce viral genome replication by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or other known to one of skill in the art.

In certain embodiments, a subject is administered a compound or a composition in an amount effective to inhibit or reduce viral protein synthesis by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In other embodiments, a subject is administered a compound or a composition in an amount effective to inhibit or reduce viral protein synthesis by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In certain embodiments, a subject is administered a compound or a composition in an amount effective to inhibit or reduce viral protein synthesis by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art.

In certain embodiments, a subject is administered a compound or a composition in an amount effective to inhibit or reduce viral infection by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered a compound or a composition in an amount effective to inhibit or reduce viral infection by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art.

In certain embodiments, a subject is administered a compound or a composition in an amount effective to inhibit or reduce viral replication by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered a compound or a composition in an amount effective to inhibit or reduce viral replication by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art. In other embodiments, a subject is administered a compound or a composition in an amount effective to inhibit or reduce viral replication by 1 log, 1.5 logs, 2 logs, 2.5 logs, 3 logs, 3.5 logs, 4 logs, 5 logs or more relative to a negative control as determined using an assay described herein or others known to one of skill in the art.

In certain embodiments, a subject is administered a compound or a composition in an amount effective to inhibit or reduce the ability of the virus to spread to other individuals by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In other embodiments, a subject is administered a compound or a composition in an amount effective to inhibit or reduce the ability of the virus to spread to other cells, tissues or organs in the subject by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art.

In certain embodiments, a subject is administered a compound or a composition in an amount effective to inhibit or reduce viral induced lipid synthesis by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In other embodiments, a subject is administered a compound or a composition in an amount effective to inhibit or reduce viral induced lipid synthesis by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In certain embodiments, a subject is administered a compound or a composition in an amount effective to inhibit or reduce viral induced lipid synthesis by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art.

In certain embodiments, a dose of a compound or a composition is administered to a subject every day, every other day, every couple of days, every third day, once a week, twice a week, three times a week, or once every two weeks. In other embodiments, two, three or four doses of a compound or a composition is administered to a subject every day, every couple of days, every third day, once a week or once every two weeks. In some embodiments, a dose(s) of a compound or a composition is administered for 2 days, 3 days, 5 days, 7 days, 14 days, or 21 days. In certain embodiments, a dose of a compound or a composition is administered for 1 month, 1.5 months, 2 months, 2.5 months, 3 months, 4 months, 5 months, 6 months or more.

The dosages of prophylactic or therapeutic agents which have been or are currently used for the prevention, treatment and/or management of a viral infection can be determined using references available to a clinician such as, e.g., the Physicians' Desk Reference (61$^{st}$ ed. 2007). Preferably, dosages lower than those which have been or are currently being used to prevent, treat and/or manage the infection are utilized in combination with one or more compounds or compositions.

For compounds which have been approved for uses other than prevention, treatment or management of viral infections, safe ranges of doses can be readily determined using references available to clinicians, such as e.g., the Physician's Desk Reference (61$^{st}$ ed. 2007).

The above-described administration schedules are provided for illustrative purposes only and should not be considered limiting. A person of ordinary skill in the art will readily understand that all doses are within the scope of the invention.

It is to be understood and expected that variations in the principles of invention herein disclosed may be made by one skilled in the art and it is intended that such modifications are to be included within the scope of the present invention.

Throughout this application, various publications are referenced. These publications are hereby incorporated into this application by reference in their entireties to more fully describe the state of the art to which this invention pertains. The following examples further illustrate the invention, but should not be construed to limit the scope of the invention in any way.

EXAMPLES

Example 1

Screen of Antiviral Targets

To identify host cell enzymes whose inhibition could decrease the production of virus progeny, an siRNA screen was performed to test for roles of specific enzymes involved directly or indirectly in lipid metabolism. The siRNA screen was designed to test for effects of inhibiting specific siRNA targets on the infectious yield of HCMV. The screen was performed in 96-well plates using a portion of an siRNA library purchased from Sigma. Each target was assayed with three different siRNAs. (See Table 2).

MRCS human fibroblasts received siRNAs by transfection, 24 h later they were infected at a multiplicity of 0.1 pfu/cell with an HCMV derivative expressing a GFP tagged protein, and 96 h after infection cells in each well were observed for spread of the GFP marker. Also at 96 h after infection, the medium was removed from each well and used to infect fibroblasts in a new 96-well plate, and infectivity was quantified by staining for immunofluorescence and counting IE1-positive cells 24 h later.

The siRNA which were found to inhibit HCMV replication are shown in Table 1. Note that, even when siRNA resulted in only a modest (e.g. ~2-fold) inhibition of viral replication, the associated enzyme may be pivotal for viral replication, as siRNA typically results in only a modest, e.g., 2- to 10-fold, reduction in enzyme activity. Further reduction in enzyme activity (e.g., using a more effective siRNA or a small molecule inhibitor) may result in greater, sometimes much greater, inhibition of viral replication.

Example 2

Antiviral Effects and Therapeutic Index of Triacsin C

Triacsin C has been administered orally to mice for two months at 10 mg/kg/day with no significant toxicities noted, and it significantly inhibited the progression of atherosclerosis (LDLR$^{-/-}$ mice) (Matsuda et al., *J. Antibiot.* 6:318-21, 2008). Also, WS-1228 A and B, compounds structurally related to triacsin C, exhibit vasodilator activity (Omura et al., *J Antibiot* 39:1211-8, 1986).

Figure 2:
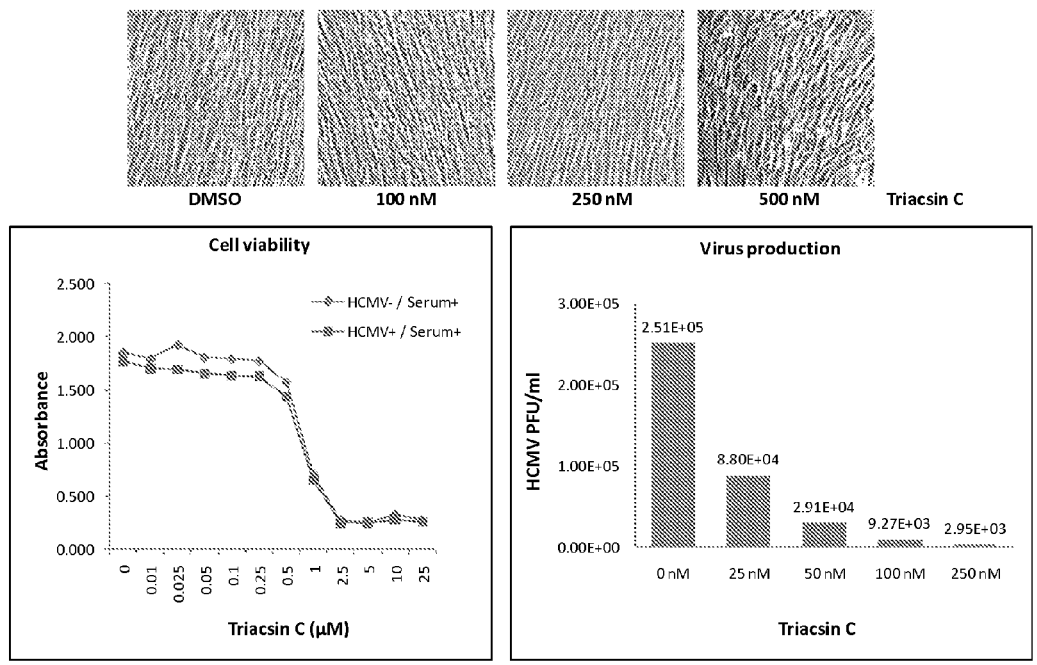
FIG. 2. Dose-dependent inhibition of human cytomegalovirus replication by triacsin C. Top panels: About 90% confluent MRCS human fibroblasts were treated with the indicated concentrations of triacsin C or the carrier in which the drug was dissolved (DMSO) in the presence of 10% fetal calf serum and photographed 96 h later. Bottom left panel: About 90% confluent MRCS fibroblasts were either mock infected or infected with the AD169 strain of HCMV at a multiplicity of (0.1 pfu/cell). The uninfected or infected cells received DMSO (solvent for the drug) or the drug for 96 h before cells were assayed for viability. Bottom right panel: About 90% confluent MRCS fibroblasts were infected with HCMV at a multiplicity of (0.1 pfu/cell) in the presence of DMSO (0 nM triacsin C) or triacsin C at the indicated concentrations. Infected fibroblasts were maintained in medium containing 10% fetal calf serum. Virus yield in the medium at 96 h after infection was determined by infecting fibrobalsts and assaying IE1 expression by immunofluorescence 24 h later. 96 h after infection, cells were harvested into culture medium and sonicated to release cell-associated virus. Virus yield in the medium was determined by infecting fibroblasts and assaying IE1 expression by immunofluorescence 24 h later.

The effect of triacsin C on the viability of MRCS human fibroblasts in culture medium containing 10% fetal calf serum was tested. At the time drug was added, cells were about 90% confluent. After 96 h the drug did not alter the appearance of cells when administered at 100 or 250 nM, but caused some cell rounding at ≤500 nM (FIG. 2, top panels). The drug had little effect on cell viability at doses of ≤500 nM (FIG. 2, bottom left). Triascin C was also tested for its effect on the viability of MRCS human fibroblasts in the absence of fetal calf serum, where it showed no discernable impact on viability at doses up to 10 µM. When added together with the infecting virus, triacsin C inhibited the production of HCMV in a dose-dependent manner, reducing the yield of infectious virus by a factor of 85 at 250 nM (FIG. 2, bottom right).

At 50 nM, triacsin C reduced the yield of infectious HCMV virus by a factor of >8-fold without discrenably impacting the viability of MRC-5 fibroblasts in the presence of serum. Thus, triacsin C shows a favorable therapeutic index as an antiviral of >10-fold. For fibroblasts in the absence of serum, the therapeutic index is yet more favorable, >100-fold. Based on the in vivo tolerability of 10 mg/kg/day, it is likely that the fibroblasts in the absence of serum are the more relevant reflection of in vivo biology (the MRC-5 fibroblasts in the absence of serum are quiescent, like most cells in vivo). Thus, triacsin C is anticipated to have an in vivo therapeutic index of >2-fold, preferably >5-fold or >10-fold, and more preferably >20-fold.

Lipid drop formation is associated with HCMV infection. Triacsin C treatment reduced lipid droplet formation induced by HCMV infection of HFF cells (not shown).

Lipid droplet formation and depletion is associated with HCMV infection. At early phase of infection (2-12 hours after infection) lipid droplets are induced within the infected cells and thereafter, a complete loss of lipid droplets is observed (48-72 hours after infection). On the other hand, the cells that do not harbor HCMV but are neighboring to the infected cells dramatically accumulate lipid droplets starting with 48 hours after infection. Triacsin C treatment reduced lipid droplet formation induced by HCMV infection of HFF cells in both cases.

Figure 3:
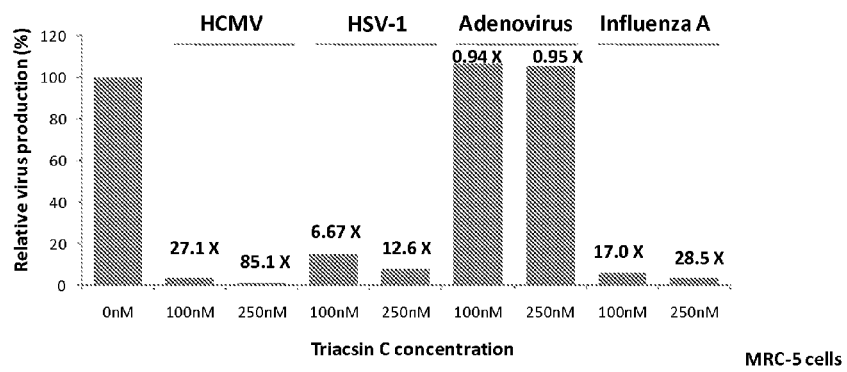
FIG. 3. Dose-dependent inhibition of multiple viruses by triacsin C. About 90% confluent MRCS fibroblasts were infected with HCMV AD169 strain (MOI=0.1 pfu/cell), HSV-1 F-strain (MOI=1 pfu/cell), adenovirus type 5 (MOI=1 pfu/cell) or influenza A strain WSN/33 (MOI=1 pfu/cell). Infected cultures received the indicated doses of drug when the virus inoculum was added, and cultures were maintained in medium plus 10% fetal calf serum plus drug until harvest. Cells were harvested at 96 h (HCMV), 72 h (adenovirus), 48 h (HSV-1) or 24 h post infection (influenza A), and infectious virus was quantified.

Triacsin C was tested for its ability to inhibit the growth of additional viruses. MRCS fibroblasts were infected with HCMV, herpes simplex virus type 1 (HSV-1), adenovirus type 5 or influenza A and treated with indicated amounts of triacsin C beginning when virus was added to cells (FIG. 3). All of the enveloped viruses (HCMV, HSV-1, influenza A) were substantially inhibited by drug treatment, while adenovirus was not.

Figure 9:
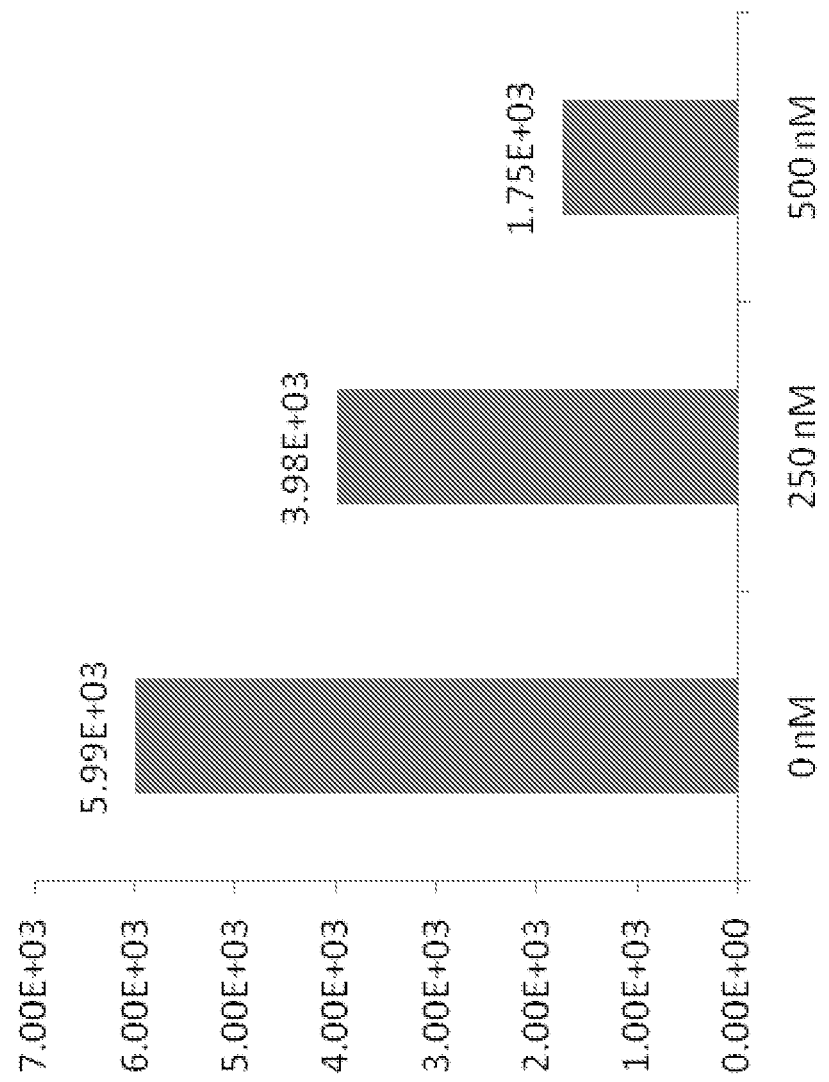
FIG. 9. Dose dependent inhibition of hepatitis C virus by triacsin C. Huh7.5 cells were infected with a derivative of HCV JFH1 strain (MOI=0.1 $TCID_{50}$/cell). Infected cells were maintained in medium containing 10% fetal calf serum plus DMSO (0 nM triacsin C) or triacsin C at the indicated concentrations. Media were harvested at 72 h and infectious virus was quantified by standard $TCID_{50}$ assay on Huh7.5 cells.

In addition, hepatitis C virus (HCV) growth was also inhibited by Triacsin C. Huh7.5 cells which are susceptible to HCV infection was infected with a derivative of JFH1 strain and treated with indicated amounts of Triacsin C (FIG. 9). The release of infectious HCV particles to the culture medium was significantly reduced by Triacsin C treatment.

Example 3

Antiviral Effects of Aminoxyacetic Acid (AOAA)

Figure 4:
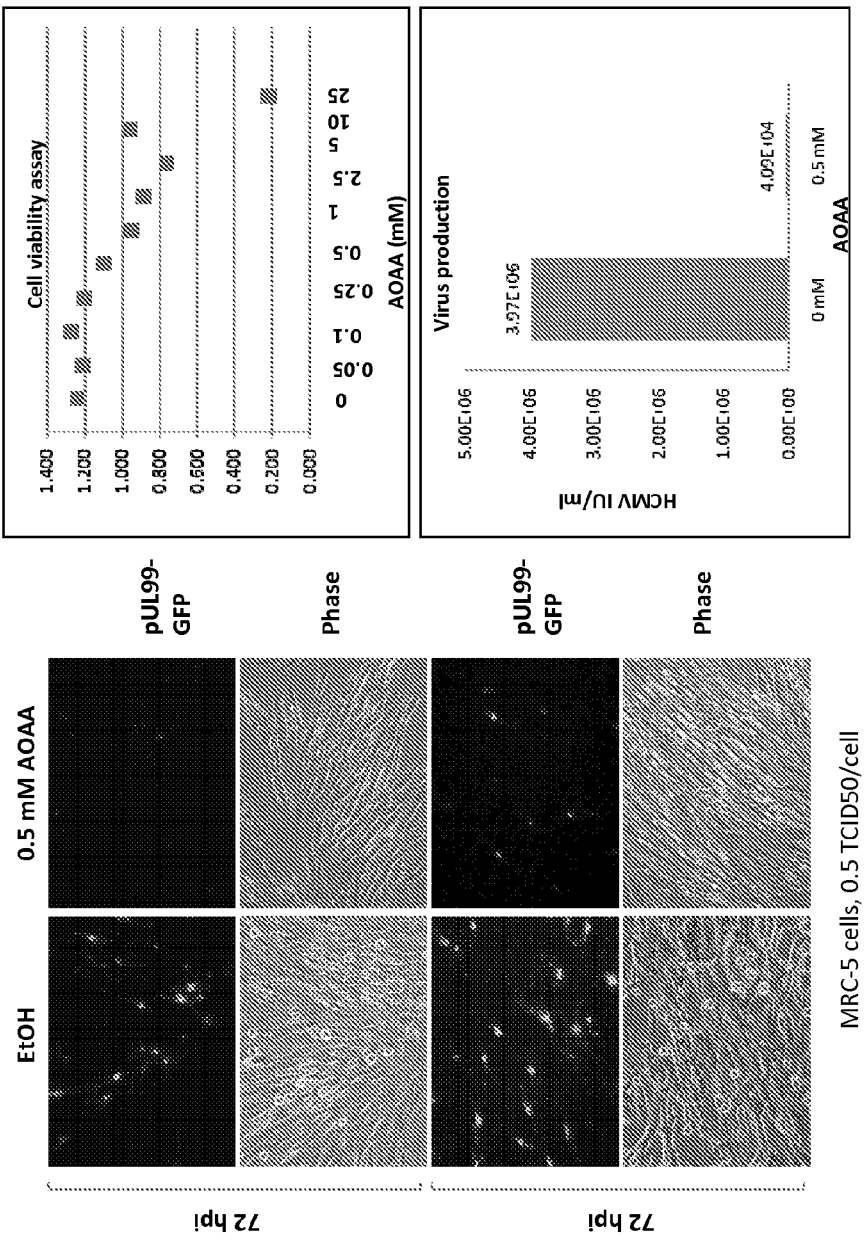
FIG. 4. Dose- and time-post-infection-dependent inhibition of HCMV by aminoxyacetic acid. MRC-5 fibroblast cells were infected with HCMV in the presence of the indicated concentrations of aminoxyacetic acid (AOAA) or the carrier in which the drug was dissolved (PBS) and photographed at indicated times after infection. Cells were harvested at 96 h and virus production was determined assaying IE1 expression in the infected fibroblasts by immunofluorescence 24 h later.

Replication of HCMV was tested in MRCS fibroblasts. 0.5 mM AOAA resulted in a 100-fold decrease in viral replication (FIG. 4), with no measurable decrease in cell viability at concentrations up to 2.5 mM (5-fold therapeutic index for 100-fold antiviral effect).

Figure 5:
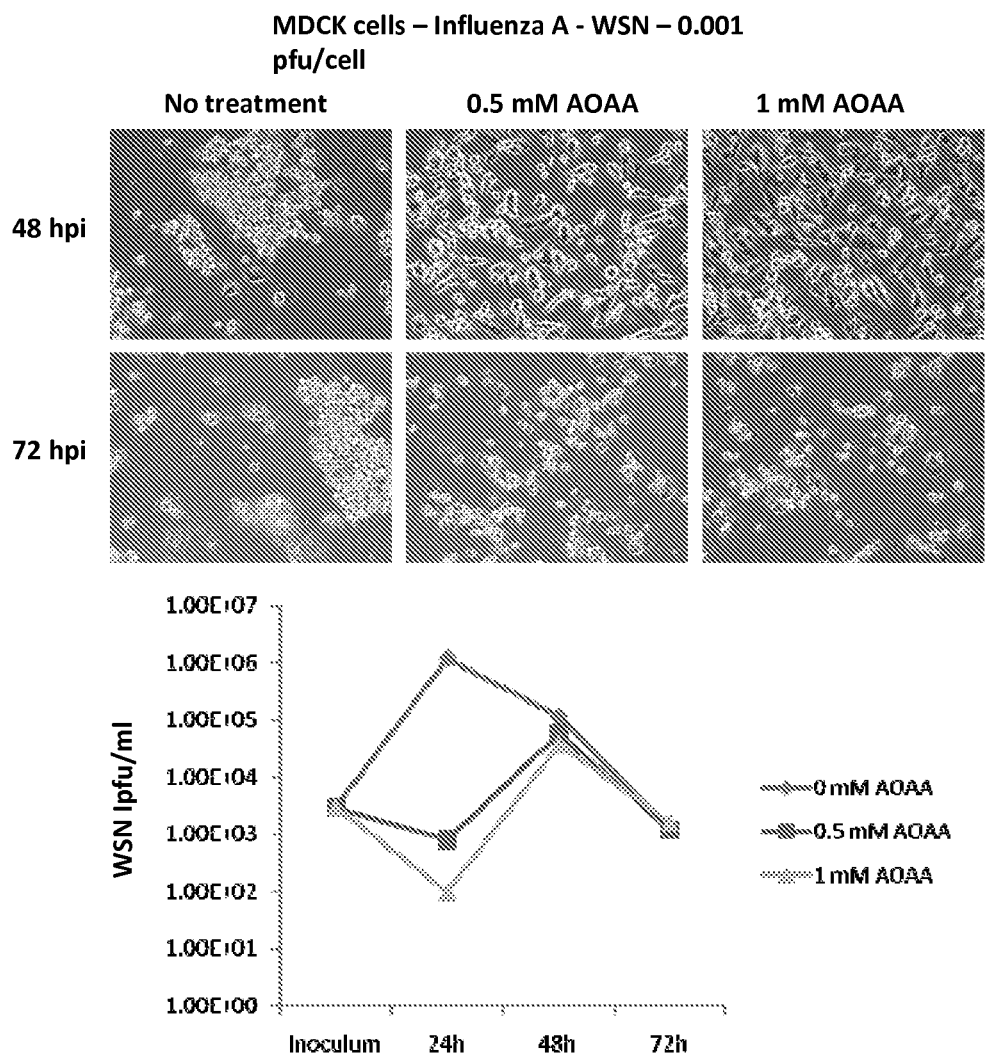
FIG. 5. Dose- and time-post-infection-dependent inhibition of influenza A by aminoxyacetic acid. Top panels: Approximately 90% confluent Madin Darby Canine Kidney (MDCK) cells were infected with WSN/33 strain of Influenza A virus in the presence of indicated concentrations of aminoxyacetic acid (AOAA) or the carrier in which the drug was dissolved (PBS) and photographed at indicated times after infection. Bottom panel: Approximately 90% confluent MDCK cells were infected with WSN/33 at a multiplicity of (0.001 pfu/cell) in the presence of PBS (0 mM) or AOAA at the indicated concentrations. Virus yield in the medium at indicated times after infection was determined by standard plaque assay on MDCK cells.

Replication of influenza A (WSN/33 strain) was measured in MDCK cells at a multiplicity of infection of 0.001 particle forming unit per cell. There was no evidence of host cell toxicity at doses of 0.5 and 1 mM based on light microscopy. Both of these doses markedly delayed the replication of influenza A, decreasing viral yields at 24 hours post infection by >1000-fold at each dose level (FIG. 5). Such a delay in viral spread is anticipated to enable effective immune clearance of the virus and therefore to prevent, eliminate, or greatly mitigate disease in an infected mammal.

Figure 6:
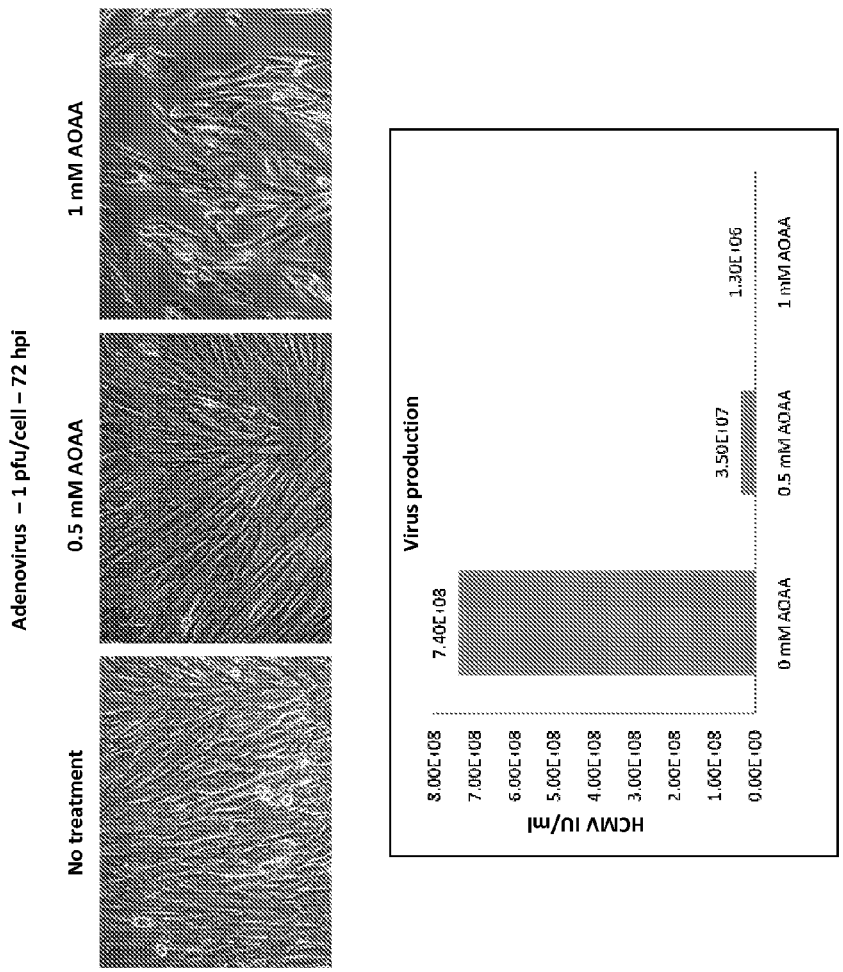
FIG. 6. Dose-dependent inhibition of adenovirus production by aminoxyacetic acid. Top panels: MRCS fibroblasts were infected with adenovirus in the presence of indicated concentrations of aminoxyacetic acid (AOAA) or the carrier in which the drug was dissolved (PBS) and photographed at 72 hours after infection. Bottom panel: Approximately 90% confluent MRCS cells were infected with adenovirus at a multiplicity of 1 pfu/cell in the presence of PBS (0 mM AOAA) or AOAA at the indicated concentrations. Virus production at 72 h after infection was determined by standard plaque assay on HeLa cells.

Replication of adenovirus was tested in MRCS fibroblasts at a multiplicity of infection of 1 particle forming unit per cell. 0.5 mM AOAA resulted in a 20-fold decrease in viral replication, and 1 mM AOAA resulted in a 500-fold decrease in viral replication (FIG. 6).

Example 4

Antiviral Effects of Meta-Iodo-Benzylguanidine (MIBG)

Figure 7:
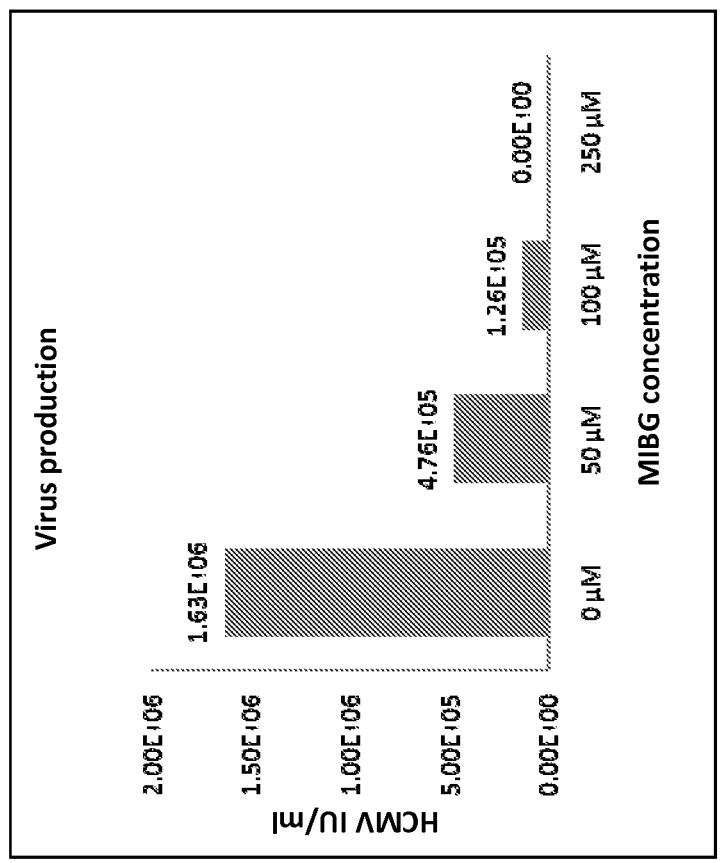
FIG. 7 Dose-dependent inhibition of HCMV production by meta-iodo-benzylguanidine (MIBG). Replication of HCMV was tested in MRCS fibroblasts. Cells were infected with HCMV and incubated at MIBG concentrations of 0 µM, 50 µM, 100 µM, and 250 µM. Virus production at 96 hours after infection was determined.

Replication of HCMV was tested in MRCS fibroblasts. Cells were infected with HCMV and incubated at MIBG concentrations of 0 µM, 50 µM, 100 µM, and 250 µM. Virus yield in the medium at 96 hours after infection was determined. 50 µM MIBG resulted in an approximately 70% decrease in virus titer, with little or no effect on cell morphology. (FIG. 7)

Example 5

Antiviral Effects of Simvastatin

Figure 8:
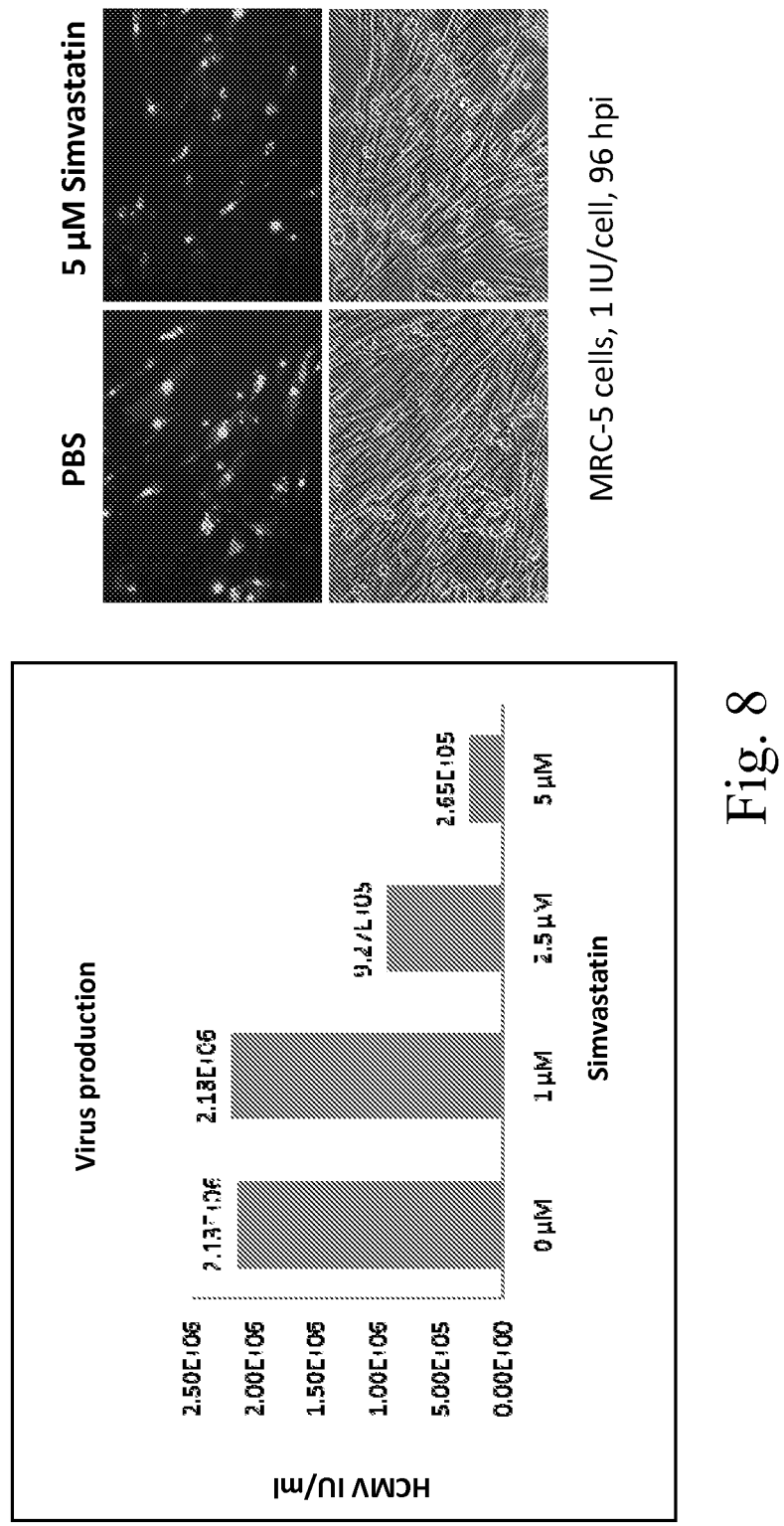
FIG. 8 Dose-dependent inhibition of HCMV production by simvastatin. Replication of HCMV was tested in MRCS fibroblasts. Cells were infected with HCMV and incubated at simvastatin concentrations of 0 µM, 1 µM, 2.5 µM, and 5 µM. Virus production at 96 hours after infection was determined.

Replication of HCMV was tested in MRC fibroblasts. Cells were infected with HCMV and incubated at simvastatin concentrations of 0 µM, 1 µM, 2.5 µM, and 5 µM. Virus yield in the medium at 96 hours after infection was determined. 5 µM simvastatin resulted in an approximately 90% decrease in virus titer. (FIG. 8)

Example 6

Antiviral Effects of PF-1052

Figure 10:
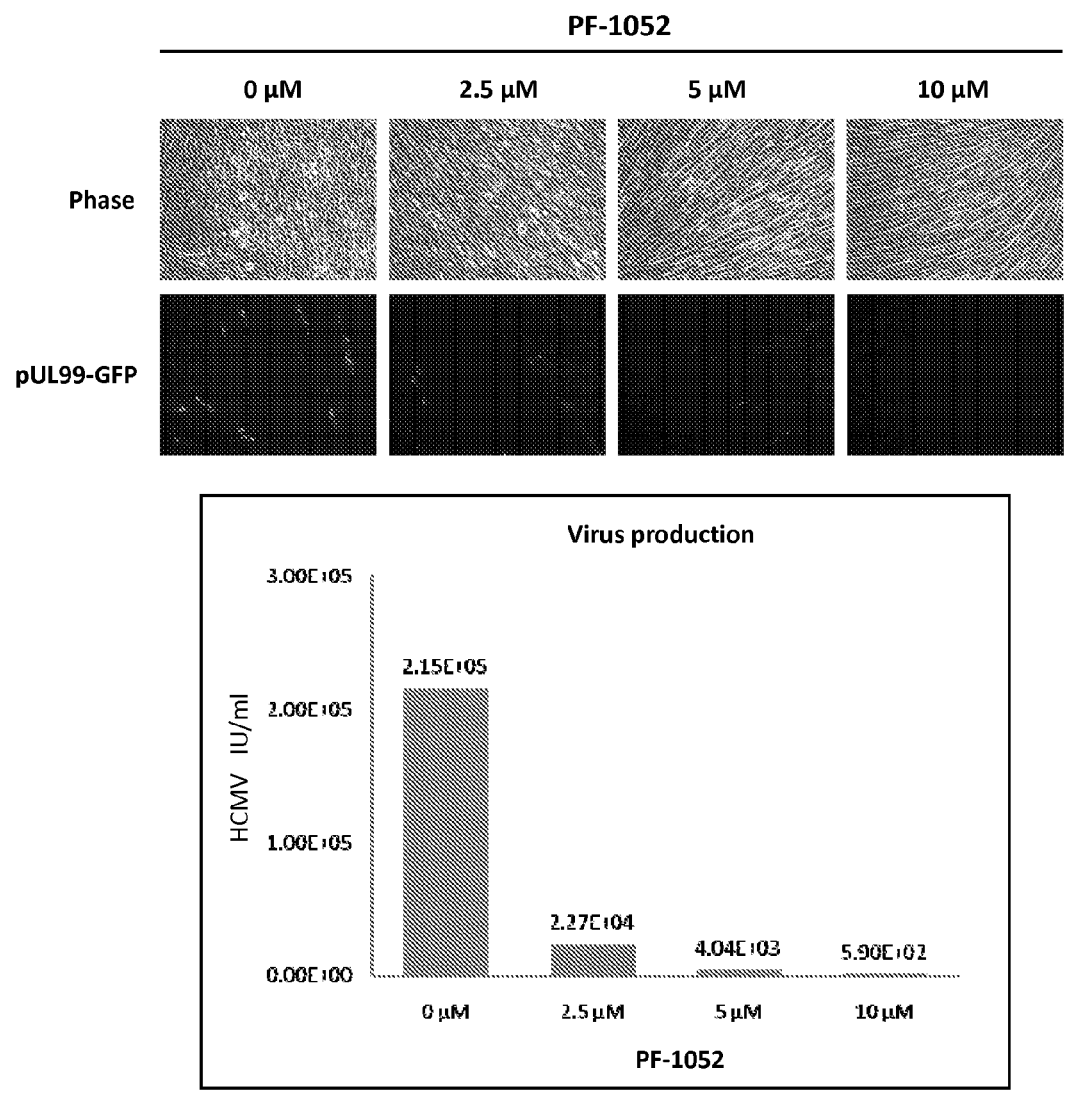
FIG. 10. Dose dependent inhibition of HCMV by PF-1052. About 90% confluent MRCS human fibroblasts were infected with HCMV. Infected cells were maintained in medium containing 10% fetal calf serum plus the indicated concentrations of PF-1052 or the carrier in which the drug was dissolved (ethanol). Top panels: The cells were photographed 96 h later. Bottom panel: Virus production at 96 h after infection was determined.

Replication of HCMV (AD169 strain) was tested in MRCS cells at a multiplicity of infection of 0.1 particle forming unit per cell. There was no evidence of host cell toxicity at doses of 5 and 10 µM based on light microscopy. Both of these doses markedly reduced the expression of late viral protein pUL99 coupled to GFP. PF-1052 reduced the viral yields at 96 hours post infection by >50-fold at 5 µM and by >300-fold at 10 µM (FIG. 10).

Figure 11:
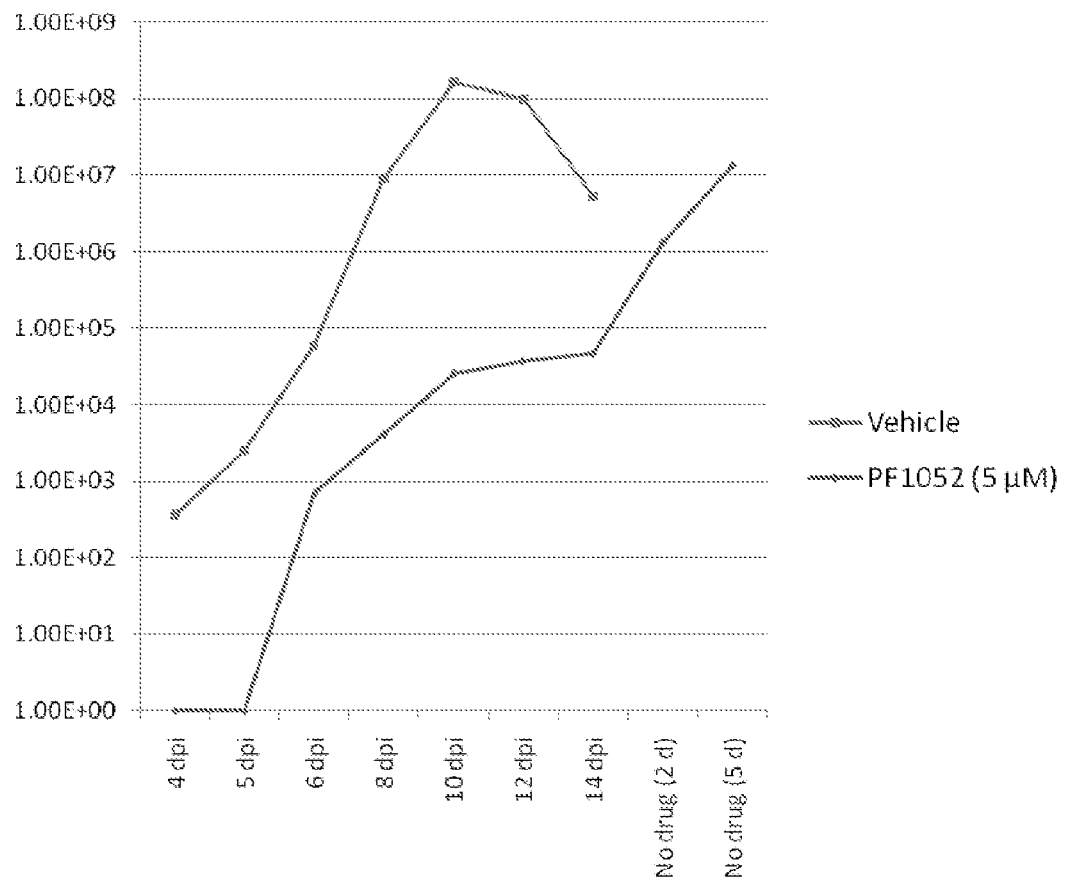
FIG. 11. Long term inhibition of HCMV by PF-1052. About 90% confluent MRCS human fibroblasts were infected with HCMV. Infected cells were maintained in medium containing 10% fetal calf serum plus 5 μM PF-1052 or the carrier in which the drug was dissolved (ethanol). The media of the cells were replaced every day. Starting from 4 days after infection, media were harvested at indicated times and infectious virus was determined. PF-1052 was no longer added to the cells 14 days after infection and infectious virus released into media were quantified 2 and 5 d after the removal of the drug.

PF-1052 was also tested for its ability to inhibit HCMV in a prolonged treatment of two weeks. The culture medium was replaced with fresh medium containing 5 µM PF-1052 or ethanol as a control every day. At 10 days after infection, PF-1052 dramatically reduced the yield of HCMV by a factor of >5000 fold (FIG. 11). After 10 days, HCMV infection in the control cells that was reduced due to the severe infection that causes cell death while the virus yields remained constant in PF-1052 treated cells. 14 days after infection, PF-1052 was removed and no longer added to the cells. The virus production was substantially increased 2 and 5 days after the removal of PF-1052, indicating that the inhibitory effect of the drug is specific and not due to a permanent change that occurs in the cells during prolonged drug treatment.

Figure 12:
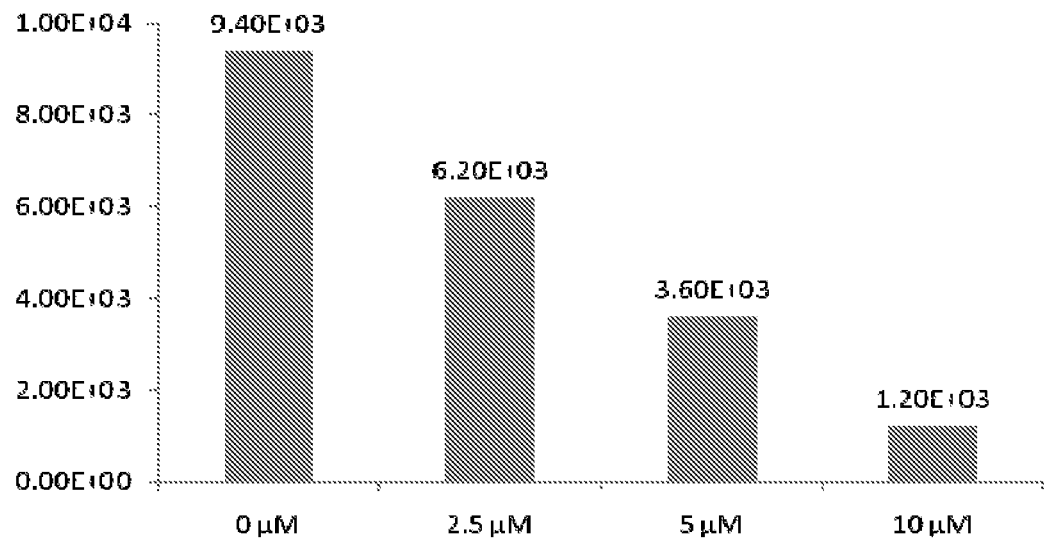
FIG. 12. Dose dependent inhibition of influenza A virus by PF-1052. MRCS cells were infected with influenza A WSN/33 strain (MOI=0.1 pfu/cell). Infected cells were maintained in medium containing 10% fetal calf serum plus the indicated concentrations of PF-1052 or the carrier in which the drug was dissolved (ethanol). Virus yield in the medium at 24 h after infection was determined.
Figure 13:
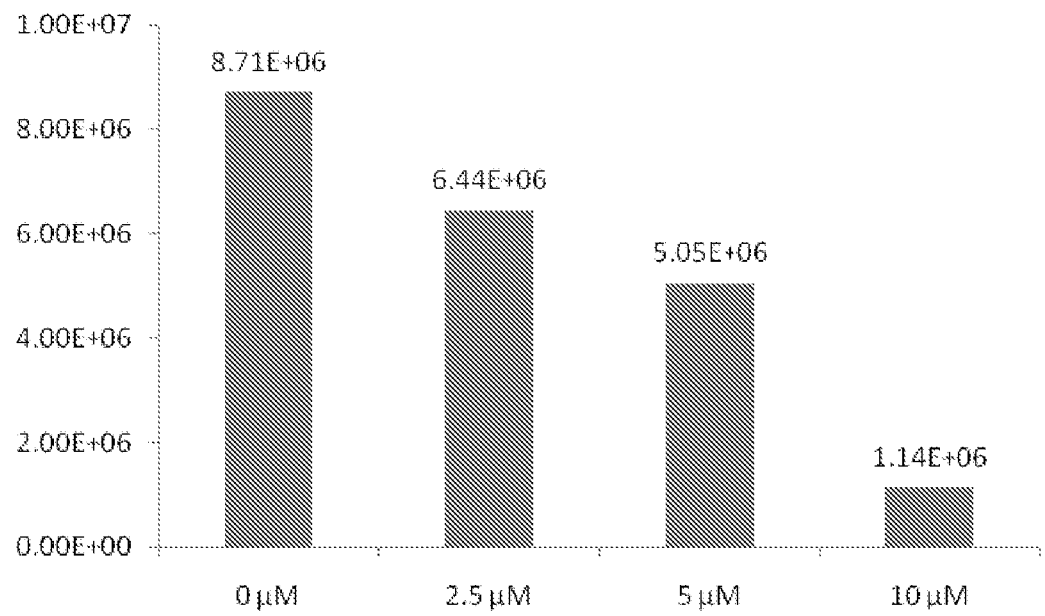
FIG. 13. Dose dependent inhibition of HSV-1 by PF-1052. MRCS cells were infected with HSV-1, KOS strain (MOI=1 pfu/cell). Infected cells were maintained in medium containing 10% fetal calf serum plus the indicated concentrations of PF-1052 or the carrier in which the drug was dissolved (ethanol). Virus yield in the medium at 24 h after infection was determined.
Figure 14:
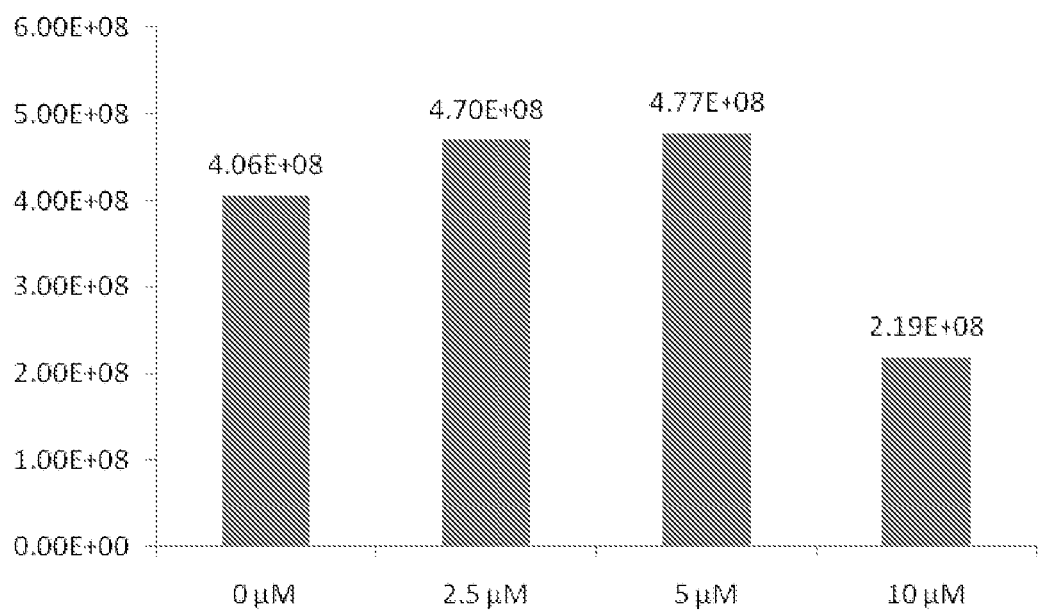
FIG. 14. Adenovirus replication is not inhibited by PF-1052. MRCS cells were infected with adenovirus type 5 (MOI=1 pfu/cell). Infected cells were maintained in medium containing 10% fetal calf serum plus the indicated concentrations of PF-1052 or the carrier in which the drug was dissolved (ethanol). Virus yield in the medium at 72 h after infection was determined.

PF-1052 was tested for its ability to inhibit the growth of additional viruses. MRCS fibroblasts were infected with HSV-1, adenovirus type 5 or influenza A and treated with indicated amounts of PF-1052 (FIGS. 12-14). HSV-1 and influenza A which contain a viral envelope were substantially inhibited by drug treatment in a dose dependent manner, while adenovirus was not.

Figure 15:
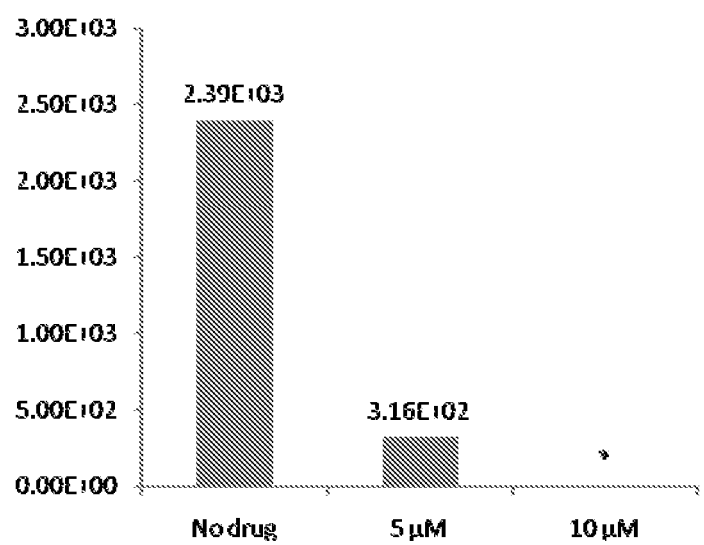
FIG. 15. Dose dependent inhibition of hepatitis C virus by PF-1052. Huh7.5 cells were infected with a derivative of HCV, JFH1 strain (MOI=0.1 $TCID_{50}$/cell) in the presence of ethanol (0 μM PF-1052) or PF-1052 at the indicated concentrations. Virus yield in the medium at 72 h after infection was determined. The star (*) indicates that the virus yield is below the detection limit which is 1.43E+0.1 $TCID_{50}$/ml for this assay.

In addition, HCV growth was also inhibited by PF-1052. Huh7.5 cells which was infected with HCV and treated with indicated amounts of PF-1052 (FIG. 15). PF-1052 inhibited the release of infectious HCV particles to the culture medium at 5 µM by a factor of 10 fold and at 10 µM by a factor of >100 fold.

Example 7

Antiviral Effects of Rubimaillin

Figure 16:
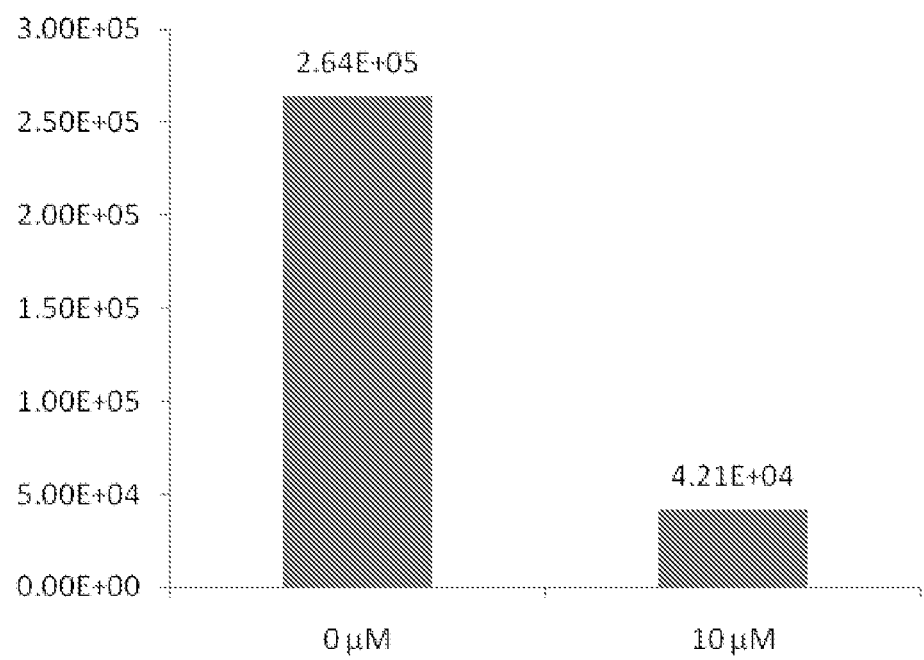
FIG. 16. Inhibition of HCMV production by rubimaillin. Replication of HCMV was tested in MRCS fibroblasts. Cells were infected with HCMV and either incubated with rubimaillin at concentration of 10 μM or the carrier in which the drug was dissolved (ethanol). Virus production at 96 h after infection was determined.

Replication of HCMV was tested in MRC fibroblasts. Cells were infected with HCMV and incubated with rubimaillin at a concentration of 10 µM. Virus yield in the medium at 96 hours after infection was determined. 5 µM rubimaillin resulted in an approximately 85% decrease in virus titer. (FIG. 16)

Example 8

Antiviral Effects of Elongase Inhibitors

Figure 17:
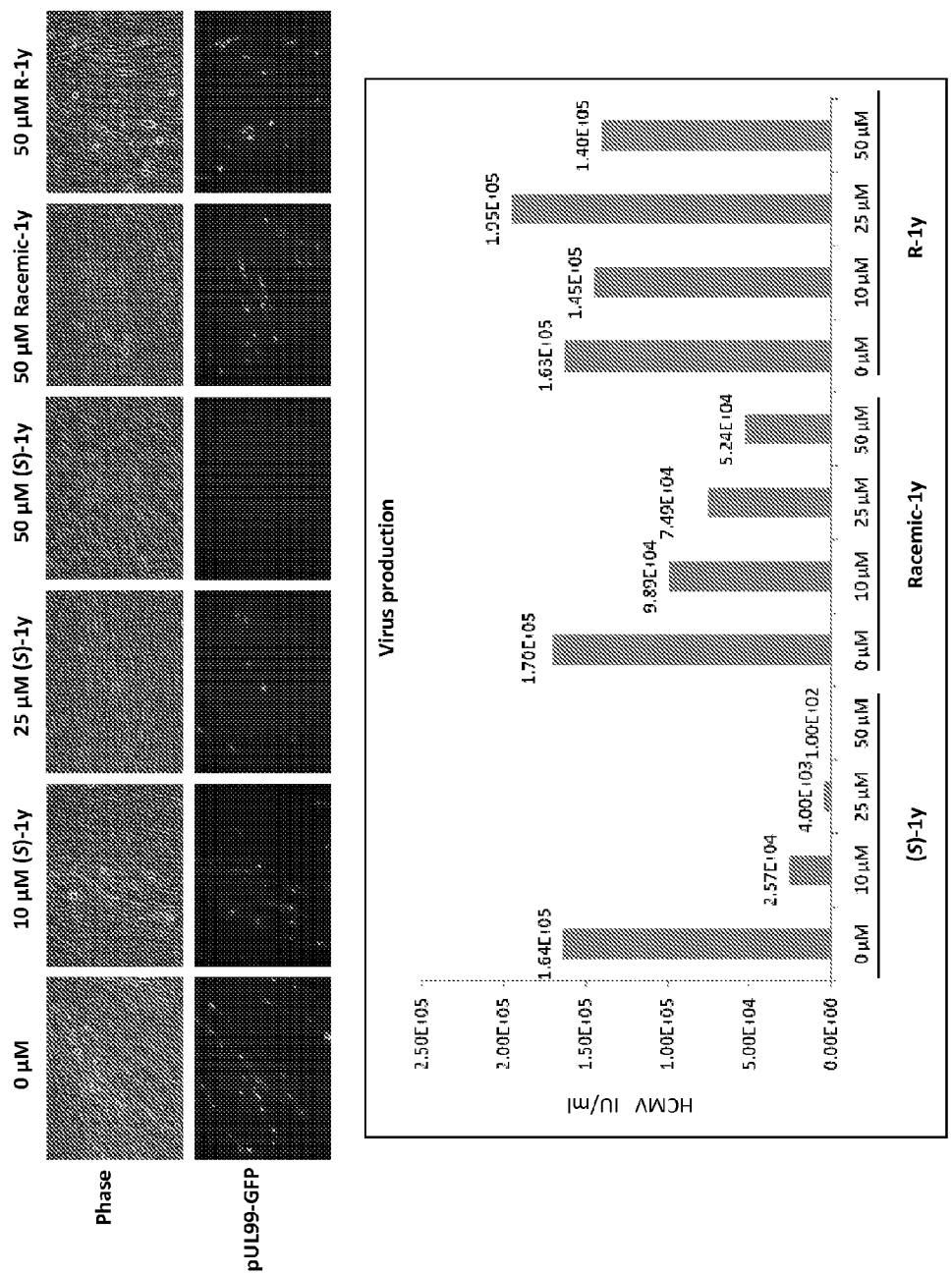
FIG. 17. Dose dependent inhibition of HCMV by the compound (S)-1y. About 90% confluent MRCS human fibroblasts were infected with HCMV. Infected cells were maintained in medium containing 10% fetal calf serum plus the indicated concentrations of (S)-1y, Racemic-1y, (R)-1y or the carrier in which the drugs were dissolved (DMSO; 0 μM). Top panels: The cells were photographed 96 h later. Bottom panel: Virus production at 96 h after infection was determined.

One class of elongase inhibitors is benzoxazinone compounds (Mizutani et al., *J. Med. Chem.*, 52: 7289-7300, 2009). Among these the most potent compound, (S)-1y shows specific inhibitory activity against human ELOVL6 with an $IC_{50}$ of ~2.6 nM and human ELOVL3 with an $IC_{50}$ of ~130 nM in vitro. Note that the plasma protein unbound fraction ratio of (S)-1y was found to be about 10% in tissue culture experiments which raises the expected inhibitory concentration cells. In line with this, the in vivo IC50 values of (S)-1y was found to be 169 nM for ELOVL6 and >5 µM for ELOVL3. Without inducing any toxicity on the cells, (S)-1y dramatically reduced HCMV late pUL99 expression in a dose dependent manner. Similarly, at 25 µM concentration, (S)-1y inhibited HCMV replication by a factor of ~40 fold, and at 50 µM by a factor of >1000 fold (FIG. 17). Whereas, it's inactive isomers R-1y and racemic-1y did not show a potent inhibitory effect on virus replication.

Figure 18:
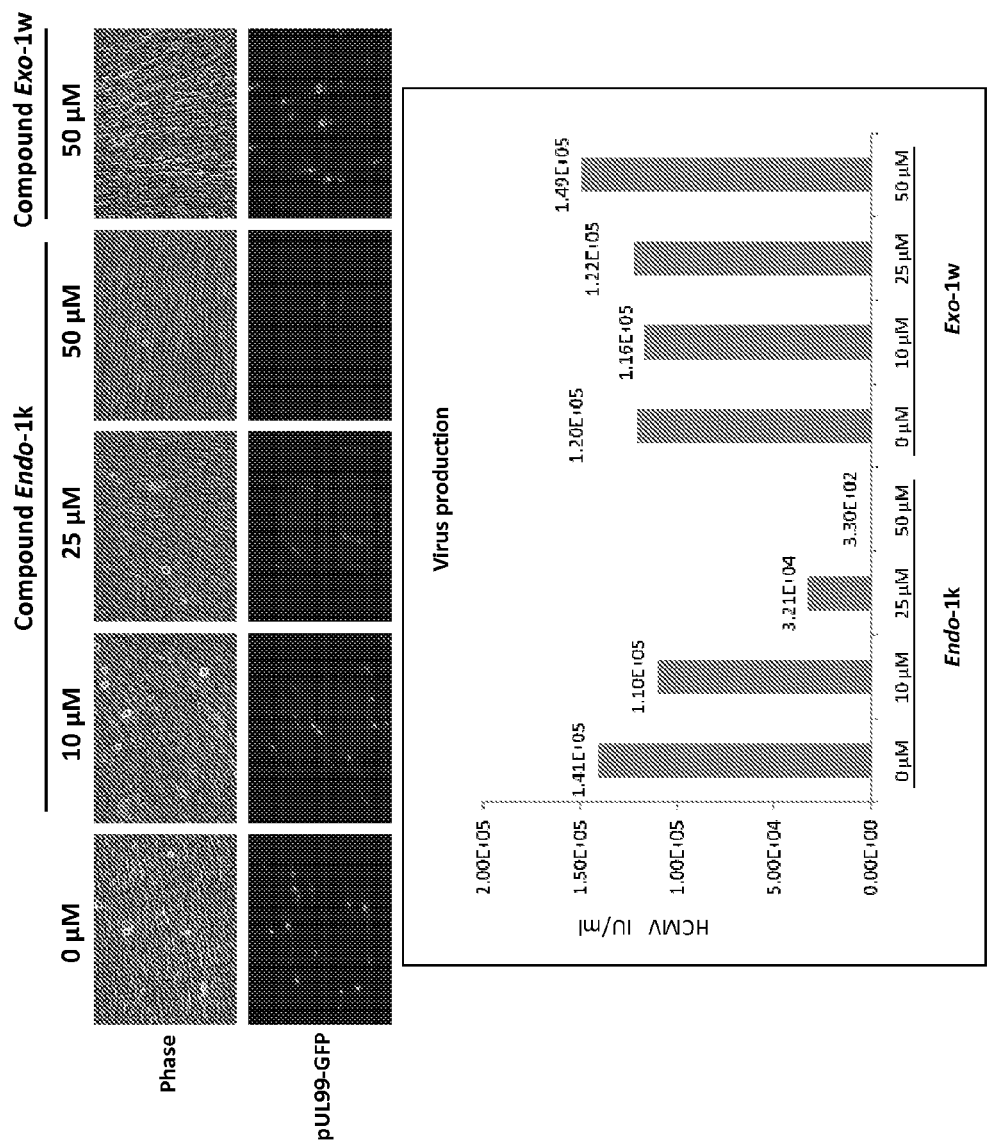
FIG. 18. Dose dependent inhibition of HCMV by the compound Endo-1k. About 90% confluent MRCS human fibroblasts were infected with HCMV. Infected cells were maintained in medium containing 10% fetal calf serum plus the indicated concentrations of Endo-1k, Exo-1w, or the carrier in which the drugs were dissolved (DMSO; 0 μM). Top panels: The cells were photographed 96 h later. Bottom panel: Virus production at 96 h after infection was determined.

Another class of elongase inhibitors is 3-sulfonyl-8-azabi-cyclo[3.2.1]octane compounds (Nagase et al., *J. Med. Chem.*, 52: 4111-4114, 2009). Among these, the endo isomer of compound 1k and 1w inhibit human ELOVL6 with an $IC_{50}$ of about 78 nM and 1w inhibits human ELOVL6 with an $IC_{50}$ of about 6.9 µM in vitro. The endo configuration of these particular compounds is essential for their inhibitory action since exo isomers are devoid of potency. The compounds Endo-1k and Exo-1w were tested for their effect on HCMV replication. MRC5 cells were infected with HCMV AD169 strain at a multiplicity of 0.1 pfu per cell. Without inducing any toxicity on the cells, Endo-1k dramatically reduced HCMV late pUL99 expression and virus yield in a dose dependent manner and at 50 µM it inhibited HCMV replication by a factor of ~400 fold (FIG. 18). Expectedly, the compound Exo-1w neither affected late viral protein expression nor HCMV yield indicating that antiviral function of Endo-1k is due to the inhibition of elongase enzymes specifically.

Figure 19:
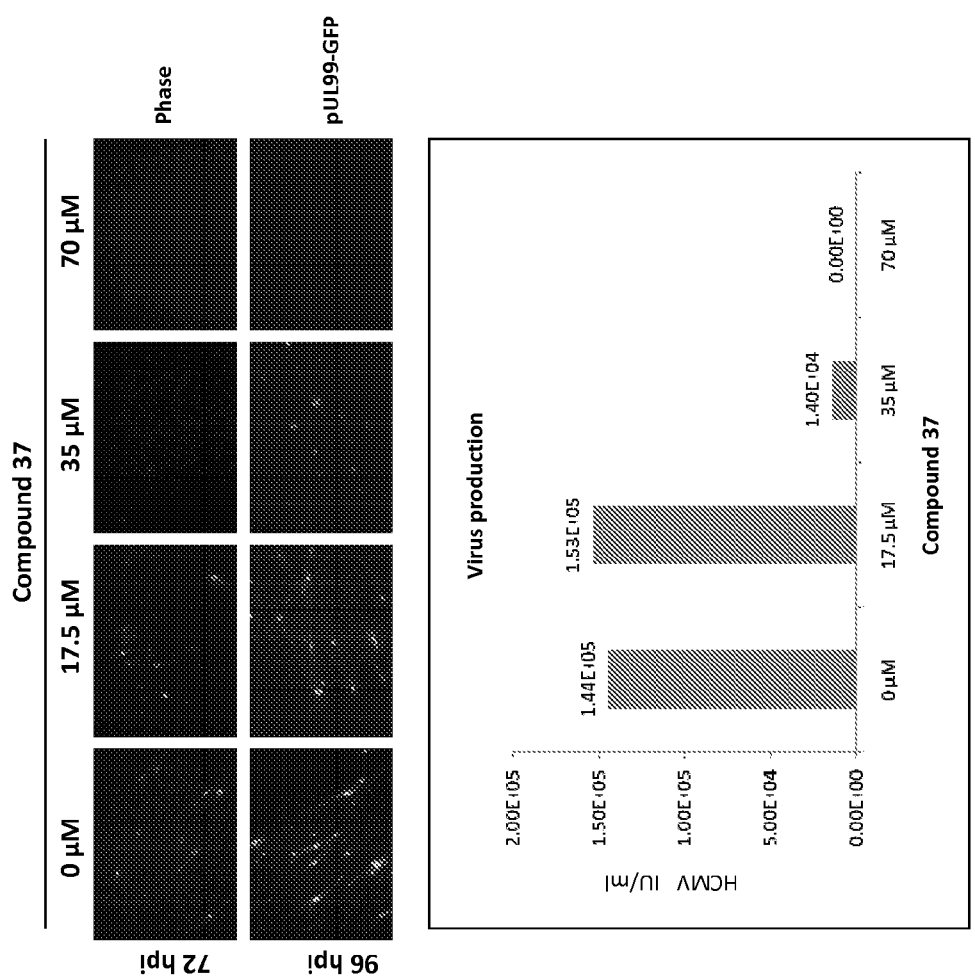
FIG. 19. Dose dependent inhibition of HCMV by the compound 37. About 90% confluent MRCS human fibroblasts were infected with HCMV. Infected cells were maintained in medium containing 10% fetal calf serum plus the indicated concentrations of compound 37 or the carrier in which the drug were dissolved (DMSO; 0 μM). Top panels: The cells were photographed 96 h later. Bottom panel: Virus production at 96 h after infection was determined.

Yet another class of elongase inhibitors is indoledione compounds which are selective for ELOVL6 and ELOVL3 over other elongases (Takahashi et al., *J. Med. Chem.*, 52: 3142-3145, 2009). Among these, Compound 37 inhibits human ELOVL6 and ELOVL3 with $IC_{50}$ of ~8.9 nM and ~337 nM respectively in vitro. The drug has been administrated orally to mice and at a dose of 10 mg/kg which resulted in 30 and 50 µM plasma and liver levels 2 hours after treatment. The effect of Compound 37 on HCMV replication was tested in MRCS cells. The cells were infected with HCMV AD169 strain at a multiplicity of 0.1 pfu per cell. Without inducing any toxicity on the cells, at 35 µM concentration, compound 37 substantially reduced late viral pUL99-GFP expression which is determined by fluorescence microscopy (FIG. 19). Similarly, at 35 µM, compound 37 inhibited HCMV replication by a factor of >10 fold, and at 70 µM, it reduced virus yield to undetectable levels.

The elongase inhibitor compounds indicated above are structurally diverse and potent inhibitors of ELOVL6 and less potent inhibitors ELOVL3. The most potent inhibitor of each classes exerted similar antiviral effects on HCMV. Thus, the compounds that inhibits ELOVL6, ELOVL3 and both ELOVL6/ELOVL3 are identified as potent antivirals.

Example 9

Gene Expression Analysis of ACSLs in HCMV Infected Cells

Figure 20:
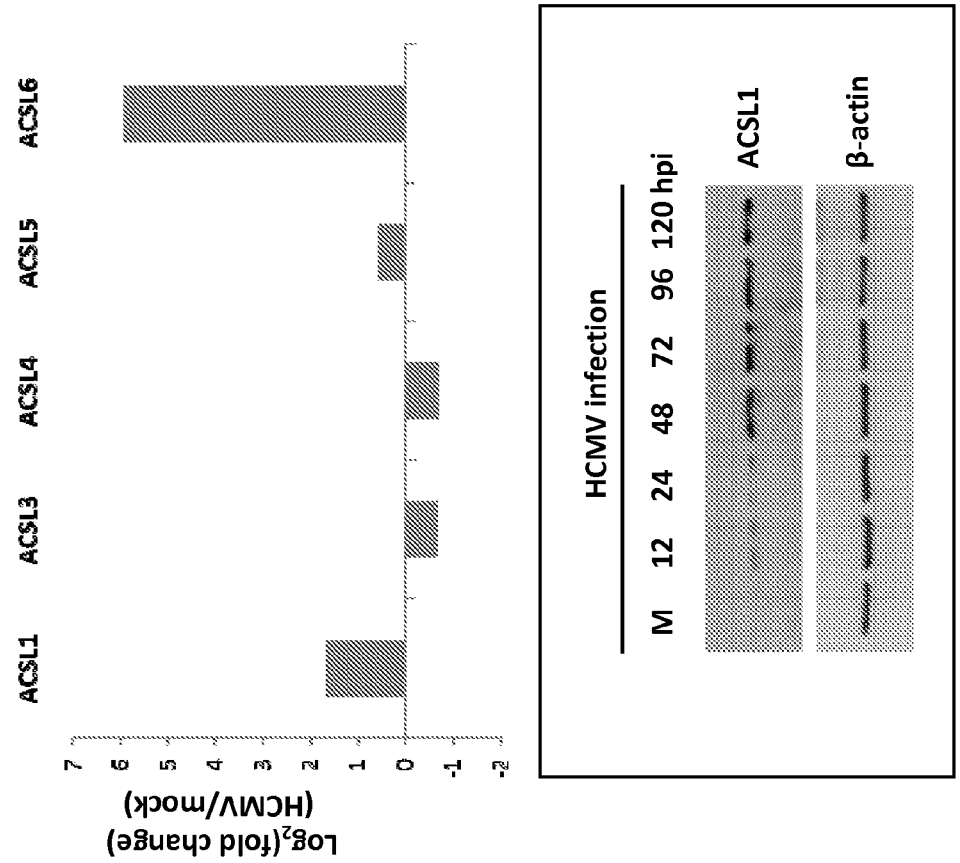
FIG. 20. Gene expression analysis of ACSLs during HCMV infection. Upper panel: MRCS cells were infected with HCMV AD169 strain (MOI=3 pfu/cell) or remained uninfected (mock). The cells were harvested 48 hours after infection and the transcript levels of all five ACSLs were determined by qRT-PCR. The change in transcript levels during infection is shown. Lower panels: MRCS cells were infected with HCMV AD169 strain (MOI=3 pfu/cell) or remained uninfected (M). The cells were harvested at indicated times after infection and processed for western blot. The level of ACSL1 was determined by using an ACSL1-specific monoclonal antibody. β-actin was employed as a loading control.

HCMV infection causes global changes in cellular mRNA levels. To evaluate whether any particular change in ACLS mRNA levels occurs in HCMV infection, the mRNA levels of all 5 ACSL isomers were analyzed by quantitative RT-PCR method. Among these 5 genes, mRNA levels of ACSL1 were elevated at 48 h after infection (FIG. 20; upper panel). In line with this, the analysis of ACSL1 protein levels showed a dramatic increase of ACSL1 during the course of infection (FIG. 20; lower panels). This together with the fact that inhibition of ACSL1 by siRNAs or triacsin C blocks HCMV replication, points ACSL1 as a preferred target for treating HCMV infections. In addition, ACSL6 mRNA levels were shown to be enhanced by HCMV infection even to a greater extent than ACSL1. Note that ACSL6 is not sensitive to triacsin C and these data predict that siRNAs or small molecule inhibitors targeting ACSL6 are potential antivirals.

Example 10

Enhanced Antiviral Effects of a Combination of an ACC Inhibitor and an ELOVL Inhibitor TOFA acts as an inhibitor of acetyl-CoA carboxylase (ACC), which produces malonyl-CoA, the substrate for both de novo fatty acid synthesis by fatty acid synthase (FAS) as well as elongation of acyl-CoAs by elongases of very long chain fatty acids (ELOVLs). The data presented herein indicate that inhibition of ACC or specific ELOVLs alone suffice to interfere with the reproduction of a number of enveloped viruses. The present example concerns the combined use of ACC inhibitors (e.g., TOFA) and ELOVL inhibitors to antagonize viral replication and spread. A non-limiting example of a rationale for a beneficial antiviral effect of a combination of ACC inhibitor and ELOVL inhibitor follows from the fact that ACC catalyzes the rate-limiting reaction for both fatty acid synthesis and elongation, and ELOVL inhibitors directly interfere with the elongation process. Since ACC inhibition by TOFA directly inhibits malonyl-CoA production and indirectly inhibits palmitate production by depriving FAS of the malonyl-CoA needed for palmitate synthesis, it depletes both the substrates for the very long chain fatty acid elongation process, which canonically begins with palmitate. Together with a direct ELOVL inhibitor this would synergistically inhibit ELOVL activity, potentially allowing one or both drugs to be used at a lower dose and prevent undesirable side effects. Non-limiting examples of assays that could be performed to assess the effect of a combination of an ACC inhibitor and an ELOVL inhibitor on HCMV, influenza A, HBV, or HCV replication follow. Assays for TOFA-mediated antiviral activity using HCMV-infected human fibroblasts, influenza A-infected MDCK cells, HIV-1-infected C8166 cells, HBV-producing HepG2-2.2.15 cells, and Huh7 ET cells that contain an HCV RNA replicon have been described in WO 2009/023059. In each assay, various concentrations of TOFA can be combined with various concentrations of different ELOVL inhibitors and assayed for their effect on virus replication. In one preferred embodiment, a physiological concentration of an ELOVL inhibitor will be held constant as the dose of TOFA is increased. Control cultures are treated with no drug, ELOVL inhibitor alone or the various concentrations of TOFA alone. Samples are taken at 24, 48, 72 and 96 hours after initiation of drug treatment. The antiviral effect of ELOVL inhibitor plus each concentration of TOFA is then compared to the activity of ELOVL inhibitor alone or the various concentrations of TOFA alone. Uptake of neutral red dye can be used to determine the relative level of toxicity in duplicate cultures at each time a sample is harvested. The concentration of TOFA required to reduce viral growth and/or replication by 10-fold is reduced by 2-fold, and sometime more, by the presence of a therapeutically effective concentration of the ELOVL inhibitor.

Example 11

Antiviral Effects of TOFA

TOFA is an allosteric inhibitor of ACACA and has been shown to block production of human cytomegalovirus progeny in cultured cells as described in WO 2009/023059. TOFA was tested for its ability to inhibit HCMV replication. At a dose of 5 µg/ml, TOFA inhibited HCMV replication by a factor of >500 fold.

Figure 21:
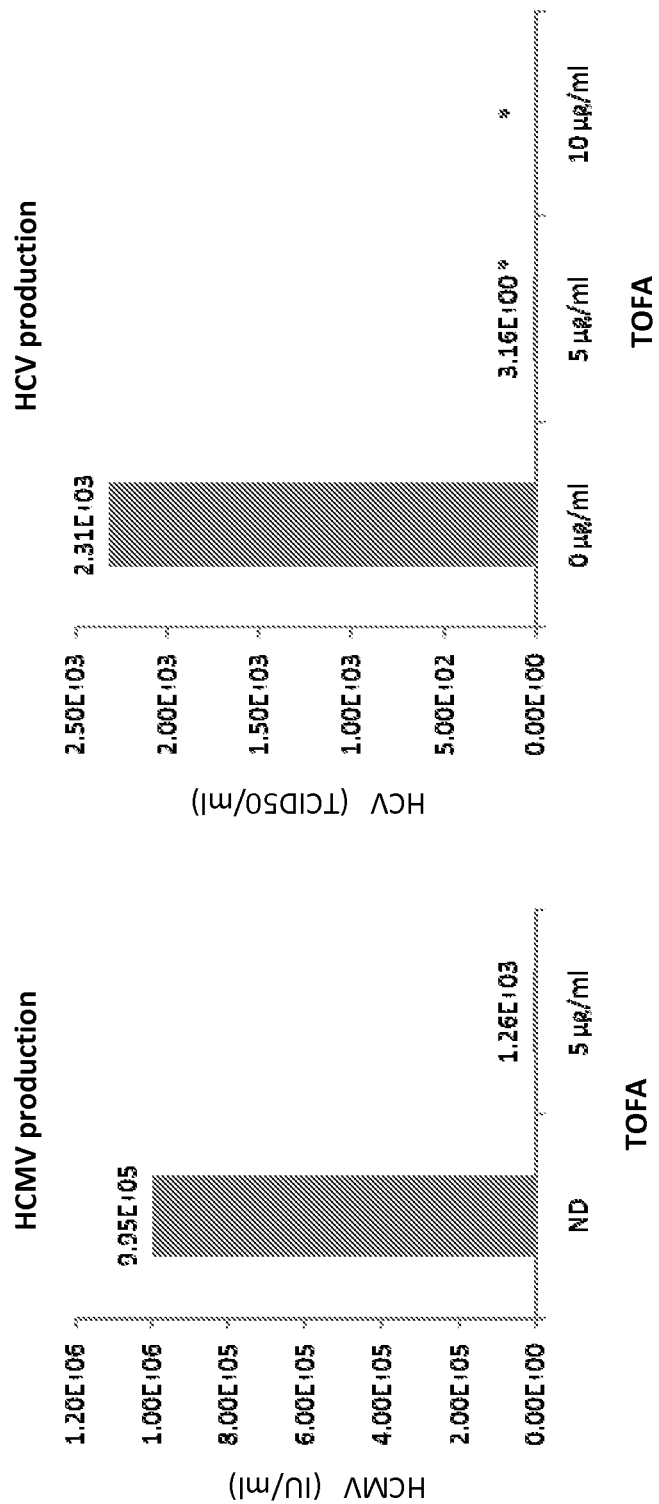
FIG. 21. Dose dependent inhibition of hepatitis C virus by triacsin C. Huh7.5 cells were infected a derivative of HCV JFH1 strain (MOI=0.1 $TCID_{50}$/cell) Infected cells were maintained in medium containing 10% fetal calf serum plus DMSO (0 μg/ml TOFA) or TOFA at the indicated doses. Media were harvested at 72 h and infectious virus was quantified by standard $TCID_{50}$ assay on Huh7.5 cells. The star (*) indicates that the virus yield is below the detection limit which is 1.43E+0.1 $TCID_{50}$/ml for this assay.

In addition, HCV growth was also inhibited by TOFA. Huh7.5 cells which was infected with HCV and treated with indicated amounts of TOFA (FIG. 21). TOFA inhibited the release of infectious HCV particles to the culture medium at 5 µg/ml by a factor of >500 fold and at 10 µg/ml by a factor of >1000 fold.

The following examples provide non-limiting examples of proposed combinations of the present invention.

Example 12

Enhanced Antiviral Effects of a Combination of an ACC Inhibitor and an ACSL1 Inhibitor Acyl-CoA synthetase (long chain) member 1 (ACSL1) activates free fatty acids, such as the palmitate derived from de novo fatty acid synthesis, by conjugating them to coenzyme A. These acyl-CoAs are the substrate for the majority of the lipid biosynthetic enzymes that act on acyl chains. The data presented herein indicate that inhibition of ACC or ACSL1 alone suffices to interfere with the reproduction of a number of enveloped viruses. The present example concerns the combined use of ACC inhibitors (e.g., TOFA) and ACSL1 inhibitor (e.g., triacsin C) to antagonize viral replication and spread. There are multiple rationales for such a combination. Non-limiting examples of such rationales include the following. While viral infection can up-regulate the de novo fatty acid biosynthetic, the major source for fatty acids in most mammalian cell types consists of the circulating lipids present in the plasma. Therefore, a TOFA-induced blockade of fatty acid biosynthesis might be partially or completely overcome through the influx of plasma fatty acids. Triacsin C co-treatment could prevent these exogenous fatty acids from being activated and utilized, thereby enhancing the efficacy of TOFA treatment. Conversely, triacsin C-induced ACSL1 inhibition might be overcome by the expression of a different, triacsin-resistant ACSL; for example, ACSL5 overexpression was shown to rescue the inhibitory effect of triacsin C on glioma cells (Mashima et al., Cancer Sci. 2009 100:1556-1562). This presents an infecting virus with a possibly host cell-dependent means of escape from triacsin C inhibition. Simultaneous treatment with TOFA, however, would deplete the substrates for all ACSL enzymes, and so prevent viral escape. Thus these drugs in combination might synergize so as to lower the effective dose of one or both, as well as lower the occurrence of treatment failure.

Non-limiting examples of assays that could be performed to assess the effect of a combination of an ACC inhibitor and an ACSL1 inhibitor on HCMV, influenza A, HBV, or HCV replication follow. Assays for TOFA-mediated antiviral activity using HCMV-infected human fibroblasts, influenza A-infected MDCK cells, HIV-1-infected C8166 cells, HBV-producing HepG2-2.2.15 cells, and Huh7 ET cells that contain an HCV RNA replicon have been described in WO 2009/023059. In each assay, various concentrations of TOFA can be combined with various concentrations of triacsin C and assayed for their effect on virus replication. In one preferred embodiment, a physiological concentration of triacsin C is held constant as the dose of TOFA is increased. Control cultures are treated with no drug, triacsin C alone or the various concentrations of TOFA alone. Samples are taken at 24, 48, 72 and 96 hours after initiation of drug treatment. The antiviral effect of triacsin C plus each concentration of TOFA is then compared to the activity of triacsin C alone or the various concentrations of TOFA alone. Uptake of neutral red dye is used to determine the relative level of toxicity in duplicate cultures at each time a sample is harvested. In the presence of a pharmacologically acceptable concentration of triacsin C, the concentration of TOFA required to produce a 10-fold reduction in HCMV replication is markedly reduced, from ~10 µg/mL to <5 µg/mL. At 10 µg/mL of TOFA, the magnitude of the therapeutic effect is increased from ~10-fold in the absence of triacsin C to ~100-fold in its presence. The combined use of TOFA and triacsin C does not increase host cell toxicity as measured by the neutral red dye assay. Similar results are obtained for other triacsins and structurally related ACSL1 inhibitors.

Example 13

Enhanced Antiviral Effects of a Combination of an ACC Inhibitor and an Inhibitor of Viral Neuraminidase Neuraminidase inhibitors are a critical component of the current standard of care for acute infection by influenza A. These virally-encoded enzymes cleave sialic acid residues from glycoproteins on the host cell surface, freeing the recently replicated virion to diffuse away and invade another cell. Neuraminidase inhibitors such as oseltamivir (TAMIFLU™) block this process, thereby blocking viral release. The present example concerns the combined use of ACC inhibitors (e.g., TOFA) and neuraminidase inhibitors (e.g., oseltamivir, zanamivir) to antagonize viral replication and spread. A non-limiting example of a rationale for a beneficial antiviral effect of a combination of ACC inhibitor and neuraminidase inhibitor follows from the fact that these drugs target different but equally necessary processes in viral replication: virion assembly and virion release. They would therefore be expected to act synergistically to inhibit viral spread, e.g., if TOFA treatment alone results in a ten-fold reduction in viable virions assembled, and oseltamivir treatment alone causes a ten-fold reduction in the virion release, then the combination would result in a hundred-fold reduction in the release of viable virions.

Non-limiting examples of assays that could be performed to assess the effect of a combination of an ACC inhibitor and a neuraminidase inhibitor on influenza A replication follow. Assays for TOFA-mediated antiviral activity using influenza A-infected MDCK cells have been described in WO 2009/023059. In each assay, various concentrations of TOFA can be combined with various concentrations of oseltamivir and assayed for their effect on virus replication. In one preferred embodiment, a physiological concentration of oseltamivir is held constant as the dose of TOFA is increased. Control cultures are treated with no drug, oseltamivir alone or the various concentrations of TOFA alone. Samples are taken at 24, 48, 72 and 96 hours after initiation of drug treatment. The antiviral effect of oseltamivir plus each concentration of TOFA is then compared to the activity of oseltamivir alone or the various concentrations of TOFA alone. Uptake of neutral red dye is used to determine the relative level of toxicity in duplicate cultures at each time a sample is harvested. In the presence of a pharmacologically acceptable concentration of oseltamivir, the concentration of TOFA required to produce a 10-fold reduction in HCMV replication is markedly reduced, from ~10 μg/mL to <5 μg/mL. At 10 μg/mL of TOFA, the magnitude of the therapeutic effect is increased from ~10-fold in the absence of oseltamivir to ~100-fold in its presence. The combined use of TOFA and oseltamivir does not increase host cell toxicity as measured by the neutral red dye assay. Similar results are obtained for other neuraminidase inhibitors.

Example 14

Enhanced Antiviral Effects of a Combination of an ACC Inhibitor and a Viral Entry Inhibitor One key step in the HIV-1 life cycle consists of the virion's recognizing, binding to, and finally fusing with the correct host cell. This is the process by which newly-synthesized virions are able to invade a new host cell, thereby spreading the infection. Viral entry is so central to the pathology of HIV-1 infection that pharmacological inhibition of binding and fusion events has proven a viable strategy in the clinical management of the disease. The present example concerns the combined use of ACC inhibitors (e.g., TOFA) and entry inhibitors (e.g., maraviroc, enfurtivide) to antagonize viral replication and spread. A non-limiting example of a rationale for a beneficial antiviral effect of a combination of ACC inhibitor and neuraminidase inhibitor follows from the fact that these drugs target different but equally necessary processes in viral replication: virion assembly and virion entry. They would therefore be expected to act synergistically to inhibit viral spread, e.g., if TOFA treatment alone results in a ten-fold reduction in viable virions assembled, and enfurtivide treatment alone causes a ten-fold reduction in the successful entry of viable virions, then the combination would result in a hundred-fold reduction in the entry of viable virions.

Non-limiting examples of assays that could be performed to assess the effect of a combination of an ACC inhibitor and an entry inhibitor on HIV-1 replication follow. Assays for TOFA-mediated antiviral activity using HIV-1-infected C8166 cells have been described in (WO 2009/023059). In each assay, various concentrations of TOFA can be combined with various concentrations of enfurtivide and assayed for their effect on virus replication. In one preferred embodiment, a physiological concentration of enfurtivide is held constant as the dose of TOFA is increased. Control cultures are treated with no drug, enfurtivide alone or the various concentrations of TOFA alone. Samples are taken at 24, 48, 72 and 96 hours after initiation of drug treatment. The antiviral effect of enfurtivide plus each concentration of TOFA is then compared to the activity of enfurtivide alone or the various concentrations of TOFA alone. Uptake of neutral red dye is used to determine the relative level of toxicity in duplicate cultures at each time a sample is harvested. In the presence of a pharmacologically acceptable concentration of enfurtivide, the concentration of TOFA required to produce a 10-fold reduction in HCMV replication is markedly reduced, from ~10 μg/mL to <5 μg/mL. At 10 μg/mL of TOFA, the magnitude of the therapeutic effect is increased from ~10-fold in the absence of enfurtivide to ~100-fold in its presence. The combined use of TOFA and enfurtivide does not increase host cell toxicity as measured by the neutral red dye assay. Similar results are obtained for other entry inhibitors.

We claim:

1. A method of treating or preventing viral infection in a mammal, comprising administering to the mammalian subject in need thereof a therapeutically effective amount of an agent that inhibits a long chain fatty acid synthesis enzyme, wherein the virus is human cytomegalovirus (HCMV) and the agent is a compound of Formula VIII

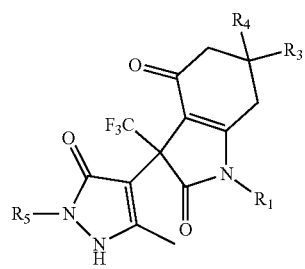

(VIII)

wherein $R_1$ is selected from H, unsubstituted phenyl; substituted phenyl where substitutents are selected from F, Me, Et, Cl, OMe, $OCF_3$ and $CF_3$; $C_{1-6}$ alkyl; and $C_{3-6}$ cycloalkyl;

wherein $R_3$ and $R_4$ are independently selected from H; $C_{1-3}$ alkyl; and phenyl; or $R_3$ and $R_4$ taken together form a cycloalkyl of formula —$(CH2)_n$— where n=2, 3, 4 and 5;

wherein $R_5$ is selected from methyl; $CF_3$; cyclopropyl; unsubstituted phenyl; mono- and disubstituted phenyl where substitutents are selected from F, Me, Et, CN, iPr, Cl, OMe, OPh, $OCF_3$, and $CF_3$; unsubstituted heteroaromatic group; and imidazole;

or prodrug thereof, or pharmaceutically acceptable salt or ester of said compound or prodrug thereof.

2. The method of claim 1, wherein $R^5$ is

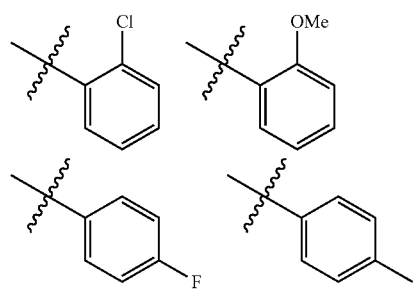

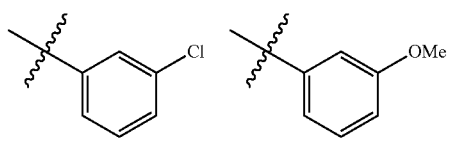

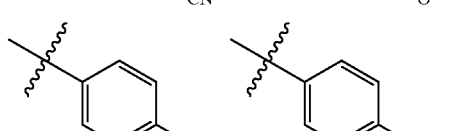

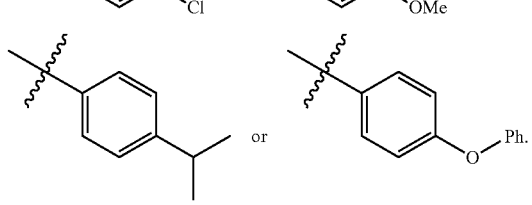

3. The method of claim 1, wherein the compound of Formula VIII is selected from the group consisting of

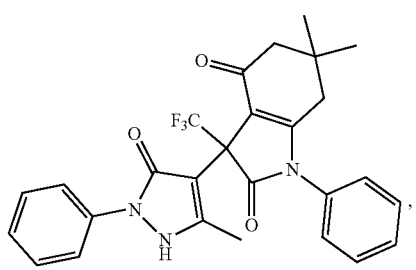

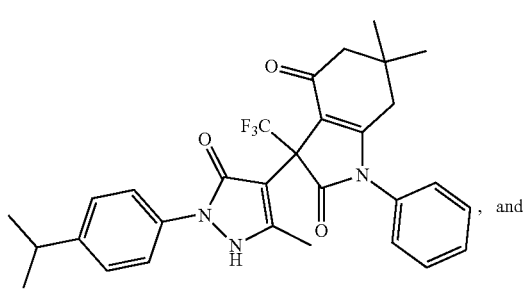

-continued
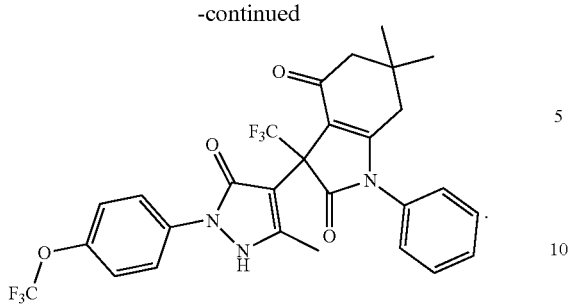
4. The method of claim 1, wherein the virus is HCMV, which further comprises administering a therapeutically effective amount of an agent that inhibits HCMV-encoded DNA polymerase, wherein the agent is selected from the group consisting of gancyclovir, valgancyclovir, cidofovir, and foscarnet.
* * * * *

SEQUENCE LISTING

<160> NUMBER OF SEQ ID NOS: 267

<210> SEQ ID NO 1
<211> LENGTH: 21
<212> TYPE: DNA
<213> ORGANISM: Artificial
<220> FEATURE:
<223> OTHER INFORMATION: siRNA

<400> SEQUENCE: 1
guuugauugu gccauacuut t                                              21

<210> SEQ ID NO 2
<211> LENGTH: 21
<212> TYPE: DNA
<213> ORGANISM: Artificial
<220> FEATURE:
<223> OTHER INFORMATION: siRNA

<400> SEQUENCE: 2
aaguauggca caaucaaact t					21

<210> SEQ ID NO 3
<211> LENGTH: 21
<212> TYPE: DNA
<213> ORGANISM: Artificial
<220> FEATURE:
<223> OTHER INFORMATION: siRNA

<400> SEQUENCE: 3
caugucuggc uugcaccuat t					21

<210> SEQ ID NO 4
<211> LENGTH: 21
<212> TYPE: DNA
<213> ORGANISM: Artificial
<220> FEATURE:
<223> OTHER INFORMATION: siRNA

<400> SEQUENCE: 4
uaggugcaag ccagacaugt t					21

<210> SEQ ID NO 5
<211> LENGTH: 21
<212> TYPE: DNA
<213> ORGANISM: Artificial
<220> FEATURE:
<223> OTHER INFORMATION: siRNA

<400> SEQUENCE: 5
gauugagaag guucuuauut t					21

<210> SEQ ID NO 6
<211> LENGTH: 21
<212> TYPE: DNA
<213> ORGANISM: Artificial
<220> FEATURE:
<223> OTHER INFORMATION: siRNA

<400> SEQUENCE: 6
aauaagaacc uucucaauct t					21

<210> SEQ ID NO 7
<211> LENGTH: 21
<212> TYPE: DNA
<213> ORGANISM: Artificial
<220> FEATURE:
<223> OTHER INFORMATION: siRNA

<400> SEQUENCE: 7
gugugaagaa gaaagcucat t					21

<210> SEQ ID NO 8
<211> LENGTH: 21
<212> TYPE: DNA
<213> ORGANISM: Artificial
<220> FEATURE:
<223> OTHER INFORMATION: siRNA

<400> SEQUENCE: 8
ugagcuuucu ucuucacact t					21

<210> SEQ ID NO 9
<211> LENGTH: 21
<212> TYPE: DNA
<213> ORGANISM: Artificial

```
<220> FEATURE:
<223> OTHER INFORMATION: siRNA

<400> SEQUENCE: 9
gaacaaggau gcuuugcuut t                                      21

<210> SEQ ID NO 10
<211> LENGTH: 21
<212> TYPE: DNA
<213> ORGANISM: Artificial
<220> FEATURE:
<223> OTHER INFORMATION: siRNA

<400> SEQUENCE: 10
aagcaaagca uccuuguuct t                                      21

<210> SEQ ID NO 11
<211> LENGTH: 21
<212> TYPE: DNA
<213> ORGANISM: Artificial
<220> FEATURE:
<223> OTHER INFORMATION: siRNA

<400> SEQUENCE: 11
gaaaugaagc caucacguat t                                      21

<210> SEQ ID NO 12
<211> LENGTH: 21
<212> TYPE: DNA
<213> ORGANISM: Artificial
<220> FEATURE:
<223> OTHER INFORMATION: siRNA

<400> SEQUENCE: 12
uacgugaugg cuucauuuct t                                      21

<210> SEQ ID NO 13
<211> LENGTH: 21
<212> TYPE: DNA
<213> ORGANISM: Artificial
<220> FEATURE:
<223> OTHER INFORMATION: siRNA

<400> SEQUENCE: 13
cccucuaugc caacaaugut t                                      21

<210> SEQ ID NO 14
<211> LENGTH: 21
<212> TYPE: DNA
<213> ORGANISM: Artificial
<220> FEATURE:
<223> OTHER INFORMATION: siRNA

<400> SEQUENCE: 14
acauuguugg cauagagggt t                                      21

<210> SEQ ID NO 15
<211> LENGTH: 21
<212> TYPE: DNA
<213> ORGANISM: Artificial
<220> FEATURE:
<223> OTHER INFORMATION: siRNA

<400> SEQUENCE: 15
ggguuuggug gacuuccgat t                                      21
```

```
<210> SEQ ID NO 16
<211> LENGTH: 21
<212> TYPE: DNA
<213> ORGANISM: Artificial
<220> FEATURE:
<223> OTHER INFORMATION: siRNA

<400> SEQUENCE: 16
ucggaagucc accaaaccct t                                              21

<210> SEQ ID NO 17
<211> LENGTH: 21
<212> TYPE: DNA
<213> ORGANISM: Artificial
<220> FEATURE:
<223> OTHER INFORMATION: siRNA

<400> SEQUENCE: 17
ccaacaaugu ucagagggut t                                              21

<210> SEQ ID NO 18
<211> LENGTH: 21
<212> TYPE: DNA
<213> ORGANISM: Artificial
<220> FEATURE:
<223> OTHER INFORMATION: siRNA

<400> SEQUENCE: 18
acccucugaa cauuguuggt t                                              21

<210> SEQ ID NO 19
<211> LENGTH: 21
<212> TYPE: DNA
<213> ORGANISM: Artificial
<220> FEATURE:
<223> OTHER INFORMATION: siRNA

<400> SEQUENCE: 19
caagcuaaag aucaguauat t                                              21

<210> SEQ ID NO 20
<211> LENGTH: 21
<212> TYPE: DNA
<213> ORGANISM: Artificial
<220> FEATURE:
<223> OTHER INFORMATION: siRNA

<400> SEQUENCE: 20
uauacugauc uuuagcuugt t                                              21

<210> SEQ ID NO 21
<211> LENGTH: 21
<212> TYPE: DNA
<213> ORGANISM: Artificial
<220> FEATURE:
<223> OTHER INFORMATION: siRNA

<400> SEQUENCE: 21
gugugaaugg aguuguccat t                                              21

<210> SEQ ID NO 22
<211> LENGTH: 21
<212> TYPE: DNA
<213> ORGANISM: Artificial
<220> FEATURE:
<223> OTHER INFORMATION: siRNA
```

-continued

<400> SEQUENCE: 22
uggacaacuc cauucacact t                                    21

<210> SEQ ID NO 23
<211> LENGTH: 21
<212> TYPE: DNA
<213> ORGANISM: Artificial
<220> FEATURE:
<223> OTHER INFORMATION: siRNA

<400> SEQUENCE: 23
gucucaugau aggcauagat t                                    21

<210> SEQ ID NO 24
<211> LENGTH: 21
<212> TYPE: DNA
<213> ORGANISM: Artificial
<220> FEATURE:
<223> OTHER INFORMATION: siRNA

<400> SEQUENCE: 24
ucuaugccua ucaugagact t                                    21

<210> SEQ ID NO 25
<211> LENGTH: 21
<212> TYPE: DNA
<213> ORGANISM: Artificial
<220> FEATURE:
<223> OTHER INFORMATION: siRNA

<400> SEQUENCE: 25
caccuaugug cuucacugat t                                    21

<210> SEQ ID NO 26
<211> LENGTH: 21
<212> TYPE: DNA
<213> ORGANISM: Artificial
<220> FEATURE:
<223> OTHER INFORMATION: siRNA

<400> SEQUENCE: 26
ucagugaagc acauaggugt t                                    21

<210> SEQ ID NO 27
<211> LENGTH: 21
<212> TYPE: DNA
<213> ORGANISM: Artificial
<220> FEATURE:
<223> OTHER INFORMATION: siRNA

<400> SEQUENCE: 27
ggaauuguca guuuagauut t                                    21

<210> SEQ ID NO 28
<211> LENGTH: 21
<212> TYPE: DNA
<213> ORGANISM: Artificial
<220> FEATURE:
<223> OTHER INFORMATION: siRNA

<400> SEQUENCE: 28
aaucuaaacu gacaauucct t                                    21

<210> SEQ ID NO 29

```
<211> LENGTH: 21
<212> TYPE: DNA
<213> ORGANISM: Artificial
<220> FEATURE:
<223> OTHER INFORMATION: siRNA

<400> SEQUENCE: 29
gguuaauagc ucuauuauat t                                              21

<210> SEQ ID NO 30
<211> LENGTH: 21
<212> TYPE: DNA
<213> ORGANISM: Artificial
<220> FEATURE:
<223> OTHER INFORMATION: siRNA

<400> SEQUENCE: 30
uauaauagag cuauuaacct t                                              21

<210> SEQ ID NO 31
<211> LENGTH: 21
<212> TYPE: DNA
<213> ORGANISM: Artificial
<220> FEATURE:
<223> OTHER INFORMATION: siRNA

<400> SEQUENCE: 31
caacugcgag uacaucaaat t                                              21

<210> SEQ ID NO 32
<211> LENGTH: 21
<212> TYPE: DNA
<213> ORGANISM: Artificial
<220> FEATURE:
<223> OTHER INFORMATION: siRNA

<400> SEQUENCE: 32
uuugauguac ucgcaguugt t                                              21

<210> SEQ ID NO 33
<211> LENGTH: 21
<212> TYPE: DNA
<213> ORGANISM: Artificial
<220> FEATURE:
<223> OTHER INFORMATION: siRNA

<400> SEQUENCE: 33
ccaaccaggu guaugcagat t                                              21

<210> SEQ ID NO 34
<211> LENGTH: 21
<212> TYPE: DNA
<213> ORGANISM: Artificial
<220> FEATURE:
<223> OTHER INFORMATION: siRNA

<400> SEQUENCE: 34
ucugcauaca ccugguuggt t                                              21

<210> SEQ ID NO 35
<211> LENGTH: 21
<212> TYPE: DNA
<213> ORGANISM: Artificial
<220> FEATURE:
<223> OTHER INFORMATION: siRNA

<400> SEQUENCE: 35
```
caagucuggg ccuugccaut t                                             21

<210> SEQ ID NO 36
<211> LENGTH: 21
<212> TYPE: DNA
<213> ORGANISM: Artificial
<220> FEATURE:
<223> OTHER INFORMATION: siRNA

<400> SEQUENCE: 36
auggcaaggc ccagacuugt t                                             21

<210> SEQ ID NO 37
<211> LENGTH: 21
<212> TYPE: DNA
<213> ORGANISM: Artificial
<220> FEATURE:
<223> OTHER INFORMATION: siRNA

<400> SEQUENCE: 37
gccauuauga gugugcauut t                                             21

<210> SEQ ID NO 38
<211> LENGTH: 21
<212> TYPE: DNA
<213> ORGANISM: Artificial
<220> FEATURE:
<223> OTHER INFORMATION: siRNA

<400> SEQUENCE: 38
aaugcacacu cauaauggct t                                             21

<210> SEQ ID NO 39
<211> LENGTH: 21
<212> TYPE: DNA
<213> ORGANISM: Artificial
<220> FEATURE:
<223> OTHER INFORMATION: siRNA

<400> SEQUENCE: 39
gccaaauggg cagcccgaat t                                             21

<210> SEQ ID NO 40
<211> LENGTH: 21
<212> TYPE: DNA
<213> ORGANISM: Artificial
<220> FEATURE:
<223> OTHER INFORMATION: siRNA

<400> SEQUENCE: 40
uucgggcugc ccauuuggct t                                             21

<210> SEQ ID NO 41
<211> LENGTH: 21
<212> TYPE: DNA
<213> ORGANISM: Artificial
<220> FEATURE:
<223> OTHER INFORMATION: siRNA

<400> SEQUENCE: 41
cucaaaucuu ucucccuaut t                                             21

<210> SEQ ID NO 42
<211> LENGTH: 21
<212> TYPE: DNA

```
<213> ORGANISM: Artificial
<220> FEATURE:
<223> OTHER INFORMATION: siRNA

<400> SEQUENCE: 42
auagggagaa agauuugagt t                                              21

<210> SEQ ID NO 43
<211> LENGTH: 21
<212> TYPE: DNA
<213> ORGANISM: Artificial
<220> FEATURE:
<223> OTHER INFORMATION: siRNA

<400> SEQUENCE: 43
guaaccuccu ggaucugaat t                                              21

<210> SEQ ID NO 44
<211> LENGTH: 21
<212> TYPE: DNA
<213> ORGANISM: Artificial
<220> FEATURE:
<223> OTHER INFORMATION: siRNA

<400> SEQUENCE: 44
uucagaucca ggagguuact t                                              21

<210> SEQ ID NO 45
<211> LENGTH: 21
<212> TYPE: DNA
<213> ORGANISM: Artificial
<220> FEATURE:
<223> OTHER INFORMATION: siRNA

<400> SEQUENCE: 45
ccaguaaccu ccuggaucut t                                              21

<210> SEQ ID NO 46
<211> LENGTH: 21
<212> TYPE: DNA
<213> ORGANISM: Artificial
<220> FEATURE:
<223> OTHER INFORMATION: siRNA

<400> SEQUENCE: 46
agauccagga gguuacuggt t                                              21

<210> SEQ ID NO 47
<211> LENGTH: 21
<212> TYPE: DNA
<213> ORGANISM: Artificial
<220> FEATURE:
<223> OTHER INFORMATION: siRNA

<400> SEQUENCE: 47
ccuaugacuu gagcagugut t                                              21

<210> SEQ ID NO 48
<211> LENGTH: 21
<212> TYPE: DNA
<213> ORGANISM: Artificial
<220> FEATURE:
<223> OTHER INFORMATION: siRNA

<400> SEQUENCE: 48
acacugcuca agucauaggt t                                              21
```

```
<210> SEQ ID NO 49
<211> LENGTH: 21
<212> TYPE: DNA
<213> ORGANISM: Artificial
<220> FEATURE:
<223> OTHER INFORMATION: siRNA

<400> SEQUENCE: 49
guaauuaaag aaaugguuat t                                              21

<210> SEQ ID NO 50
<211> LENGTH: 21
<212> TYPE: DNA
<213> ORGANISM: Artificial
<220> FEATURE:
<223> OTHER INFORMATION: siRNA

<400> SEQUENCE: 50
uaaccauuuc uuuaauuact t                                              21

<210> SEQ ID NO 51
<211> LENGTH: 21
<212> TYPE: DNA
<213> ORGANISM: Artificial
<220> FEATURE:
<223> OTHER INFORMATION: siRNA

<400> SEQUENCE: 51
gcuaucaacu agaucgacat t                                              21

<210> SEQ ID NO 52
<211> LENGTH: 21
<212> TYPE: DNA
<213> ORGANISM: Artificial
<220> FEATURE:
<223> OTHER INFORMATION: siRNA

<400> SEQUENCE: 52
ugucgaucua guugauagct t                                              21

<210> SEQ ID NO 53
<211> LENGTH: 21
<212> TYPE: DNA
<213> ORGANISM: Artificial
<220> FEATURE:
<223> OTHER INFORMATION: siRNA

<400> SEQUENCE: 53
gauaauaaau ucaacuauut t                                              21

<210> SEQ ID NO 54
<211> LENGTH: 21
<212> TYPE: DNA
<213> ORGANISM: Artificial
<220> FEATURE:
<223> OTHER INFORMATION: siRNA

<400> SEQUENCE: 54
aauaguugaa uuuauuauct t                                              21

<210> SEQ ID NO 55
<211> LENGTH: 21
<212> TYPE: DNA
<213> ORGANISM: Artificial
<220> FEATURE:
```

```
<223> OTHER INFORMATION: siRNA

<400> SEQUENCE: 55
gcuacaacuu acagugucat t                                              21

<210> SEQ ID NO 56
<211> LENGTH: 21
<212> TYPE: DNA
<213> ORGANISM: Artificial
<220> FEATURE:
<223> OTHER INFORMATION: siRNA

<400> SEQUENCE: 56
ugacacugua aguuguagct t                                              21

<210> SEQ ID NO 57
<211> LENGTH: 21
<212> TYPE: DNA
<213> ORGANISM: Artificial
<220> FEATURE:
<223> OTHER INFORMATION: siRNA

<400> SEQUENCE: 57
caaaguuucu uuggaccaat t                                              21

<210> SEQ ID NO 58
<211> LENGTH: 21
<212> TYPE: DNA
<213> ORGANISM: Artificial
<220> FEATURE:
<223> OTHER INFORMATION: siRNA

<400> SEQUENCE: 58
uugguccaaa gaaacuuugt t                                              21

<210> SEQ ID NO 59
<211> LENGTH: 21
<212> TYPE: DNA
<213> ORGANISM: Artificial
<220> FEATURE:
<223> OTHER INFORMATION: siRNA

<400> SEQUENCE: 59
cguuagucau ccucuucuut t                                              21

<210> SEQ ID NO 60
<211> LENGTH: 21
<212> TYPE: DNA
<213> ORGANISM: Artificial
<220> FEATURE:
<223> OTHER INFORMATION: siRNA

<400> SEQUENCE: 60
aagaagagga ugacuaacgt t                                              21

<210> SEQ ID NO 61
<211> LENGTH: 21
<212> TYPE: DNA
<213> ORGANISM: Artificial
<220> FEATURE:
<223> OTHER INFORMATION: siRNA

<400> SEQUENCE: 61
ggaguauugg gcaaccucat t                                              21
```

```
<210> SEQ ID NO 62
<211> LENGTH: 21
<212> TYPE: DNA
<213> ORGANISM: Artificial
<220> FEATURE:
<223> OTHER INFORMATION: siRNA

<400> SEQUENCE: 62
ugagguugcc caauacucct t                                              21

<210> SEQ ID NO 63
<211> LENGTH: 21
<212> TYPE: DNA
<213> ORGANISM: Artificial
<220> FEATURE:
<223> OTHER INFORMATION: siRNA

<400> SEQUENCE: 63
gaaugauuag guugccuuat t                                              21

<210> SEQ ID NO 64
<211> LENGTH: 21
<212> TYPE: DNA
<213> ORGANISM: Artificial
<220> FEATURE:
<223> OTHER INFORMATION: siRNA

<400> SEQUENCE: 64
uaaggcaacc uaaucauuct t                                              21

<210> SEQ ID NO 65
<211> LENGTH: 21
<212> TYPE: DNA
<213> ORGANISM: Artificial
<220> FEATURE:
<223> OTHER INFORMATION: siRNA

<400> SEQUENCE: 65
cacuuauucu gguccuucat t                                              21

<210> SEQ ID NO 66
<211> LENGTH: 21
<212> TYPE: DNA
<213> ORGANISM: Artificial
<220> FEATURE:
<223> OTHER INFORMATION: siRNA

<400> SEQUENCE: 66
ugaaggacca gaauaagugt t                                              21

<210> SEQ ID NO 67
<211> LENGTH: 21
<212> TYPE: DNA
<213> ORGANISM: Artificial
<220> FEATURE:
<223> OTHER INFORMATION: siRNA

<400> SEQUENCE: 67
ggcuuaugca uuugugcuat t                                              21

<210> SEQ ID NO 68
<211> LENGTH: 21
<212> TYPE: DNA
<213> ORGANISM: Artificial
<220> FEATURE:
<223> OTHER INFORMATION: siRNA
```

```
<400> SEQUENCE: 68
uagcacaaau gcauaagcct t                                              21

<210> SEQ ID NO 69
<211> LENGTH: 21
<212> TYPE: DNA
<213> ORGANISM: Artificial
<220> FEATURE:
<223> OTHER INFORMATION: siRNA

<400> SEQUENCE: 69
caauggaccu gucagcaaat t                                              21

<210> SEQ ID NO 70
<211> LENGTH: 21
<212> TYPE: DNA
<213> ORGANISM: Artificial
<220> FEATURE:
<223> OTHER INFORMATION: siRNA

<400> SEQUENCE: 70
uuugcugaca gguccauugt t                                              21

<210> SEQ ID NO 71
<211> LENGTH: 21
<212> TYPE: DNA
<213> ORGANISM: Artificial
<220> FEATURE:
<223> OTHER INFORMATION: siRNA

<400> SEQUENCE: 71
caugucagug uugacuuuat t                                              21

<210> SEQ ID NO 72
<211> LENGTH: 21
<212> TYPE: DNA
<213> ORGANISM: Artificial
<220> FEATURE:
<223> OTHER INFORMATION: siRNA

<400> SEQUENCE: 72
uaaagucaac acugacaugt t                                              21

<210> SEQ ID NO 73
<211> LENGTH: 21
<212> TYPE: DNA
<213> ORGANISM: Artificial
<220> FEATURE:
<223> OTHER INFORMATION: siRNA

<400> SEQUENCE: 73
cuaacaaggu ggaccaccat t                                              21

<210> SEQ ID NO 74
<211> LENGTH: 21
<212> TYPE: DNA
<213> ORGANISM: Artificial
<220> FEATURE:
<223> OTHER INFORMATION: siRNA

<400> SEQUENCE: 74
ugguggucca ccuuguuagt t                                              21

<210> SEQ ID NO 75
<211> LENGTH: 21
```

```
<212> TYPE: DNA
<213> ORGANISM: Artificial
<220> FEATURE:
<223> OTHER INFORMATION: siRNA

<400> SEQUENCE: 75
cuaaccaucc cugagaucat t                                              21

<210> SEQ ID NO 76
<211> LENGTH: 21
<212> TYPE: DNA
<213> ORGANISM: Artificial
<220> FEATURE:
<223> OTHER INFORMATION: siRNA

<400> SEQUENCE: 76
ugaucucagg gaugguuagt t                                              21

<210> SEQ ID NO 77
<211> LENGTH: 21
<212> TYPE: DNA
<213> ORGANISM: Artificial
<220> FEATURE:
<223> OTHER INFORMATION: siRNA

<400> SEQUENCE: 77
gccuauaguc ucagaguuat t                                              21

<210> SEQ ID NO 78
<211> LENGTH: 21
<212> TYPE: DNA
<213> ORGANISM: Artificial
<220> FEATURE:
<223> OTHER INFORMATION: siRNA

<400> SEQUENCE: 78
uaacucugag acuauaggct t                                              21

<210> SEQ ID NO 79
<211> LENGTH: 21
<212> TYPE: DNA
<213> ORGANISM: Artificial
<220> FEATURE:
<223> OTHER INFORMATION: siRNA

<400> SEQUENCE: 79
gagacauccu gauaguugut t                                              21

<210> SEQ ID NO 80
<211> LENGTH: 21
<212> TYPE: DNA
<213> ORGANISM: Artificial
<220> FEATURE:
<223> OTHER INFORMATION: siRNA

<400> SEQUENCE: 80
acaacuauca ggaugucuct t                                              21

<210> SEQ ID NO 81
<211> LENGTH: 21
<212> TYPE: DNA
<213> ORGANISM: Artificial
<220> FEATURE:
<223> OTHER INFORMATION: siRNA

<400> SEQUENCE: 81
```
caaauggcuu uccaugaaut t                                              21

<210> SEQ ID NO 82
<211> LENGTH: 21
<212> TYPE: DNA
<213> ORGANISM: Artificial
<220> FEATURE:
<223> OTHER INFORMATION: siRNA

<400> SEQUENCE: 82
auucauggaa agccauuugt t                                              21

<210> SEQ ID NO 83
<211> LENGTH: 21
<212> TYPE: DNA
<213> ORGANISM: Artificial
<220> FEATURE:
<223> OTHER INFORMATION: siRNA

<400> SEQUENCE: 83
cauuaaaguu aacauucgut t                                              21

<210> SEQ ID NO 84
<211> LENGTH: 21
<212> TYPE: DNA
<213> ORGANISM: Artificial
<220> FEATURE:
<223> OTHER INFORMATION: siRNA

<400> SEQUENCE: 84
acgaauguua acuuuaaugt t                                              21

<210> SEQ ID NO 85
<211> LENGTH: 21
<212> TYPE: DNA
<213> ORGANISM: Artificial
<220> FEATURE:
<223> OTHER INFORMATION: siRNA

<400> SEQUENCE: 85
cacucaugac ugaggucaut t                                              21

<210> SEQ ID NO 86
<211> LENGTH: 21
<212> TYPE: DNA
<213> ORGANISM: Artificial
<220> FEATURE:
<223> OTHER INFORMATION: siRNA

<400> SEQUENCE: 86
augaccucag ucaugagugt t                                              21

<210> SEQ ID NO 87
<211> LENGTH: 21
<212> TYPE: DNA
<213> ORGANISM: Artificial
<220> FEATURE:
<223> OTHER INFORMATION: siRNA

<400> SEQUENCE: 87
ccugucuugu gugaggugut t                                              21

<210> SEQ ID NO 88
<211> LENGTH: 21
<212> TYPE: DNA
<213> ORGANISM: Artificial

```
<220> FEATURE:
<223> OTHER INFORMATION: siRNA

<400> SEQUENCE: 88
acaccucaca caagacaggt t                                              21

<210> SEQ ID NO 89
<211> LENGTH: 21
<212> TYPE: DNA
<213> ORGANISM: Artificial
<220> FEATURE:
<223> OTHER INFORMATION: siRNA

<400> SEQUENCE: 89
ccagcauuca ccaaugagut t                                              21

<210> SEQ ID NO 90
<211> LENGTH: 21
<212> TYPE: DNA
<213> ORGANISM: Artificial
<220> FEATURE:
<223> OTHER INFORMATION: siRNA

<400> SEQUENCE: 90
acucauuggu gaaugcuggt t                                              21

<210> SEQ ID NO 91
<211> LENGTH: 21
<212> TYPE: DNA
<213> ORGANISM: Artificial
<220> FEATURE:
<223> OTHER INFORMATION: siRNA

<400> SEQUENCE: 91
guuauuagaa uguuacgaat t                                              21

<210> SEQ ID NO 92
<211> LENGTH: 21
<212> TYPE: DNA
<213> ORGANISM: Artificial
<220> FEATURE:
<223> OTHER INFORMATION: siRNA

<400> SEQUENCE: 92
uucguaacau ucuaauaact t                                              21

<210> SEQ ID NO 93
<211> LENGTH: 21
<212> TYPE: DNA
<213> ORGANISM: Artificial
<220> FEATURE:
<223> OTHER INFORMATION: siRNA

<400> SEQUENCE: 93
gaguguagca agagguguut t                                              21

<210> SEQ ID NO 94
<211> LENGTH: 21
<212> TYPE: DNA
<213> ORGANISM: Artificial
<220> FEATURE:
<223> OTHER INFORMATION: siRNA

<400> SEQUENCE: 94
aacaccucuu gcuacacuct t                                              21
```

```
<210> SEQ ID NO 95
<211> LENGTH: 21
<212> TYPE: DNA
<213> ORGANISM: Artificial
<220> FEATURE:
<223> OTHER INFORMATION: siRNA

<400> SEQUENCE: 95
gcauguuugc caccaaugut t                                              21

<210> SEQ ID NO 96
<211> LENGTH: 21
<212> TYPE: DNA
<213> ORGANISM: Artificial
<220> FEATURE:
<223> OTHER INFORMATION: siRNA

<400> SEQUENCE: 96
acauuggugg caaacaugct t                                              21

<210> SEQ ID NO 97
<211> LENGTH: 21
<212> TYPE: DNA
<213> ORGANISM: Artificial
<220> FEATURE:
<223> OTHER INFORMATION: siRNA

<400> SEQUENCE: 97
gacgucuuug cauaugugut t                                              21

<210> SEQ ID NO 98
<211> LENGTH: 21
<212> TYPE: DNA
<213> ORGANISM: Artificial
<220> FEATURE:
<223> OTHER INFORMATION: siRNA

<400> SEQUENCE: 98
acacauaugc aaagacguct t                                              21

<210> SEQ ID NO 99
<211> LENGTH: 21
<212> TYPE: DNA
<213> ORGANISM: Artificial
<220> FEATURE:
<223> OTHER INFORMATION: siRNA

<400> SEQUENCE: 99
cuguucgagc ggacguucat t                                              21

<210> SEQ ID NO 100
<211> LENGTH: 21
<212> TYPE: DNA
<213> ORGANISM: Artificial
<220> FEATURE:
<223> OTHER INFORMATION: siRNA

<400> SEQUENCE: 100
ugaacguccg cucgaacagt t                                              21

<210> SEQ ID NO 101
<211> LENGTH: 21
<212> TYPE: DNA
<213> ORGANISM: Artificial
<220> FEATURE:
<223> OTHER INFORMATION: siRNA
```

```
<400> SEQUENCE: 101
caguaccugu ucgagcggat t                                              21

<210> SEQ ID NO 102
<211> LENGTH: 21
<212> TYPE: DNA
<213> ORGANISM: Artificial
<220> FEATURE:
<223> OTHER INFORMATION: siRNA

<400> SEQUENCE: 102
uccgcucgaa cagguacugt t                                              21

<210> SEQ ID NO 103
<211> LENGTH: 21
<212> TYPE: DNA
<213> ORGANISM: Artificial
<220> FEATURE:
<223> OTHER INFORMATION: siRNA

<400> SEQUENCE: 103
gccauuuacc caguauaaut t                                              21

<210> SEQ ID NO 104
<211> LENGTH: 21
<212> TYPE: DNA
<213> ORGANISM: Artificial
<220> FEATURE:
<223> OTHER INFORMATION: siRNA

<400> SEQUENCE: 104
auuauacugg guaaauggct t                                              21

<210> SEQ ID NO 105
<211> LENGTH: 21
<212> TYPE: DNA
<213> ORGANISM: Artificial
<220> FEATURE:
<223> OTHER INFORMATION: siRNA

<400> SEQUENCE: 105
gguaucaguu uaugaggcat t                                              21

<210> SEQ ID NO 106
<211> LENGTH: 21
<212> TYPE: DNA
<213> ORGANISM: Artificial
<220> FEATURE:
<223> OTHER INFORMATION: siRNA

<400> SEQUENCE: 106
ugccucauaa acugauacct t                                              21

<210> SEQ ID NO 107
<211> LENGTH: 21
<212> TYPE: DNA
<213> ORGANISM: Artificial
<220> FEATURE:
<223> OTHER INFORMATION: siRNA

<400> SEQUENCE: 107
caugaacuuu auuucgccat t                                              21

<210> SEQ ID NO 108
```

```
<210> SEQ ID NO 108
<211> LENGTH: 21
<212> TYPE: DNA
<213> ORGANISM: Artificial
<220> FEATURE:
<223> OTHER INFORMATION: siRNA

<400> SEQUENCE: 108
uggcgaaaua aaguucaugt t                                              21

<210> SEQ ID NO 109
<211> LENGTH: 21
<212> TYPE: DNA
<213> ORGANISM: Artificial
<220> FEATURE:
<223> OTHER INFORMATION: siRNA

<400> SEQUENCE: 109
gucccuguac gagcgguuat t                                              21

<210> SEQ ID NO 110
<211> LENGTH: 21
<212> TYPE: DNA
<213> ORGANISM: Artificial
<220> FEATURE:
<223> OTHER INFORMATION: siRNA

<400> SEQUENCE: 110
uaaccgcucg uacagggact t                                              21

<210> SEQ ID NO 111
<211> LENGTH: 21
<212> TYPE: DNA
<213> ORGANISM: Artificial
<220> FEATURE:
<223> OTHER INFORMATION: siRNA

<400> SEQUENCE: 111
gcgguuaagu cagaggaugt t                                              21

<210> SEQ ID NO 112
<211> LENGTH: 21
<212> TYPE: DNA
<213> ORGANISM: Artificial
<220> FEATURE:
<223> OTHER INFORMATION: siRNA

<400> SEQUENCE: 112
cauccucuga cuuaaccgct t                                              21

<210> SEQ ID NO 113
<211> LENGTH: 21
<212> TYPE: DNA
<213> ORGANISM: Artificial
<220> FEATURE:
<223> OTHER INFORMATION: siRNA

<400> SEQUENCE: 113
cuguacgagc gguuaaguct t                                              21

<210> SEQ ID NO 114
<211> LENGTH: 21
<212> TYPE: DNA
<213> ORGANISM: Artificial
<220> FEATURE:
<223> OTHER INFORMATION: siRNA

<400> SEQUENCE: 114
```

| | |
|---|---|
| gacuuaaccg cucguacagt t | 21 |

<210> SEQ ID NO 115
<211> LENGTH: 21
<212> TYPE: DNA
<213> ORGANISM: Artificial
<220> FEATURE:
<223> OTHER INFORMATION: siRNA

<400> SEQUENCE: 115

| | |
|---|---|
| gcgaguacuu cccgcuguut t | 21 |

<210> SEQ ID NO 116
<211> LENGTH: 21
<212> TYPE: DNA
<213> ORGANISM: Artificial
<220> FEATURE:
<223> OTHER INFORMATION: siRNA

<400> SEQUENCE: 116

| | |
|---|---|
| aacagcggga aguacucgct t | 21 |

<210> SEQ ID NO 117
<211> LENGTH: 21
<212> TYPE: DNA
<213> ORGANISM: Artificial
<220> FEATURE:
<223> OTHER INFORMATION: siRNA

<400> SEQUENCE: 117

| | |
|---|---|
| gccggcaucu ucuuucaugt t | 21 |

<210> SEQ ID NO 118
<211> LENGTH: 21
<212> TYPE: DNA
<213> ORGANISM: Artificial
<220> FEATURE:
<223> OTHER INFORMATION: siRNA

<400> SEQUENCE: 118

| | |
|---|---|
| caugaaagaa gaugccggct t | 21 |

<210> SEQ ID NO 119
<211> LENGTH: 21
<212> TYPE: DNA
<213> ORGANISM: Artificial
<220> FEATURE:
<223> OTHER INFORMATION: siRNA

<400> SEQUENCE: 119

| | |
|---|---|
| gggucgccgg caucuucuut t | 21 |

<210> SEQ ID NO 120
<211> LENGTH: 21
<212> TYPE: DNA
<213> ORGANISM: Artificial
<220> FEATURE:
<223> OTHER INFORMATION: siRNA

<400> SEQUENCE: 120

| | |
|---|---|
| aagaagaugc cggcgaccct t | 21 |

<210> SEQ ID NO 121
<211> LENGTH: 21
<212> TYPE: DNA

```
<213> ORGANISM: Artificial
<220> FEATURE:
<223> OTHER INFORMATION: siRNA

<400> SEQUENCE: 121
ccaagauuuc ucuacauuut t                                              21

<210> SEQ ID NO 122
<211> LENGTH: 21
<212> TYPE: DNA
<213> ORGANISM: Artificial
<220> FEATURE:
<223> OTHER INFORMATION: siRNA

<400> SEQUENCE: 122
aaauguagag aaaucuuggt t                                              21

<210> SEQ ID NO 123
<211> LENGTH: 21
<212> TYPE: DNA
<213> ORGANISM: Artificial
<220> FEATURE:
<223> OTHER INFORMATION: siRNA

<400> SEQUENCE: 123
gauuuauggu ugguagagat t                                              21

<210> SEQ ID NO 124
<211> LENGTH: 21
<212> TYPE: DNA
<213> ORGANISM: Artificial
<220> FEATURE:
<223> OTHER INFORMATION: siRNA

<400> SEQUENCE: 124
ucucuaccaa ccauaaauct t                                              21

<210> SEQ ID NO 125
<211> LENGTH: 21
<212> TYPE: DNA
<213> ORGANISM: Artificial
<220> FEATURE:
<223> OTHER INFORMATION: siRNA

<400> SEQUENCE: 125
caucaugccc uucacuuaat t                                              21

<210> SEQ ID NO 126
<211> LENGTH: 21
<212> TYPE: DNA
<213> ORGANISM: Artificial
<220> FEATURE:
<223> OTHER INFORMATION: siRNA

<400> SEQUENCE: 126
uuaagugaag ggcaugaugt t                                              21

<210> SEQ ID NO 127
<211> LENGTH: 21
<212> TYPE: DNA
<213> ORGANISM: Artificial
<220> FEATURE:
<223> OTHER INFORMATION: siRNA

<400> SEQUENCE: 127
guguauccuc ccuucuuaut t                                              21
```

```
<210> SEQ ID NO 128
<211> LENGTH: 21
<212> TYPE: DNA
<213> ORGANISM: Artificial
<220> FEATURE:
<223> OTHER INFORMATION: siRNA

<400> SEQUENCE: 128
auaagaaggg aggauacact t                                              21

<210> SEQ ID NO 129
<211> LENGTH: 21
<212> TYPE: DNA
<213> ORGANISM: Artificial
<220> FEATURE:
<223> OTHER INFORMATION: siRNA

<400> SEQUENCE: 129
cuggauuguu ggacgaguut t                                              21

<210> SEQ ID NO 130
<211> LENGTH: 21
<212> TYPE: DNA
<213> ORGANISM: Artificial
<220> FEATURE:
<223> OTHER INFORMATION: siRNA

<400> SEQUENCE: 130
aacucgucca acaauccagt t                                              21

<210> SEQ ID NO 131
<211> LENGTH: 21
<212> TYPE: DNA
<213> ORGANISM: Artificial
<220> FEATURE:
<223> OTHER INFORMATION: siRNA

<400> SEQUENCE: 131
guguuuacca cccgcguaut t                                              21

<210> SEQ ID NO 132
<211> LENGTH: 21
<212> TYPE: DNA
<213> ORGANISM: Artificial
<220> FEATURE:
<223> OTHER INFORMATION: siRNA

<400> SEQUENCE: 132
auacgcgggu gguaaacact t                                              21

<210> SEQ ID NO 133
<211> LENGTH: 21
<212> TYPE: DNA
<213> ORGANISM: Artificial
<220> FEATURE:
<223> OTHER INFORMATION: siRNA

<400> SEQUENCE: 133
caucgaauuu caaccgagat t                                              21

<210> SEQ ID NO 134
<211> LENGTH: 21
<212> TYPE: DNA
<213> ORGANISM: Artificial
<220> FEATURE:
```

<223> OTHER INFORMATION: siRNA

<400> SEQUENCE: 134
ucucgguuga aauucgaugt t                                      21

<210> SEQ ID NO 135
<211> LENGTH: 21
<212> TYPE: DNA
<213> ORGANISM: Artificial
<220> FEATURE:
<223> OTHER INFORMATION: siRNA

<400> SEQUENCE: 135
gugauaguuc aaguaagaat t                                      21

<210> SEQ ID NO 136
<211> LENGTH: 21
<212> TYPE: DNA
<213> ORGANISM: Artificial
<220> FEATURE:
<223> OTHER INFORMATION: siRNA

<400> SEQUENCE: 136
uucuuacuug aacuaucact t                                      21

<210> SEQ ID NO 137
<211> LENGTH: 21
<212> TYPE: DNA
<213> ORGANISM: Artificial
<220> FEATURE:
<223> OTHER INFORMATION: siRNA

<400> SEQUENCE: 137
ccaucaaugc acgcaagaut t                                      21

<210> SEQ ID NO 138
<211> LENGTH: 21
<212> TYPE: DNA
<213> ORGANISM: Artificial
<220> FEATURE:
<223> OTHER INFORMATION: siRNA

<400> SEQUENCE: 138
aucuugcgug cauugauggt t                                      21

<210> SEQ ID NO 139
<211> LENGTH: 21
<212> TYPE: DNA
<213> ORGANISM: Artificial
<220> FEATURE:
<223> OTHER INFORMATION: siRNA

<400> SEQUENCE: 139
cagagauuca gaugugguat t                                      21

<210> SEQ ID NO 140
<211> LENGTH: 21
<212> TYPE: DNA
<213> ORGANISM: Artificial
<220> FEATURE:
<223> OTHER INFORMATION: siRNA

<400> SEQUENCE: 140
uaccacaucu gaaucucugt t                                      21

```
<210> SEQ ID NO 141
<211> LENGTH: 21
<212> TYPE: DNA
<213> ORGANISM: Artificial
<220> FEATURE:
<223> OTHER INFORMATION: siRNA

<400> SEQUENCE: 141
gccuuauucc guugguugut t                                              21

<210> SEQ ID NO 142
<211> LENGTH: 21
<212> TYPE: DNA
<213> ORGANISM: Artificial
<220> FEATURE:
<223> OTHER INFORMATION: siRNA

<400> SEQUENCE: 142
acaaccaacg gaauaaggct t                                              21

<210> SEQ ID NO 143
<211> LENGTH: 21
<212> TYPE: DNA
<213> ORGANISM: Artificial
<220> FEATURE:
<223> OTHER INFORMATION: siRNA

<400> SEQUENCE: 143
gaaaugagca gguacggcat t                                              21

<210> SEQ ID NO 144
<211> LENGTH: 21
<212> TYPE: DNA
<213> ORGANISM: Artificial
<220> FEATURE:
<223> OTHER INFORMATION: siRNA

<400> SEQUENCE: 144
ugccguaccu gcucauuuct t                                              21

<210> SEQ ID NO 145
<211> LENGTH: 21
<212> TYPE: DNA
<213> ORGANISM: Artificial
<220> FEATURE:
<223> OTHER INFORMATION: siRNA

<400> SEQUENCE: 145
ccuucaacug gagcauguat t                                              21

<210> SEQ ID NO 146
<211> LENGTH: 21
<212> TYPE: DNA
<213> ORGANISM: Artificial
<220> FEATURE:
<223> OTHER INFORMATION: siRNA

<400> SEQUENCE: 146
uacaugcucc aguugaaggt t                                              21

<210> SEQ ID NO 147
<211> LENGTH: 21
<212> TYPE: DNA
<213> ORGANISM: Artificial
<220> FEATURE:
<223> OTHER INFORMATION: siRNA
```

```
<400> SEQUENCE: 147
gacaucacca ugacagauut t                                              21

<210> SEQ ID NO 148
<211> LENGTH: 21
<212> TYPE: DNA
<213> ORGANISM: Artificial
<220> FEATURE:
<223> OTHER INFORMATION: siRNA

<400> SEQUENCE: 148
aaucugucau ggugauguct t                                              21

<210> SEQ ID NO 149
<211> LENGTH: 21
<212> TYPE: DNA
<213> ORGANISM: Artificial
<220> FEATURE:
<223> OTHER INFORMATION: siRNA

<400> SEQUENCE: 149
cccucaucga cauugguuct t                                              21

<210> SEQ ID NO 150
<211> LENGTH: 21
<212> TYPE: DNA
<213> ORGANISM: Artificial
<220> FEATURE:
<223> OTHER INFORMATION: siRNA

<400> SEQUENCE: 150
gaaccaaugu cgaugagggt t                                              21

<210> SEQ ID NO 151
<211> LENGTH: 21
<212> TYPE: DNA
<213> ORGANISM: Artificial
<220> FEATURE:
<223> OTHER INFORMATION: siRNA

<400> SEQUENCE: 151
gcaacguggc caccaucaat t                                              21

<210> SEQ ID NO 152
<211> LENGTH: 21
<212> TYPE: DNA
<213> ORGANISM: Artificial
<220> FEATURE:
<223> OTHER INFORMATION: siRNA

<400> SEQUENCE: 152
uugauggugg ccacguugct t                                              21

<210> SEQ ID NO 153
<211> LENGTH: 21
<212> TYPE: DNA
<213> ORGANISM: Artificial
<220> FEATURE:
<223> OTHER INFORMATION: siRNA

<400> SEQUENCE: 153
ccagauaccu gggagcguut t                                              21

<210> SEQ ID NO 154
<211> LENGTH: 21
```

```
<212> TYPE: DNA
<213> ORGANISM: Artificial
<220> FEATURE:
<223> OTHER INFORMATION: siRNA

<400> SEQUENCE: 154
aacgcuccca gguaucuggt t                                          21

<210> SEQ ID NO 155
<211> LENGTH: 21
<212> TYPE: DNA
<213> ORGANISM: Artificial
<220> FEATURE:
<223> OTHER INFORMATION: siRNA

<400> SEQUENCE: 155
cgcugaagug gaugggccat t                                          21

<210> SEQ ID NO 156
<211> LENGTH: 21
<212> TYPE: DNA
<213> ORGANISM: Artificial
<220> FEATURE:
<223> OTHER INFORMATION: siRNA

<400> SEQUENCE: 156
uggcccaucc acuucagcgt t                                          21

<210> SEQ ID NO 157
<211> LENGTH: 21
<212> TYPE: DNA
<213> ORGANISM: Artificial
<220> FEATURE:
<223> OTHER INFORMATION: siRNA

<400> SEQUENCE: 157
cacaagagga ccagauuaat t                                          21

<210> SEQ ID NO 158
<211> LENGTH: 21
<212> TYPE: DNA
<213> ORGANISM: Artificial
<220> FEATURE:
<223> OTHER INFORMATION: siRNA

<400> SEQUENCE: 158
uuaaucuggu ccucuugugt t                                          21

<210> SEQ ID NO 159
<211> LENGTH: 21
<212> TYPE: DNA
<213> ORGANISM: Artificial
<220> FEATURE:
<223> OTHER INFORMATION: siRNA

<400> SEQUENCE: 159
gcaacacggg cgagaucaat t                                          21

<210> SEQ ID NO 160
<211> LENGTH: 21
<212> TYPE: DNA
<213> ORGANISM: Artificial
<220> FEATURE:
<223> OTHER INFORMATION: siRNA

<400> SEQUENCE: 160
```
uugaucucgc ccguguugct t       21

<210> SEQ ID NO 161
<211> LENGTH: 21
<212> TYPE: DNA
<213> ORGANISM: Artificial
<220> FEATURE:
<223> OTHER INFORMATION: siRNA

<400> SEQUENCE: 161
cgaauucuua uaaagcugut t       21

<210> SEQ ID NO 162
<211> LENGTH: 21
<212> TYPE: DNA
<213> ORGANISM: Artificial
<220> FEATURE:
<223> OTHER INFORMATION: siRNA

<400> SEQUENCE: 162
acagcuuuau aagaauucgt t       21

<210> SEQ ID NO 163
<211> LENGTH: 21
<212> TYPE: DNA
<213> ORGANISM: Artificial
<220> FEATURE:
<223> OTHER INFORMATION: siRNA

<400> SEQUENCE: 163
gucguuugug gauguggcat t       21

<210> SEQ ID NO 164
<211> LENGTH: 21
<212> TYPE: DNA
<213> ORGANISM: Artificial
<220> FEATURE:
<223> OTHER INFORMATION: siRNA

<400> SEQUENCE: 164
ugccacaucc acaaacgact t       21

<210> SEQ ID NO 165
<211> LENGTH: 21
<212> TYPE: DNA
<213> ORGANISM: Artificial
<220> FEATURE:
<223> OTHER INFORMATION: siRNA

<400> SEQUENCE: 165
caugcaaagc caaugccgat t       21

<210> SEQ ID NO 166
<211> LENGTH: 21
<212> TYPE: DNA
<213> ORGANISM: Artificial
<220> FEATURE:
<223> OTHER INFORMATION: siRNA

<400> SEQUENCE: 166
ucggcauugg cuuugcaugt t       21

<210> SEQ ID NO 167
<211> LENGTH: 21
<212> TYPE: DNA
<213> ORGANISM: Artificial

```
<220> FEATURE:
<223> OTHER INFORMATION: siRNA

<400> SEQUENCE: 167
gguauucugg caggcuucut t                                              21

<210> SEQ ID NO 168
<211> LENGTH: 21
<212> TYPE: DNA
<213> ORGANISM: Artificial
<220> FEATURE:
<223> OTHER INFORMATION: siRNA

<400> SEQUENCE: 168
agaagccugc cagaauacct t                                              21

<210> SEQ ID NO 169
<211> LENGTH: 21
<212> TYPE: DNA
<213> ORGANISM: Artificial
<220> FEATURE:
<223> OTHER INFORMATION: siRNA

<400> SEQUENCE: 169
guuucuauuc aguuaaagat t                                              21

<210> SEQ ID NO 170
<211> LENGTH: 21
<212> TYPE: DNA
<213> ORGANISM: Artificial
<220> FEATURE:
<223> OTHER INFORMATION: siRNA

<400> SEQUENCE: 170
ucuuuaacug aauagaaact t                                              21

<210> SEQ ID NO 171
<211> LENGTH: 21
<212> TYPE: DNA
<213> ORGANISM: Artificial
<220> FEATURE:
<223> OTHER INFORMATION: siRNA

<400> SEQUENCE: 171
gagacauugg cucuuaagat t                                              21

<210> SEQ ID NO 172
<211> LENGTH: 21
<212> TYPE: DNA
<213> ORGANISM: Artificial
<220> FEATURE:
<223> OTHER INFORMATION: siRNA

<400> SEQUENCE: 172
ucuuaagagc caaugucuct t                                              21

<210> SEQ ID NO 173
<211> LENGTH: 21
<212> TYPE: DNA
<213> ORGANISM: Artificial
<220> FEATURE:
<223> OTHER INFORMATION: siRNA

<400> SEQUENCE: 173
gaacuucgac auggugauat t                                              21
```

```
<210> SEQ ID NO 174
<211> LENGTH: 21
<212> TYPE: DNA
<213> ORGANISM: Artificial
<220> FEATURE:
<223> OTHER INFORMATION: siRNA

<400> SEQUENCE: 174
uaucaccaug ucgaaguuct t                                              21

<210> SEQ ID NO 175
<211> LENGTH: 21
<212> TYPE: DNA
<213> ORGANISM: Artificial
<220> FEATURE:
<223> OTHER INFORMATION: siRNA

<400> SEQUENCE: 175
ccuauuuauu cacucgacat t                                              21

<210> SEQ ID NO 176
<211> LENGTH: 21
<212> TYPE: DNA
<213> ORGANISM: Artificial
<220> FEATURE:
<223> OTHER INFORMATION: siRNA

<400> SEQUENCE: 176
ugucgaguga auaaauaggt t                                              21

<210> SEQ ID NO 177
<211> LENGTH: 21
<212> TYPE: DNA
<213> ORGANISM: Artificial
<220> FEATURE:
<223> OTHER INFORMATION: siRNA

<400> SEQUENCE: 177
gagauacgag uacgaguuut t                                              21

<210> SEQ ID NO 178
<211> LENGTH: 21
<212> TYPE: DNA
<213> ORGANISM: Artificial
<220> FEATURE:
<223> OTHER INFORMATION: siRNA

<400> SEQUENCE: 178
aaacucguac ucguaucuct t                                              21

<210> SEQ ID NO 179
<211> LENGTH: 21
<212> TYPE: DNA
<213> ORGANISM: Artificial
<220> FEATURE:
<223> OTHER INFORMATION: siRNA

<400> SEQUENCE: 179
ccuuaaggga cuaaauuaat t                                              21

<210> SEQ ID NO 180
<211> LENGTH: 21
<212> TYPE: DNA
<213> ORGANISM: Artificial
<220> FEATURE:
<223> OTHER INFORMATION: siRNA
```

```
<400> SEQUENCE: 180
uuaauuuagu cccuuaaggt t                                              21

<210> SEQ ID NO 181
<211> LENGTH: 21
<212> TYPE: DNA
<213> ORGANISM: Homo sapiens

<400> SEQUENCE: 181
aagaaccaag ggcatataaa g                                              21

<210> SEQ ID NO 182
<211> LENGTH: 21
<212> TYPE: DNA
<213> ORGANISM: Artificial
<220> FEATURE:
<223> OTHER INFORMATION: siRNA

<400> SEQUENCE: 182
gaaccaaggg cauauaaagt t                                              21

<210> SEQ ID NO 183
<211> LENGTH: 21
<212> TYPE: DNA
<213> ORGANISM: Artificial
<220> FEATURE:
<223> OTHER INFORMATION: siRNA

<400> SEQUENCE: 183
cuuuauaugc ccuugguuct t                                              21

<210> SEQ ID NO 184
<211> LENGTH: 21
<212> TYPE: DNA
<213> ORGANISM: Homo sapiens

<400> SEQUENCE: 184
aaccaagggc atataaagac a                                              21

<210> SEQ ID NO 185
<211> LENGTH: 21
<212> TYPE: DNA
<213> ORGANISM: Artificial
<220> FEATURE:
<223> OTHER INFORMATION: siRNA

<400> SEQUENCE: 185
ccaagggcau auaaagacat t                                              21

<210> SEQ ID NO 186
<211> LENGTH: 21
<212> TYPE: DNA
<213> ORGANISM: Artificial
<220> FEATURE:
<223> OTHER INFORMATION: siRNA

<400> SEQUENCE: 186
ugucuuuaua ugcccuuggt t                                              21

<210> SEQ ID NO 187
<211> LENGTH: 21
<212> TYPE: DNA
<213> ORGANISM: Homo sapiens
```

<400> SEQUENCE: 187
aagggcatat aaagacagat g                                              21

<210> SEQ ID NO 188
<211> LENGTH: 21
<212> TYPE: DNA
<213> ORGANISM: Artificial
<220> FEATURE:
<223> OTHER INFORMATION: siRNA

<400> SEQUENCE: 188
gggcauauaa agacagaugt t                                              21

<210> SEQ ID NO 189
<211> LENGTH: 21
<212> TYPE: DNA
<213> ORGANISM: Artificial
<220> FEATURE:
<223> OTHER INFORMATION: siRNA

<400> SEQUENCE: 189
caucugucuu uauaugccct t                                              21

<210> SEQ ID NO 190
<211> LENGTH: 21
<212> TYPE: DNA
<213> ORGANISM: Homo sapiens

<400> SEQUENCE: 190
aaagacagat gggaggagac c                                              21

<210> SEQ ID NO 191
<211> LENGTH: 21
<212> TYPE: DNA
<213> ORGANISM: Artificial
<220> FEATURE:
<223> OTHER INFORMATION: siRNA

<400> SEQUENCE: 191
agacagaugg gaggagacct t                                              21

<210> SEQ ID NO 192
<211> LENGTH: 21
<212> TYPE: DNA
<213> ORGANISM: Artificial
<220> FEATURE:
<223> OTHER INFORMATION: siRNA

<400> SEQUENCE: 192
ggucuccucc caucugucut t                                              21

<210> SEQ ID NO 193
<211> LENGTH: 21
<212> TYPE: DNA
<213> ORGANISM: Homo sapiens

<400> SEQUENCE: 193
aagaagcatc tacataggta c                                              21

<210> SEQ ID NO 194
<211> LENGTH: 21
<212> TYPE: DNA
<213> ORGANISM: Artificial
<220> FEATURE:
<223> OTHER INFORMATION: siRNA -continued

<400> SEQUENCE: 194
gaagcaucua cauagguact t                                         21

<210> SEQ ID NO 195
<211> LENGTH: 21
<212> TYPE: DNA
<213> ORGANISM: Artificial
<220> FEATURE:
<223> OTHER INFORMATION: siRNA

<400> SEQUENCE: 195
guaccuaugu agaugcuuct t                                         21

<210> SEQ ID NO 196
<211> LENGTH: 21
<212> TYPE: DNA
<213> ORGANISM: Artificial
<220> FEATURE:
<223> OTHER INFORMATION: siRNA

<400> SEQUENCE: 196
cgucauacuc caacuauuat t                                         21

<210> SEQ ID NO 197
<211> LENGTH: 21
<212> TYPE: DNA
<213> ORGANISM: Artificial
<220> FEATURE:
<223> OTHER INFORMATION: siRNA

<400> SEQUENCE: 197
uaauaguugg aguaugacgt t                                         21

<210> SEQ ID NO 198
<211> LENGTH: 21
<212> TYPE: DNA
<213> ORGANISM: Artificial
<220> FEATURE:
<223> OTHER INFORMATION: siRNA

<400> SEQUENCE: 198
caaaucugcu gccauguuat t                                         21

<210> SEQ ID NO 199
<211> LENGTH: 21
<212> TYPE: DNA
<213> ORGANISM: Artificial
<220> FEATURE:
<223> OTHER INFORMATION: siRNA

<400> SEQUENCE: 199
uaacauggca gcagauuugt t                                         21

<210> SEQ ID NO 200
<211> LENGTH: 21
<212> TYPE: DNA
<213> ORGANISM: Artificial
<220> FEATURE:
<223> OTHER INFORMATION: siRNA

<400> SEQUENCE: 200
cgaauaugcc uuggcuguut t                                         21

<210> SEQ ID NO 201

```
<211> LENGTH: 21
<212> TYPE: DNA
<213> ORGANISM: Artificial
<220> FEATURE:
<223> OTHER INFORMATION: siRNA

<400> SEQUENCE: 201
aacagccaag gcauauucgt t                                            21

<210> SEQ ID NO 202
<211> LENGTH: 19
<212> TYPE: DNA
<213> ORGANISM: Artificial
<220> FEATURE:
<223> OTHER INFORMATION: siRNA

<400> SEQUENCE: 202
gcuauacaau ccuacccau                                               19

<210> SEQ ID NO 203
<211> LENGTH: 19
<212> TYPE: DNA
<213> ORGANISM: Artificial
<220> FEATURE:
<223> OTHER INFORMATION: siRNA

<400> SEQUENCE: 203
auggguagga uuguauagc                                               19

<210> SEQ ID NO 204
<211> LENGTH: 19
<212> TYPE: DNA
<213> ORGANISM: Artificial
<220> FEATURE:
<223> OTHER INFORMATION: siRNA

<400> SEQUENCE: 204
cugauacucu uccuuguca                                               19

<210> SEQ ID NO 205
<211> LENGTH: 19
<212> TYPE: DNA
<213> ORGANISM: Artificial
<220> FEATURE:
<223> OTHER INFORMATION: siRNA

<400> SEQUENCE: 205
ugacaaggaa gaguaucag                                               19

<210> SEQ ID NO 206
<211> LENGTH: 19
<212> TYPE: DNA
<213> ORGANISM: Artificial
<220> FEATURE:
<223> OTHER INFORMATION: siRNA

<400> SEQUENCE: 206
cgaucuuggu ccugccaua                                               19

<210> SEQ ID NO 207
<211> LENGTH: 19
<212> TYPE: DNA
<213> ORGANISM: Artificial
<220> FEATURE:
<223> OTHER INFORMATION: siRNA

<400> SEQUENCE: 207
```
uauggcagga ccaagaucg                                                19

<210> SEQ ID NO 208
<211> LENGTH: 21
<212> TYPE: DNA
<213> ORGANISM: Artificial
<220> FEATURE:
<223> OTHER INFORMATION: siRNA

<400> SEQUENCE: 208
ccaguuugcu ccuuggucat t                                             21

<210> SEQ ID NO 209
<211> LENGTH: 21
<212> TYPE: DNA
<213> ORGANISM: Artificial
<220> FEATURE:
<223> OTHER INFORMATION: siRNA

<400> SEQUENCE: 209
ugaccaagga gcaaacuggt t                                             21

<210> SEQ ID NO 210
<211> LENGTH: 21
<212> TYPE: DNA
<213> ORGANISM: Artificial
<220> FEATURE:
<223> OTHER INFORMATION: siRNA

<400> SEQUENCE: 210
cacugaaggg ccgcguggut t                                             21

<210> SEQ ID NO 211
<211> LENGTH: 21
<212> TYPE: DNA
<213> ORGANISM: Artificial
<220> FEATURE:
<223> OTHER INFORMATION: siRNA

<400> SEQUENCE: 211
accacgcggc ccuucagugt t                                             21

<210> SEQ ID NO 212
<211> LENGTH: 21
<212> TYPE: DNA
<213> ORGANISM: Artificial
<220> FEATURE:
<223> OTHER INFORMATION: siRNA

<400> SEQUENCE: 212
gagacucaag caauaauuat t                                             21

<210> SEQ ID NO 213
<211> LENGTH: 21
<212> TYPE: DNA
<213> ORGANISM: Artificial
<220> FEATURE:
<223> OTHER INFORMATION: siRNA

<400> SEQUENCE: 213
uaauuauugc uugagucuct t                                             21

<210> SEQ ID NO 214
<211> LENGTH: 21
<212> TYPE: DNA

```
<213> ORGANISM: Artificial
<220> FEATURE:
<223> OTHER INFORMATION: siRNA

<400> SEQUENCE: 214
cccugaaugu gguguuccut t                                              21

<210> SEQ ID NO 215
<211> LENGTH: 21
<212> TYPE: DNA
<213> ORGANISM: Artificial
<220> FEATURE:
<223> OTHER INFORMATION: siRNA

<400> SEQUENCE: 215
aggaacacca cauucagggt t                                              21

<210> SEQ ID NO 216
<211> LENGTH: 21
<212> TYPE: DNA
<213> ORGANISM: Artificial
<220> FEATURE:
<223> OTHER INFORMATION: siRNA

<400> SEQUENCE: 216
gaggcuuccu gaugcucuat t                                              21

<210> SEQ ID NO 217
<211> LENGTH: 21
<212> TYPE: DNA
<213> ORGANISM: Artificial
<220> FEATURE:
<223> OTHER INFORMATION: siRNA

<400> SEQUENCE: 217
uagagcauca ggaagccuct t                                              21

<210> SEQ ID NO 218
<211> LENGTH: 21
<212> TYPE: DNA
<213> ORGANISM: Artificial
<220> FEATURE:
<223> OTHER INFORMATION: siRNA

<400> SEQUENCE: 218
ggcaaugaga ccaacaccut t                                              21

<210> SEQ ID NO 219
<211> LENGTH: 21
<212> TYPE: DNA
<213> ORGANISM: Artificial
<220> FEATURE:
<223> OTHER INFORMATION: siRNA

<400> SEQUENCE: 219
agguguuggu cucauugcct t                                              21

<210> SEQ ID NO 220
<211> LENGTH: 21
<212> TYPE: DNA
<213> ORGANISM: Artificial
<220> FEATURE:
<223> OTHER INFORMATION: siRNA

<400> SEQUENCE: 220
caauaagaac cgagacgaat t                                              21
```

<210> SEQ ID NO 221
<211> LENGTH: 21
<212> TYPE: DNA
<213> ORGANISM: Artificial
<220> FEATURE:
<223> OTHER INFORMATION: siRNA

<400> SEQUENCE: 221
uucgucucgg uucuuauugt t                                         21

<210> SEQ ID NO 222
<211> LENGTH: 21
<212> TYPE: DNA
<213> ORGANISM: Artificial
<220> FEATURE:
<223> OTHER INFORMATION: siRNA

<400> SEQUENCE: 222
gugaaacacu gcaagcguut t                                         21

<210> SEQ ID NO 223
<211> LENGTH: 21
<212> TYPE: DNA
<213> ORGANISM: Artificial
<220> FEATURE:
<223> OTHER INFORMATION: siRNA

<400> SEQUENCE: 223
aacgcuugca guguuucact t                                         21

<210> SEQ ID NO 224
<211> LENGTH: 21
<212> TYPE: DNA
<213> ORGANISM: Artificial
<220> FEATURE:
<223> OTHER INFORMATION: siRNA

<400> SEQUENCE: 224
gagacuuccu ccaaauggut t                                         21

<210> SEQ ID NO 225
<211> LENGTH: 21
<212> TYPE: DNA
<213> ORGANISM: Artificial
<220> FEATURE:
<223> OTHER INFORMATION: siRNA

<400> SEQUENCE: 225
accauuugga ggaagucuct t                                         21

<210> SEQ ID NO 226
<211> LENGTH: 21
<212> TYPE: DNA
<213> ORGANISM: Artificial
<220> FEATURE:
<223> OTHER INFORMATION: siRNA

<400> SEQUENCE: 226
caauggaucc cgagacuuut t                                         21

<210> SEQ ID NO 227
<211> LENGTH: 21
<212> TYPE: DNA
<213> ORGANISM: Artificial
<220> FEATURE:

```
<223> OTHER INFORMATION: siRNA

<400> SEQUENCE: 227
aaagucucgg gauccauugt t                                              21

<210> SEQ ID NO 228
<211> LENGTH: 21
<212> TYPE: DNA
<213> ORGANISM: Artificial
<220> FEATURE:
<223> OTHER INFORMATION: siRNA

<400> SEQUENCE: 228
guacaauccg cauccaacut t                                              21

<210> SEQ ID NO 229
<211> LENGTH: 21
<212> TYPE: DNA
<213> ORGANISM: Artificial
<220> FEATURE:
<223> OTHER INFORMATION: siRNA

<400> SEQUENCE: 229
aguuggaugc ggauuguact t                                              21

<210> SEQ ID NO 230
<211> LENGTH: 21
<212> TYPE: DNA
<213> ORGANISM: Artificial
<220> FEATURE:
<223> OTHER INFORMATION: siRNA

<400> SEQUENCE: 230
gagauaugga aucagauuat t                                              21

<210> SEQ ID NO 231
<211> LENGTH: 21
<212> TYPE: DNA
<213> ORGANISM: Artificial
<220> FEATURE:
<223> OTHER INFORMATION: siRNA

<400> SEQUENCE: 231
uaaucugauu ccauaucuct t                                              21

<210> SEQ ID NO 232
<211> LENGTH: 21
<212> TYPE: DNA
<213> ORGANISM: Artificial
<220> FEATURE:
<223> OTHER INFORMATION: siRNA

<400> SEQUENCE: 232
gcauagaaug cagcaauuut t                                              21

<210> SEQ ID NO 233
<211> LENGTH: 21
<212> TYPE: DNA
<213> ORGANISM: Artificial
<220> FEATURE:
<223> OTHER INFORMATION: siRNA

<400> SEQUENCE: 233
aaauugcugc auucuaugct t                                              21
```

```
<210> SEQ ID NO 234
<211> LENGTH: 21
<212> TYPE: DNA
<213> ORGANISM: Artificial
<220> FEATURE:
<223> OTHER INFORMATION: siRNA

<400> SEQUENCE: 234
gaaagaauuu gcggcaauut t                                              21

<210> SEQ ID NO 235
<211> LENGTH: 21
<212> TYPE: DNA
<213> ORGANISM: Artificial
<220> FEATURE:
<223> OTHER INFORMATION: siRNA

<400> SEQUENCE: 235
aauugccgca aauucuuuct t                                              21

<210> SEQ ID NO 236
<211> LENGTH: 21
<212> TYPE: DNA
<213> ORGANISM: Artificial
<220> FEATURE:
<223> OTHER INFORMATION: siRNA

<400> SEQUENCE: 236
cagaguacgu ucgacgggat t                                              21

<210> SEQ ID NO 237
<211> LENGTH: 21
<212> TYPE: DNA
<213> ORGANISM: Artificial
<220> FEATURE:
<223> OTHER INFORMATION: siRNA

<400> SEQUENCE: 237
ucccgucgaa cguacucugt t                                              21

<210> SEQ ID NO 238
<211> LENGTH: 21
<212> TYPE: DNA
<213> ORGANISM: Artificial
<220> FEATURE:
<223> OTHER INFORMATION: siRNA

<400> SEQUENCE: 238
gacgguucuu guuccaguat t                                              21

<210> SEQ ID NO 239
<211> LENGTH: 21
<212> TYPE: DNA
<213> ORGANISM: Artificial
<220> FEATURE:
<223> OTHER INFORMATION: siRNA

<400> SEQUENCE: 239
uacuggaaca agaaccguct t                                              21

<210> SEQ ID NO 240
<211> LENGTH: 21
<212> TYPE: DNA
<213> ORGANISM: Artificial
<220> FEATURE:
<223> OTHER INFORMATION: siRNA
```

```
<400> SEQUENCE: 240
ccauuaccag gauggugcat t                                              21

<210> SEQ ID NO 241
<211> LENGTH: 21
<212> TYPE: DNA
<213> ORGANISM: Artificial
<220> FEATURE:
<223> OTHER INFORMATION: siRNA

<400> SEQUENCE: 241
ugcaccaucc ugguaauggt t                                              21

<210> SEQ ID NO 242
<211> LENGTH: 21
<212> TYPE: DNA
<213> ORGANISM: Artificial
<220> FEATURE:
<223> OTHER INFORMATION: siRNA

<400> SEQUENCE: 242
ccguuuauca ccugaccgat t                                              21

<210> SEQ ID NO 243
<211> LENGTH: 21
<212> TYPE: DNA
<213> ORGANISM: Artificial
<220> FEATURE:
<223> OTHER INFORMATION: siRNA

<400> SEQUENCE: 243
ucggucaggu gauaaacggt t                                              21

<210> SEQ ID NO 244
<211> LENGTH: 21
<212> TYPE: DNA
<213> ORGANISM: Artificial
<220> FEATURE:
<223> OTHER INFORMATION: siRNA

<400> SEQUENCE: 244
gaguaugcga ugugcuuaat t                                              21

<210> SEQ ID NO 245
<211> LENGTH: 21
<212> TYPE: DNA
<213> ORGANISM: Artificial
<220> FEATURE:
<223> OTHER INFORMATION: siRNA

<400> SEQUENCE: 245
uuaagcacau cgcauacuct t                                              21

<210> SEQ ID NO 246
<211> LENGTH: 21
<212> TYPE: DNA
<213> ORGANISM: Artificial
<220> FEATURE:
<223> OTHER INFORMATION: siRNA

<400> SEQUENCE: 246
caguauaagu gcgauuguat t                                              21

<210> SEQ ID NO 247
<211> LENGTH: 21
```

-continued

```
<212> TYPE: DNA
<213> ORGANISM: Artificial
<220> FEATURE:
<223> OTHER INFORMATION: siRNA

<400> SEQUENCE: 247
uacaaucgca cuuauacugt t                                              21

<210> SEQ ID NO 248
<211> LENGTH: 21
<212> TYPE: DNA
<213> ORGANISM: Artificial
<220> FEATURE:
<223> OTHER INFORMATION: siRNA

<400> SEQUENCE: 248
guaugagugu gggauuugat t                                              21

<210> SEQ ID NO 249
<211> LENGTH: 21
<212> TYPE: DNA
<213> ORGANISM: Artificial
<220> FEATURE:
<223> OTHER INFORMATION: siRNA

<400> SEQUENCE: 249
ucaaauccca cacucauact t                                              21

<210> SEQ ID NO 250
<211> LENGTH: 21
<212> TYPE: DNA
<213> ORGANISM: Artificial
<220> FEATURE:
<223> OTHER INFORMATION: siRNA

<400> SEQUENCE: 250
gacuacuucu ggcauccuut t                                              21

<210> SEQ ID NO 251
<211> LENGTH: 21
<212> TYPE: DNA
<213> ORGANISM: Artificial
<220> FEATURE:
<223> OTHER INFORMATION: siRNA

<400> SEQUENCE: 251
aaggaugcca gaaguaguct t                                              21

<210> SEQ ID NO 252
<211> LENGTH: 21
<212> TYPE: DNA
<213> ORGANISM: Artificial
<220> FEATURE:
<223> OTHER INFORMATION: siRNA

<400> SEQUENCE: 252
caaccuagug gagaacacat t                                              21

<210> SEQ ID NO 253
<211> LENGTH: 21
<212> TYPE: DNA
<213> ORGANISM: Artificial
<220> FEATURE:
<223> OTHER INFORMATION: siRNA

<400> SEQUENCE: 253
```

```
uguguucucc acuagguugt t                                              21

<210> SEQ ID NO 254
<211> LENGTH: 21
<212> TYPE: DNA
<213> ORGANISM: Artificial
<220> FEATURE:
<223> OTHER INFORMATION: siRNA

<400> SEQUENCE: 254
caaagcuuac cgugacaaut t                                              21

<210> SEQ ID NO 255
<211> LENGTH: 21
<212> TYPE: DNA
<213> ORGANISM: Artificial
<220> FEATURE:
<223> OTHER INFORMATION: siRNA

<400> SEQUENCE: 255
auugucacgg uaagcuuugt t                                              21

<210> SEQ ID NO 256
<211> LENGTH: 21
<212> TYPE: DNA
<213> ORGANISM: Artificial
<220> FEATURE:
<223> OTHER INFORMATION: siRNA

<400> SEQUENCE: 256
cugucagccu cuuccgggat t                                              21

<210> SEQ ID NO 257
<211> LENGTH: 21
<212> TYPE: DNA
<213> ORGANISM: Artificial
<220> FEATURE:
<223> OTHER INFORMATION: siRNA

<400> SEQUENCE: 257
ucccggaaga ggcugacagt t                                              21

<210> SEQ ID NO 258
<211> LENGTH: 21
<212> TYPE: DNA
<213> ORGANISM: Artificial
<220> FEATURE:
<223> OTHER INFORMATION: siRNA

<400> SEQUENCE: 258
cccuucagac cagcgggaat t                                              21

<210> SEQ ID NO 259
<211> LENGTH: 21
<212> TYPE: DNA
<213> ORGANISM: Artificial
<220> FEATURE:
<223> OTHER INFORMATION: siRNA

<400> SEQUENCE: 259
uucccgcugg ucugaagggt t                                              21

<210> SEQ ID NO 260
<211> LENGTH: 21
<212> TYPE: DNA
<213> ORGANISM: Artificial
```

```
<220> FEATURE:
<223> OTHER INFORMATION: siRNA

<400> SEQUENCE: 260
cugaccuggu guggucucat t                                              21

<210> SEQ ID NO 261
<211> LENGTH: 21
<212> TYPE: DNA
<213> ORGANISM: Artificial
<220> FEATURE:
<223> OTHER INFORMATION: siRNA

<400> SEQUENCE: 261
ugagaccaca ccaggucagt t                                              21

<210> SEQ ID NO 262
<211> LENGTH: 21
<212> TYPE: DNA
<213> ORGANISM: Artificial
<220> FEATURE:
<223> OTHER INFORMATION: siRNA

<400> SEQUENCE: 262
caaguuguca gggacaugat t                                              21

<210> SEQ ID NO 263
<211> LENGTH: 21
<212> TYPE: DNA
<213> ORGANISM: Artificial
<220> FEATURE:
<223> OTHER INFORMATION: siRNA

<400> SEQUENCE: 263
ucaugucccu gacaacuugt t                                              21

<210> SEQ ID NO 264
<211> LENGTH: 21
<212> TYPE: DNA
<213> ORGANISM: Artificial
<220> FEATURE:
<223> OTHER INFORMATION: siRNA

<400> SEQUENCE: 264
gaaauaaccu ccggagcaut t                                              21

<210> SEQ ID NO 265
<211> LENGTH: 21
<212> TYPE: DNA
<213> ORGANISM: Artificial
<220> FEATURE:
<223> OTHER INFORMATION: siRNA

<400> SEQUENCE: 265
augcuccgga gguuauuuct t                                              21

<210> SEQ ID NO 266
<211> LENGTH: 21
<212> TYPE: DNA
<213> ORGANISM: Artificial
<220> FEATURE:
<223> OTHER INFORMATION: siRNA

<400> SEQUENCE: 266
caguuauguu ggaagauuut t                                              21
```

```
<210> SEQ ID NO 267
<211> LENGTH: 21
<212> TYPE: DNA
<213> ORGANISM: Artificial
<220> FEATURE:
<223> OTHER INFORMATION: siRNA

<400> SEQUENCE: 267
aaaucuucca acauaacugt t                                            21
```